(12) United States Patent
Short et al.

(10) Patent No.: US 9,533,970 B2
(45) Date of Patent: Jan. 3, 2017

(54) MULTISUBSTITUTED AROMATIC COMPOUNDS AS SERINE PROTEASE INHIBITORS

(71) Applicant: VERSEON CORPORATION, Fremont, CA (US)

(72) Inventors: Kevin Michael Short, Fremont, CA (US); Son Minh Pham, Fremont, CA (US); David Charles Williams, Fremont, CA (US); David Ben Kita, Fremont, CA (US)

(73) Assignee: VERSEON CORPORATION, Fremont, CA (US)

( * ) Notice: Subject to any disclaimer, the term of this patent is extended or adjusted under 35 U.S.C. 154(b) by 0 days.

(21) Appl. No.: 14/776,612

(22) PCT Filed: Mar. 17, 2014

(86) PCT No.: PCT/US2014/030853
§ 371 (c)(1),
(2) Date: Sep. 14, 2015

(87) PCT Pub. No.: WO2014/145986
PCT Pub. Date: Sep. 18, 2014

(65) Prior Publication Data
US 2016/0024047 A1    Jan. 28, 2016

Related U.S. Application Data

(60) Provisional application No. 61/789,358, filed on Mar. 15, 2013.

(51) Int. Cl.
| | | |
|---|---|---|
| *A61K 31/535* | (2006.01) | |
| *C07D 401/04* | (2006.01) | |
| *A61K 31/4439* | (2006.01) | |
| *A61K 31/415* | (2006.01) | |
| *A61K 31/4545* | (2006.01) | |
| *A61K 31/506* | (2006.01) | |
| *A61K 31/5377* | (2006.01) | |
| *C07D 405/14* | (2006.01) | |
| *C07D 231/38* | (2006.01) | |
| *C07D 403/04* | (2006.01) | |
| *C07D 409/14* | (2006.01) | |
| *A61K 9/00* | (2006.01) | |
| *A61K 31/444* | (2006.01) | |

(52) U.S. Cl.
CPC ........... *C07D 401/04* (2013.01); *A61K 9/0048* (2013.01); *A61K 31/415* (2013.01); *A61K 31/444* (2013.01); *A61K 31/4439* (2013.01); *A61K 31/4545* (2013.01); *A61K 31/506* (2013.01); *A61K 31/5377* (2013.01); *C07D 231/38* (2013.01); *C07D 403/04* (2013.01); *C07D 405/14* (2013.01); *C07D 409/14* (2013.01)

(58) Field of Classification Search
CPC .................................................... C07D 401/04
USPC ....................................................... 514/236.2
See application file for complete search history.

(56) References Cited

U.S. PATENT DOCUMENTS

| | | | |
|---|---|---|---|
| 3,250,761 | A | 5/1966 | Schmidt et al. |
| 3,926,999 | A | 12/1975 | Poetsch |
| 4,008,249 | A | 2/1977 | Fischer et al. |
| 4,160,452 | A | 7/1979 | Theeuwes |
| 4,256,108 | A | 3/1981 | Theeuwes |
| 4,265,874 | A | 5/1981 | Bonsen et al. |
| 4,861,760 | A | 8/1989 | Mazuel et al. |
| 4,911,920 | A | 3/1990 | Jani et al. |
| 5,212,162 | A | 5/1993 | Missel et al. |
| 5,403,841 | A | 4/1995 | Lang et al. |
| 5,466,823 | A | 11/1995 | Talley et al. |
| 5,739,083 | A | 4/1998 | Endo et al. |
| 5,753,688 | A | 5/1998 | Talley et al. |
| 5,792,761 | A | 8/1998 | Fraley et al. |
| 5,902,852 | A | 5/1999 | Schulz et al. |
| 6,589,997 | B2 | 7/2003 | Pillarisetti et al. |
| 7,625,944 | B2 | 12/2009 | Sinha et al. |
| 2002/0055639 | A1 | 5/2002 | Nebel et al. |
| 2002/0091116 | A1 | 7/2002 | Zhu et al. |
| 2003/0144309 | A1 | 7/2003 | Choon-Moon |
| 2004/0132726 | A1 | 7/2004 | Arora et al. |
| 2005/0009827 | A1 | 1/2005 | Nazare et al. |
| 2005/0065144 | A1 | 3/2005 | Feng et al. |

(Continued)

FOREIGN PATENT DOCUMENTS

| | | | |
|---|---|---|---|
| CH | WO 2004/035564 | * | 4/2004 |
| EP | 0246888 A2 | | 11/1987 |

(Continued)

OTHER PUBLICATIONS

Hughes, "First oral warfarin alternative approved in the US," Nature Reviews Drug Discovery, 9. pp. 903-906. Dec. 2010. Published ahead of print Oct. 29, 2010.
Inaba et al., "Suppression of experimental autoimmune encephalomyelitis by dermatan sulfate," Cellular Immunology, 198(2). pp. 96-102. Dec. 15, 1999.
International Search Report and Written Opinion mailed Jul. 17, 2014, International Patent Application No. PCT/US2014/030853, filed Mar. 17, 2014.
Kakkar et al., "Low Molecular Weight Heparin, Therapy With Dalteparin, and Survival in Advanced Cancer. The Fragmin Advanced Malignancy Outcome Study (FAMOUS)," Journal of Clinical Oncology, 22(10). pp. 1944-1948. May 15, 2004.

(Continued)

*Primary Examiner* — Nizal Chandrakumar
(74) *Attorney, Agent, or Firm* — Davis Wright Tremaine LLP

(57) ABSTRACT

There are provided inter alia multisubstituted aromatic compounds useful for the inhibition of kallikrein, which compounds include substituted pyrazolyl or substituted triazolyl. There are additionally provided pharmaceutical compositions. There are additionally provided methods of treating and preventing certain diseases or disorders, which disease or disorder is amenable to treatment or prevention by the inhibition of kallikrein.

25 Claims, No Drawings

(56) References Cited

U.S. PATENT DOCUMENTS

| | | |
|---|---|---|
| 2005/0203127 A1 | 9/2005 | Cezanne et al. |
| 2008/0188527 A1 | 8/2008 | Cashman |
| 2008/0269293 A1 | 10/2008 | Chi et al. |
| 2008/0275070 A1 | 11/2008 | Liu et al. |
| 2009/0105253 A1 | 4/2009 | Kubo et al. |
| 2009/0163545 A1 | 6/2009 | Goldfarb |
| 2010/0016320 A1 | 1/2010 | Dyckman et al. |
| 2010/0210696 A1 | 8/2010 | Nishida et al. |
| 2011/0071182 A1 | 3/2011 | Seefeld et al. |
| 2013/0040950 A1 | 2/2013 | Short et al. |

FOREIGN PATENT DOCUMENTS

| | | |
|---|---|---|
| EP | 0854723 A1 | 7/1998 |
| JP | S50-117936 A | 9/1975 |
| JP | H10-509708 A | 9/1998 |
| WO | 9605309 A2 | 2/1996 |
| WO | 9614843 A2 | 5/1996 |
| WO | 9828269 A1 | 7/1998 |
| WO | 0009500 A2 | 2/2000 |
| WO | 0041716 A | 7/2000 |
| WO | 0112189 A1 | 2/2001 |
| WO | 02092573 A2 | 11/2002 |
| WO | 03048155 A1 | 6/2003 |
| WO | 03061682 A1 | 7/2003 |
| WO | 03062206 A2 | 7/2003 |
| WO | 2004000785 A2 | 12/2003 |
| WO | 2004058721 A2 | 7/2004 |
| WO | 2004058722 A1 | 7/2004 |
| WO | 2004089911 A1 | 10/2004 |
| WO | 2004098589 A1 | 11/2004 |
| WO | 2004101555 A1 | 11/2004 |
| WO | 2008009638 A2 | 1/2008 |
| WO | 2009010560 A1 | 1/2009 |
| WO | 2009041447 A1 | 4/2009 |
| WO | 2010020600 A1 | 2/2010 |
| WO | 2010020601 A1 | 2/2010 |
| WO | 2010020602 A1 | 2/2010 |
| WO | 2010127855 A1 | 11/2010 |
| WO | 2011126903 A2 | 10/2011 |
| WO | 2012065019 A2 | 5/2012 |
| WO | 2012154880 A1 | 11/2012 |
| WO | 2013049591 A2 | 4/2013 |
| WO | 2014145986 A1 | 9/2014 |
| WO | 2014149139 A2 | 9/2014 |

OTHER PUBLICATIONS

Kantlehner et al., "Orthoamide, XXXII. Umsetzungen von tert-Butoxy-N,N,N',N'-tetramethylmethandiamin mit NH-und CH-aciden Verbindungen," Liebigs Annalen der Chemie, 1980(3). pp. 344-357. Mar. 1980.

Katritzky et al. "Selective Reactivity of sp3 and sp2 Carbanions of 1-Substituted 1,2,4-Triazoles. A Comparative Approach," Journal of Organic Chemsitry, 63(13). pp. 4323-4331. Jun. 5, 1998.

Keel et al., "Pathophysiology of polytrauma," Injury, 36(6). pp. 691-709. Jun. 2005.

Klerk et al., "The Effect of Low Molecular Weight Heparin on Survival in Patients With Advanced Malignancy," Journal of Clinical Oncology, 23(10). pp. 2130-2135. Apr. 1, 2005.

Kokolis et al., "Anticoagulation strategies for patients undergoing percutaneous coronary intervention: unfractionated heparin, low-molecular-weight heparins, and direct thrombin inhibitors." Progress in Cardiovascular Disease, 46(6):506-523. May-Jun. 2004.

Kranjc et al., "Dual Inhibitors of the Blood Coagulation Enzymes" Current Medicinal Chemistry, 11(19). pp. 2535-2547. Oct. 2004.

Kumar et al., "Efficient Routes to Pyrazolo[3,4-b]indoles and Pyrazolo[1,5-a]benzimidazoles via Palladium- and Copper-Catalyzed Intramolecular C—C and C—N Bond Formation", The Journal of Organic Chemistry, 74(18). pp. 7046-7051. Sep. 18, 2009. Published ahead of print Aug. 11, 2009.

Labanauskas et al., "Synthesis of 3-(3,4-Dimethoxyphenyl)-1H-1,2,4,-Triazole-5-Thiol and 2-Amino-5-(3,4-Dimethopheny)-1,3,4-Thiadiazole Derivatives Exhibiting Anti-Inflammatory Activity," Die Pharmazie, 56(8). pp. 617-619. Aug. 2001.

Langer et al., "New methods of drug delivery," Science, 249(4976). pp. 1527-1533. Sep. 28, 1990.

Lee et al., "Randomized comparison of low molecular weight heparin and coumarin derivatives on the survival of patients with cancer and venous thromboembolism," Journal of Clinical Oncology, 23(10). pp. 2123-2129. Apr. 1, 2005.

Lewis et al., "Argatroban anticoagulation during percutaneous coronary intervention in patients with heparin-induced Thrombocytopenia." Catheterization & Cardiovascular Interventions, 57(2):177-184. Oct. 2002. Published ahead of print Sep. 30, 2002.

Lloyd et al., "Benzopyran sulfonamides as Kv1.5 potassium channel blockers," Bioorganic & Medicinal Chemistry Letters, 17(12). pp. 3271-3275. Jun. 15, 2007.

Lottenberg et al., "The action of thrombin on peptide p-Nitroanilide substrates: Substrate selectivity and examination of hydrolysis under different reaction condtions," Biochimica et Biophysica Acta (BBA)—Protein Structure and Molecular Enzymology, 742(3). pp. 539-557. Feb. 15, 1983.

Luo et al., "The Role of Thrombin and Thrombin Receptors in the Brain," in Thrombin: Physiology and Disease, XII. Maragoudakis et al. (eds.). pp. 133-159. 2009.

Miller Keane et al., Miller-Keane Encyclopedia & Dictionary of Medicine, Nursing & Allied Health, 5th Ed. pp. 1651 and 1708. O'Toole (ed.). W.B. Saunders, Philadephia, PA. 1992.

Miura "Transactivation of KDR/Flk-1 by the B2 receptor induces tube formation in human coronary endothelial cells" Hypertension, 41(5). pp. 1118-1123. Published ahead of print Mar. 24, 2001.

Montoya et al., "Regioselective formation of N-alkyl-3,5-pyrazole derived ligands. A synthetic and computational study," Tetrahedron, 61(52). pp. 12377-12385. Dec. 26, 2005.

Moreau et al., "The kallikrein-kinin system: current and future pharmacological targets," Journal of Pharmacological Sciences, 99(1). pp. 6-38. Sep. 22, 2005.

Narita et al, "Protease-activated receptor-1 and platelet-derived growth factor in spinal cord neurons are implicated n neuropathic pain after nerve injury," The Journal of Neuroscience, 25(43). pp. 10000-10009. Oct. 26, 2005.

Nieman et al., "Oral thrombostatin FM19 inhibits prostate cancer," Thrombosis and Haemostasis, 104(5). pp. 1044-1048. Nov. 2010. Published ahead of print Sep. 30, 2010.

Nieman et al., "Thrombostatin FM compounds: direct thrombin inhibitors—mechanism of action in vitro and in vivo," Journal of Thrombosis and Haemostasis, 6(5). pp. 837-845. May 2008. Published ahead of print Feb. 26, 2008.

Olsson et al., "Stroke prevention with the oral direct thrombin inhibitor ximelagatran compared with warfarin in patients with non-valvular atrial fibrillation (SPORTIF III): randomised controlled trial.," Lancet, 362(9397): 1691-1698, Nov. 22, 2003.

Pinto et al., "Discovery of 1[3-(Aminomethyl)phenyl]-N-[3-fluoro-2'-(methylsulfony1)-[1,1'-biphenyl]-4-yl]-3-(trifiuoromethyl)-1H-pyrazole-5-carboxamide (DPC423), a Highly Potent, Selective, and Orally Bioavailable Inhibitor of Blood Coagulation Factor Xa," Journal of Medicinal Chemistry, 44(4). pp. 566-578. Jan. 24, 2001.

Prezelj et al., "Recent Advances in Serine Protease Inhibitors as Anticoagulant Agents," Current Pharmaceutical Design, 13(3). pp. 287-312. Jan. 2007.

Reiter et al., "On Triazoles. VI. The acylation of 5-amino-1,2,4-triazoles," Journal of Heterocyclic Chemistry, 24(1). pp. 127-142. Jan. 1987.

Renné, "Plasma kallikrein: Novel functions for an old protease," Thrombosis and Haemostasis, 107(6). pp. 1012-1013. Jun. 2012.

Saalfrank et al., "Geminate Vinyldiazide, VI. 4,5-Dihydro-1H-tetrazol-5-ylidene aus 3,3-Diazido-2-cyanacrylsáureestem und Hydrazinen, Hydraziden sowie O-substituierten Hydroxylaminen," Chemische Berichte, 122(3). pp. 519-522. Mar. 1989.

Schepetkin et al., "N-Benzoylpyrazoles Are Novel Small-Molecule Inhibitors of Human Neutrophil Elastase," Journal of Medicinal Chemistry, 50(20). pp. 4928-4938. Oct. 4, 2007. Published ahead of print Sep. 12, 2007.

(56) References Cited

OTHER PUBLICATIONS

Schneider et al., "Critical role of kallikrein in hereditary angioedema pathogenesis: a clinical trial of ecallantide, a novel kallikrein inhibitor," Journal of Allergy and Clinical Immunology, 120(2). pp. 416-422. Aug. 2007.
Silver et al., "Dabigatran Etexilate, An Oral Direct Thrombin Inhibitor, Represses Fibrotic Changes in a Murine Model of Pulmonary Fibrosis." American Journal of Respiratory and Critical Care Medicine, 181. p. A6780. 2010.
Simiti et al., "Kondensation von 3-MerKapto-5-phenyl-1,2,4-triazole mit Monochloracetaldehyd," Archie Der Pharmazie, 320(1). pp. 528-534. Jan. 1, 1987.
Smorenburg et al., "The effects of unfractionated heparin on survival in patients with malignancy—a systematic review," Thrombosis and Haemostasis, 82. pp. 1600-1604. 1999.
Sotiropoulou et al., "Targeting the kallikrein-related peptidases for drug development," Trends in Pharmacological Sciences, 33(12). pp. 623-634. Dec. 2012.
Stella, "Prodrugs: An Overview and Definition." Pro-drugs as Novel Drug Delivery Systems, vol. 14, Chapter 1. 115 pages. American Chemical Society. Jun. 1, 1975.
STN International File caplus [Online], AN 2007:157737, DN 147: 385893, SO: Zhumal Organichnoi ta Farmatsevtichnoi Kimii 2006, 4(1), p. 32-37, CAS registration No. RN:882238-17-7, 882238-21-3, 882238-25-7, 382239-13-6, 882239-17-0, 882239-21-6.
STN International File Registry [Online]. CAS registration No. RN: 1189909-54-3, 1007171-70-1, 956442-20-9, 956441-56-8, 956375-74-9, 882239-05-6.
STN International Registry File [Online] May 14, 2008, CAS Registration No. RN 1020709-18-5.
Syed et al., "Wet AMD market," Nature Reviews Drug Discovery, 11. pp. 827-828. Nov. 2012.
Telander, "Inflammation and age-related macular degeneration (AMD)," Seminars in Ophthalmology, 26(3). pp. 192-197. Published online May 24, 2011.
The National Formulary, 14th Ed. American Pharmaceutical Association. Washington, D.C. pp. 1-5. Jul. 1, 1975.
The National Formulary, 14th Ed. American Pharmaceutical Association. Washington, D.C. pp. 6-19. Jul. 1, 1975.
Van Noorden et al., "Experimental and clinical effects of anticoagulants on cancer progression," Thrombosis Search, 125, Supplment 2. pp. S77-S79. Apr. 2010.
Vaughan et al., "Protease nexin-1, a potent thrombin inhibitor, is reduced around cerebral blood vessels in Alzheimer's disease," Brain Research, 668(1-2). pp. 160-170. Dec. 30, 1994.
Wardakhan et al., "Synthesis of novel pyrazole, coumarin, and pyridazine derivatives evaluated as potential antimicrobial and antifungal agents," Journal of the Chilean Chemical Society, 52(2). pp. 1145-1149. Jun. 2007.
Wiedermann et al., "The anti-inflammatory actions of antithrombin—a review," Acta Medica Austriaca, 29(3). pp. 39-92. Jul. 29, 2002.
Wieland et al., "Approaches in anticoagulation: rationales for target positiong," Current Opinion in Investigational Drugs, 4(3). pp. 264-271. Mar. 2003.
Wong et al., "Nonpeptide Factor Xa Inhibitors III: Effects of DPC423, an Orally-Active Pyrazole Antithrombotic Agent, on Arterial Thrombosis in Rabbits." The Journal of Pharmacolor and Experimental Therapeutics, 303(3). pp. 993-1000. Dec. 1, 2002.
Xiong et al., "Discovery and Structure-Activity Relationship of 3-Methoxy-N-(3-(1-methyl-1 H-pyrazol-5-y-l)-4-(2-morpholinoethoxy)phenyl)benzamide (APD791): A Highly Selective 5-Hydroxytryptamine 2A Receptor Inverse Agonist for the Treatment of Arterial Thrombosis," Journal of Medicinal Chemistry 53(11):4412-4421, Jun. 10, 2010, ISSN:0022-2623, DOI: 10.1021/jm100044a.
Yin et al., "Brain endothelial cells synthesize neurotoxic thrombin in Alzheimer's disease.", The American Journal of Pathology, 176(4). pp. 1600-1606. Apr. 2010.

Young et al., "Selective and dual action orally active inhibitors of thrombin and factor Xa" Bioorganic & Medicinal Chemistry Letters, 17(10). pp. 2927-2930. May 15, 2007.
Yu et al., "Synthesis and biological activities of 5-substituted benzamide triazole," Journal of Central China Normal University, Natural Sciences Edition, 37(4). pp. 505-503. 2003. Accessed from Database CAPLUS. Database accession No. 2004:240714.
Zacharski et al., "Heparin as an anticancer therapeutic," Expert Opinion on Investigational Drugs, 17(7). pp. 1029-1037. Jun. 12, 2008.
Abdel-Salam et al., "A study of unfractionated and low molecular weight heparins in a model of cholestatic liver injury in the rat," Pharmacological Research, 51(1). pp. 59-67. Jan. 2005.
Abe et al., "Low molecular weight heparin prevents hepatic fibrogenesis caused by carbon tetrachloride in the rat," Journal of Hepatology, 46(2). pp. 286-294. Feb. 2007.
Akerblom et al., "Nitrofuryttriazole derivatives as potential urinary tract antibacterial agents," Journal of Medicinal Chemistry, 16(4). pp. 312-319. Apr. 1973.
Akiyama et al., "Thrombin accumulation in brains of patients with Alzheimer's disease," Neuroscience Letters, 146(2). pp. 152-154. Nov. 9, 1992.
Akl et al., "Parenteral anticoagulation may prolong the survival of patients with limited small cell lung cancer a Cochrane systematic review," Journal of Experimental & Clinical Cancer Research, 27(4). 10 pages. May 15, 2008.
Altinbas et al., "A randomized clinical trial of combination chemotherapy with and without low-molecular-weight heparin in small cell lung cancer," Journal of Thrombosis and Haemostasis, 2(8). pp. 1266-1271. Aug. 2004.
Assy et al., "The beneficial effect of aspirin and enoxaparin on fibrosis progression and regenerative activity in a rat model of cirrhosis," Digestive Diseases and Sciences, 52(5). pp. 1187-1193. May 2007.
Bader, "Kallikrein-Kinin System in Neovascularization," Arteriosclerosis, Thombosis, and Vascular Biology, 29(5). pp. 617-619. May 2009.
Berge et al., "Pharmaceutical Salts," Journal of Pharmaceutical Sciences, 66(1). pp. 1-19. Jan. 1977.
Bird et al., "Effects of plasma kallikrein deficiency on haemostasis and thrombosis in mice: Murine Ortholog of the Fletcher Trait," Thrombosis and Haemostasis, 107(6). pp. 1141-1150. Jun. 2012.
Bogatkevich et al., "Dabigatran, a direct thrombin inhibitor, demonstrates antifibrotic effects on lung fibroblasts," Arthritis & Rheumatism, 60(11). pp. 3455-3464. Nov. 2009. Published ahead of print Oct. 29, 2009.
Brent et al., "Fomepizole for the treatment of ethylene glycol poisoning," The New England Journal of Medicine, 340 (11). pp. 832-838. Mar. 18, 1999.
Caliendo et al., "Kallikrein Protease Activated Receptor (PAR) Axis: An Attractive Target for Drug Development," Journal of Medicinal Chemistry, 55(15). pp. 6669-6686. May 18, 2012.
Calvaruso et al. "Cogaulation and fibrosis in chronic liver disease," Gut, 57(12). pp. 1722-1727. Dec. 2008.
Chambers et al., "Coagulation cascade proteases and tissue fibrosis," Biochemical Society Transactions, 30(2). pp. 194-200. Apr. 2002.
Chambers et al., "Procoagulant signalling mechanisms in lung inflammation and fibrosis: novel opportunities for pharmacological intervention?" British Journal of Pharmacology, 153(S1). pp. S367-S378. Mar. 2008. Published ahead of print Jan. 28, 2008.
Chang et al., "Synthesis and structure-activity relationships of quatemary ammonium cephalosporins with 3-pyrazolylpyridinium derivatives," Bioorganic & Medicinal Chemistry Letters, 10(11). pp. 1211-1214. Jun. 5, 2000.
Chelmicka-Szorc et al., "Partial suppression of experimental allergic encephalomyelitis with heparin," Archives of Neurology, 27(2). pp. 153-158. Aug. 1972.
Chen et al., "Interaction of Novel Positive Allosteric Modulators of Metabotropic Glutamate Receptor 5 with the Negative Allosteric Antagonist Site is Required for Potentiation of Receptor Responses," Molecular Pharmacology, 71 (5). pp. 1389-1398. May 2007. Published ahead of print Feb. 15, 2007.

(56) References Cited

OTHER PUBLICATIONS

Cherton et al., "Réactivité du nucléophile azoture vis-à-vis de cations hétérocycliques aromatiques. VIII. Réarrangement de β-tétrazolo-trans-benzalacétophenones," Canadian Journal of Chemistry, 63(10). pp. 2601-2607. Oct. 1985.
Cipens et al., "Aminoguanidine derivatives and their transformations. V. Alkyl- and arylamino substituted 1,2,4-triazoles and," Proceedings of the Academy of Science of Latvian SSR, Chemistry Series, 2. pp. 255-261. 1962. Accessed through CAPLUS. Database accession No. 1963:469125.
Defeo et al., "Dabigatran etexilate blocks breast cancer progression in vitro and in a 4T1 breast cancer tumor model in mice," Thrombosis Research, 125, Supplement 2. p. S188. Apr. 2010.
Defeo et al., "Use of dabigatran etexilate to reduce breast cancer progression," Cancer Biology & Therapy, 10(10). pp. 1001-1008. Nov. 15, 2010.
Deng et al., "Development of an oxazolopyridine series of dual thrombin/factor Xa inhibitors via structure-guided lead optimization," Bioorganic & Medicinal Chemistry Letters, 15(20). pp. 4411-4416. Oct. 15, 2005.
Diener et al., "Stroke prevention using the oral direct thrombin inhibitor ximelagatran in patients with non-valvular atrial fibrillation. Pooled analysis from the SPORTIF III and V studies." Cerebrovascular Diseases, 21(4):279-293. Mar. 2006.
Dubau et al., "Malonylierungsreaktionen an 4-monosubstituierten Pyrazolidin-3,5-dionen," Chemische Berichte, 108 (7). pp. 2189-2201. Jul. 1975.
Duplantier et al., "A role for thrombin in liver fibrosis," Gut, 53(11). pp. 1682-1687. Nov. 2004.
Dzygiel et al., "Synthesis, Structure and Properties of N-Acetylated Derivatives of Methyl 5-Amino-1H-[1,2,4] triazole-3-carboxylate," Chemical and Pharaceutical Bulletin, 52(2). pp. 192-198. Feb. 1, 2004.
Eliel et al., Stereochemistry of Organic Compounds, Chapter 1. pp. 1-16. Wiley. Sep. 1994.
Eriksson et al., "Direct thrombin inhibitor melagatran followed by oral ximelagatran in comparison with enoxaparin for prevention of venous thromboembolism after total hip or knee replacement." Thrombosis and Haemostasis, 89 (2):288-296. Feb. 2003.
Falanga et al., "Effect of anticoagulant drugs in cancer," Current Opinion in Pulmonary Medicine, 11(5). pp. 403-407. Sep. 2005.
Farghaly et al., "Synthesis of some new azoles with antiviral protential," ARKIVOC XI. pp. 76-90. 2006.
Favreau et al., "Anti-thrombin therapy during warm ischemia and cold preservation prevents chronic kidney graft fibrosis in a DCD model," American Journal of Transplantation, 10(1). pp. 30-39. Jan. 2010. Published ahead of print Dec. 2, 2009.
Feener et al., "Plasma Kallikrein and Diabetic Macular Edema," Current Diabetes Reports, 10(4). pp. 270-275. Published ahead of print, Jun. 10, 2010.
Francis et al., "Ximelagatran versus warfarin for the prevention of venous thromboembolism after total knee arthroplasty. A randomized, double-blind trial." Annals of Internal Medicine, 137(8):648-655. Oct. 15, 2002.
Freitas et al., "Isomannide derivatives as new class of inhibitors for human kallikrein 7," Bioorganic & Medicinal Chemistry Letters, 22(19). pp. 6072-6075. Oct. 1, 2012.
Garcia et al., "The role of thrombin and protease-activated receptors in pain mechanisms," Thrombosis and Haemostasis, 103(6). pp. 1145-1151. Jun. 2010. Published ahead of print Apr. 29, 2010.
Giardino, E. C., et al., "Cooperative antithrombotic effect from the simultaneous inhibition of thrombin and factor Xa", Blood Coagulation and Fibrinolysis, 21(2). pp. 128-134. Mar. 2010.
Goding, Monoclonal Antibodies: Prinicples and Practice. p. 104. Academic Press. 1986.
Gross et al., "New anticoagulants for treatment of venous thromboembolism," Arteriosclerosis, Thrombosis, and Vascular Biology, 28(3). pp. 380-386. Mar. 2008.
Han et al., "Proteomic analysis of active multiple sclerosis lesions reveals therapeutic targets," Nature, 451. pp. 1076-1081. Feb. 28, 2008. Published ahead of print Feb. 17, 2008.
Hankey et al, "Antithrombotic Drugs for Patients with Ischaemic Stroke and Transient Ischaemic Attack to Prevent Recurrent Major Vascular Events," The Lancet Neurology, 9(3):273-284, Mar. 2010.
Heit et al., "Comparison of the Oral Direct Thrombin Inhibitor Ximelagatran With Enoxaparin as Prophylaxis Against Venous Thromboembolism After Total Knee Replacement: A Phase 2 Dose-Finding Study," Archives of Internal Medicine 161(18): 2215-2221, Oct. 8, 2001.
Herrera et al., "Regio- and Stereoselectivity of Captodative Olefins in 1,3-Dipolar Cydoadditions. A DFT/HSAB Theory Rationale for the Observed Regiochemistry of Nitrones," The Journal of Organic Chemistry, 66(4). pp. 1252-1263. Feb. 9, 2001. Published ahead of print Jan. 27, 2001.
Hettiarachchi et al., "Do Heparins Do More Than Just Treat Thrombosis? The Influence of Heparins on Cancer Spread," Thrombosis and Haemostasis, 82(2). pp. 947-952. 1999.
Hirsh et al., "New anticoagulants," Blood, 105(2). pp. 453-463. Jan. 2005. Published ahead of print Jun. 10, 2004.
Howell et al., "Direct thrombin inhibition reduces lung collagen, accumulation, and connective tissue growth factor nRNA levels in bleomycin-induced pulmonary fibrosis.," American Journal of Pathology, 159(4). pp. 1383-1395. Oct. 2001.
Hu et al., "Role of endogenous thrombin in tumor implantation, seeding, and spontaneous metastasis," Blood, 104(9). pp. 2746-2751. Nov. 1, 2004.
Hua et al., "Systemic use of argatroban reduces tumor mass, attenuates neurological deficits and prolongs survival :ime in rat glioma models," Acta Neurochirurgica Supplement, 95. pp. 403-406. 2005.
Hua et al., "The role of thrombin in gliomas," Journal of Thrombosis and Haemostasis, 3(9). pp. 1917-1923. Sep. 2005. Published ahead of print Jun. 24, 2005.
Ramalakshmi et al., "Synthesis, Characterization and Biological Screening of Some Novel 1,3,5 Trisubstituted 2-Pyrazolines," Rasayan Journal of Chemistry 2(2):393-396, Apr. 2009.

\* cited by examiner

MULTISUBSTITUTED AROMATIC COMPOUNDS AS SERINE PROTEASE INHIBITORS

CROSS-REFERENCE TO RELATED APPLICATIONS

The present application is a U.S. National Stage entry under 35 U.S.C. §371 of International Application No. PCT/US2014/030853, filed on Mar. 17, 2014, designating the United States of America and published in English on Sep. 18, 2014, which in turn claims priority to U.S. Provisional Application No. 61/789,358, filed on Mar. 15, 2013, each of which is hereby incorporated by reference in its entirety.

BACKGROUND OF THE INVENTION

The present disclosure relates to compounds, e.g., multisubstituted aromatic compounds, which exhibit biological activity, e.g., inhibitory action, against serine proteases, including thrombin and various kallikreins.

Kallikreins are a subgroup of serine proteases, divided into plasma kallikrein and tissue kallikreins. Plasma kallikrein (KLKB1) liberates kinins (bradykinin and kallidin) from the kininogens, peptides responsible for the regulation of blood pressure and activation of inflammation. In the contact activation pathway of the coagulation cascade, plasma kallikrein assists in the conversion of factor XII to factor XIIa (Keel, M.; Trentz, O. *Injury* 2005, 36, 691-709). Factor XIIa converts FXI into FXIa, which in turn activates FIX, which with its co-factor FVIIIa forms the tenase complex, which finally activates FX to FXa. In the fibrinolysis part of the coagulation cascade, plasma kallikrein serves to convert plasminogen to plasmin. Thus, it has been proposed that plasma kallikrein inhibitors can be useful in the treatment of thrombotic and fibrinolytic diseases and disease conditions (U.S. Pat. No. 7,625,944; Bird et al. *Thrombosis and Hemostasis* 2012, 107, 1141).

In rodent models, it has been shown that activation of plasma kallikrein in the eye increases retinal vascular permeability; whereas inhibition of the kallikrein-kinin system reduces retinal leakage induced by diabetes and hypertension. These findings suggest that intraocular activation of the plasma kallikrein pathway can contribute to excessive retinal vascular permeability that can lead to diabetic macular edema (DME). Thus, evidence suggests that plasma kallikrein inhibitors can provide a new therapeutic opportunity to reduce retinal vascular permeability (Feener, E. P. *Curr Diab Rep* 2010, 10, 270).

The Kallikrein-kinin system is involved in the regulation of vascular endothelial growth factor (VEGF), endothelial NO synthase, and fibroblast growth factor 2, all of which are involved in angiogenesis (Bader M. 2009, *Arteriosclerosis, Thrombosis, and Vascular Biology*, 29: 617). Tissue kallikrein (KLK1) has been linked to blood vessel growth (Miura S., 2003, *Hypertension*, 41, 1118). Therapies that moderate angiogenesis have been proposed for the treatment of both diabetic macular edema (DME) and age-related macular degeneration (AMD) (Syed, B. A.; Evans, J. B.; Bielory, L., 2012, *Nature Reviews Drug Discovery*, 11, 827). Without further wishing to be bound by any theory, it is therefore reasonable to conclude that KLKinhibitors can be useful in the treatment of diabetic retinopathy, DME, and AMD.

Studies have shown that inflammation plays an important role in the origin and development of AMD, and treatment often includes anti-inflammatories such as corticosteroid (Telander, D., 2011, *Seminars in Ophthalmology*, 26(3), 192). The connection between the kallikrein-kinin system and inflammation is also well established (Duchene, 2011, "Kallikrein-kinin kystem in inflammatory diseases". Kinins. De Gruyter. 261). Without further wishing to be bound by any theory, it is reasonable to conclude that the anti-inflammatory nature of kallikrein (e.g. KLK1 and KLKB1) inhibitors can be useful in the treatment of AMD.

Ecallantide (Kalbitor) is a 60-amino acid recombinant protein that acts as a potent reversible inhibitor of plasma kallikrein (Schneider L, et al., *J Allergy Clin Immunol* 2007, 120, 416). Ecallantide has been approvied by the FDA for the treatment of acute attacks of hereditary angioedema (HAE). Without further wishing to be bound by any theory, it is reasonable to believe that plasma kallikrein inhibition in general can be a useful treatment for HAE, and thus there is strong interest in the development of plasma kallikrein inhibitors as a therapy for HAE.

Tissue kallikreins (KLKs, for example, KLK1) are subdivided into various types, and have been extensively investigated in cancer and inflammation biology. Various kallikrein KLKs have been found to be up- or down-regulated in various cancer types, such as cervical-, testicular-, and non-small-cell lung adenocarcinoma (Caliendo et al. *J. Med. Chem.*, 2012, 55, 6669). Furthermore, overexpression of various KLKs in the skin has led to the recognition that certain kallikrein inhibitors can be useful for certain dermatological conditions, including atopic dermatitis, psoriasis and rare skin diseases such as Netherton Syndrome (Freitas et al. *Bioorganic & Medicinal Chemistry Letters* 2012, 22, 6072-6075). A thorough discussion of tissue kallikrein, plasma kallikreins, their functions and potential roles in various diseases can be found in a variety of references, including the following which are incorporated herein by reference in their entireties and for all purposes: Renné, T.; Gruber, A. *Thromb Haemost* 2012, 107, 1012-3; Sotiropoulou, G.; Pampalakis, G. *Trends in Pharmacological Sciences* 2012, 33, 623-634; Pampalakis, G.; Sotiropoulou, G. *Chapter 9 Pharmacological Targeting of Human Tissue Kallikrein-Related Peptidases. In Proteinases as Drug Targets*, Dunn, B., Ed. The Royal Society of Chemistry: 2012; pp 199-228; Caliendo, G.; Santagada, V.; Perissutti, E.; Severino, B.; Fiorino, F.; Frecentese, F.; Juliano, L. *J Med Chem* 2012, 55, 6669-86.

In mammalian systems, blood vessel injuries result in bleeding events, which are dealt with by the blood coagulation cascade. The cascade includes the extrinsic and intrinsic pathways, involving the activation of at least 13 interconnected factors and a variety of co-factors and other regulatory proteins. Upon vascular injury, plasma factor VII interacts with exposed Tissue Factor (TF), and the resultant TF-fVIIa complex initiates a complex series of events. Factor fXa is produced directly 'downstream' from the TF-fVIIa complex, and amplified manifold via the intrinsic Pathway. FXa then serves as the catalyst for formation of thrombin (fIIa), which in turn is the direct precursor to fibrinolysis. The outcome is a fibrinolytic clot, which stops the bleeding. Fibrinolysis of the polymeric clot into fibrin monomers leads to dissolution and a return of the system to the pre-clot state. The cascade is a complex balance of factors and co-factors and is tightly regulated. In disease states, undesired up- or down-regulation of any factor leads to conditions such as bleeding or thrombosis. Historically, anticoagulants have been used in patients at risk of suffering from thrombotic complications, such as angina, stroke and heart attack. Warfarin has enjoyed dominance as a first-inline anticoagulant therapeutic. Developed in the 1940s, it is a Vitamin K antagonist and inhibits factors II, VII, IX and X, amongst others. It is administered orally, but its ease of use is tempered by other effects: it has a very long half-life (>2 days) and has serious drug-drug interactions. Importantly, since Vitamin K is a ubiquitous cofactor within the coagulation cascade, antagonism results in the simultaneous inhibition of many clotting factors and thus can lead to significant bleeding complications.

Much attention has been focused on heparin, the naturally-occurring polysaccharide that activates AT III, the endogenous inhibitor of many of the factors in the coagulation cascade. The need for parenteral administration for the heparin-derived therapeutics, and the inconvenient requirements for close supervision for the orally available warfarin, has resulted in a drive to discover and develop orally available drugs with wide therapeutic windows for safety and efficacy. Indeed, the position of thrombin in the coagulation cascade has made it a popular target for drug discovery. Without wishing to be bound by any theory, it is believed that the ultimate development of direct thrombin inhibitors (DTIs) is usefully based upon the classical D-Phe-Pro-Arg motif, a sequence that mimics fibrinogen, which is a natural substrate of thrombin. Without further wishing to be bound by any theory, it is believed that the use of DTIs is very well precedented, such as with the hirudin-based anticoagulants, and thus there is strong interest in the discovery and development of novel DTIs.

A thorough discussion of thrombin and its roles in the coagulation process can be found in a variety of references, including the following which are incorporated herein by reference in their entireties and for all purposes: Wieland, H. A., et al., 2003, *Curr Opin Investig Drugs*, 4:264-71; Gross, P. L. & Weitz, J. I., 2008, *Arterioscler Thromb Vasc Biol*, 28:380-6; Hirsh, J., et al., 2005, *Blood*, 105:453-63; Prezelj, A., et al., 2007, *Curr Pharm Des*, 13:287-312.

BRIEF SUMMARY OF THE INVENTION

Embodiments of the invention encompass methods for treating or preventing a kallikrein-related disease or disorder in a subject, the methods including administering a compound of Formula (Ia):

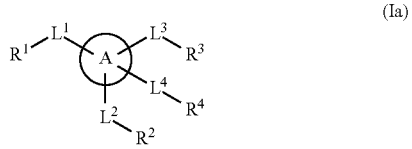

or a pharmaceutical composition including the compound and a pharmaceutically acceptable excipient, to a subject in need thereof in an amount effective to treat or prevent said disease or disorder, wherein: Ring A can be substituted or unsubstituted pyrazolyl, or substituted or unsubstituted triazolyl; $L^1$, $L^2$, and $L^4$ can be independently absent, a bond, substituted or unsubstituted alkylene, substituted or unsubstituted heteroalkylene, —S—, —SO—, —SO$_2$—, —O—, —NHSO$_2$—, or —NR$^7$—; $L^3$ can be a bond, substituted or unsubstituted alkylene, substituted or unsubstituted heteroalkylene, —S—, —SO—, —SO$_2$—, —O—, —NHSO$_2$—, or —NR$^7$—; $R^1$, $R^2$, and $R^4$ can be independently absent, hydrogen, halogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl, provided that $R^1$ can be absent when $L^1$ can be absent, $R^2$ can be absent when $L^2$ can be absent, and $R^4$ can be absent when $L^4$ can be absent; $R^3$ can be hydrogen, halogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl, provided that $R^2$ can be absent when $L^2$ can be absent, $R^3$ can be absent when $L^3$ can be absent, and $R^4$ can be absent when $L^4$ can be absent; and $R^7$ can be hydrogen, substituted or unsubstituted alkyl, substituted or unsubstituted heteroalkyl, substituted or unsubstituted alkylene, substituted or unsubstituted heteroalkylene, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl. In some embodiments of the methods $L^4$ and $R^4$ can be absent.

In some embodiments, the compound can have the structure of Formula (IIa):

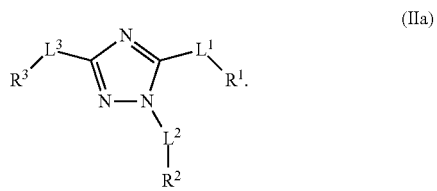

In some embodiments, $L^3$ can be a bond, and $R^3$ can be substituted or unsubstituted heterocycloalkyl, substituted or unsubstituted aryl, substituted or unsubstituted fused ring aryl, or substituted or unsubstituted heteroaryl. In some embodiments, the heteroaryl can be pyridyl, pyridazinyl, pyrimidinyl, thienyl, or furyl. In some embodiments, $R^3$ can be substituted or unsubstituted phenyl, substituted or unsubstituted morpholinyl, substituted or unsubstituted oxanyl, substituted or unsubstituted oxetanyl, substituted or unsubstituted naphthyl or substituted or unsubstituted benzodioxinyl. In some embodiments, $L^3$ can be a bond or substituted or unsubstituted alkylene, and $R^3$ can be substituted or unsubstituted aryl, or substituted or unsubstituted heterocycloalkyl. In some embodiments, $L^3$ can be —C(O)O—, and $R^3$ can be substituted or unsubstituted alkyl. In some embodiments, $L^3$ can be —C(O)NR$^5$—, $R^5$ can be hydrogen or alkyl, and $R^3$ can be substituted or unsubstituted alkyl, or substituted or unsubstituted aryl. In some embodiments, $L^1$ can be —S—, —NR$^4$—, substituted or unsubstituted alkylene, or substituted or unsubstituted heteroalkylene, and $R^1$ can be hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, the heteroaryl can be pyridyl, pyridazinyl, pyrimidinyl, thienyl, or furyl. In some embodiments, $R^1$ can be chloro-substituted thienyl. In some embodiments, $R^1$ can be substituted or unsubstituted phenyl, substituted or unsubstituted morpholinyl, substituted or unsubstituted oxanyl, substituted or unsubstituted oxetanyl, substituted or unsubstituted naphthyl or substituted or unsubstituted benzodioxinyl. In some embodiments, $L^2$ and $R^2$ can be absent. In some embodiments, $L^3$ and $R^3$ can be absent. In some embodiments, $L^2$ can be substituted or unsubstituted alkylene or —C(O)—, and $R^2$ can be hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, the heteroaryl can be pyridyl, pyridazinyl, pyrimidinyl, thienyl, or furyl. In some embodiments, $R^2$ can be substituted or unsubstituted phenyl, substituted or unsubstituted morpholinyl, substituted or unsubstituted oxanyl, substituted or unsubstituted oxetanyl, substituted or unsubstituted naphthyl or substituted or unsubstituted benzodioxinyl.

In some embodiments, the compound can have the structure of Formula (III):

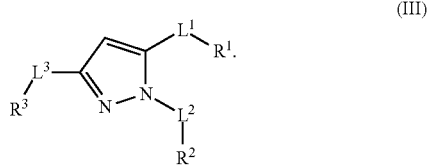

(III)

In some embodiments, $L^3$ can be a bond, or substituted or unsubstituted alkylene, and $R^3$ can be substituted or unsubstituted aryl, substituted or unsubstituted fused ring aryl, substituted or unsubstituted heteroaryl, substituted or unsubstituted heterocycloalkyl, or substituted or unsubstituted heterocycloalkyl. In some embodiments, $R^3$ can be phenyl, naphthyl, pyridyl, pyridazinyl, pyrimidinyl, thienyl, furyl, morpholinyl, oxanyl, oxetanyl, or benzodioxinyl. In some embodiments, $L^3$ can be —C(O)O—, and $R^3$ can be substituted or unsubstituted alkyl. In some embodiments, $L^3$ can be —C(O)NR'—, R' can be hydrogen or alkyl, and $R^3$ can be substituted or unsubstituted alkyl, or substituted or unsubstituted aryl. In some embodiments, $L^1$ can be —S—, —$NR^7$—, substituted or unsubstituted alkylene, or substituted or unsubstituted heteroalkylene, $R^7$ can be a hydrogen or alkyl, and $R^1$ can be hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, the heteroaryl can be pyridyl, pyridazinyl, pyrimidinyl, thienyl, or furyl. In some embodiments, $R^1$ can be chloro-substituted thienyl. In some embodiments, $R^1$ can be substituted or unsubstituted phenyl, substituted or unsubstituted morpholinyl, substituted or unsubstituted oxanyl, substituted or unsubstituted oxetanyl, substituted or unsubstituted naphthyl or substituted or unsubstituted benzodioxinyl. In some embodiments, $L^2$ can be a bond and $R^2$ can be hydrogen. In some embodiments, $L^2$ can be substituted or unsubstituted alkylene or —C(O)—, and $R^2$ can be hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, the heteroaryl can be pyridyl, pyridazinyl, pyrimidinyl, thienyl, or furyl. In some embodiments, $R^2$ can be substituted or unsubstituted phenyl, substituted or unsubstituted morpholinyl, substituted or unsubstituted oxanyl, substituted or unsubstituted oxetanyl, substituted or unsubstituted naphthyl or substituted or unsubstituted benzodioxinyl.

In some embodiments, the compound has the following structure of Formula (IV):

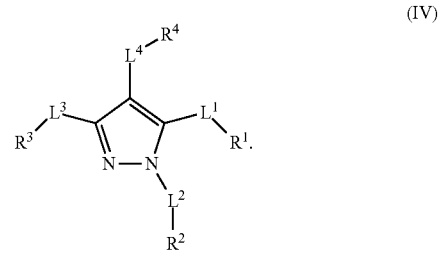

(IV)

In some embodiments, $L^4$ can be a bond, and $R^4$ can be hydrogen, halogen, substituted or unsubstituted alkyl, substituted or unsubstituted heteroalkyl, substituted or unsubstituted aryl, or substituted or unsubstituted heteroaryl. In some embodiments, $R^4$ can be halogen. In some embodiments, $R^4$ can be unsubstituted alkyl. In some embodiments, $R^4$ can be phenyl, naphthyl, pyridyl, pyridazinyl, pyrimidinyl, thienyl, or furyl.

In some embodiments, the compound can be selected from any of Tables B or C. In some embodiments, the kallikrein-related disorder can be a thrombotic disease, a fibrinolytic disease, a type of cancer, an inflammatory condition, or a dermatological condition. In some embodiments, the kallikrein-related disorder can be an ophthalmic disease. In some embodiments, the ophthalmic disease can be diabetic macular edema, age-related macular degeneration, or diabetic retinopathy. In some embodiments, the type of cancer can be cervical-, testicular-, or non-small-cell lung adenocarcinoma. In some embodiments, the inflammatory condition can be sepsis, inflammatory bowel disease, systemic inflammatory response syndrome, or rheumatoid arthritis. In some embodiments, the dermatological condition can be atopic dermatitis, psoriasis, or Netherton Syndrome. In some embodiments, the compound acts by inhibiting kallikrein. In some embodiments, the compound acts by inhibiting tissue kallikrein. In some embodiments, the compound acts by inhibiting plasma kallikrein. In some embodiments, the compound or pharmaceutical composition can be administered in the form of an ophthalmic composition applied topically to the eye. In some embodiments, the ophthalmic composition can be in the form of eye drops. In some embodiments, the compound or pharmaceutical composition can be administered in the form of an ophthalmic composition via intravitreal injection. Embodiments of the invention also encompass methods for treating or preventing a kallikrein-related disease or disorder in a subject, including administering a compound from Table D or a pharmaceutical composition including compound and a pharmaceutically acceptable excipient, to a subject in need thereof in an amount effective to treat or prevent the disease or disorder.

Embodiments of the invention also encompass compounds with structure of Formula (V):

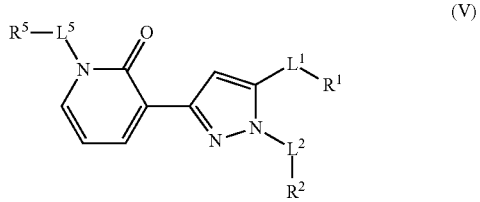

(V)

or pharmaceutically acceptable salt, ester, solvate, or prodrug thereof; wherein $L^1$ can be a bond, substituted or unsubstituted alkylene, substituted or unsubstituted heteroalkylene, —S—, —SO—, —$SO_2$—, —O—, —$NHSO_2$—, or —$NR^7$—; $L^2$ and $L^5$ can be independently absent, a bond, substituted or unsubstituted alkylene, substituted or unsubstituted heteroalkylene, —S—, —SO—, —$SO_2$—, —O—, —$NHSO_2$—, or —$NR^7$—; $R^1$ can be hydrogen, halogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl; $R^2$ and $R^5$ can be independently absent, hydrogen, halogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl; and $R^7$ can be hydrogen, substituted or unsubstituted alkyl, substituted or unsubstituted heteroalkyl, substituted or unsubstituted alkylene, substituted or unsubstituted heteroalkylene, substituted or unsubstituted cycloalkyl, substituted or unsubstituted heterocycloalkyl, substituted or unsubstituted aryl, or substituted or unsubstituted heteroaryl. In some embodiments, $L^5$ and $R^5$ can be absent. In some embodiments, $L^2$ and $R^2$ can be absent. In some embodiments, $L^2$ can be —C(O)—, and $R^2$ can be substituted or unsubstituted alkyl, substituted or unsubstituted cycloalkyl, substituted or unsubstituted cycloalkenyl, substituted or unsubstituted heteroalkyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl. In some embodiments, $R^2$ can be substituted or unsubstituted aryl or substituted or unsubstituted heteroaryl. In some embodiments, the heteroaryl can be pyridyl, pyridazinyl, pyrimidinyl, thienyl, or furyl. In some embodiments, $R^2$ can be substituted or unsubstituted alkyl, substituted or unsubstituted cycloalkyl, or substituted or unsubstituted heterocycloalkyl. In some embodiments, the heterocycloalkyl can be oxanyl, oxetanyl, or morpholinyl. In some embodiments, the fused ring aryl can be benzodioxinyl or naphthyl. In some embodiments, $L^1$ can be bond, —S—, —$NR^7$—, substituted or unsubstituted alkylene, or substituted or unsubstituted heteroalkylene, and $R^1$ can be hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, the heteroaryl can be pyridyl, pyridazinyl, pyrimidinyl, thienyl, or furyl. In some embodiments, $R^1$ can be chloro-substituted thienyl. In some embodiments, the heterocycloalkyl can be morpholinyl, oxanyl, or oxetanyl. In some embodiments, the fused ring aryl can be benzodioxinyl or naphthyl. In some embodiments, $L^5$ can be a bond or substituted or unsubstituted alkylene, and $R^5$ can be substituted or unsubstituted aryl, substituted or unsubstituted fused ring aryl, or substituted or unsubstituted heteroaryl. In some embodiments, the heteroaryl can be pyridyl, pyridazinyl, pyrimidinyl, thienyl, or furyl. In some embodiments, the fused ring aryl can be benzodioxinyl or naphthyl. In some embodiments, $L^5$ can be substituted or unsubstituted alkylene, and $R^5$ can be substituted or unsubstituted heterocycloalkyl. In some embodiments, the heterocycloalkyl can be morpholinyl, oxanyl, or oxetanyl.

Embodiments of the invention also encompass pharmaceutical compositions including such compounds, or a compound as set forth in Table A, and a pharmaceutically acceptable excipient. Embodiments of the invention also encompass methods for treating a disease or disorder in a subject, including administering such compounds or pharmaceutical compositions to a subject in need thereof in an amount effective to treat or prevent said disease or disorder. In some embodiments, the disease or disorder can be a thrombotic disorder. In some embodiments, the thrombotic disorder can be acute coronary syndrome, venous thromboembolism, arterial thromboembolism, cardiogenic thromboembolism, disseminated intravascular coagulation, or a blood clot thrombus. In some embodiments, the disease or disorder can be fibrosis. In some embodiments, the disease or disorder can be Alzheimer's Disease. In some embodiments, the disease or disorder can be multiple sclerosis. In some embodiments, the disease or disorder can be pain. In some embodiments, the disease or disorder can be cancer. In some embodiments, the compound acts by inhibiting thrombin. In some embodiments, the disease or disorder can be a kallikrein-related disorder. In some embodiments, the kallikrein-related disorder can be a thrombotic disease, a fibrinolytic disease, a type of cancer, an inflammatory condition, or a dermatological condition. In some embodiments, the kallikrein-related disorder can be an ophthalmic disease. In some embodiments, the ophthalmic disease can be diabetic macular edema, age-related macular degeneration, or diabetic retinopathy. In some embodiments, the type of cancer can be cervical-, testicular-, or non-small-cell lung adenocarcinoma. In some embodiments, the inflammatory condition can be sepsis, inflammatory bowel disease, systemic inflammatory response syndrome, or rheumatoid arthritis. In some embodiments, the dermatological condition can be atopic dermatitis, psoriasis, or Netherton Syndrome. In some embodiments, the compound acts by inhibiting kallikrein. In some embodiments, the compound acts by inhibiting tissue kallikrein. In some embodiments, the compound acts by inhibiting plasma kallikrein. In some embodiments, the compound or pharmaceutical composition can be administered in the form of an ophthalmic composition applied topically to the eye. In some embodiments, the ophthalmic composition can be in the form of eye drops. In some embodiments, the compound or pharmaceutical composition can be administered in the form of an ophthalmic composition via intravitreal injection.

BRIEF DESCRIPTION OF THE DRAWINGS

Not applicable.

DETAILED DESCRIPTION OF THE INVENTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

As used herein, the term "attached" signifies a stable covalent bond, certain preferred points of attachment being apparent to those of ordinary skill in the art.

The terms "halogen" or "halo" include fluorine, chlorine, bromine, and iodine. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "alkyl," by itself or as part of another substituent, means, unless otherwise stated, a straight (i.e., unbranched) or branched chain, or combination thereof, which can be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Accordingly, the term "alkyl" can refer to $C_1$-$C_{16}$ straight chain saturated, $C_1$-$C_{16}$ branched saturated, $C_3$-$C_8$ cyclic saturated and $C_1$-$C_{16}$ straight chain or branched saturated aliphatic hydrocarbon groups substituted with $C_3$-$C_8$ cyclic saturated aliphatic hydrocarbon groups having the specified number of carbon atoms. For example, this definition shall include but is not limited to methyl (Me), ethyl (Et), propyl (Pr), butyl (Bu), pentyl, hexyl, heptyl, octyl, nonyl, decyl, undecyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopropylmethyl, and the like.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the compounds disclosed herein. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms can optionally be oxidized, and the nitrogen heteroatom can optionally be quaternized. The heteroatom(s) O, N, P, S, and Si can be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms can be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The term "alkenyl" includes $C_2$-$C_{16}$ straight chain unsaturated, $C_2$-$C_{11}$ branched unsaturated, $C_5$-$C_8$ unsaturated cyclic, and $C_2$-$C_{16}$ straight chain or branched unsaturated aliphatic hydrocarbon groups substituted with $C_3$-$C_8$ cyclic saturated and unsaturated aliphatic hydrocarbon groups having the specified number of carbon atoms. Double bonds can occur in any stable point along the chain and the carbon-carbon double bonds can have either the cis or trans configuration. For example, this definition shall include but is not limited to ethenyl, propenyl, butenyl, pentenyl, hexenyl, heptenyl, octenyl, nonenyl, decenyl, undecenyl, 1,5-octadienyl, 1,4,7-nonatrienyl, cyclopentenyl, cyclohexenyl, cycloheptenyl, cyclooctenyl, ethylcyclohexenyl, butenylcyclopentyl, 1-pentenyl-3-cyclohexenyl, and the like. Similarly, "heteroalkenyl" refers to heteroalkyl having one or more double bonds.

The term "alkynyl" refers in the customary sense to alkyl additionally having one or more triple bonds. The term "cycloalkenyl" refers to cycloalkyl additionally having one or more double bonds. The term "heterocycloalkenyl" refers to heterocycloalkyl additionally having one or more double bonds.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

Each of the above terms (e.g., "alkyl," "heteroalkyl," "aryl," and "heteroaryl") includes both substituted and unsubstituted forms of the indicated radical. Preferred substituents for each type of radical are provided herein.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", and R''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound disclosed herein includes more than one R group, for example, each of the R groups is independently selected as are each R', R", and R''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound disclosed herein includes more than one R group, for example, each of the R groups is independently selected as are each R', R", and R''' groups when more than one of these groups is present.

Two or more substituents can optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring can optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring can optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed can optionally be replaced with a double bond. Alternatively, two of the substituents on adjacent atoms of the aryl or heteroaryl ring can optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

The term "alkyloxy" (e.g. methoxy, ethoxy, propyloxy, allyloxy, cyclohexyloxy) represents an alkyl group as defined above having the indicated number of carbon atoms attached through an oxygen bridge (—O—).

The term "alkylthio" (e.g. methylthio, ethylthio, propylthio, cyclohexylthio and the like) represents an alkyl group as defined above having the indicated number of carbon atoms attached through a sulfur bridge (—S—).

The term "alkylamino" represents one or two alkyl groups as defined above having the indicated number of carbon atoms attached through an amine bridge. The two alkyl groups can be taken together with the nitrogen to which they are attached forming a cyclic system containing 3 to 8 carbon atoms with or without one C$_1$-C$_{16}$alkyl, arylC$_0$-C$_{16}$alkyl, or C$_0$-C$_{16}$alkylaryl substituent.

The term "alkylaminoalkyl" represents an alkylamino group attached through an alkyl group as defined above having the indicated number of carbon atoms.

The term "alkyloxy(alkyl)amino" (e.g. methoxy(methyl) amine, ethoxy(propyl)amine) represents an alkyloxy group as defined above attached through an amino group, the amino group itself having an alkyl substituent.

The term "alkylcarbonyl" (e.g. cyclooctylcarbonyl, pentylcarbonyl, 3-hexylcarbonyl) represents an alkyl group as defined above having the indicated number of carbon atoms attached through a carbonyl group.

The term "alkylcarboxy" (e.g. heptylcarboxy, cyclopropylcarboxy, 3-pentenylcarboxy) represents an alkylcarbonyl group as defined above wherein the carbonyl is in turn attached through an oxygen.

The term "alkylcarboxyalkyl" represents an alkylcarboxy group attached through an alkyl group as defined above having the indicated number of carbon atoms.

The term "alkylcarbonylamino" (e.g. hexylcarbonylamino, cyclopentylcarbonylaminomethyl, methylcarbonylaminophenyl) represents an alkylcarbonyl group as defined above wherein the carbonyl is in turn attached through the nitrogen atom of an amino group.

The nitrogen group can itself be substituted with an alkyl or aryl group.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Accordingly, the term "aryl" can represent an unsubstituted, mono-, di- or trisubstituted monocyclic, polycyclic, biaryl and heterocyclic aromatic groups covalently attached at any ring position capable of forming a stable covalent bond, certain preferred points of attachment being apparent to those skilled in the art (e.g. 3-indolyl, 4-imidazolyl). The aryl substituents are independently selected from the group consisting of halo, nitro, cyano, trihalomethyl, $C_{1-16}$alkyl, aryl$C_{1-16}$alkyl, $C_{0-16}$alkyloxy$C_{0-16}$alkyl, aryl$C_{0-16}$alkyloxy$C_{0-16}$alkyl, $C_{0-16}$alkylthio$C_{0-16}$alkyl, aryl$C_{0-16}$alkylthio$C_{0-16}$alkyl, $C_{0-16}$alkylamino$C_{0-16}$alkyl, aryl$C_{0-16}$alkylamino$C_{0-16}$alkyl, di(aryl$C_{1-16}$alkyl)amino$C_{0-16}$alkyl, $C_{1-16}$alkylcarbonyl$C_{0-16}$alkyl, aryl$C_{1-16}$alkylcarbonyl$C_{0-16}$alkyl, $C_{1-16}$alkylcarboxy$C_{0-16}$alkyl, aryl$C_{1-16}$alkylcarboxy$C_{0-16}$alkyl, $C_{1-16}$alkylcarbonylamino$C_{0-16}$alkyl, aryl$C_{1-16}$alkylcarbonylamino$C_{0-16}$alkyl, —$C_{0-16}$alkyl-COOR$_4$, —$C_{0-16}$alkylCONR$_5$R$_6$ wherein R$_4$, R$_5$ and R$_6$ are independently selected from hydrogen, $C_1$-$C_{11}$alkyl, aryl$C_0$-$C_{11}$ alkyl, or R$_5$ and R$_6$ are taken together with the nitrogen to which they are attached forming a cyclic system containing 3 to 8 carbon atoms with or without one $C_{1-16}$alkyl, aryl$C_0$-$C_{16}$alkyl, or $C_0$-$Cl_{16}$alkylaryl substituent. Aryl includes but is not limited to pyrazolyl and triazolyl.

For brevity, the term "aryl" when used in combination with other terms (e.g., aryloxy, arylthioxy, arylalkyl) includes both aryl and heteroaryl rings as defined above. Thus, the terms "arylalkyl," "aralkyl" and the like are meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like), or a sulfur atom. Accordingly, the terms "arylalkyl" and the like (e.g. (4-hydroxyphenyl)ethyl, (2-aminonaphthyl)hexyl, pyridylcyclopentyl) represents an aryl group as defined above attached through an alkyl group as defined above having the indicated number of carbon atoms.

The term "oxo," as used herein, means an oxygen that is double bonded to a carbon atom.

The term "alkylsulfonyl," as used herein, means a moiety having the formula —S(O$_2$)—R', where R' is an alkyl group as defined above. R' can have a specified number of carbons (e.g., "$C_1$-$C_4$ alkylsulfonyl").

The term "carbonyloxy" represents a carbonyl group attached through an oxygen bridge.

In the above definitions, the terms "alkyl" and "alkenyl" can be used interchangeably in so far as a stable chemical entity is formed, as would be apparent to those skilled in the art.

The term "linker" refers to attachment groups interposed between substituents, e.g., $R^1$, $R^2$, $R^3$ or $R^4$ described herein, e.g., Formula (Ia) and generically referred to as R″, and the group which is substituted, e.g., "ring A" group of e.g., Formula (Ia). In some embodiments, the linker includes amido (—CONH—R″ or —NHCO—R″), thioamido (—CSNH—R″ or —NHCS—R″), carboxyl (—CO$_2$—R″ or —OCOR″), carbonyl (—CO—R″), urea (—NHCONH—R″), thiourea (—NHCSNH—R″), sulfonamido (—NHSO$_2$—R″ or —SO$_2$NH—R″), ether (—O—R″), sulfonyl (—SO$_2$—R″), sulfoxyl (—SO—R″), carbamoyl (—NHCO$_2$—R″ or —OCONH—R″), or amino (—NHR″) linking moieties.

A "substituent group," as used herein, means a group selected from the following moieties:

(A) —OH, —NH$_2$, —SH, —CN, —CF$_3$, —NO$_2$, oxo, halogen, —COOH, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, —COOH, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, —COOH, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, —COOH, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2-20-membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4-8-membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2-8-membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5-7-membered heterocycloalkyl.

The term "about" used in the context of a numeric value indicates a range of +/−10% of the numeric value, unless expressly indicated otherwise.

II. Compounds

In one aspect, there is provided a compound with structure of Formula (Ia):

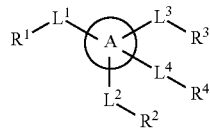

(Ia)

or pharmaceutically acceptable salt, ester, solvate, or prodrug thereof. Ring A is substituted or unsubstituted pyrazolyl, or substituted or unsubstituted triazolyl. $L^1$, $L^2$ and $L^3$ are independently absent, a bond, substituted or unsubstituted alkylene, substituted or unsubstituted heteroalkylene, —S—, —SO—, —SO$_2$—, —O—, —NHSO$_2$—, or —NR$^7$—. $L^4$ is absent, a bond, substituted or unsubstituted alkylene, substituted or unsubstituted heteroalkylene, —S—, —SO—, —SO$_2$—, —O—, —NHSO$_2$—, or —NR$^7$—. $R^1$, $R^2$, and $R^4$ are independently absent, hydrogen, halogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted heteroaryl, substituted or unsubstituted cycloalkenyl, substituted or unsubstituted heterocycloalkenyl, or substituted or unsubstituted fused ring aryl. In some embodiments, $R^1$ can be absent provided $L^1$ is also absent. In some embodiments, $R^2$ can be absent provided $L^2$ is also absent. In some embodiments, $R^4$ can be absent provided $L^4$ is also absent. $R^3$ is hydrogen, halogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl. $R^7$ is hydrogen, substituted or unsubstituted alkyl, substituted or unsubstituted heteroalkyl, substituted or unsubstituted alkylene, substituted or unsubstituted heteroalkylene, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl.

In some embodiments, the compound is a pharmaceutically acceptable salt, ester, solvate, or prodrug of a compound of Formula (Ia). In some embodiments, the compound is not an ester, not a solvate, and not a prodrug.

In some embodiments, $L^4$ and $R^4$ are absent, providing a compound with structure of Formula (Ib) following.

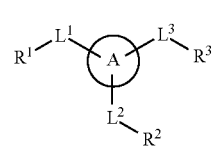

(Ib)

In some embodiments, there is provided a compound according to Formula (Ib) with structure of Formula (IIa) following.

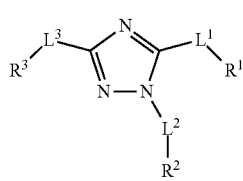

(IIa)

In some embodiments, the compound has the structure of Formula (IIa), wherein $L^3$ is a bond, and $R^3$ is substituted or unsubstituted aryl, substituted or unsubstituted fused ring aryl, substituted or unsubstituted heterocycloalkyl, or substituted or unsubstituted heteroaryl. In some embodiments, $R^3$ is unsubstituted aryl, preferably phenyl. In some embodiments, $R^3$ is substituted aryl, preferably halogen-substituted phenyl. In some embodiments, $R^3$ is substituted or unsubstituted phenyl, or substituted or unsubstituted thienyl. In some embodiments, $R^3$ is unsubstituted thienyl. In some embodiments, $R^3$ is a chloro-substituted thienyl. In some embodiments, $R^3$ is substituted or unsubstituted pyridyl, or substituted or unsubstituted pyridazinyl. In some embodiments, $R^3$ is unsubstituted pyridyl. In some embodiments, $R^3$ is unsubstituted pyridazinyl. In some embodiments, $R^3$ is substituted or unsubstituted pyrimidinyl, or substituted or unsubstituted furyl. In some embodiments, $R^3$ is unsubstituted pyrimidinyl. In some embodiments, $R^3$ is unsubstituted furyl. In some embodiments, $R^3$ is substituted or unsubstituted morpholinyl, or substituted or unsubstituted oxanyl, or substituted or unsubstituted oxetanyl. In some embodiments, R³ is unsubstituted morpholinyl. In some embodiments, R³ is unsubstituted oxanyl. In some embodiments, R³ is unsubstituted oxetanyl. In some embodiments, R³ is substituted or unsubstituted benzodioxinyl, or substituted or unsubstituted naphthyl. In some embodiments, R³ is unsubstituted benzodioxinyl. In some embodiments, R³ is unsubstituted naphthyl.

In some embodiments, a compound is provided with structure of Formula (IIa), wherein L³ is a bond, substituted or unsubstituted alkylene, and R³ is substituted or unsubstituted aryl, or substituted or unsubstituted heterocycloalkyl.

In some embodiments, the compound has the structure of Formula (IIa), wherein L³ is —C(O)O—, and R³ is substituted or unsubstituted alkyl, preferably unsubstituted alkyl, more preferably unsubstituted lower alkyl.

In some embodiments, the compound has the structure of Formula (IIa), wherein L³ is —C(O)NR⁵—, R⁵ is hydrogen or alkyl, and R³ is substituted or unsubstituted alkyl, or substituted or unsubstituted aryl.

Further to any embodiment above wherein the compound has the structure of Formula (IIa), in some embodiments L¹ is —S—, —NR⁷—, substituted or unsubstituted alkylene, or substituted or unsubstituted heteroalkylene, where R⁷ is as described in formula Ia, and R¹ is hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, R¹ is substituted or unsubstituted phenyl. In some embodiments is an R¹ is unsubstituted phenyl. In some embodiments, R¹ is a substituted or unsubstituted pyridyl. In some embodiments, R¹ is a substituted or unsubstituted pyridazinyl. In some embodiments, R¹ is a substituted or unsubstituted pyrimidinyl. In some embodiments, R¹ is a substituted or unsubstituted thienyl. In some embodiments, R¹ is a substituted or unsubstituted furyl. In some embodiments, R¹ is an unsubstituted pyridyl. In some embodiments, R¹ is an unsubstituted pyridazinyl. In some embodiments, R¹ is an unsubstituted pyrimidinyl. In some embodiments, R¹ is an unsubstituted thienyl. In some embodiments, R¹ is a chloro-substituted thienyl. In some embodiments, R¹ is an unsubstituted furyl. In some embodiments, R¹ is a substituted or unsubstituted morpholinyl. In some embodiments, R¹ is a substituted or unsubstituted oxanyl. In some embodiments, R¹ is a substituted or unsubstituted oxetanyl. In some embodiments, R¹ is an unsubstituted morpholinyl. In some embodiments, R¹ is an unsubstituted oxanyl. In some embodiments, R¹ is an unsubstituted oxetanyl. In some embodiments, R¹ is substituted or unsubstituted benzodioxinyl. In some embodiments, R¹ is substituted or unsubstituted naphthyl. In some embodiments, R¹ is unsubstituted benzodioxinyl. In some embodiments, R¹ is unsubstituted naphthyl. In some embodiments, R³ is substituted or unsubstituted aryl. In some embodiments, R³ is unsubstituted aryl. In some embodiments, L³ and R³ are absent. In some embodiments, L² and R² are absent. In some embodiments, L² is a bond. In some embodiments, L² is a bond and R² is hydrogen.

Further to any embodiment above wherein the compound has the structure of Formula (IIa), R² is hydrogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl. In some embodiments, R² is substituted or unsubstituted phenyl. In some embodiments is an R² is unsubstituted phenyl. In some embodiments, R² is a substituted or unsubstituted pyridyl. In some embodiments, R² is a substituted or unsubstituted pyridazinyl. In some embodiments, R² is a substituted or unsubstituted pyrimidinyl. In some embodiments, R² is a substituted or unsubstituted thienyl. In some embodiments, R² is a substituted or unsubstituted furyl. In some embodiments, R² is an unsubstituted pyridyl. In some embodiments, R² is an unsubstituted pyridazinyl. In some embodiments, R² is an unsubstituted pyrimidinyl. In some embodiments, R² is an unsubstituted thienyl. In some embodiments, R² is a chloro-substituted thienyl. In some embodiments, R² is an unsubstituted furyl. In some embodiments, R² is a substituted or unsubstituted morpholinyl. In some embodiments, R² is a substituted or unsubstituted oxanyl. In some embodiments, R² is a substituted or unsubstituted oxetanyl. In some embodiments, R² is an unsubstituted morpholinyl. In some embodiments, R² is an unsubstituted oxanyl. In some embodiments, R² is an unsubstituted oxetanyl. In some embodiments, R² is substituted or unsubstituted benzodioxinyl. In some embodiments, R² is substituted or unsubstituted naphthyl. In some embodiments, R² is unsubstituted benzodioxinyl. In some embodiments, R² is unsubstituted naphthyl.

In some embodiments, the compound of Formula (IIa) has the structure of Formula (IIb) following, wherein L¹ is —NH—(CH₂)ₙ—, n is 0 to 6, preferably 1, and R¹ is hydrogen, substituted or unsubstituted alkyl, substituted or unsubstituted aryl, substituted or unsubstituted heteroaryl, or substituted or unsubstituted heterocycloalkyl.

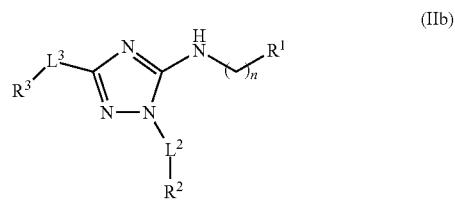

(IIb)

In some embodiments of the compound of Formula (IIb), L¹ is —NHCH₂— or —NH(CH₂)₂—, and R¹ is substituted or unsubstituted aryl. In some embodiments, R¹ is unsubstituted aryl. In some embodiments, R¹ is aryl, preferably phenyl, substituted with halogen, —CN or alkyloxy, preferably methoxy. In some embodiments, R¹ is unsubstituted alkyl, preferably lower alkyl, more preferably methyl or ethyl. In some embodiments, n is 0, and R¹ is hydrogen.

In some embodiments, the compound of Formula (IIa) has the structure of Formula (IIc) following, wherein L¹ is a bond, and R¹ is unsubstituted alkyl, or substituted or unsubstituted aryl. In some embodiments, R¹ is unsubstituted alkyl, preferably lower alkyl. In some embodiments, R¹ is substituted aryl, preferably halogen-substituted phenyl.

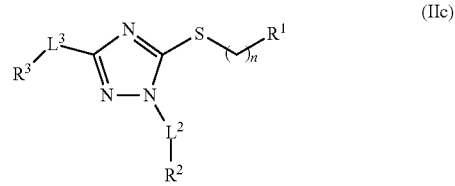

(IIc)

In some embodiments, there is provided a compound according to Formula (Ib) with structure of Formula (III) following.

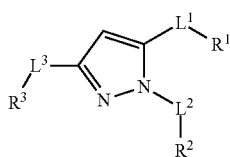
(III)

In some embodiments, the compound has the structure of Formula (III). In some embodiments, $L^3$ is a bond, or substituted or unsubstituted alkylene, and $R^3$ is substituted or unsubstituted aryl, substituted or unsubstituted fused ring aryl, substituted or unsubstituted heterocycloalkyl, or substituted or unsubstituted heterocycloalkyl. In some embodiments, $R^3$ is substituted or unsubstituted phenyl, or substituted or unsubstituted thienyl. In some embodiments, $R^3$ is unsubstituted phenyl. In some embodiments, $R^3$ is unsubstituted thienyl. In some embodiments, $R^3$ is a chloro-substituted thienyl. In some embodiments, $R^3$ is substituted or unsubstituted pyridyl, or substituted or unsubstituted pyridazinyl. In some embodiments, $R^3$ is unsubstituted pyridyl. In some embodiments, $R^3$ is unsubstituted pyridazinyl. In some embodiments, $R^3$ is substituted or unsubstituted pyrimidinyl, or substituted or unsubstituted furyl. In some embodiments, $R^3$ is unsubstituted pyrimidinyl. In some embodiments, $R^3$ is unsubstituted furyl. In some embodiments, $R^3$ is substituted or unsubstituted morpholinyl, or substituted or unsubstituted oxanyl, or substituted or unsubstituted oxetanyl. In some embodiments, $R^3$ is unsubstituted morpholinyl. In some embodiments, $R^3$ is unsubstituted oxanyl. In some embodiments, $R^3$ is unsubstituted oxetanyl. In some embodiments, $R^3$ is substituted or unsubstituted benzodioxinyl, or substituted or unsubstituted naphthyl. In some embodiments, $R^3$ is unsubstituted benzodioxinyl. In some embodiments, $R^3$ is unsubstituted naphthyl.

In some embodiments, the compound has the structure of Formula (III) wherein $L^3$ is —C(O)O—, and $R^3$ is substituted or unsubstituted alkyl. In some embodiments, the compound has the structure of Formula (III) wherein $L^3$ is —C(O)NR$^7$, R$^7$ is hydrogen or alkyl, and $R^3$ is substituted or unsubstituted alkyl, or substituted or unsubstituted aryl.

Further to any embodiment above wherein the compound has the structure of Formula (III), in some embodiments, $L^1$ is —S—, —NR$^7$—, substituted or unsubstituted alkylene, or substituted or unsubstituted heteroalkylene, where $R^7$ is as described in Formula (Ia), and $R^1$ is hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, $R^1$ is substituted or unsubstituted phenyl. In some embodiments is an $R^1$ is unsubstituted phenyl. In some embodiments, $R^1$ is a substituted or unsubstituted pyridyl. In some embodiments, $R^1$ is a substituted or unsubstituted pyridazinyl. In some embodiments, $R^1$ is a substituted or unsubstituted pyrimidinyl. In some embodiments, $R^1$ is a substituted or unsubstituted thienyl. In some embodiments, $R^1$ is a substituted or unsubstituted furyl. In some embodiments, $R^1$ is an unsubstituted pyridyl. In some embodiments, $R^1$ is an unsubstituted pyridazinyl. In some embodiments, $R^1$ is an unsubstituted pyrimidinyl. In some embodiments, $R^1$ is an unsubstituted thienyl. In some embodiments, $R^1$ is a chloro-substituted thienyl. In some embodiments, $R^1$ is an unsubstituted furyl. In some embodiments, $R^1$ is a substituted or unsubstituted morpholinyl. In some embodiments, $R^1$ is a substituted or unsubstituted oxanyl. In some embodiments, $R^1$ is a substituted or unsubstituted oxetanyl. In some embodiments, $R^1$ is an unsubstituted morpholinyl. In some embodiments, $R^1$ is an unsubstituted oxanyl. In some embodiments, $R^1$ is an unsubstituted oxetanyl. In some embodiments, $R^1$ is substituted or unsubstituted benzodioxinyl. In some embodiments, $R^1$ is substituted or unsubstituted naphthyl. In some embodiments, $R^1$ is unsubstituted benzodioxinyl. In some embodiments, $R^1$ is unsubstituted naphthyl.

Further to any embodiment above wherein the compound has the structure of Formula (III), in some embodiments, $L^2$ is a bond. In some embodiments, $R^2$ is hydrogen. In some embodiments, $L^2$ is substituted or unsubstituted alkylene or —C(O)—, and $R^2$ is hydrogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl. In some embodiments, $R^2$ is substituted or unsubstituted phenyl. In some embodiments is an $R^2$ is unsubstituted phenyl. In some embodiments, $R^2$ is a substituted or unsubstituted pyridyl. In some embodiments, $R^2$ is a substituted or unsubstituted pyridazinyl. In some embodiments, $R^2$ is a substituted or unsubstituted pyrimidinyl. In some embodiments, $R^2$ is a substituted or unsubstituted thienyl. In some embodiments, $R^2$ is a substituted or unsubstituted furyl. In some embodiments, $R^2$ is an unsubstituted pyridyl. In some embodiments, $R^2$ is an unsubstituted pyridazinyl. In some embodiments, $R^2$ is an unsubstituted pyrimidinyl. In some embodiments, $R^2$ is an unsubstituted thienyl. In some embodiments, $R^2$ is a chloro-substituted thienyl. In some embodiments, $R^2$ is an unsubstituted furyl. In some embodiments, $R^2$ is a substituted or unsubstituted morpholinyl. In some embodiments, $R^2$ is a substituted or unsubstituted oxanyl. In some embodiments, $R^2$ is a substituted or unsubstituted oxetanyl. In some embodiments, $R^2$ is an unsubstituted morpholinyl. In some embodiments, $R^2$ is an unsubstituted oxanyl. In some embodiments, $R^2$ is an unsubstituted oxetanyl. In some embodiments, $R^2$ is substituted or unsubstituted benzodioxinyl. In some embodiments, $R^2$ is substituted or unsubstituted naphthyl. In some embodiments, $R^2$ is unsubstituted benzodioxinyl. In some embodiments, $R^2$ is unsubstituted naphthyl.

In some embodiments, there is provided a compound according to Formula (Ia) with structure of Formula (IV) following.

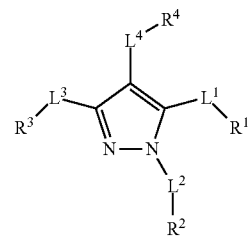
(IV)

In some embodiments, there is provided a compound according to Formula (IV) wherein $L^4$ is a bond; and $R^4$ is hydrogen, halogen, substituted or unsubstituted alkyl, or substituted or unsubstituted heteroalkyl, substituted or unsubstituted aryl, or substituted or unsubstituted heteroaryl. In some embodiments, $R^4$ is halogen. In some embodiments, $R^4$ is unsubstituted alkyl. In some embodiments, $R^4$ is substituted or unsubstituted aryl or substituted or unsubstituted heteroaryl. In some embodiments, $R^4$ is phenyl, naphthyl, pyridyl, pyridazinyl, pyrimidinyl, thienyl, or furyl.

In some embodiments, there is provided a compound according to Formula (III) with structure of Formula (V) following.

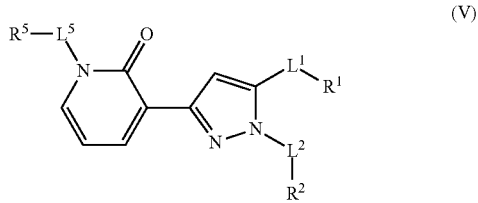

(V)

In some embodiments, the compound is a pharmaceutically acceptable salt, ester, solvate, or prodrug of a compound of Formula (V). In some embodiments, the compound is not an ester, not a solvate, and not a prodrug. In some embodiments, there is provided a compound according to Formula (V) wherein $L^1$ is a bond, substituted or unsubstituted alkylene, substituted or unsubstituted heteroalkylene, —S—, —SO—, —SO$_2$—, —O—, —NHSO$_2$—, or —NR$^7$—. $R^1$ is hydrogen, a halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted cycloalkenyl, substituted or unsubstituted heterocycloalkenyl, substituted or unsubstituted fused ring aryl, or substituted or unsubstituted heteroaryl. $L^2$ is absent, a bond, substituted or unsubstituted alkylene, substituted or unsubstituted heteroalkylene, —S—, —SO—, —SO$_2$—, —O—, —NHSO$_2$—, or —NR$^7$. $L^5$ is absent, a bond, substituted or unsubstituted alkylene, substituted or unsubstituted heteroalkylene, —S—, —SO—, —SO$_2$—, —O—, —NHSO$_2$—, or —NR$^7$. $R^2$ is absent, hydrogen, a halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted cycloalkenyl, substituted or unsubstituted heterocycloalkenyl, substituted or unsubstituted fused ring aryl, or substituted or unsubstituted heteroaryl. In some embodiments, $R^2$ is absent provided $L^2$ is also absent. $R^5$ is absent, hydrogen, a halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted cycloalkenyl, substituted or unsubstituted heterocycloalkenyl, substituted or unsubstituted fused ring aryl, or substituted or unsubstituted heteroaryl. In some embodiments, $R^5$ is absent provided $L^5$ is also absent. $R^7$ is hydrogen, substituted or unsubstituted alkyl, substituted or unsubstituted heteroalkyl, substituted or unsubstituted alkylene, substituted or unsubstituted heteroalkylene, substituted or unsubstituted cycloalkyl, substituted or unsubstituted heterocycloalkyl, substituted or unsubstituted aryl, substituted or unsubstituted cycloalkenyl, substituted or unsubstituted heterocycloalkenyl, substituted or unsubstituted fused ring aryl, or substituted or unsubstituted heteroaryl.

Further to any embodiment above wherein the compound has the structure of Formula (V), in some embodiments, $L^2$ is a bond. In some embodiments, $R^2$ is hydrogen. In some embodiments, $L^2$ is substituted or unsubstituted alkylene or —C(O)—, and $R^2$ is hydrogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl. In some embodiments, $R^2$ is substituted or unsubstituted phenyl. In some embodiments is an $R^2$ is unsubstituted phenyl. In some embodiments, $R^2$ is a substituted or unsubstituted pyridyl. In some embodiments, $R^2$ is a substituted or unsubstituted pyridazinyl. In some embodiments, $R^2$ is a substituted or unsubstituted pyrimidinyl. In some embodiments, $R^2$ is a substituted or unsubstituted thienyl. In some embodiments, $R^2$ is a substituted or unsubstituted furyl. In some embodiments, $R^2$ is an unsubstituted pyridyl. In some embodiments, $R^2$ is an unsubstituted pyridazinyl. In some embodiments, $R^2$ is an unsubstituted pyrimidinyl. In some embodiments, $R^2$ is an unsubstituted thienyl. In some embodiments, $R^2$ is a chloro-substituted thienyl. In some embodiments, $R^2$ is an unsubstituted furyl. In some embodiments, $R^2$ is a substituted or unsubstituted morpholinyl. In some embodiments, $R^2$ is a substituted or unsubstituted oxanyl. In some embodiments, $R^2$ is a substituted or unsubstituted oxetanyl. In some embodiments, $R^2$ is an unsubstituted morpholinyl. In some embodiments, $R^2$ is an unsubstituted oxanyl. In some embodiments, $R^2$ is an unsubstituted oxetanyl. In some embodiments, $R^2$ is substituted or unsubstituted benzodioxinyl. In some embodiments, $R^2$ is substituted or unsubstituted naphthyl. In some embodiments, $R^2$ is unsubstituted benzodioxinyl. In some embodiments, $R^2$ is unsubstituted naphthyl.

Further to any embodiment above wherein the compound has the structure of Formula (V), in some embodiments, $L^5$ is a bond, or substituted or unsubstituted alkylene, and $R^5$ is substituted or unsubstituted aryl, substituted or unsubstituted fused ring aryl, substituted or unsubstituted heterocycloalkyl, or substituted or unsubstituted heterocycloalkyl. In some embodiments, $R^5$ is substituted or unsubstituted phenyl, or substituted or unsubstituted thienyl. In some embodiments, $R^5$ is unsubstituted phenyl. In some embodiments, $R^5$ is unsubstituted thienyl. In some embodiments, $R^5$ is a chloro-substituted thienyl. In some embodiments, $R^5$ is substituted or unsubstituted pyridyl, or substituted or unsubstituted pyridazinyl. In some embodiments, $R^5$ is unsubstituted pyridyl. In some embodiments, $R^5$ is unsubstituted pyridazinyl. In some embodiments, $R^5$ is substituted or unsubstituted pyrimidinyl, or substituted or unsubstituted furyl. In some embodiments, $R^5$ is unsubstituted pyrimidinyl. In some embodiments, $R^5$ is unsubstituted furyl. In some embodiments, $R^5$ is substituted or unsubstituted morpholinyl, or substituted or unsubstituted oxanyl, or substituted or unsubstituted oxetanyl. In some embodiments, $R^5$ is unsubstituted morpholinyl. In some embodiments, $R^5$ is unsubstituted oxanyl. In some embodiments, $R^5$ is unsubstituted oxetanyl. In some embodiments, $R^5$ is substituted or unsubstituted benzodioxinyl, or substituted or unsubstituted naphthyl. In some embodiments, $R^5$ is unsubstituted benzodioxinyl. In some embodiments, $R^5$ is unsubstituted naphthyl.

Further to any embodiment above wherein the compound has the structure of Formula (V), in some embodiments, $L^1$ is —S—, —NR$^7$—, substituted or unsubstituted alkylene, or substituted or unsubstituted heteroalkylene, where $R^7$ is as described in formula Ia, and $R^1$ is hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, $R^1$ is substituted or unsubstituted phenyl. In some embodiments is an $R^1$ is unsubstituted phenyl. In some embodiments, $R^1$ is a substituted or unsubstituted pyridyl. In some embodiments, $R^1$ is a substituted or unsubstituted pyridazinyl. In some embodiments, $R^1$ is a substituted or unsubstituted pyrimidinyl. In some embodiments, $R^1$ is a substituted or unsubstituted thienyl. In some embodiments, $R^1$ is a substituted or unsubstituted furyl. In some embodiments, $R^1$ is an unsubstituted pyridyl. In some embodiments, $R^1$ is an unsubstituted pyridazinyl. In some embodiments, $R^1$ is an unsubstituted pyrimidinyl. In some embodiments, $R^1$ is an unsubstituted thienyl. In some embodiments, $R^1$ is a chloro-substituted thienyl. In some embodiments, $R^1$ is an unsubstituted furyl. In some embodiments, $R^1$ is a substituted or unsubstituted morpholinyl. In some embodiments, $R^1$ is a substituted or unsubstituted oxanyl. In some embodiments, $R^1$ is a substituted or unsubstituted oxetanyl. In some embodiments, $R^1$ is an unsubstituted morpholinyl. In some embodiments, $R^1$ is an unsubstituted oxanyl. In some embodiments, $R^1$ is an unsubstituted oxetanyl. In some embodiments, $R^1$ is substituted or unsubstituted benzodioxinyl. In some embodiments, $R^1$ is substituted or unsubstituted naphthyl. In some embodiments, $R^1$ is unsubstituted benzodioxinyl. In some embodiments, $R^1$ is unsubstituted naphthyl.

In some embodiments, there is provided a compound according to Formula (V) and its listed embodiments, wherein $L^2$ and $R^2$ are absent, providing a compound with structure of Formula (VI) following.

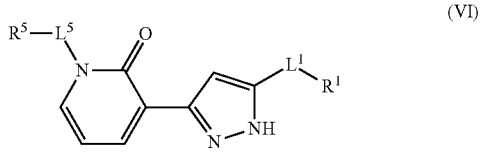

(VI)

In some embodiments, the compound is a pharmaceutically acceptable salt, ester, solvate, or prodrug of a compound of Formula (VI). In some embodiments, the compound is not an ester, not a solvate, and not a prodrug.

In some embodiments, there is provided a compound according to Formula (V) and its listed embodiments, wherein $L^5$ and $R^5$ are absent, providing a compound with structure of Formula (VII) following.

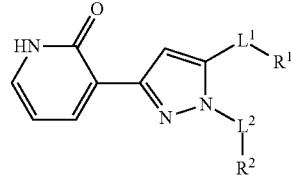

(VII)

In some embodiments, the compound is a pharmaceutically acceptable salt, ester, solvate, or prodrug of a compound of Formula (VII). In some embodiments, the compound is not an ester, not a solvate, and not a prodrug.

Exemplary compounds, e.g., multisubstituted aromatic compounds, in accordance with the present disclosure are provided herein. In Table A, B, C, and D following, compound (Cmpd) number, chemical name (i.e., International Union of Pure and Applied Chemistry [IUPAC] name), calculated molecular weight (MW) and biological activity (i.e., inhibition activity in thrombin, KLK1 and KLKB1 assays) are disclosed.

For Table A following, the disclosed compounds were assayed for inhibition of the protease activity of thrombin as described herein. In Table A, the level of inhibition in the thrombin assay is indicated as follows: a $IC_{50} \leq 0.1$ μM; b: $0.1$ μM$<IC_{50}<1$ μM; c: $1$ μM$<IC_{50}<10$ μM; d: $10$ μM$<IC_{50}<100$ μM; e: $IC_{50} \geq 100$ μM. Accordingly, in some embodiments, there is provided a compound as expressly set forth in Table A following.

TABLE A

| Cmpd No. | IUPAC name | MW | Thrombin Activity |
|---|---|---|---|
| 1 | 3-(5-amino-1H-pyrazol-3-yl)-1,2-dihydropyridin-2-one | 176 | e |
| 2 | 3-(5-[(5-chlorothiophen-2-yl)methyl]amino-1H-pyrazol-3-yl)-1,2-dihydropyridin-2-one | 307 | e |
| 3 | 3-(5-[(5-chlorothiophen-2-yl)methyl]amino-1-(2,2-dimethylpropanoyl)-1H-pyrazol-3-yl)-1,2-dihydropyridin-2-one | 391 | a |
| 4 | 3-(5-[(5-chlorothiophen-2-yl)methyl]amino-1-[(furan-3-yl)carbonyl]-1H-pyrazol-3-yl)-1,2-dihydropyridin-2-one | 401 | a |
| 5 | 3-(5-[(5-chlorothiophen-2-yl)methyl]amino-1-[(furan-3-yl)carbonyl]-1H-pyrazol-3-yl)-1-(thiophen-2-ylmethyl)-1,2-dihydropyridin-2-one | 497 | a |
| 6 | 3-(5-[(5-chlorothiophen-2-yl)methyl]amino-1-[(furan-3-yl)carbonyl]-1H-pyrazol-3-yl)-1-(pyridin-4-ylmethyl)-1,2-dihydropyridin-2-one | 492 | a |
| 23 | 3-(5-[(5-chlorothiophen-2-yl)methyl]amino-1-[(furan-3-yl)carbonyl]-1H-pyrazol-3-yl)-1-methyl-1,2-dihydropyridin-2-one | 415 | a |
| 25 | 3-(5-[(5-chlorothiophen-2-yl)methyl]amino-1-[(furan-3-yl)carbonyl]-1H-pyrazol-3-yl)-1-(pyridin-2-ylmethyl)-1,2-dihydropyridin-2-one | 492 | a |
| 26 | 3-(5-[(5-chlorothiophen-2-yl)methyl]amino-1-[(furan-3-yl)carbonyl]-1H-pyrazol-3-yl)-1-(furan-2-ylmethyl)-1,2-dihydropyridin-2-one | 481 | a |
| 27 | 1-[(2-chlorophenyl)methyl]-3-(5-[(5-chlorothiophen-2-yl)methyl]amino-1-(2,2-dimethylpropanoyl)-1H-pyrazol-3-yl)-1,2-dihydropyridin-2-one | 516 | a |

TABLE A-continued

| Cmpd No. | IUPAC name | MW | Thrombin Activity |
|---|---|---|---|
| 28 | 1-[(2-chlorophenyl)methyl]-3-(5-[(5-chlorothiophen-2-yl)methyl]amino-1-[(2-methoxyphenyl)carbonyl]-1H-pyrazol-3-yl)-1,2-dihydropyridin-2-one | 566 | a |
| 29 | 1-[(2-chlorophenyl)methyl]-3-(5-[(5-chlorothiophen-2-yl)methyl]amino-1-[(furan-3-yl)carbonyl]-1H-pyrazol-3-yl)-1,2-dihydropyridin-2-one | 525 | a |
| 30 | 1-[(2-chlorophenyl)methyl]-3-(5-[(5-chlorothiophen-2-yl)methyl]amino-1H-pyrazol-3-yl)-1,2-dihydropyridin-2-one | 431 | d |
| 31 | 1-[(3-chlorophenyl)methyl]-3-(5-[(5-chlorothiophen-2-yl)methyl]amino-1-(2,2-dimethylpropanoyl)-1H-pyrazol-3-yl)-1,2-dihydropyridin-2-one | 516 | a |
| 32 | 1-[(3-chlorophenyl)methyl]-3-(5-[(5-chlorothiophen-2-yl)methyl]amino-1-[(2-methoxyphenyl)carbonyl]-1H-pyrazol-3-yl)-1,2-dihydropyridin-2-one | 566 | a |
| 33 | 1-[(3-chlorophenyl)methyl]-3-(5-[(5-chlorothiophen-2-yl)methyl]amino-1-[(furan-3-yl)carbonyl]-1H-pyrazol-3-yl)-1,2-dihydropyridin-2-one | 525 | a |
| 34 | 1-[(3-chlorophenyl)methyl]-3-(5-[(5-chlorothiophen-2-yl)methyl]amino-1H-pyrazol-3-yl)-1,2-dihydropyridin-2-one | 431 | c |
| 35 | 1-[(4-chlorophenyl)methyl]-3-(5-[(5-chlorothiophen-2-yl)methyl]amino-1-(2,2-dimethylpropanoyl)-1H-pyrazol-3-yl)-1,2-dihydropyridin-2-one | 516 | a |
| 36 | 1-[(4-chlorophenyl)methyl]-3-(5-[(5-chlorothiophen-2-yl)methyl]amino-1-[(2-methoxyphenyl)carbonyl]-1H-pyrazol-3-yl)-1,2-dihydropyridin-2-one | 566 | a |
| 37 | 1-[(4-chlorophenyl)methyl]-3-(5-[(5-chlorothiophen-2-yl)methyl]amino-1-[(furan-3-yl)carbonyl]-1H-pyrazol-3-yl)-1,2-dihydropyridin-2-one | 525 | a |
| 38 | 1-[(4-chlorophenyl)methyl]-3-(5-[(5-chlorothiophen-2-yl)methyl]amino-1H-pyrazol-3-yl)-1,2-dihydropyridin-2-one | 431 | e |
| 39 | 1-[(5-chlorothiophen-2-yl)methyl]-3-(5-[(5-chlorothiophen-2-yl)methyl]amino-1-(2,2-dimethylpropanoyl)-1H-pyrazol-3-yl)-1,2-dihydropyridin-2-one | 522 | a |
| 40 | 1-[(5-chlorothiophen-2-yl)methyl]-3-(5-[(5-chlorothiophen-2-yl)methyl]amino-1-[(2-methoxyphenyl)carbonyl]-1H-pyrazol-3-yl)-1,2-dihydropyridin-2-one | 572 | a |
| 41 | 1-[(5-chlorothiophen-2-yl)methyl]-3-(5-[(5-chlorothiophen-2-yl)methyl]amino-1-[(furan-3-yl)carbonyl]-1H-pyrazol-3-yl)-1,2-dihydropyridin-2-one | 531 | a |
| 42 | 1-[(5-chlorothiophen-2-yl)methyl]-3-(5-[(5-chlorothiophen-2-yl)methyl]amino-1H-pyrazol-3-yl)-1,2-dihydropyridin-2-one | 437 | e |
| 43 | 1-benzyl-3-(5-[(5-chlorothiophen-2-yl)methyl]amino-1-(2,2-dimethylpropanoyl)-1H-pyrazol-3-yl)-1,2-dihydropyridin-2-one | 481 | a |
| 44 | 1-benzyl-3-(5-[(5-chlorothiophen-2-yl)methyl]amino-1-(3-methoxy-2,2-dimethylpropanoyl)-1H-pyrazol-3-yl)-1,2-dihydropyridin-2-one | 511 | a |
| 45 | 1-benzyl-3-(5-[(5-chlorothiophen-2-yl)methyl]amino-1-[(2,3-dihydro-1,4-benzodioxin-5-yl)carbonyl]-1H-pyrazol-3-yl)-1,2-dihydropyridin-2-one | 559 | a |
| 46 | 1-benzyl-3-(5-[(5-chlorothiophen-2-yl)methyl]amino-1-[(2,4-dimethoxyphenyl)carbonyl]-1H-pyrazol-3-yl)-1,2-dihydropyridin-2-one | 561 | a |
| 47 | 1-benzyl-3-(5-[(5-chlorothiophen-2-yl)methyl]amino-1-[(2-methoxyphenyl)carbonyl]-1H-pyrazol-3-yl)-1,2-dihydropyridin-2-one | 531 | a |
| 48 | 1-benzyl-3-(5-[(5-chlorothiophen-2-yl)methyl]amino-1-[(4-methyloxan-4-yl)carbonyl]-1H-pyrazol-3-yl)-1,2-dihydropyridin-2-one | 523 | a |
| 49 | 1-benzyl-3-(5-[(5-chlorothiophen-2-yl)methyl]amino-1-[(furan-2-yl)carbonyl]-1H-pyrazol-3-yl)-1,2-dihydropyridin-2-one | 491 | a |
| 50 | 1-benzyl-3-(5-[(5-chlorothiophen-2-yl)methyl]amino-1-[(furan-3-yl)carbonyl]-1H-pyrazol-3-yl)-1,2-dihydropyridin-2-one | 491 | a |
| 51 | 1-benzyl-3-(5-[(5-chlorothiophen-2-yl)methyl]amino-1-[(thiophen-2-yl)carbonyl]-1H-pyrazol-3-yl)-1,2-dihydropyridin-2-one | 507 | a |
| 52 | 1-benzyl-3-(5-[(5-chlorothiophen-2-yl)methyl]amino-1-[(thiophen-3-yl)carbonyl]-1H-pyrazol-3-yl)-1,2-dihydropyridin-2-one | 507 | a |

TABLE A-continued

| Cmpd No. | IUPAC name | MW | Thrombin Activity |
|---|---|---|---|
| 53 | 1-benzyl-3-(5-[(5-chlorothiophen-2-yl)methyl]amino-1-[4-(morpholin-4-yl)phenyl]carbonyl-1H-pyrazol-3-yl)-1,2-dihydropyridin-2-one | 586 | a |
| 54 | 1-benzyl-3-(5-[(5-chlorothiophen-2-yl)methyl]amino-1H-pyrazol-3-yl)-1,2-dihydropyridin-2-one | 397 | c |
| 55 | 1-benzyl-3-1-[(2-chlorophenyl)carbonyl]-5-[(5-chlorothiophen-2-yl)methyl]amino-1H-pyrazol-3-yl-1,2-dihydropyridin-2-one | 535 | a |
| 56 | 2-[3-(5-[(5-chlorothiophen-2-yl)methyl]amino-1-(2,2-dimethylpropanoyl)-1H-pyrazol-3-yl)-2-oxo-1,2-dihydropyridin-1-yl]acetonitrile | 430 | a |
| 57 | 2-[3-(5-[(5-chlorothiophen-2-yl)methyl]amino-1-[(2-methoxyphenyl)carbonyl]-1H-pyrazol-3-yl)-2-oxo-1,2-dihydropyridin-1-yl]acetonitrile | 480 | a |
| 58 | 2-[3-(5-[(5-chlorothiophen-2-yl)methyl]amino-1-[(furan-3-yl)carbonyl]-1H-pyrazol-3-yl)-2-oxo-1,2-dihydropyridin-1-yl]acetonitrile | 440 | a |
| 59 | 2-[3-(5-[(5-chlorothiophen-2-yl)methyl]amino-1H-pyrazol-3-yl)-2-oxo-1,2-dihydropyridin-1-yl]acetic acid | 365 | d |
| 60 | 2-[3-(5-[(5-chlorothiophen-2-yl)methyl]amino-1H-pyrazol-3-yl)-2-oxo-1,2-dihydropyridin-1-yl]acetonitrile | 346 | d |
| 61 | 3-(1-benzoyl-5-[(5-chlorothiophen-2-yl)methyl]amino-1H-pyrazol-3-yl)-1,2-dihydropyridin-2-one | 411 | a |
| 62 | 3-(1-benzoyl-5-[(5-chlorothiophen-2-yl)methyl]amino-1H-pyrazol-3-yl)-1-(2-methoxyethyl)-1,2-dihydropyridin-2-one | 469 | a |
| 63 | 3-(1-benzoyl-5-[(5-chlorothiophen-2-yl)methyl]amino-1H-pyrazol-3-yl)-1-(furan-2-ylmethyl)-1,2-dihydropyridin-2-one | 491 | a |
| 64 | 3-(1-benzoyl-5-[(5-chlorothiophen-2-yl)methyl]amino-1H-pyrazol-3-yl)-1-(furan-3-ylmethyl)-1,2-dihydropyridin-2-one | 491 | a |
| 65 | 3-(1-benzoyl-5-[(5-chlorothiophen-2-yl)methyl]amino-1H-pyrazol-3-yl)-1-(pyridazin-3-ylmethyl)-1,2-dihydropyridin-2-one | 503 | a |
| 66 | 3-(1-benzoyl-5-[(5-chlorothiophen-2-yl)methyl]amino-1H-pyrazol-3-yl)-1-(pyridin-2-ylmethyl)-1,2-dihydropyridin-2-one | 502 | a |
| 67 | 3-(1-benzoyl-5-[(5-chlorothiophen-2-yl)methyl]amino-1H-pyrazol-3-yl)-1-(pyridin-3-ylmethyl)-1,2-dihydropyridin-2-one | 502 | a |
| 68 | 3-(1-benzoyl-5-[(5-chlorothiophen-2-yl)methyl]amino-1H-pyrazol-3-yl)-1-(pyridin-4-ylmethyl)-1,2-dihydropyridin-2-one | 502 | e |
| 69 | 3-(1-benzoyl-5-[(5-chlorothiophen-2-yl)methyl]amino-1H-pyrazol-3-yl)-1-(pyrimidin-2-ylmethyl)-1,2-dihydropyridin-2-one | 503 | a |
| 70 | 3-(1-benzoyl-5-[(5-chlorothiophen-2-yl)methyl]amino-1H-pyrazol-3-yl)-1-(thiophen-2-ylmethyl)-1,2-dihydropyridin-2-one | 507 | a |
| 71 | 3-(1-benzoyl-5-[(5-chlorothiophen-2-yl)methyl]amino-1H-pyrazol-3-yl)-1-(thiophen-3-ylmethyl)-1,2-dihydropyridin-2-one | 507 | a |
| 72 | 3-(1-benzoyl-5-[(5-chlorothiophen-2-yl)methyl]amino-1H-pyrazol-3-yl)-1-benzyl-1,2-dihydropyridin-2-one | 501 | a |
| 73 | 3-(1-benzoyl-5-[(5-chlorothiophen-2-yl)methyl]amino-1H-pyrazol-3-yl)-1-methyl-1,2-dihydropyridin-2-one | 425 | a |
| 74 | 3-(5-[(4-fluorophenyl)methyl]amino-1-[(furan-2-yl)carbonyl]-1H-pyrazol-3-yl)-1-(pyridin-2-ylmethyl)-1,2-dihydropyridin-2-one | 470 | a |
| 75 | 3-(5-[(5-chlorothiophen-2-yl)methyl]amino-1-(2,2-dimethylpropanoyl)-1H-pyrazol-3-yl)-1-(2-methoxyethyl)-1,2-dihydropyridin-2-one | 449 | a |
| 76 | 3-(5-[(5-chlorothiophen-2-yl)methyl]amino-1-(2,2-dimethylpropanoyl)-1H-pyrazol-3-yl)-1-(2-phenylethyl)-1,2-dihydropyridin-2-one | 495 | a |
| 77 | 3-(5-[(5-chlorothiophen-2-yl)methyl]amino-1-(2,2-dimethylpropanoyl)-1H-pyrazol-3-yl)-1-(furan-2-ylmethyl)-1,2-dihydropyridin-2-one | 471 | a |
| 78 | 3-(5-[(5-chlorothiophen-2-yl)methyl]amino-1-(2,2-dimethylpropanoyl)-1H-pyrazol-3-yl)-1-(furan-3-ylmethyl)-1,2-dihydropyridin-2-one | 471 | a |
| 79 | 3-(5-[(5-chlorothiophen-2-yl)methyl]amino-1-(2,2-dimethylpropanoyl)-1H-pyrazol-3-yl)-1-(naphthalen-1-ylmethyl)-1,2-dihydropyridin-2-one | 531 | a |
| 80 | 3-(5-[(5-chlorothiophen-2-yl)methyl]amino-1-(2,2-dimethylpropanoyl)-1H-pyrazol-3-yl)-1-(naphthalen-2-ylmethyl)-1,2-dihydropyridin-2-one | 531 | a |

TABLE A-continued

| Cmpd No. | IUPAC name | MW | Thrombin Activity |
|---|---|---|---|
| 81 | 3-(5-[(5-chlorothiophen-2-yl)methyl]amino-1-(2,2-dimethylpropanoyl)-1H-pyrazol-3-yl)-1-(pyridazin-3-ylmethyl)-1,2-dihydropyridin-2-one | 483 | a |
| 82 | 3-(5-[(5-chlorothiophen-2-yl)methyl]amino-1-(2,2-dimethylpropanoyl)-1H-pyrazol-3-yl)-1-(pyridin-2-ylmethyl)-1,2-dihydropyridin-2-one | 482 | a |
| 83 | 3-(5-[(5-chlorothiophen-2-yl)methyl]amino-1-(2,2-dimethylpropanoyl)-1H-pyrazol-3-yl)-1-(pyridin-3-ylmethyl)-1,2-dihydropyridin-2-one | 482 | a |
| 84 | 3-(5-[(5-chlorothiophen-2-yl)methyl]amino-1-(2,2-dimethylpropanoyl)-1H-pyrazol-3-yl)-1-(pyridin-4-ylmethyl)-1,2-dihydropyridin-2-one | 482 | a |
| 85 | 3-(5-[(5-chlorothiophen-2-yl)methyl]amino-1-(2,2-dimethylpropanoyl)-1H-pyrazol-3-yl)-1-(pyrimidin-2-ylmethyl)-1,2-dihydropyridin-2-one | 483 | a |
| 86 | 3-(5-[(5-chlorothiophen-2-yl)methyl]amino-1-(2,2-dimethylpropanoyl)-1H-pyrazol-3-yl)-1-(thiophen-2-ylmethyl)-1,2-dihydropyridin-2-one | 487 | a |
| 87 | 3-(5-[(5-chlorothiophen-2-yl)methyl]amino-1-(2,2-dimethylpropanoyl)-1H-pyrazol-3-yl)-1-(thiophen-3-ylmethyl)-1,2-dihydropyridin-2-one | 487 | a |
| 88 | 3-(5-[(5-chlorothiophen-2-yl)methyl]amino-1-(2,2-dimethylpropanoyl)-1H-pyrazol-3-yl)-1-[2-(morpholin-4-yl)-2-oxoethyl]-1,2-dihydropyridin-2-one | 518 | a |
| 89 | 3-(5-[(5-chlorothiophen-2-yl)methyl]amino-1-(2,2-dimethylpropanoyl)-1H-pyrazol-3-yl)-1-[2-(morpholin-4-yl)ethyl]-1,2-dihydropyridin-2-one | 504 | a |
| 90 | 3-(5-[(5-chlorothiophen-2-yl)methyl]amino-1-(2,2-dimethylpropanoyl)-1H-pyrazol-3-yl)-1-methyl-1,2-dihydropyridin-2-one | 405 | a |
| 91 | 3-(5-[(5-chlorothiophen-2-yl)methyl]amino-1-(3-hydroxy-2,2-dimethylpropanoyl)-1H-pyrazol-3-yl)-1,2-dihydropyridin-2-one | 407 | a |
| 92 | 3-(5-[(5-chlorothiophen-2-yl)methyl]amino-1-(3-hydroxy-2,2-dimethylpropanoyl)-1H-pyrazol-3-yl)-1-(2-methoxyethyl)-1,2-dihydropyridin-2-one | 465 | a |
| 93 | 3-(5-[(5-chlorothiophen-2-yl)methyl]amino-1-(3-hydroxy-2,2-dimethylpropanoyl)-1H-pyrazol-3-yl)-1-(furan-2-ylmethyl)-1,2-dihydropyridin-2-one | 487 | a |
| 94 | 3-(5-[(5-chlorothiophen-2-yl)methyl]amino-1-(3-hydroxy-2,2-dimethylpropanoyl)-1H-pyrazol-3-yl)-1-(pyridin-3-ylmethyl)-1,2-dihydropyridin-2-one | 498 | a |
| 95 | 3-(5-[(5-chlorothiophen-2-yl)methyl]amino-1-(3-hydroxy-2,2-dimethylpropanoyl)-1H-pyrazol-3-yl)-1-(thiophen-2-ylmethyl)-1,2-dihydropyridin-2-one | 503 | a |
| 96 | 3-(5-[(5-chlorothiophen-2-yl)methyl]amino-1-(3-methoxy-2,2-dimethylpropanoyl)-1H-pyrazol-3-yl)-1,2-dihydropyridin-2-one | 421 | a |
| 97 | 3-(5-[(5-chlorothiophen-2-yl)methyl]amino-1-(3-methoxy-2,2-dimethylpropanoyl)-1H-pyrazol-3-yl)-1-(2-methoxyethyl)-1,2-dihydropyridin-2-one | 479 | a |
| 98 | 3-(5-[(5-chlorothiophen-2-yl)methyl]amino-1-(3-methoxy-2,2-dimethylpropanoyl)-1H-pyrazol-3-yl)-1-(furan-2-ylmethyl)-1,2-dihydropyridin-2-one | 501 | a |
| 99 | 3-(5-[(5-chlorothiophen-2-yl)methyl]amino-1-(3-methoxy-2,2-dimethylpropanoyl)-1H-pyrazol-3-yl)-1-(furan-3-ylmethyl)-1,2-dihydropyridin-2-one | 501 | a |
| 100 | 3-(5-[(5-chlorothiophen-2-yl)methyl]amino-1-(3-methoxy-2,2-dimethylpropanoyl)-1H-pyrazol-3-yl)-1-(pyridazin-3-ylmethyl)-1,2-dihydropyridin-2-one | 513 | a |
| 101 | 3-(5-[(5-chlorothiophen-2-yl)methyl]amino-1-(3-methoxy-2,2-dimethylpropanoyl)-1H-pyrazol-3-yl)-1-(pyridin-2-ylmethyl)-1,2-dihydropyridin-2-one | 512 | a |
| 102 | 3-(5-[(5-chlorothiophen-2-yl)methyl]amino-1-(3-methoxy-2,2-dimethylpropanoyl)-1H-pyrazol-3-yl)-1-(pyridin-3-ylmethyl)-1,2-dihydropyridin-2-one | 512 | a |
| 103 | 3-(5-[(5-chlorothiophen-2-yl)methyl]amino-1-(3-methoxy-2,2-dimethylpropanoyl)-1H-pyrazol-3-yl)-1-(pyridin-4-ylmethyl)-1,2-dihydropyridin-2-one | 512 | a |
| 104 | 3-(5-[(5-chlorothiophen-2-yl)methyl]amino-1-(3-methoxy-2,2-dimethylpropanoyl)-1H-pyrazol-3-yl)-1-(pyrimidin-2-ylmethyl)-1,2-dihydropyridin-2-one | 513 | a |
| 105 | 3-(5-[(5-chlorothiophen-2-yl)methyl]amino-1-(3-methoxy-2,2-dimethylpropanoyl)-1H-pyrazol-3-yl)-1-(thiophen-2-ylmethyl)-1,2-dihydropyridin-2-one | 517 | a |

TABLE A-continued

| Cmpd No. | IUPAC name | MW | Thrombin Activity |
|---|---|---|---|
| 106 | 3-(5-[(5-chlorothiophen-2-yl)methyl]amino-1-(3-methoxy-2,2-dimethylpropanoyl)-1H-pyrazol-3-yl)-1-(thiophen-3-ylmethyl)-1,2-dihydropyridin-2-one | 517 | a |
| 107 | 3-(5-[(5-chlorothiophen-2-yl)methyl]amino-1-(3-methoxy-2,2-dimethylpropanoyl)-1H-pyrazol-3-yl)-1-[2-(morpholin-4-yl)ethyl]-1,2-dihydropyridin-2-one | 534 | a |
| 108 | 3-(5-[(5-chlorothiophen-2-yl)methyl]amino-1-[(2,3-dihydro-1,4-benzodioxin-5-yl)carbonyl]-1H-pyrazol-3-yl)-1,2-dihydropyridin-2-one | 469 | a |
| 109 | 3-(5-[(5-chlorothiophen-2-yl)methyl]amino-1-[(2,3-dihydro-1,4-benzodioxin-5-yl)carbonyl]-1H-pyrazol-3-yl)-1-(2-methoxyethyl)-1,2-dihydropyridin-2-one | 527 | a |
| 110 | 3-(5-[(5-chlorothiophen-2-yl)methyl]amino-1-[(2,3-dihydro-1,4-benzodioxin-5-yl)carbonyl]-1H-pyrazol-3-yl)-1-(furan-2-ylmethyl)-1,2-dihydropyridin-2-one | 549 | a |
| 111 | 3-(5-[(5-chlorothiophen-2-yl)methyl]amino-1-[(2,3-dihydro-1,4-benzodioxin-5-yl)carbonyl]-1H-pyrazol-3-yl)-1-(furan-3-ylmethyl)-1,2-dihydropyridin-2-one | 549 | a |
| 112 | 3-(5-[(5-chlorothiophen-2-yl)methyl]amino-1-[(2,3-dihydro-1,4-benzodioxin-5-yl)carbonyl]-1H-pyrazol-3-yl)-1-(pyridazin-3-ylmethyl)-1,2-dihydropyridin-2-one | 561 | a |
| 113 | 3-(5-[(5-chlorothiophen-2-yl)methyl]amino-1-[(2,3-dihydro-1,4-benzodioxin-5-yl)carbonyl]-1H-pyrazol-3-yl)-1-(pyridin-2-ylmethyl)-1,2-dihydropyridin-2-one | 560 | a |
| 114 | 3-(5-[(5-chlorothiophen-2-yl)methyl]amino-1-[(2,3-dihydro-1,4-benzodioxin-5-yl)carbonyl]-1H-pyrazol-3-yl)-1-(pyridin-3-ylmethyl)-1,2-dihydropyridin-2-one | 560 | a |
| 115 | 3-(5-[(5-chlorothiophen-2-yl)methyl]amino-1-[(2,3-dihydro-1,4-benzodioxin-5-yl)carbonyl]-1H-pyrazol-3-yl)-1-(pyridin-4-ylmethyl)-1,2-dihydropyridin-2-one | 560 | a |
| 116 | 3-(5-[(5-chlorothiophen-2-yl)methyl]amino-1-[(2,3-dihydro-1,4-benzodioxin-5-yl)carbonyl]-1H-pyrazol-3-yl)-1-(pyrimidin-2-ylmethyl)-1,2-dihydropyridin-2-one | 561 | a |
| 117 | 3-(5-[(5-chlorothiophen-2-yl)methyl]amino-1-[(2,3-dihydro-1,4-benzodioxin-5-yl)carbonyl]-1H-pyrazol-3-yl)-1-(thiophen-2-ylmethyl)-1,2-dihydropyridin-2-one | 565 | a |
| 118 | 3-(5-[(5-chlorothiophen-2-yl)methyl]amino-1-[(2,3-dihydro-1,4-benzodioxin-5-yl)carbonyl]-1H-pyrazol-3-yl)-1-(thiophen-3-ylmethyl)-1,2-dihydropyridin-2-one | 565 | a |
| 119 | 3-(5-[(5-chlorothiophen-2-yl)methyl]amino-1-[(2,3-dihydro-1,4-benzodioxin-5-yl)carbonyl]-1H-pyrazol-3-yl)-1-[2-(morpholin-4-yl)ethyl]-1,2-dihydropyridin-2-one | 582 | a |
| 120 | 3-(5-[(5-chlorothiophen-2-yl)methyl]amino-1-[(2,3-dihydro-1,4-benzodioxin-5-yl)carbonyl]-1H-pyrazol-3-yl)-1-methyl-1,2-dihydropyridin-2-one | 483 | a |
| 121 | 3-(5-[(5-chlorothiophen-2-yl)methyl]amino-1-[(2,4-dimethoxyphenyl)carbonyl]-1H-pyrazol-3-yl)-1,2-dihydropyridin-2-one | 471 | a |
| 122 | 3-(5-[(5-chlorothiophen-2-yl)methyl]amino-1-[(2,4-dimethoxyphenyl)carbonyl]-1H-pyrazol-3-yl)-1-(2-methoxyethyl)-1,2-dihydropyridin-2-one | 529 | a |
| 123 | 3-(5-[(5-chlorothiophen-2-yl)methyl]amino-1-[(2,4-dimethoxyphenyl)carbonyl]-1H-pyrazol-3-yl)-1-(furan-3-ylmethyl)-1,2-dihydropyridin-2-one | 551 | a |
| 124 | 3-(5-[(5-chlorothiophen-2-yl)methyl]amino-1-[(2,4-dimethoxyphenyl)carbonyl]-1H-pyrazol-3-yl)-1-(pyridazin-3-ylmethyl)-1,2-dihydropyridin-2-one | 563 | a |
| 125 | 3-(5-[(5-chlorothiophen-2-yl)methyl]amino-1-[(2,4-dimethoxyphenyl)carbonyl]-1H-pyrazol-3-yl)-1-(pyridin-2-ylmethyl)-1,2-dihydropyridin-2-one | 562 | a |
| 126 | 3-(5-[(5-chlorothiophen-2-yl)methyl]amino-1-[(2,4-dimethoxyphenyl)carbonyl]-1H-pyrazol-3-yl)-1-(pyridin-3-ylmethyl)-1,2-dihydropyridin-2-one | 562 | a |
| 127 | 3-(5-[(5-chlorothiophen-2-yl)methyl]amino-1-[(2,4-dimethoxyphenyl)carbonyl]-1H-pyrazol-3-yl)-1-(pyridin-4-ylmethyl)-1,2-dihydropyridin-2-one | 562 | a |
| 128 | 3-(5-[(5-chlorothiophen-2-yl)methyl]amino-1-[(2,4-dimethoxyphenyl)carbonyl]-1H-pyrazol-3-yl)-1-(pyrimidin-2-ylmethyl)-1,2-dihydropyridin-2-one | 563 | e |
| 129 | 3-(5-[(5-chlorothiophen-2-yl)methyl]amino-1-[(2,4-dimethoxyphenyl)carbonyl]-1H-pyrazol-3-yl)-1-(thiophen-2-ylmethyl)-1,2-dihydropyridin-2-one | 567 | a |
| 130 | 3-(5-[(5-chlorothiophen-2-yl)methyl]amino-1-[(2,4-dimethoxyphenyl)carbonyl]-1H-pyrazol-3-yl)-1-(thiophen-3-ylmethyl)-1,2-dihydropyridin-2-one | 567 | a |

TABLE A-continued

| Cmpd No. | IUPAC name | MW | Thrombin Activity |
|---|---|---|---|
| 131 | 3-(5-[(5-chlorothiophen-2-yl)methyl]amino-1-[(2,4-dimethoxyphenyl)carbonyl]-1H-pyrazol-3-yl)-1-[2-(morpholin-4-yl)ethyl]-1,2-dihydropyridin-2-one | 584 | a |
| 132 | 3-(5-[(5-chlorothiophen-2-yl)methyl]amino-1-[(2-methoxyphenyl)carbonyl]-1H-pyrazol-3-yl)-1,2-dihydropyridin-2-one | 441 | a |
| 133 | 3-(5-[(5-chlorothiophen-2-yl)methyl]amino-1-[(2-methoxyphenyl)carbonyl]-1H-pyrazol-3-yl)-1-(2-methoxyethyl)-1,2-dihydropyridin-2-one | 499 | a |
| 134 | 3-(5-[(5-chlorothiophen-2-yl)methyl]amino-1-[(2-methoxyphenyl)carbonyl]-1H-pyrazol-3-yl)-1-(2-phenylethyl)-1,2-dihydropyridin-2-one | 545 | a |
| 135 | 3-(5-[(5-chlorothiophen-2-yl)methyl]amino-1-[(2-methoxyphenyl)carbonyl]-1H-pyrazol-3-yl)-1-(furan-2-ylmethyl)-1,2-dihydropyridin-2-one | 521 | a |
| 136 | 3-(5-[(5-chlorothiophen-2-yl)methyl]amino-1-[(2-methoxyphenyl)carbonyl]-1H-pyrazol-3-yl)-1-(furan-3-ylmethyl)-1,2-dihydropyridin-2-one | 521 | a |
| 137 | 3-(5-[(5-chlorothiophen-2-yl)methyl]amino-1-[(2-methoxyphenyl)carbonyl]-1H-pyrazol-3-yl)-1-(naphthalen-2-ylmethyl)-1,2-dihydropyridin-2-one | 581 | a |
| 138 | 3-(5-[(5-chlorothiophen-2-yl)methyl]amino-1-[(2-methoxyphenyl)carbonyl]-1H-pyrazol-3-yl)-1-(pyridazin-3-ylmethyl)-1,2-dihydropyridin-2-one | 533 | a |
| 139 | 3-(5-[(5-chlorothiophen-2-yl)methyl]amino-1-[(2-methoxyphenyl)carbonyl]-1H-pyrazol-3-yl)-1-(pyridin-2-ylmethyl)-1,2-dihydropyridin-2-one | 532 | a |
| 140 | 3-(5-[(5-chlorothiophen-2-yl)methyl]amino-1-[(2-methoxyphenyl)carbonyl]-1H-pyrazol-3-yl)-1-(pyridin-3-ylmethyl)-1,2-dihydropyridin-2-one | 532 | a |
| 141 | 3-(5-[(5-chlorothiophen-2-yl)methyl]amino-1-[(2-methoxyphenyl)carbonyl]-1H-pyrazol-3-yl)-1-(pyridin-4-ylmethyl)-1,2-dihydropyridin-2-one | 532 | a |
| 142 | 3-(5-[(5-chlorothiophen-2-yl)methyl]amino-1-[(2-methoxyphenyl)carbonyl]-1H-pyrazol-3-yl)-1-(pyrimidin-2-ylmethyl)-1,2-dihydropyridin-2-one | 533 | a |
| 143 | 3-(5-[(5-chlorothiophen-2-yl)methyl]amino-1-[(2-methoxyphenyl)carbonyl]-1H-pyrazol-3-yl)-1-(thiophen-2-ylmethyl)-1,2-dihydropyridin-2-one | 537 | a |
| 144 | 3-(5-[(5-chlorothiophen-2-yl)methyl]amino-1-[(2-methoxyphenyl)carbonyl]-1H-pyrazol-3-yl)-1-(thiophen-3-ylmethyl)-1,2-dihydropyridin-2-one | 537 | a |
| 145 | 3-(5-[(5-chlorothiophen-2-yl)methyl]amino-1-[(2-methoxyphenyl)carbonyl]-1H-pyrazol-3-yl)-1-[2-(morpholin-4-yl)-2-oxoethyl]-1,2-dihydropyridin-2-one | 568 | a |
| 146 | 3-(5-[(5-chlorothiophen-2-yl)methyl]amino-1-[(2-methoxyphenyl)carbonyl]-1H-pyrazol-3-yl)-1-[2-(morpholin-4-yl)ethyl]-1,2-dihydropyridin-2-one | 554 | a |
| 147 | 3-(5-[(5-chlorothiophen-2-yl)methyl]amino-1-[(2-methoxyphenyl)carbonyl]-1H-pyrazol-3-yl)-1-methyl-1,2-dihydropyridin-2-one | 455 | a |
| 148 | 3-(5-[(5-chlorothiophen-2-yl)methyl]amino-1-[(3-methyloxetan-3-yl)carbonyl]-1H-pyrazol-3-yl)-1-methyl-1,2-dihydropyridin-2-one | 419 | b |
| 149 | 3-(5-[(5-chlorothiophen-2-yl)methyl]amino-1-[(4-methyloxan-4-yl)carbonyl]-1H-pyrazol-3-yl-1-(2-methoxyethyl)-1,2-dihydropyridin-2-one | 491 | e |
| 150 | 3-(5-[(5-chlorothiophen-2-yl)methyl]amino-1-[(4-methyloxan-4-yl)carbonyl]-1H-pyrazol-3-yl-1-(furan-2-ylmethyl)-1,2-dihydropyridin-2-one | 513 | a |
| 151 | 3-(5-[(5-chlorothiophen-2-yl)methyl]amino-1-[(4-methyloxan-4-yl)carbonyl]-1H-pyrazol-3-yl-1-(furan-3-ylmethyl)-1,2-dihydropyridin-2-one | 513 | a |
| 152 | 3-(5-[(5-chlorothiophen-2-yl)methyl]amino-1-[(4-methyloxan-4-yl)carbonyl]-1H-pyrazol-3-yl-1-(pyridazin-3-ylmethyl)-1,2-dihydropyridin-2-one | 525 | a |
| 153 | 3-(5-[(5-chlorothiophen-2-yl)methyl]amino-1-[(4-methyloxan-4-yl)carbonyl]-1H-pyrazol-3-yl-1-(pyridin-2-ylmethyl)-1,2-dihydropyridin-2-one | 524 | a |
| 154 | 3-(5-[(5-chlorothiophen-2-yl)methyl]amino-1-[(4-methyloxan-4-yl)carbonyl]-1H-pyrazol-3-yl1-(pyridin-3-ylmethyl)-1,2-dihydropyridin-2-one | 524 | a |
| 155 | 3-(5-[(5-chlorothiophen-2-yl)methyl]amino-1-[(4-methyloxan-4-yl)carbonyl]-1H-pyrazol-3-yl-1-(pyridin-4-ylmethyl)-1,2-dihydropyridin-2-one | 524 | a |

TABLE A-continued

| Cmpd No. | IUPAC name | MW | Thrombin Activity |
|---|---|---|---|
| 156 | 3-(5-[(5-chlorothiophen-2-yl)methyl]amino-1-[(4-methyloxan-4-yl)carbonyl]-1H-pyrazol-3-yl-1-(pyrimidin-2-ylmethyl)-1,2-dihydropyridin-2-one | 525 | a |
| 157 | 3-(5-[(5-chlorothiophen-2-yl)methyl]amino-1-[(4-methyloxan-4-yl)carbonyl]-1H-pyrazol-3-yl-1-(thiophen-2-ylmethyl)-1,2-dihydropyridin-2-one | 529 | a |
| 158 | 3-(5-[(5-chlorothiophen-2-yl)methyl]amino-1-[(4-methyloxan-4-yl)carbonyl]-1H-pyrazol-3-yl-1-(thiophen-3-ylmethyl)-1,2-dihydropyridin-2-one | 529 | a |
| 159 | 3-(5-[(5-chlorothiophen-2-yl)methyl]amino-1-[(4-methyloxan-4-yl)carbonyl]-1H-pyrazol-3-yl)-1-[2-(morpholin-4-yl)ethyl]-1,2-dihydropyridin-2-one | 546 | e |
| 160 | 3-(5-[(5-chlorothiophen-2-yl)methyl]amino-1-[(furan-2-yl)carbonyl]-1H-pyrazol-3-yl)-1-(2-methoxyethyl)-1,2-dihydropyridin-2-one | 459 | e |
| 161 | 3-(5-[(5-chlorothiophen-2-yl)methyl]amino-1-[(furan-2-yl)carbonyl]-1H-pyrazol-3-yl)-1-(furan-2-ylmethyl)-1,2-dihydropyridin-2-one | 481 | a |
| 162 | 3-(5-[(5-chlorothiophen-2-yl)methyl]amino-1-[(furan-2-yl)carbonyl]-1H-pyrazol-3-yl)-1-(furan-3-ylmethyl)-1,2-dihydropyridin-2-one | 481 | a |
| 163 | 3-(5-[(5-chlorothiophen-2-yl)methyl]amino-1-[(furan-2-yl)carbonyl]-1H-pyrazol-3-yl)-1-(pyridazin-3-ylmethyl)-1,2-dihydropyridin-2-one | 493 | e |
| 164 | 3-(5-[(5-chlorothiophen-2-yl)methyl]amino-1-[(furan-2-yl)carbonyl]-1H-pyrazol-3-yl)-1-(pyridin-2-ylmethyl)-1,2-dihydropyridin-2-one | 492 | a |
| 165 | 3-(5-[(5-chlorothiophen-2-yl)methyl]amino-1-[(furan-2-yl)carbonyl]-1H-pyrazol-3-yl)-1-(pyridin-3-ylmethyl)-1,2-dihydropyridin-2-one | 492 | a |
| 166 | 3-(5-[(5-chlorothiophen-2-yl)methyl]amino-1-[(furan-2-yl)carbonyl]-1H-pyrazol-3-yl)-1-(pyridin-4-ylmethyl)-1,2-dihydropyridin-2-one | 492 | a |
| 167 | 3-(5-[(5-chlorothiophen-2-yl)methyl]amino-1-[(furan-2-yl)carbonyl]-1H-pyrazol-3-yl)-1-(pyrimidin-2-ylmethyl)-1,2-dihydropyridin-2-one | 493 | a |
| 168 | 3-(5-[(5-chlorothiophen-2-yl)methyl]amino-1-[(furan-2-yl)carbonyl]-1H-pyrazol-3-yl)-1-(thiophen-2-ylmethyl)-1,2-dihydropyridin-2-one | 497 | a |
| 169 | 3-(5-[(5-chlorothiophen-2-yl)methyl]amino-1-[(furan-2-yl)carbonyl]-1H-pyrazol-3-yl)-1-(thiophen-3-ylmethyl)-1,2-dihydropyridin-2-one | 497 | a |
| 170 | 3-(5-[(5-chlorothiophen-2-yl)methyl]amino-1-[(furan-2-yl)carbonyl]-1H-pyrazol-3-yl)-1-[2-(morpholin-4-yl)ethyl]-1,2-dihydropyridin-2-one | 514 | e |
| 171 | 3-(5-[(5-chlorothiophen-2-yl)methyl]amino-1-[(furan-3-yl)carbonyl]-1H-pyrazol-3-yl)-1-(2-methoxyethyl)-1,2-dihydropyridin-2-one | 459 | e |
| 172 | 3-(5-[(5-chlorothiophen-2-yl)methyl]amino-1-[(furan-3-yl)carbonyl]-1H-pyrazol-3-yl)-1-(2-phenylethyl)-1,2-dihydropyridin-2-one | 505 | a |
| 173 | 3-(5-[(5-chlorothiophen-2-yl)methyl]amino-1-[(furan-3-yl)carbonyl]-1H-pyrazol-3-yl)-1-(furan-3-ylmethyl)-1,2-dihydropyridin-2-one | 481 | a |
| 174 | 3-(5-[(5-chlorothiophen-2-yl)methyl]amino-1-[(furan-3-yl)carbonyl]-1H-pyrazol-3-yl)-1-(naphthalen-1-ylmethyl)-1,2-dihydropyridin-2-one | 541 | a |
| 175 | 3-(5-[(5-chlorothiophen-2-yl)methyl]amino-1-[(furan-3-yl)carbonyl]-1H-pyrazol-3-yl)-1-(naphthalen-2-ylmethyl)-1,2-dihydropyridin-2-one | 541 | a |
| 176 | 3-(5-[(5-chlorothiophen-2-yl)methyl]amino-1-[(furan-3-yl)carbonyl]-1H-pyrazol-3-yl)-1-(pyridazin-3-ylmethyl)-1,2-dihydropyridin-2-one | 493 | a |
| 177 | 3-(5-[(5-chlorothiophen-2-yl)methyl]amino-1-[(furan-3-yl)carbonyl]-1H-pyrazol-3-yl)-1-(pyridin-3-ylmethyl)-1,2-dihydropyridin-2-one | 492 | a |
| 178 | 3-(5-[(5-chlorothiophen-2-yl)methyl]amino-1-[(furan-3-yl)carbonyl]-1H-pyrazol-3-yl)-1-(pyrimidin-2-ylmethyl)-1,2-dihydropyridin-2-one | 493 | a |
| 179 | 3-(5-[(5-chlorothiophen-2-yl)methyl]amino-1-[(furan-3-yl)carbonyl]-1H-pyrazol-3-yl)-1-(thiophen-3-ylmethyl)-1,2-dihydropyridin-2-one | 497 | a |
| 180 | 3-(5-[(5-chlorothiophen-2-yl)methyl]amino-1-[(furan-3-yl)carbonyl]-1H-pyrazol-3-yl)-1-[2-(morpholin-4-yl)-2-oxoethyl]-1,2-dihydropyridin-2-one | 528 | a |

TABLE A-continued

| Cmpd No. | IUPAC name | MW | Thrombin Activity |
|---|---|---|---|
| 181 | 3-(5-[(5-chlorothiophen-2-yl)methyl]amino-1-[(furan-3-yl)carbonyl]-1H-pyrazol-3-yl)-1-[2-(morpholin-4-yl)ethyl]-1,2-dihydropyridin-2-one | 514 | a |
| 182 | 3-(5-[(5-chlorothiophen-2-yl)methyl]amino-1-[(thiophen-2-yl)carbonyl]-1H-pyrazol-3-yl)-1-(2-methoxyethyl)-1,2-dihydropyridin-2-one | 475 | a |
| 183 | 3-(5-[(5-chlorothiophen-2-yl)methyl]amino-1-[(thiophen-2-yl)carbonyl]-1H-pyrazol-3-yl)-1-(furan-2-ylmethyl)-1,2-dihydropyridin-2-one | 497 | a |
| 184 | 3-(5-[(5-chlorothiophen-2-yl)methyl]amino-1-[(thiophen-2-yl)carbonyl]-1H-pyrazol-3-yl)-1-(furan-3-ylmethyl)-1,2-dihydropyridin-2-one | 497 | a |
| 185 | 3-(5-[(5-chlorothiophen-2-yl)methyl]amino-1-[(thiophen-2-yl)carbonyl]-1H-pyrazol-3-yl)-1-(pyridazin-3-ylmethyl)-1,2-dihydropyridin-2-one | 509 | e |
| 186 | 3-(5-[(5-chlorothiophen-2-yl)methyl]amino-1-[(thiophen-2-yl)carbonyl]-1H-pyrazol-3-yl)-1-(pyridin-2-ylmethyl)-1,2-dihydropyridin-2-one | 508 | a |
| 187 | 3-(5-[(5-chlorothiophen-2-yl)methyl]amino-1-[(thiophen-2-yl)carbonyl]-1H-pyrazol-3-yl)-1-(pyridin-3-ylmethyl)-1,2-dihydropyridin-2-one | 508 | a |
| 188 | 3-(5-[(5-chlorothiophen-2-yl)methyl]amino-1-[(thiophen-2-yl)carbonyl]-1H-pyrazol-3-yl)-1-(pyridin-4-ylmethyl)-1,2-dihydropyridin-2-one | 508 | a |
| 189 | 3-(5-[(5-chlorothiophen-2-yl)methyl]amino-1-[(thiophen-2-yl)carbonyl]-1H-pyrazol-3-yl)-1-(pyrimidin-2-ylmethyl)-1,2-dihydropyridin-2-one | 509 | a |
| 190 | 3-(5-[(5-chlorothiophen-2-yl)methyl]amino-1-[(thiophen-2-yl)carbonyl]-1H-pyrazol-3-yl)-1-(thiophen-2-ylmethyl)-1,2-dihydropyridin-2-one | 513 | a |
| 191 | 3-(5-[(5-chlorothiophen-2-yl)methyl]amino-1-[(thiophen-2-yl)carbonyl]-1H-pyrazol-3-yl)-1-(thiophen-3-ylmethyl)-1,2-dihydropyridin-2-one | 513 | a |
| 192 | 3-(5-[(5-chlorothiophen-2-yl)methyl]amino-1-[(thiophen-2-yl)carbonyl]-1H-pyrazol-3-yl)-1-[2-(morpholin-4-yl)ethyl]-1,2-dihydropyridin-2-one | 530 | e |
| 193 | 3-(5-[(5-chlorothiophen-2-yl)methyl]amino-1-[(thiophen-3-yl)carbonyl]-1H-pyrazol-3-yl)-1,2-dihydropyridin-2-one | 417 | a |
| 194 | 3-(5-[(5-chlorothiophen-2-yl)methyl]amino-1-[(thiophen-3-yl)carbonyl]-1H-pyrazol-3-yl)-1-(2-methoxyethyl)-1,2-dihydropyridin-2-one | 475 | a |
| 195 | 3-(5-[(5-chlorothiophen-2-yl)methyl]amino-1-[(thiophen-3-yl)carbonyl]-1H-pyrazol-3-yl)-1-(furan-2-ylmethyl)-1,2-dihydropyridin-2-one | 497 | a |
| 196 | 3-(5-[(5-chlorothiophen-2-yl)methyl]amino-1-[(thiophen-3-yl)carbonyl]-1H-pyrazol-3-yl)-1-(furan-3-ylmethyl)-1,2-dihydropyridin-2-one | 497 | a |
| 197 | 3-(5-[(5-chlorothiophen-2-yl)methyl]amino-1-[(thiophen-3-yl)carbonyl]-1H-pyrazol-3-yl)-1-(pyridazin-3-ylmethyl)-1,2-dihydropyridin-2-one | 509 | a |
| 198 | 3-(5-[(5-chlorothiophen-2-yl)methyl]amino-1-[(thiophen-3-yl)carbonyl]-1H-pyrazol-3-yl)-1-(pyridin-2-ylmethyl)-1,2-dihydropyridin-2-one | 508 | a |
| 199 | 3-(5-[(5-chlorothiophen-2-yl)methyl]amino-1-[(thiophen-3-yl)carbonyl]-1H-pyrazol-3-yl)-1-(pyridin-3-ylmethyl)-1,2-dihydropyridin-2-one | 508 | e |
| 200 | 3-(5-[(5-chlorothiophen-2-yl)methyl]amino-1-[(thiophen-3-yl)carbonyl]-1H-pyrazol-3-yl)-1-(pyridin-4-ylmethyl)-1,2-dihydropyridin-2-one | 508 | a |
| 201 | 3-(5-[(5-chlorothiophen-2-yl)methyl]amino-1-[(thiophen-3-yl)carbonyl]-1H-pyrazol-3-yl)-1-(pyrimidin-2-ylmethyl)-1,2-dihydropyridin-2-one | 509 | a |
| 202 | 3-(5-[(5-chlorothiophen-2-yl)methyl]amino-1-[(thiophen-3-yl)carbonyl]-1H-pyrazol-3-yl)-1-(thiophen-2-ylmethyl)-1,2-dihydropyridin-2-one | 513 | a |
| 203 | 3-(5-[(5-chlorothiophen-2-yl)methyl]amino-1-[(thiophen-3-yl)carbonyl]-1H-pyrazol-3-yl)-1-(thiophen-3-ylmethyl)-1,2-dihydropyridin-2-one | 513 | a |
| 204 | 3-(5-[(5-chlorothiophen-2-yl)methyl]amino-1-[(thiophen-3-yl)carbonyl]-1H-pyrazol-3-yl)-1-[2-(morpholin-4-yl)ethyl]-1,2-dihydropyridin-2-one | 530 | a |
| 205 | 3-(5-[(5-chlorothiophen-2-yl)methyl]amino-1-[2-(morpholin-4-yl)phenyl]carbonyl-1H-pyrazol-3-yl)-1,2-dihydropyridin-2-one | 496 | c |
| 206 | 3-(5-[(5-chlorothiophen-2-yl)methyl]amino-1-[4-(2-methoxyethoxy)phenyl]carbonyl-1H-pyrazol-3-yl)-1,2-dihydropyridin-2-one | 485 | a |

TABLE A-continued

| Cmpd No. | IUPAC name | MW | Thrombin Activity |
|---|---|---|---|
| 207 | 3-(5-[(5-chlorothiophen-2-yl)methyl]amino-1-[4-(morpholin-4-yl)phenyl]carbonyl-1H-pyrazol-3-yl)-1,2-dihydropyridin-2-one | 496 | a |
| 208 | 3-(5-[(5-chlorothiophen-2-yl)methyl]amino-1-[4-(morpholin-4-yl)phenyl]carbonyl-1H-pyrazol-3-yl)-1-(2-methoxyethyl)-1,2-dihydropyridin-2-one | 554 | a |
| 209 | 3-(5-[(5-chlorothiophen-2-yl)methyl]amino-1-[4-(morpholin-4-yl)phenyl]carbonyl-1H-pyrazol-3-yl)-1-(furan-2-ylmethyl)-1,2-dihydropyridin-2-one | 576 | a |
| 210 | 3-(5-[(5-chlorothiophen-2-yl)methyl]amino-1-[4-(morpholin-4-yl)phenyl]carbonyl-1H-pyrazol-3-yl)-1-(furan-3-ylmethyl)-1,2-dihydropyridin-2-one | 576 | a |
| 211 | 3-(5-[(5-chlorothiophen-2-yl)methyl]amino-1-[4-(morpholin-4-yl)phenyl]carbonyl-1H-pyrazol-3-yl)-1-(pyridazin-3-ylmethyl)-1,2-dihydropyridin-2-one | 588 | a |
| 212 | 3-(5-[(5-chlorothiophen-2-yl)methyl]amino-1-[4-(morpholin-4-yl)phenyl]carbonyl-1H-pyrazol-3-yl)-1-(pyridin-2-ylmethyl)-1,2-dihydropyridin-2-one | 587 | a |
| 213 | 3-(5-[(5-chlorothiophen-2-yl)methyl]amino-1-[4-(morpholin-4-yl)phenyl]carbonyl-1H-pyrazol-3-yl)-1-(pyridin-3-ylmethyl)-1,2-dihydropyridin-2-one | 587 | a |
| 214 | 3-(5-[(5-chlorothiophen-2-yl)methyl]amino-1-[4-(morpholin-4-yl)phenyl]carbonyl-1H-pyrazol-3-yl)-1-(pyridin-4-ylmethyl)-1,2-dihydropyridin-2-one | 587 | a |
| 215 | 3-(5-[(5-chlorothiophen-2-yl)methyl]amino-1-[4-(morpholin-4-yl)phenyl]carbonyl-1H-pyrazol-3-yl)-1-(pyrimidin-2-ylmethyl)-1,2-dihydropyridin-2-one | 588 | a |
| 216 | 3-(5-[(5-chlorothiophen-2-yl)methyl]amino-1-[4-(morpholin-4-yl)phenyl]carbonyl-1H-pyrazol-3-yl)-1-(thiophen-2-ylmethyl)-1,2-dihydropyridin-2-one | 592 | a |
| 217 | 3-(5-[(5-chlorothiophen-2-yl)methyl]amino-1-[4-(morpholin-4-yl)phenyl]carbonyl-1H-pyrazol-3-yl)-1-(thiophen-3-ylmethyl)-1,2-dihydropyridin-2-one | 592 | a |
| 218 | 3-(5-[(5-chlorothiophen-2-yl)methyl]amino-1-[4-(morpholin-4-yl)phenyl]carbonyl-1H-pyrazol-3-yl)-1-[2-(morpholin-4-yl)ethyl]-1,2-dihydropyridin-2-one | 609 | a |
| 219 | 3-(5-[(5-chlorothiophen-2-yl)methyl]amino-1H-pyrazol-3-yl)-1-(1H-1,2,3,4-tetrazol-5-ylmethyl)-1,2-dihydropyridin-2-one | 389 | d |
| 220 | 3-(5-[(5-chlorothiophen-2-yl)methyl]amino-1H-pyrazol-3-yl)-1-(2-methoxyethyl)-1,2-dihydropyridin-2-one | 365 | d |
| 221 | 3-(5-[(5-chlorothiophen-2-yl)methyl]amino-1H-pyrazol-3-yl)-1-(2-phenylethyl)-1,2-dihydropyridin-2-one | 411 | d |
| 222 | 3-(5-[(5-chlorothiophen-2-yl)methyl]amino-1H-pyrazol-3-yl)-1-(furan-2-ylmethyl)-1,2-dihydropyridin-2-one | 387 | e |
| 223 | 3-(5-[(5-chlorothiophen-2-yl)methyl]amino-1H-pyrazol-3-yl)-1-(furan-3-ylmethyl)-1,2-dihydropyridin-2-one | 387 | c |
| 224 | 3-(5-[(5-chlorothiophen-2-yl)methyl]amino-1H-pyrazol-3-yl)-1-(naphthalen-1-ylmethyl)-1,2-dihydropyridin-2-one | 447 | e |
| 225 | 3-(5-[(5-chlorothiophen-2-yl)methyl]amino-1H-pyrazol-3-yl)-1-(naphthalen-2-ylmethyl)-1,2-dihydropyridin-2-one | 447 | e |
| 226 | 3-(5-[(5-chlorothiophen-2-yl)methyl]amino-1H-pyrazol-3-yl)-1-(pyridazin-3-ylmethyl)-1,2-dihydropyridin-2-one | 399 | d |
| 227 | 3-(5-[(5-chlorothiophen-2-yl)methyl]amino-1H-pyrazol-3-yl)-1-(pyridin-2-ylmethyl)-1,2-dihydropyridin-2-one | 398 | c |
| 228 | 3-(5-[(5-chlorothiophen-2-yl)methyl]amino-1H-pyrazol-3-yl)-1-(pyridin-3-ylmethyl)-1,2-dihydropyridin-2-one | 398 | c |
| 229 | 3-(5-[(5-chlorothiophen-2-yl)methyl]amino-1H-pyrazol-3-yl)-1-(pyridin-4-ylmethyl)-1,2-dihydropyridin-2-one | 398 | c |
| 230 | 3-(5-[(5-chlorothiophen-2-yl)methyl]amino-1H-pyrazol-3-yl)-1-(pyrimidin-2-ylmethyl)-1,2-dihydropyridin-2-one | 399 | e |
| 231 | 3-(5-[(5-chlorothiophen-2-yl)methyl]amino-1H-pyrazol-3-yl)-1-(thiophen-2-ylmethyl)-1,2-dihydropyridin-2-one | 403 | c |
| 232 | 3-(5-[(5-chlorothiophen-2-yl)methyl]amino-1H-pyrazol-3-yl)-1-(thiophen-3-ylmethyl)-1,2-dihydropyridin-2-one | 403 | c |
| 233 | 3-(5-[(5-chlorothiophen-2-yl)methyl]amino-1H-pyrazol-3-yl)-1-[2-(morpholin-4-yl)-2-oxoethyl]-1,2-dihydropyridin-2-one | 434 | c |
| 234 | 3-(5-[(5-chlorothiophen-2-yl)methyl]amino-1H-pyrazol-3-yl)-1-[2-(morpholin-4-yl)ethyl]-1,2-dihydropyridin-2-one | 420 | d |
| 235 | 3-(5-[(5-chlorothiophen-2-yl)methyl]amino-1H-pyrazol-3-yl)-1-[2-(pyridin-2-yl)ethyl]-1,2-dihydropyridin-2-one | 412 | d |
| 236 | 3-(5-[(5-chlorothiophen-2-yl)methyl]amino-1H-pyrazol-3-yl)-1-methyl-1,2-dihydropyridin-2-one | 321 | d |
| 237 | 3-[5-(benzylamino)-1-[(furan-2-yl)carbonyl]-1H-pyrazol-3-yl]-1,2-dihydropyridin-2-one | 360 | b |

TABLE A-continued

| Cmpd No. | IUPAC name | MW | Thrombin Activity |
|---|---|---|---|
| 238 | 3-[5-(benzylamino)-1-[(furan-2-yl)carbonyl]-1H-pyrazol-3-yl]-1-(pyridin-2-ylmethyl)-1,2-dihydropyridin-2-one | 452 | a |
| 239 | 3-[5-(dimethylamino)-1-[(furan-2-yl)carbonyl]-1H-pyrazol-3-yl]-1,2-dihydropyridin-2-one | 298 | e |
| 240 | 3-[5-(dimethylamino)-1-[(furan-2-yl)carbonyl]-1H-pyrazol-3-yl]-1-(pyridin-2-ylmethyl)-1,2-dihydropyridin-2-one | 389 | e |
| 241 | 3-1-[(2-aminophenyl)carbonyl]-5-[(5-chlorothiophen-2-yl)methyl]amino-1H-pyrazol-3-yl-1,2-dihydropyridin-2-one | 426 | a |
| 242 | 3-1-[(2-chlorophenyl)carbonyl]-5-[(5-chlorothiophen-2-yl)methyl]amino-1H-pyrazol-3-yl-1-(2-methoxyethyl)-1,2-dihydropyridin-2-one | 503 | a |
| 243 | 3-1-[(2-chlorophenyl)carbonyl]-5-[(5-chlorothiophen-2-yl)methyl]amino-1H-pyrazol-3-yl-1-(furan-2-ylmethyl)-1,2-dihydropyridin-2-one | 525 | a |
| 244 | 3-1-[(2-chlorophenyl)carbonyl]-5-[(5-chlorothiophen-2-yl)methyl]amino-1H-pyrazol-3-yl-1-(furan-3-ylmethyl)-1,2-dihydropyridin-2-one | 525 | a |
| 245 | 3-1-[(2-chlorophenyl)carbonyl]-5-[(5-chlorothiophen-2-yl)methyl]amino-1H-pyrazol-3-yl-1-(pyridazin-3-ylmethyl)-1,2-dihydropyridin-2-one | 537 | a |
| 246 | 3-1-[(2-chlorophenyl)carbonyl]-5-[(5-chlorothiophen-2-yl)methyl]amino-1H-pyrazol-3-yl-1-(pyridin-2-ylmethyl)-1,2-dihydropyridin-2-one | 536 | a |
| 247 | 3-1-[(2-chlorophenyl)carbonyl]-5-[(5-chlorothiophen-2-yl)methyl]amino-1H-pyrazol-3-yl-1-(pyridin-3-ylmethyl)-1,2-dihydropyridin-2-one | 536 | a |
| 248 | 3-1-[(2-chlorophenyl)carbonyl]-5-[(5-chlorothiophen-2-yl)methyl]amino-1H-pyrazol-3-yl-1-(pyridin-4-ylmethyl)-1,2-dihydropyridin-2-one | 536 | a |
| 249 | 3-1-[(2-chlorophenyl)carbonyl]-5-[(5-chlorothiophen-2-yl)methyl]amino-1H-pyrazol-3-yl-1-(pyrimidin-2-ylmethyl)-1,2-dihydropyridin-2-one | 537 | a |
| 250 | 3-1-[(2-chlorophenyl)carbonyl]-5-[(5-chlorothiophen-2-yl)methyl]amino-1H-pyrazol-3-yl-1-(thiophen-2-ylmethyl)-1,2-dihydropyridin-2-one | 542 | a |
| 251 | 3-1-[(2-chlorophenyl)carbonyl]-5-[(5-chlorothiophen-2-yl)methyl]amino-1H-pyrazol-3-yl-1-(thiophen-3-ylmethyl)-1,2-dihydropyridin-2-one | 542 | a |
| 252 | 3-1-[(2-chlorophenyl)carbonyl]-5-[(5-chlorothiophen-2-yl)methyl]amino-1H-pyrazol-3-yl-1-[2-(morpholin-4-yl)ethyl]-1,2-dihydropyridin-2-one | 558 | a |
| 253 | 3-1-[(4-tert-butylphenyl)carbonyl]-5-[(5-chlorothiophen-2-yl)methyl]amino-1H-pyrazol-3-yl-1,2-dihydropyridin-2-one | 467 | a |
| 254 | 3-1-[(4-tert-butylphenyl)carbonyl]-5-[(5-chlorothiophen-2-yl)methyl]amino-1H-pyrazol-3-yl-1-methyl-1,2-dihydropyridin-2-one | 481 | a |
| 255 | 3-5-amino-1-[(furan-2-yl)carbonyl]-1H-pyrazol-3-yl-1,2-dihydropyridin-2-one | 270 | c |
| 256 | 3-5-amino-1-[(furan-2-yl)carbonyl]-1H-pyrazol-3-yl-1-(pyridin-2-ylmethyl)-1,2-dihydropyridin-2-one | 361 | c |
| 257 | ethyl 2-[3-(5-[(5-chlorothiophen-2-yl)methyl]amino-1-(2,2-dimethylpropanoyl)-1H-pyrazol-3-yl)-2-oxo-1,2-dihydropyridin-1-yl]acetate | 477 | a |
| 258 | ethyl 2-[3-(5-[(5-chlorothiophen-2-yl)methyl]amino-1-[(2-methoxyphenyl)carbonyl]-1H-pyrazol-3-yl)-2-oxo-1,2-dihydropyridin-1-yl]acetate | 527 | a |
| 259 | ethyl 2-[3-(5-[(5-chlorothiophen-2-yl)methyl]amino-1-[(furan-3-yl)carbonyl]-1H-pyrazol-3-yl)-2-oxo-1,2-dihydropyridin-1-yl]acetate | 487 | a |
| 260 | ethyl 2-[3-(5-[(5-chlorothiophen-2-yl)methyl]amino-1H-pyrazol-3-yl)-2-oxo-1,2-dihydropyridin-1-yl]acetate | 393 | d |
| 261 | tert-butyl 2-[3-(5-[(5-chlorothiophen-2-yl)methyl]amino-1-(2,2-dimethylpropanoyl)-1H-pyrazol-3-yl)-2-oxo-1,2-dihydropyridin-1-yl]acetate | 505 | a |
| 262 | tert-butyl 2-[3-(5-[(5-chlorothiophen-2-yl)methyl]amino-1-[(2-methoxyphenyl)carbonyl]-1H-pyrazol-3-yl)-2-oxo-1,2-dihydropyridin-1-yl]acetate | 555 | a |
| 263 | tert-butyl 2-[3-(5-[(5-chlorothiophen-2-yl)methyl]amino-1-[(furan-3-yl)carbonyl]-1H-pyrazol-3-yl)-2-oxo-1,2-dihydropyridin-1-yl]acetate | 515 | a |
| 264 | tert-butyl 2-[3-(5-[(5-chlorothiophen-2-yl)methyl]amino-1H-pyrazol-3-yl)-2-oxo-1,2-dihydropyridin-1-yl]acetate | 421 | e |
| 265 | 1-[(5-[(5-chlorothiophen-2-yl)methyl]amino-3-(1-methyl-2-oxo-1,2-dihydropyridin-3-yl)-1H-pyrazol-1-yl)carbonyl]cyclopropylmethyl 1-(hydroxymethyl)cyclopropane-1-carboxylate | 517 | a |

For Table B following, the disclosed compounds were assayed for inhibition of the protease activity of KLK1 and KLKB1 as described herein. In Table B, C, and D, the level of inhibition in the KLK1 and KLKB1 assays are indicated as follows: a: $IC_{50} \leq 0.1$ μM; b: $0.1$ μM$<IC_{50}<1$ μM; c: $1$ μM$<IC_{50}<10$ μM; d: $10$ μM$<IC_{50}<100$ μM; e: $IC_{50} \geq 100$ μM. Accordingly, in some embodiments, there is provided a compound as expressly set forth in Table B following.

TABLE B

| Cmpd No. | IUPAC name | MW | KLK1 Activity | KLKB1 Activity |
|---|---|---|---|---|
| 4 | 3-(5-[(5-chlorothiophen-2-yl)methyl]amino-1-[(furan-3-yl)carbonyl]-1H-pyrazol-3-yl)-1,2-dihydropyridin-2-one | 401 | d | c |
| 5 | 3-(5-[(5-chlorothiophen-2-yl)methyl]amino-1-[(furan-3-yl)carbonyl]-1H-pyrazol-3-yl)-1-(thiophen-2-ylmethyl)-1,2-dihydropyridin-2-one | 497 | | c |
| 19 | 1-(5-[(4-fluorophenyl)methyl]amino-3-phenyl-1H-pyrazol-1-yl)-2,2-dimethylpropan-1-one | 351 | | e |
| 20 | 1-(5-[(4-fluorophenyl)methyl]amino-3-(pyridin-2-yl)-1H-pyrazol-1-yl)-2,2-dimethylpropan-1-one | 352 | | e |
| 21 | ethyl 3-[(4-fluorophenyl)methyl]amino-1-(pyridin-2-yl)-1H-pyrazole-4-carboxylate | 340 | | e |
| 23 | 3-(5-[(5-chlorothiophen-2-yl)methyl]amino-1-[(furan-3-yl)carbonyl]-1H-pyrazol-3-yl)-1-methyl-1,2-dihydropyridin-2-one | 415 | d | c |
| 24 | 1-(5-[(5-chlorothiophen-2-yl)methyl]amino-4-fluoro-3-(piperidin-4-yl)-1H-pyrazol-1-yl)-2,2-dimethylpropan-1-one | 399 | | b |
| 25 | 3-(5-[(5-chlorothiophen-2-yl)methyl]amino-1-[(furan-3-yl)carbonyl]-1H-pyrazol-3-yl)-1-(pyridin-2-ylmethyl)-1,2-dihydropyridin-2-one | 492 | d | b |
| 26 | 3-(5-[(5-chlorothiophen-2-yl)methyl]amino-1-[(furan-3-yl)carbonyl]-1H-pyrazol-3-yl)-1-(furan-2-ylmethyl)-1,2-dihydropyridin-2-one | 481 | d | c |
| 46 | 1-benzyl-3-(5-[(5-chlorothiophen-2-yl)methyl]amino-1-[(2,4-dimethoxyphenyl)carbonyl]-1H-pyrazol-3-yl)-1,2-dihydropyridin-2-one | 561 | | d |
| 48 | 1-benzyl-3-(5-[(5-chlorothiophen-2-yl)methyl]amino-1-[(4-methyloxan-4-yl)carbonyl]-1H-pyrazol-3-yl)-1,2-dihydropyridin-2-one | 523 | | e |
| 49 | 1-benzyl-3-(5-[(5-chlorothiophen-2-yl)methyl]amino-1-[(furan-2-yl)carbonyl]-1H-pyrazol-3-yl)-1,2-dihydropyridin-2-one | 491 | | b |
| 50 | 1-benzyl-3-(5-[(5-chlorothiophen-2-yl)methyl]amino-1-[(furan-3-yl)carbonyl]-1H-pyrazol-3-yl)-1,2-dihydropyridin-2-one | 491 | | d |
| 51 | 1-benzyl-3-(5-[(5-chlorothiophen-2-yl)methyl]amino-1-[(thiophen-2-yl)carbonyl]-1H-pyrazol-3-yl)-1,2-dihydropyridin-2-one | 507 | | e |
| 52 | 1-benzyl-3-(5-[(5-chlorothiophen-2-yl)methyl]amino-1-[(thiophen-3-yl)carbonyl]-1H-pyrazol-3-yl)-1,2-dihydropyridin-2-one | 507 | | b |
| 53 | 1-benzyl-3-(5-[(5-chlorothiophen-2-yl)methyl]amino-1-[4-(morpholin-4-yl)phenyl]carbonyl-1H-pyrazol-3-yl)-1,2-dihydropyridin-2-one | 586 | | e |
| 59 | 2-[3-(5-[(5-chlorothiophen-2-yl)methyl]amino-1H-pyrazol-3-yl)-2-oxo-1,2-dihydropyridin-1-yl]acetic acid | 365 | e | c |
| 62 | 3-(1-benzoyl-5-[(5-chlorothiophen-2-yl)methyl]amino-1H-pyrazol-3-yl)-1-(2-methoxyethyl)-1,2-dihydropyridin-2-one | 469 | | c |
| 73 | 3-(1-benzoyl-5-[(5-chlorothiophen-2-yl)methyl]amino-1H-pyrazol-3-yl)-1-methyl-1,2-dihydropyridin-2-one | 425 | | e |
| 77 | 3-(5-[(5-chlorothiophen-2-yl)methyl]amino-1-(2,2-dimethylpropanoyl)-1H-pyrazol-3-yl)-1-(furan-2-ylmethyl)-1,2-dihydropyridin-2-one | 471 | | e |
| 81 | 3-(5-[(5-chlorothiophen-2-yl)methyl]amino-1-(2,2-dimethylpropanoyl)-1H-pyrazol-3-yl)-1-(pyridazin-3-ylmethyl)-1,2-dihydropyridin-2-one | 483 | e | c |
| 92 | 3-(5-[(5-chlorothiophen-2-yl)methyl]amino-1-(3-hydroxy-2,2-dimethylpropanoyl)-1H-pyrazol-3-yl)-1-(2-methoxyethyl)-1,2-dihydropyridin-2-one | 465 | | d |
| 93 | 3-(5-[(5-chlorothiophen-2-yl)methyl]amino-1-(3-hydroxy-2,2-dimethylpropanoyl)-1H-pyrazol-3-yl)-1-(furan-2-ylmethyl)-1,2-dihydropyridin-2-one | 487 | | d |
| 94 | 3-(5-[(5-chlorothiophen-2-yl)methyl]amino-1-(3-hydroxy-2,2-dimethylpropanoyl)-1H-pyrazol-3-yl)-1-(pyridin-3-ylmethyl)-1,2-dihydropyridin-2-one | 498 | | c |
| 97 | 3-(5-[(5-chlorothiophen-2-yl)methyl]amino-1-(3-methoxy-2,2-dimethylpropanoyl)-1H-pyrazol-3-yl)-1-(2-methoxyethyl)-1,2-dihydropyridin-2-one | 479 | | d |

TABLE B-continued

| Cmpd No. | IUPAC name | MW | KLK1 Activity | KLKB1 Activity |
|---|---|---|---|---|
| 98 | 3-(5-[(5-chlorothiophen-2-yl)methyl]amino-1-(3-methoxy-2,2-dimethylpropanoyl)-1H-pyrazol-3-yl)-1-(furan-2-ylmethyl)-1,2-dihydropyridin-2-one | 501 | | e |
| 100 | 3-(5-[(5-chlorothiophen-2-yl)methyl]amino-1-(3-methoxy-2,2-dimethylpropanoyl)-1H-pyrazol-3-yl)-1-(pyridazin-3-ylmethyl)-1,2-dihydropyridin-2-one | 513 | | c |
| 101 | 3-(5-[(5-chlorothiophen-2-yl)methyl]amino-1-(3-methoxy-2,2-dimethylpropanoyl)-1H-pyrazol-3-yl)-1-(pyridin-2-ylmethyl)-1,2-dihydropyridin-2-one | 512 | | d |
| 102 | 3-(5-[(5-chlorothiophen-2-yl)methyl]amino-1-(3-methoxy-2,2-dimethylpropanoyl)-1H-pyrazol-3-yl)-1-(pyridin-3-ylmethyl)-1,2-dihydropyridin-2-one | 512 | | d |
| 103 | 3-(5-[(5-chlorothiophen-2-yl)methyl]amino-1-(3-methoxy-2,2-dimethylpropanoyl)-1H-pyrazol-3-yl)-1-(pyridin-4-ylmethyl)-1,2-dihydropyridin-2-one | 512 | | d |
| 104 | 3-(5-[(5-chlorothiophen-2-yl)methyl]amino-1-(3-methoxy-2,2-dimethylpropanoyl)-1H-pyrazol-3-yl)-1-(pyrimidin-2-ylmethyl)-1,2-dihydropyridin-2-one | 513 | | c |
| 105 | 3-(5-[(5-chlorothiophen-2-yl)methyl]amino-1-(3-methoxy-2,2-dimethylpropanoyl)-1H-pyrazol-3-yl)-1-(thiophen-2-ylmethyl)-1,2-dihydropyridin-2-one | 517 | | e |
| 106 | 3-(5-[(5-chlorothiophen-2-yl)methyl]amino-1-(3-methoxy-2,2-dimethylpropanoyl)-1H-pyrazol-3-yl)-1-(thiophen-3-ylmethyl)-1,2-dihydropyridin-2-one | 517 | | e |
| 109 | 3-(5-[(5-chlorothiophen-2-yl)methyl]amino-1-[(2,3-dihydro-1,4-benzodioxin-5-yl)carbonyl]-1H-pyrazol-3-yl)-1-(2-methoxyethyl)-1,2-dihydropyridin-2-one | 527 | | c |
| 113 | 3-(5-[(5-chlorothiophen-2-yl)methyl]amino-1-[(2,3-dihydro-1,4-benzodioxin-5-yl)carbonyl]-1H-pyrazol-3-yl)-1-(pyridin-2-ylmethyl)-1,2-dihydropyridin-2-one | 560 | d | b |
| 116 | 3-(5-[(5-chlorothiophen-2-yl)methyl]amino-1-[(2,3-dihydro-1,4-benzodioxin-5-yl)carbonyl]-1H-pyrazol-3-yl)-1-(pyrimidin-2-ylmethyl)-1,2-dihydropyridin-2-one | 561 | | c |
| 117 | 3-(5-[(5-chlorothiophen-2-yl)methyl]amino-1-[(2,3-dihydro-1,4-benzodioxin-5-yl)carbonyl]-1H-pyrazol-3-yl)-1-(thiophen-2-ylmethyl)-1,2-dihydropyridin-2-one | 565 | | e |
| 122 | 3-(5-[(5-chlorothiophen-2-yl)methyl]amino-1-[(2,4-dimethoxyphenyl)carbonyl]-1H-pyrazol-3-yl)-1-(2-methoxyethyl)-1,2-dihydropyridin-2-one | 529 | | c |
| 123 | 3-(5-[(5-chlorothiophen-2-yl)methyl]amino-1-[(2,4-dimethoxyphenyl)carbonyl]-1H-pyrazol-3-yl)-1-(furan-3-ylmethyl)-1,2-dihydropyridin-2-one | 551 | | d |
| 125 | 3-(5-[(5-chlorothiophen-2-yl)methyl]amino-1-[(2,4-dimethoxyphenyl)carbonyl]-1H-pyrazol-3-yl)-1-(pyridin-2-ylmethyl)-1,2-dihydropyridin-2-one | 562 | | c |
| 126 | 3-(5-[(5-chlorothiophen-2-yl)methyl]amino-1-[(2,4-dimethoxyphenyl)carbonyl]-1H-pyrazol-3-yl)-1-(pyridin-3-ylmethyl)-1,2-dihydropyridin-2-one | 562 | e | c |
| 131 | 3-(5-[(5-chlorothiophen-2-yl)methyl]amino-1-[(2,4-dimethoxyphenyl)carbonyl]-1H-pyrazol-3-yl)-1-[2-(morpholin-4-yl)ethyl]-1,2-dihydropyridin-2-one | 584 | | b |
| 132 | 3-(5-[(5-chlorothiophen-2-yl)methyl]amino-1-[(2-methoxyphenyl)carbonyl]-1H-pyrazol-3-yl)-1,2-dihydropyridin-2-one | 441 | e | c |
| 138 | 3-(5-[(5-chlorothiophen-2-yl)methyl]amino-1-[(2-methoxyphenyl)carbonyl]-1H-pyrazol-3-yl)-1-(pyridazin-3-ylmethyl)-1,2-dihydropyridin-2-one | 533 | e | b |
| 140 | 3-(5-[(5-chlorothiophen-2-yl)methyl]amino-1-[(2-methoxyphenyl)carbonyl]-1H-pyrazol-3-yl)-1-(pyridin-3-ylmethyl)-1,2-dihydropyridin-2-one | 532 | | b |
| 145 | 3-(5-[(5-chlorothiophen-2-yl)methyl]amino-1-[(2-methoxyphenyl)carbonyl]-1H-pyrazol-3-yl)-1-[2-(morpholin-4-yl)-2-oxoethyl]-1,2-dihydropyridin-2-one | 568 | e | c |
| 149 | 3-(5-[(5-chlorothiophen-2-yl)methyl]amino-1-[(4-methyloxan-4-yl)carbonyl]-1H-pyrazol-3-yl)-1-(2-methoxyethyl)-1,2-dihydropyridin-2-one | 491 | e | c |
| 157 | 3-(5-[(5-chlorothiophen-2-yl)methyl]amino-1-[(4-methyloxan-4-yl)carbonyl]-1H-pyrazol-3-yl)-1-(thiophen-2-ylmethyl)-1,2-dihydropyridin-2-one | 529 | | e |
| 160 | 3-(5-[(5-chlorothiophen-2-yl)methyl]amino-1-[(furan-2-yl)carbonyl]-1H-pyrazol-3-yl)-1-(2-methoxyethyl)-1,2-dihydropyridin-2-one | 459 | | b |
| 179 | 3-(5-[(5-chlorothiophen-2-yl)methyl]amino-1-[(furan-3-yl)carbonyl]-1H-pyrazol-3-yl)-1-(thiophen-3-ylmethyl)-1,2-dihydropyridin-2-one | 497 | | d |

TABLE B-continued

| Cmpd No. | IUPAC name | MW | KLK1 Activity | KLKB1 Activity |
|---|---|---|---|---|
| 182 | 3-(5-[(5-chlorothiophen-2-yl)methyl]amino-1-[(thiophen-2-yl)carbonyl]-1H-pyrazol-3-yl)-1-(2-methoxyethyl)-1,2-dihydropyridin-2-one | 475 | | c |
| 184 | 3-(5-[(5-chlorothiophen-2-yl)methyl]amino-1-[(thiophen-2-yl)carbonyl]-1H-pyrazol-3-yl)-1-(furan-3-ylmethyl)-1,2-dihydropyridin-2-one | 497 | | d |
| 194 | 3-(5-[(5-chlorothiophen-2-yl)methyl]amino-1-[(thiophen-3-yl)carbonyl]-1H-pyrazol-3-yl)-1-(2-methoxyethyl)-1,2-dihydropyridin-2-one | 475 | | b |
| 196 | 3-(5-[(5-chlorothiophen-2-yl)methyl]amino-1-[(thiophen-3-yl)carbonyl]-1H-pyrazol-3-yl)-1-(furan-3-ylmethyl)-1,2-dihydropyridin-2-one | 497 | | b |
| 198 | 3-(5-[(5-chlorothiophen-2-yl)methyl]amino-1-[(thiophen-3-yl)carbonyl]-1H-pyrazol-3-yl)-1-(pyridin-2-ylmethyl)-1,2-dihydropyridin-2-one | 508 | | b |
| 201 | 3-(5-[(5-chlorothiophen-2-yl)methyl]amino-1-[(thiophen-3-yl)carbonyl]-1H-pyrazol-3-yl)-1-(pyrimidin-2-ylmethyl)-1,2-dihydropyridin-2-one | 509 | | b |
| 203 | 3-(5-[(5-chlorothiophen-2-yl)methyl]amino-1-[(thiophen-3-yl)carbonyl]-1H-pyrazol-3-yl)-1-(thiophen-3-ylmethyl)-1,2-dihydropyridin-2-one | 513 | | b |
| 208 | 3-(5-[(5-chlorothiophen-2-yl)methyl]amino-1-[4-(morpholin-4-yl)phenyl]carbonyl-1H-pyrazol-3-yl)-1-(2-methoxyethyl)-1,2-dihydropyridin-2-one | 554 | | c |
| 210 | 3-(5-[(5-chlorothiophen-2-yl)methyl]amino-1-[4-(morpholin-4-yl)phenyl]carbonyl-1H-pyrazol-3-yl)-1-(furan-3-ylmethyl)-1,2-dihydropyridin-2-one | 576 | | d |
| 213 | 3-(5-[(5-chlorothiophen-2-yl)methyl]amino-1-[4-(morpholin-4-yl)phenyl]carbonyl-1H-pyrazol-3-yl)-1-(pyridin-3-ylmethyl)-1,2-dihydropyridin-2-one | 587 | e | b |
| 214 | 3-(5-[(5-chlorothiophen-2-yl)methyl]amino-1-[4-(morpholin-4-yl)phenyl]carbonyl-1H-pyrazol-3-yl)-1-(pyridin-4-ylmethyl)-1,2-dihydropyridin-2-one | 587 | | b |
| 218 | 3-(5-[(5-chlorothiophen-2-yl)methyl]amino-1-[4-(morpholin-4-yl)phenyl]carbonyl-1H-pyrazol-3-yl)-1-[2-(morpholin-4-yl)ethyl]-1,2-dihydropyridin-2-one | 609 | | b |
| 227 | 3-(5-[(5-chlorothiophen-2-yl)methyl]amino-1H-pyrazol-3-yl)-1-(pyridin-2-ylmethyl)-1,2-dihydropyridin-2-one | 398 | | e |
| 229 | 3-(5-[(5-chlorothiophen-2-yl)methyl]amino-1H-pyrazol-3-yl)-1-(pyridin-4-ylmethyl)-1,2-dihydropyridin-2-one | 398 | | e |
| 235 | 3-(5-[(5-chlorothiophen-2-yl)methyl]amino-1H-pyrazol-3-yl)-142-(pyridin-2-yl)ethyl]-1,2-dihydropyridin-2-one | 412 | | d |
| 237 | 3-[5-(benzylamino)-1-[(furan-2-yl)carbonyl]-1H-pyrazol-3-yl]-1,2-dihydropyridin-2-one | 360 | | d |
| 238 | 3-[5-(benzylamino)-1-[(furan-2-yl)carbonyl]-1H-pyrazol-3-yl]-1-(pyridin-2-ylmethyl)-1,2-dihydropyridin-2-one | 452 | | c |
| 242 | 3-1-[(2-chlorophenyl)carbonyl]-5-[(5-chlorothiophen-2-yl)methyl]amino-1H-pyrazol-3-yl-1-(2-methoxyethyl)-1,2-dihydropyridin-2-one | 503 | e | b |
| 243 | 3-1-[(2-chlorophenyl)carbonyl]-5-[(5-chlorothiophen-2-yl)methyl]amino-1H-pyrazol-3-yl-1-(furan-2-ylmethyl)-1,2-dihydropyridin-2-one | 525 | | b |
| 244 | 3-1-[(2-chlorophenyl)carbonyl]-5-[(5-chlorothiophen-2-yl)methyl]amino-1H-pyrazol-3-yl-1-(furan-3-ylmethyl)-1,2-dihydropyridin-2-one | 525 | | b |
| 247 | 3-1-[(2-chlorophenyl)carbonyl]-5-[(5-chlorothiophen-2-yl)methyl]amino-1H-pyrazol-3-yl-1-(pyridin-3-ylmethyl)-1,2-dihydropyridin-2-one | 536 | e | a |
| 248 | 3-1-[(2-chlorophenyl)carbonyl]-5-[(5-chlorothiophen-2-yl)methyl]amino-1H-pyrazol-3-yl-1-(pyridin-4-ylmethyl)-1,2-dihydropyridin-2-one | 536 | e | b |
| 265 | 1-[(5-[(5-chlorothiophen-2-yl)methyl]amino-3-(1-methyl-2-oxo-1,2-dihydropyridin-3-yl)-1H-pyrazol-1-yl)carbonyl]cyclopropylmethyl 1-(hydroxymethyl)cyclopropane-1-carboxylate | 517 | | c |
| 266 | 1-(5-[(4-fluorophenyl)methyl]amino-3-(pyridazin-3-yl)-1H-pyrazol-1-yl)-2,2-dimethylpropan-1-one | 353 | | e |
| 267 | 1-(5-[(4-fluorophenyl)methyl]amino-3-(pyrimidin-4-yl)-1H-pyrazol-1-yl)-2,2-dimethylpropan-1-one | 353 | | e |
| 268 | 1-(5-[(4-fluorophenyl)methyl]amino-3-phenyl-1H-pyrazol-1-yl)propan-1-one | 323 | | e |
| 269 | 1-(5-[(5-chlorothiophen-2-yl)methyl]amino-3-(3-fluoropyridin-2-yl)-1H-pyrazol-1-yl)-2,2-dimethylpropan-1-one | 393 | | e |
| 270 | 1-(5-[(5-chlorothiophen-2-yl)methyl]amino-3-(furan-2-yl)-1H-pyrazol-1-yl)-2,2-dimethylpropan-1-one | 364 | | e |

TABLE B-continued

| Cmpd No. | IUPAC name | MW | KLK1 Activity | KLKB1 Activity |
|---|---|---|---|---|
| 271 | 1-(5-[(5-chlorothiophen-2-yl)methyl]amino-3-(pyridin-2-yl)-1H-pyrazol-1-yl)-2,2-dimethylpropan-1-one | 375 | | e |
| 272 | 1-(5-[(5-chlorothiophen-2-yl)methyl]amino-3-(pyridin-2-yl)-1H-pyrazol-1-yl)-3-methoxy-2,2-dimethylpropan-1-one | 405 | | e |
| 273 | 1-(5-[(5-chlorothiophen-2-yl)methyl]amino-4-fluoro-3-(oxan-4-yl)-1H-pyrazol-1-yl)-3-hydroxy-2,2-dimethylpropan-1-one | 416 | | d |
| 274 | 1-(5-[(5-chlorothiophen-2-yl)methyl]amino-4-fluoro-3-(piperidin-4-yl)-1H-pyrazol-1-yl)-3-hydroxy-2,2-dimethylpropan-1-one | 415 | | c |
| 275 | 1-(5-[(5-chlorothiophen-2-yl)methyl]amino-4-fluoro-3-phenyl-1H-pyrazol-1-yl)-3-hydroxy-2,2-dimethylpropan-1-one | 408 | | e |
| 276 | 1-[(2-aminophenyl)carbonyl]-N-[(5-chlorothiophen-2-yl)methyl]-3-(3-fluoropyridin-2-yl)-1H-pyrazol-5-amine | 428 | d | c |
| 277 | 1-[(2-aminophenyl)carbonyl]-N-[(5-chlorothiophen-2-yl)methyl]-3-(furan-2-yl)-1H-pyrazol-5-amine | 399 | d | c |
| 278 | 1-[(2-methoxyphenyl)carbonyl]-3-(pyridin-2-yl)-N-(thiophen-2-ylmethyl)-1H-pyrazol-5-amine | 390 | | e |
| 279 | 1-[5-(benzylamino)-4-fluoro-3-(pyridin-2-yl)-1H-pyrazol-1-yl]-2,2-dimethylpropan-1-one | 352 | | e |
| 280 | 1-5-[(furan-2-ylmethyl)amino-3-(pyridin-2-yl)-1H-pyrazol-1-yl-2,2-dimethylpropan-1-one | 324 | | e |
| 281 | 2,2-dimethyl-1-[3-(pyridin-2-yl)-5-[(thiophen-2-ylmethyl)amino]-1H-pyrazol-1-yl]propan-1-one | 340 | | e |
| 282 | 245-[(5-chlorothiophen-2-yl)methyl]amino-1-[(2-methoxyphenyl)carbonyl]-1H-pyrazol-3-yl)cyclohexan-1-ol | 446 | e | c |
| 283 | N-(furan-2-ylmethyl)-1-[(2-methoxyphenyl)carbonyl]-3-(pyridin-2-yl)-1H-pyrazol-5-amine | 374 | | e |
| 284 | N-[(5-chlorothiophen-2-yl)methyl]-1-[(2-methoxyphenyl)carbonyl]-3-(oxan-4-yl)-1H-pyrazol-5-amine | 432 | | e |
| 285 | N-[(5-chlorothiophen-2-yl)methyl]-1-[(2-methoxyphenyl)carbonyl]-3-(pyridin-2-yl)-1H-pyrazol-5-amine | 425 | d | c |
| 286 | N-[(5-chlorothiophen-2-yl)methyl]-1-[(2-phenoxyphenyl)carbonyl]-3-(pyridin-2-yl)-1H-pyrazol-5-amine | 487 | | e |
| 287 | N-[(5-chlorothiophen-2-yl)methyl]-1-[(4-methyloxan-4-yl)carbonyl]-3-(pyridin-2-yl)-1H-pyrazol-5-amine | 417 | | d |
| 288 | N-[(5-chlorothiophen-2-yl)methyl]-1-[(furan-3-yl)carbonyl]-3-(pyridin-2-yl)-1H-pyrazol-5-amine | 385 | | d |
| 289 | N-[(5-chlorothiophen-2-yl)methyl]-1-[(furan-3-yl)carbonyl]-3-(thiophen-2-yl)-1H-pyrazol-5-amine | 390 | | e |
| 290 | N-[(5-chlorothiophen-2-yl)methyl]-3-(3-fluoropyridin-2-yl)-1-[(2-methoxyphenyl)carbonyl]-1H-pyrazol-5-amine | 443 | | e |
| 291 | N-[(5-chlorothiophen-2-yl)methyl]-3-(3-fluoropyridin-2-yl)-1-[(furan-3-yl)carbonyl]-1H-pyrazol-5-amine | 403 | | e |
| 292 | N-[(5-chlorothiophen-2-yl)methyl]-3-(pyridazin-3-yl)-1-[(thiophen-3-yl)carbonyl]-1H-pyrazol-5-amine | 402 | e | b |
| 293 | N-[(5-chlorothiophen-2-yl)methyl]-3-(pyridin-2-yl)-1-[(thiophen-3-yl)carbonyl]-1H-pyrazol-5-amine | 401 | e | b |
| 294 | N-[(5-chlorothiophen-2-yl)methyl]-4-fluoro-1-[(furan-3-yl)carbonyl]-3-(oxan-4-yl)-1H-pyrazol-5-amine | 410 | e | c |
| 295 | N-[(5-chlorothiophen-2-yl)methyl]-4-fluoro-1-[(furan-3-yl)carbonyl]-3-phenyl-1H-pyrazol-5-amine | 402 | | e |
| 296 | N-benzyl-4-fluoro-1-[(2-methoxyphenyl)carbonyl]-3-phenyl-1H-pyrazol-5-amine | 401 | | e |
| 297 | tert-butyl 4-(5-[(5-chlorothiophen-2-yl)methyl]amino-1-(2,2-dimethylpropanoyl)-1H-pyrazol-3-yl)piperidine-1-carboxylate | 481 | | e |
| 298 | tert-butyl 4-(5-[(5-chlorothiophen-2-yl)methyl]amino-1-[(thiophen-3-yl)carbonyl]-1H-pyrazol-3-yl)piperidine-1-carboxylate | 507 | | e |

In some embodiments, there is provided a compound as expressly set forth in Table C following.

TABLE C

| Cmpd No. | IUPAC name | MW | KLK1 Activity | KLKB1 Activity |
|---|---|---|---|---|
| 7 | 1-(5-[(4-fluorophenyl)methyl]amino-3-(pyridin-3-yl)-1H-1,2,4-triazol-1-yl)propan-1-one | 325 | | d |
| 8 | N-benzyl-1-[(furan-2-yl)carbonyl]-3-(pyridin-2-yl)-1H-1,2,4-triazol-5-amine | 345 | | c |
| 9 | 1-[5-(benzylamino)-3-(pyridin-2-yl)-1H-1,2,4-triazol-1-yl]-3-phenylpropan-1-one | 383 | | e |
| 10 | N-[(4-fluorophenyl)methyl]-3-(pyridin-2-yl)-1-[(thiophen-2-yl)carbonyl]-1H-1,2,4-triazol-5-amine | 379 | | c |
| 11 | N-[(4-fluorophenyl)methyl]-3-(pyridin-4-yl)-1-[(thiophen-3-yl)carbonyl]-1H-1,2,4-triazol-5-amine | 379 | | c |
| 12 | N-[(4-fluorophenyl)methyl]-1-[(morpholin-4-yl)carbonyl]-3-(pyridin-3-yl)-1H-1,2,4-triazol-5-amine | 382 | | e |
| 13 | 1-[5-(dimethylamino)-3-(pyridin-3-yl)-1H-1,2,4-triazol-1-yl]propan-1-one | 245 | | e |
| 14 | 3-(5-[(4-fluorophenyl)methyl]sulfanyl-1-[(2-methoxyphenyl)carbonyl]-1H-1,2,4-triazol-3-yl)pyridine | 420 | | b |
| 15 | 1-[(2-methoxyphenyl)carbonyl]-5-(methylsulfanyl)-3-(thiophen-2-yl)-1H-1,2,4-triazole | 331 | c | c |
| 16 | N-benzyl-1-[(2-methoxyphenyl)carbonyl]-3-(pyrimidin-4-yl)-1H-1,2,4-triazol-5-amine | 386 | | b |
| 17 | N-benzyl-1-[(2-methoxyphenyl)carbonyl]-3-(pyrimidin-5-yl)-1H-1,2,4-triazol-5-amine | 386 | | b |
| 18 | N-benzyl-1-[(2-methoxyphenyl)carbonyl]-3-(pyrimidin-2-yl)-1H-1,2,4-triazol-5-amine | 386 | d | b |
| 22 | N-[(5-chlorothiophen-2-yl)methyl]-1-[(2-methoxyphenyl)carbonyl]-3-(pyridin-2-yl)-1H-1,2,4-triazol-5-amine | 426 | d | a |
| 299 | 1-(1,3-benzothiazol-2-yl)-N-[(4-fluorophenyl)methyl]-3-(pyridin-2-yl)-1H-1,2,4-triazol-5-amine | 402 | | e |
| 300 | 1-(5-[(4-fluorophenyl)methyl]amino-3-(furan-2-yl)-1H-1,2,4-triazol-1-yl)-2,2-dimethylpropan-1-one | 342 | | d |
| 301 | 1-(5-[(4-fluorophenyl)methyl]amino-3-(pyridin-2-yl)-1H-1,2,4-triazol-1-yl)-2,2-dimethylpropan-1-one | 353 | | d |
| 302 | 1-(5-[(4-fluorophenyl)methyl]amino-3-(pyridin-2-yl)-1H-1,2,4-triazol-1-yl)-2-methylpropan-1-one | 339 | | d |
| 303 | 1-(5-[(4-fluorophenyl)methyl]amino-3-(pyridin-2-yl)-1H-1,2,4-triazol-1-yl)-2-phenylethan-1-one | 387 | | c |
| 304 | 1-(5-[(4-fluorophenyl)methyl]amino-3-(pyridin-2-yl)-1H-1,2,4-triazol-1-yl)-3-methylbutan-1-one | 353 | | d |
| 305 | 1-(5-[(4-fluorophenyl)methyl]amino-3-(pyridin-2-yl)-1H-1,2,4-triazol-1-yl)-3-phenylpropan-1-one | 401 | | d |
| 306 | 1-(5-[(4-fluorophenyl)methyl]amino-3-(pyridin-2-yl)-1H-1,2,4-triazol-1-yl)butan-1-one | 339 | | d |
| 307 | 1-(5-[(4-fluorophenyl)methyl]amino-3-(pyridin-2-yl)-1H-1,2,4-triazol-1-yl)propan-1-one | 325 | | d |
| 308 | 1-(5-[(4-fluorophenyl)methyl]amino-3-(pyridin-3-yl)-1H-1,2,4-triazol-1-yl)-2,2-dimethylpropan-1-one | 353 | | d |
| 309 | 1-(5-[(4-fluorophenyl)methyl]amino-3-(pyridin-3-yl)-1H-1,2,4-triazol-1-yl)-2-methoxyethan-1-one | 341 | | e |
| 310 | 1-(5-[(4-fluorophenyl)methyl]amino-3-(pyridin-3-yl)-1H-1,2,4-triazol-1-yl)-2-methylpropan-1-one | 339 | | d |
| 311 | 1-(5-[(4-fluorophenyl)methyl]amino-3-(pyridin-3-yl)-1H-1,2,4-triazol-1-yl)-2-phenylethan-1-one | 387 | | c |
| 312 | 1-(5-[(4-fluorophenyl)methyl]amino-3-(pyridin-3-yl)-1H-1,2,4-triazol-1-yl)-3-methylbutan-1-one | 353 | | d |
| 313 | 1-(5-[(4-fluorophenyl)methyl]amino-3-(pyridin-3-yl)-1H-1,2,4-triazol-1-yl)-3-phenylpropan-1-one | 401 | | d |
| 314 | 1-(5-[(4-fluorophenyl)methyl]amino-3-(pyridin-3-yl)-1H-1,2,4-triazol-1-yl)butan-1-one | 339 | | d |
| 315 | 1-(5-[(4-fluorophenyl)methyl]amino-3-(pyridin-4-yl)-1H-1,2,4-triazol-1-yl)-2-methylpropan-1-one | 339 | | d |
| 316 | 1-(5-[(4-fluorophenyl)methyl]amino-3-(pyridin-4-yl)-1H-1,2,4-triazol-1-yl)-3-methylbutan-1-one | 353 | | e |
| 317 | 1-(5-[(4-fluorophenyl)methyl]amino-3-(pyridin-4-yl)-1H-1,2,4-triazol-1-yl)butan-1-one | 339 | | e |
| 318 | 1-(5-[(4-fluorophenyl)methyl]amino-3-(pyridin-4-yl)-1H-1,2,4-triazol-1-yl)propan-1-one | 325 | | e |
| 319 | 1-(5-[(4-methoxyphenyl)methyl]amino-3-(pyridin-2-yl)-1H-1,2,4-triazol-1-yl)-2,2-dimethylpropan-1-one | 365 | | d |
| 320 | 1-(5-[(4-methoxyphenyl)methyl]amino-3-(pyridin-2-yl)-1H-1,2,4-triazol-1-yl)-2-methylpropan-1-one | 351 | | e |
| 321 | 1-(5-[(4-methoxyphenyl)methyl]amino-3-(pyridin-2-yl)-1H-1,2,4-triazol-1-yl)-2-phenylethan-1-one | 399 | | d |

TABLE C-continued

| Cmpd No. | IUPAC name | MW | KLK1 Activity | KLKB1 Activity |
|---|---|---|---|---|
| 322 | 1-(5-[(4-methoxyphenyl)methyl]amino-3-(pyridin-2-yl)-1H-1,2,4-triazol-1-yl)-3-methylbutan-1-one | 365 | | d |
| 323 | 1-(5-[(4-methoxyphenyl)methyl]amino-3-(pyridin-2-yl)-1H-1,2,4-triazol-1-yl)-3-phenylpropan-1-one | 414 | d | c |
| 324 | 1-(5-[(4-methoxyphenyl)methyl]amino-3-(pyridin-2-yl)-1H-1,2,4-triazol-1-yl)butan-1-one | 351 | | d |
| 325 | 1-(5-[(4-methoxyphenyl)methyl]amino-3-(pyridin-2-yl)-1H-1,2,4-triazol-1-yl)propan-1-one | 337 | | d |
| 326 | 1-(5-[(4-methoxyphenyl)methyl]amino-3-(pyridin-3-yl)-1H-1,2,4-triazol-1-yl)-2,2-dimethylpropan-1-one | 365 | | e |
| 327 | 1-(5-[(4-methoxyphenyl)methyl]amino-3-(pyridin-3-yl)-1H-1,2,4-triazol-1-yl)-2-phenylethan-1-one | 399 | | d |
| 328 | 1-(5-[(4-methoxyphenyl)methyl]amino-3-(pyridin-3-yl)-1H-1,2,4-triazol-1-yl)-3-methylbutan-1-one | 365 | | e |
| 329 | 1-(5-[(4-methoxyphenyl)methyl]amino-3-(pyridin-3-yl)-1H-1,2,4-triazol-1-yl)-3-phenylpropan-1-one | 414 | | e |
| 330 | 1-(5-[(4-methoxyphenyl)methyl]amino-3-(pyridin-3-yl)-1H-1,2,4-triazol-1-yl)butan-1-one | 351 | | d |
| 331 | 1-(5-[(5-chlorothiophen-2-yl)methyl]amino-3-(oxolan-2-yl)-1H-1,2,4-triazol-1-yl)-2,2-dimethylpropan-1-one | 369 | | c |
| 332 | 1-[(2-methoxyphenyl)carbonyl]-3-(pyridin-2-yl)-N-(1,3-thiazol-2-ylmethyl)-1H-1,2,4-triazol-5-amine | 392 | b | d |
| 333 | 1-[(2-methoxyphenyl)carbonyl]-3-phenyl-N-(1,3-thiazol-2-ylmethyl)-1H-1,2,4-triazol-5-amine | 391 | | e |
| 334 | 1-[(2-methoxyphenyl)carbonyl]-3-phenyl-N-(thiophen-2-ylmethyl)-1H-1,2,4-triazol-5-amine | 390 | | d |
| 335 | 1-[(2-methoxyphenyl)carbonyl]-3-phenyl-N-(thiophen-3-ylmethyl)-1H-1,2,4-triazol-5-amine | 390 | | d |
| 336 | 1-[(furan-2-yl)carbonyl]-N-[(4-methoxyphenyl)methyl]-3-(pyridin-2-yl)-1H-1,2,4-triazol-5-amine | 375 | | c |
| 337 | 1-[(furan-2-yl)carbonyl]-N-[(4-methoxyphenyl)methyl]-3-(pyridin-4-yl)-1H-1,2,4-triazol-5-amine | 375 | | e |
| 338 | 1-[(furan-3-yl)carbonyl]-N-[(4-methoxyphenyl)methyl]-3-(pyridin-2-yl)-1H-1,2,4-triazol-5-amine | 375 | | d |
| 339 | 1-[(furan-3-yl)carbonyl]-N-[(4-methoxyphenyl)methyl]-3-(pyridin-3-yl)-1H-1,2,4-triazol-5-amine | 375 | | e |
| 340 | 1-[3-(pyridin-3-yl)-5-[(thiophen-2-ylmethyl)amino]-1H-1,2,4-triazol-1-yl]propan-1-one | 313 | | d |
| 341 | 1-[4-(5-[(5-chlorothiophen-2-yl)methyl]amino-1-[(2-methoxyphenyl)carbonyl]-1H-1,2,4-triazol-3-yl)piperidin-1-yl]-2,2-dimethylpropan-1-one | 516 | | b |
| 342 | 1-[5-(benzylamino)-3-(furan-2-yl)-1H-1,2,4-triazol-1-yl]-2,2-dimethylpropan-1-one | 324 | | e |
| 343 | 1-[5-(benzylamino)-3-(furan-2-yl)-1H-1,2,4-triazol-1-yl]-2-phenylethan-1-one | 358 | | e |
| 344 | 1-[5-(benzylamino)-3-(pyridin-2-yl)-1H-1,2,4-triazol-1-yl]-2,2-dimethylpropan-1-one | 335 | | d |
| 345 | 1-[5-(benzylamino)-3-(pyridin-2-yl)-1H-1,2,4-triazol-1-yl]-2-methylpropan-1-one | 321 | | d |
| 346 | 1-[5-(benzylamino)-3-(pyridin-2-yl)-1H-1,2,4-triazol-1-yl]-3-methylbutan-1-one | 335 | | d |
| 347 | 1-[5-(benzylamino)-3-(pyridin-2-yl)-1H-1,2,4-triazol-1-yl]butan-1-one | 321 | | d |
| 348 | 1-[5-(benzylamino)-3-(pyridin-2-yl)-1H-1,2,4-triazol-1-yl]propan-1-one | 307 | | d |
| 349 | 1-[5-(benzylamino)-3-(pyridin-3-yl)-1H-1,2,4-triazol-1-yl]propan-1-one | 307 | | d |
| 350 | 1-[5-(benzylamino)-3-(pyridin-4-yl)-1H-1,2,4-triazol-1-yl]-2,2-dimethylpropan-1-one | 335 | | e |
| 351 | 1-[5-(benzylamino)-3-(pyridin-4-yl)-1H-1,2,4-triazol-1-yl]-2-methylpropan-1-one | 321 | | c |
| 352 | 1-[5-(benzylamino)-3-(pyridin-4-yl)-1H-1,2,4-triazol-1-yl]-2-phenylethan-1-one | 369 | | e |
| 353 | 1-[5-(benzylamino)-3-(pyridin-4-yl)-1H-1,2,4-triazol-1-yl]-3-methylbutan-1-one | 335 | | e |
| 354 | 1-[5-(benzylamino)-3-(pyridin-4-yl)-1H-1,2,4-triazol-1-yl]-3-phenylpropan-1-one | 383 | | e |
| 355 | 1-[5-(benzylamino)-3-(pyridin-4-yl)-1H-1,2,4-triazol-1-yl]butan-1-one | 321 | | e |
| 356 | 1-[5-(benzylamino)-3-(pyridin-4-yl)-1H-1,2,4-triazol-1-yl]propan-1-one | 307 | | e |
| 357 | 1-[5-(benzylamino)-3-(thiophen-2-yl)-1H-1,2,4-triazol-1-yl]-2,2-dimethylpropan-1-one | 340 | | e |
| 358 | 1-benzoyl-N-[(4-fluorophenyl)methyl]-3-(pyridin-2-yl)-1H-1,2,4-triazol-5-amine | 373 | d | b |
| 359 | 1-benzoyl-N-[(4-fluorophenyl)methyl]-3-(pyridin-3-yl)-1H-1,2,4-triazol-5-amine | 373 | | b |

TABLE C-continued

| Cmpd No. | IUPAC name | MW | KLK1 Activity | KLKB1 Activity |
|---|---|---|---|---|
| 360 | 1-benzoyl-N-[(4-methoxyphenyl)methyl]-3-(pyridin-2-yl)-1H-1,2,4-triazol-5-amine | 385 | c | c |
| 361 | 1-benzoyl-N-[(4-methoxyphenyl)methyl]-3-(pyridin-3-yl)-1H-1,2,4-triazol-5-amine | 385 | c | c |
| 362 | 1-benzoyl-N-benzyl-3-(pyridin-2-yl)-1H-1,2,4-triazol-5-amine | 355 | d | b |
| 363 | 1-benzoyl-N-benzyl-3-(pyridin-4-yl)-1H-1,2,4-triazol-5-amine | 355 |   | b |
| 364 | 3-(5-[(5-chlorothiophen-2-yl)methyl]amino-1-[(2-methoxyphenyl)carbonyl]-1H-1,2,4-triazol-3-yl)-N,N-dimethylazetidine-1-sulfonamide | 511 |   | a |
| 365 | 3-(pyridin-3-yl)-1-[(pyridin-3-yl)carbonyl]-N-(thiophen-2-ylmethyl)-1H-1,2,4-triazol-5-amine | 362 |   | c |
| 366 | 3-1-[(2-methoxyphenyl)carbonyl]-5-(methylsulfanyl)-1H-1,2,4-triazol-3-ylpyridine | 326 | c | c |
| 367 | N-[(4-fluorophenyl)methyl]-1-[(2-methoxyphenyl)carbonyl]-3-(pyridin-2-yl)-1H-1,2,4-triazol-5-amine | 403 |   | c |
| 368 | N-[(4-fluorophenyl)methyl]-1-[(2-methoxyphenyl)carbonyl]-3-(pyridin-3-yl)-1H-1,2,4-triazol-5-amine | 403 |   | c |
| 369 | N-[(4-fluorophenyl)methyl]-1-[(furan-2-yl)carbonyl]-3-(pyridin-2-yl)-1H-1,2,4-triazol-5-amine | 363 |   | c |
| 370 | N-[(4-fluorophenyl)methyl]-1-[(furan-2-yl)carbonyl]-3-(pyridin-3-yl)-1H-1,2,4-triazol-5-amine | 363 |   | c |
| 371 | N-[(4-fluorophenyl)methyl]-1-[(furan-3-yl)carbonyl]-3-(pyridin-2-yl)-1H-1,2,4-triazol-5-amine | 363 |   | c |
| 372 | N-[(4-fluorophenyl)methyl]-1-[(furan-3-yl)carbonyl]-3-(pyridin-3-yl)-1H-1,2,4-triazol-5-amine | 363 |   | c |
| 373 | N-[(4-fluorophenyl)methyl]-1-[(furan-3-yl)carbonyl]-3-(pyridin-4-yl)-1H-1,2,4-triazol-5-amine | 363 |   | e |
| 374 | N-[(4-fluorophenyl)methyl]-1-propyl-3-(pyridin-2-yl)-1H-1,2,4-triazol-5-amine | 311 |   | e |
| 375 | N-[(4-fluorophenyl)methyl]-3-(pyridin-2-yl)-1-[(thiophen-3-yl)carbonyl]-1H-1,2,4-triazol-5-amine | 379 |   | b |
| 376 | N-[(4-fluorophenyl)methyl]-3-(pyridin-3-yl)-1-[(thiophen-2-yl)carbonyl]-1H-1,2,4-triazol-5-amine | 379 |   | c |
| 377 | N-[(4-fluorophenyl)methyl]-3-(pyridin-3-yl)-1-[(thiophen-3-yl)carbonyl]-1H-1,2,4-triazol-5-amine | 379 |   | b |
| 378 | N-[(4-fluorophenyl)methyl]-3-(pyridin-4-yl)-1-[(thiophen-2-yl)carbonyl]-1H-1,2,4-triazol-5-amine | 379 |   | e |
| 379 | N-[(4-methoxyphenyl)methyl]-3-(pyridin-2-yl)-1-[(thiophen-2-yl)carbonyl]-1H-1,2,4-triazol-5-amine | 391 |   | e |
| 380 | N-[(4-methoxyphenyl)methyl]-3-(pyridin-2-yl)-1-[(thiophen-3-yl)carbonyl]-1H-1,2,4-triazol-5-amine | 391 |   | c |
| 381 | N-[(4-methoxyphenyl)methyl]-3-(pyridin-3-yl)-1-[(thiophen-2-yl)carbonyl]-1H-1,2,4-triazol-5-amine | 391 |   | e |
| 382 | N-[(4-methoxyphenyl)methyl]-3-(pyridin-3-yl)-1-[(thiophen-3-yl)carbonyl]-1H-1,2,4-triazol-5-amine | 391 |   | c |
| 383 | N-[(5-chlorofuran-2-yl)methyl]-1-[(2-methoxyphenyl)carbonyl]-3-phenyl-1H-1,2,4-triazol-5-amine | 409 |   | e |
| 384 | N-[(5-chlorothiophen-2-yl)methyl]-1-[(2,4-dimethoxyphenyl)carbonyl]-3-(oxan-4-yl)-1H-1,2,4-triazol-5-amine | 463 | d | b |
| 385 | N-[(5-chlorothiophen-2-yl)methyl]-1-[(2-methoxyphenyl)carbonyl]-3-(oxan-4-yl)-1H-1,2,4-triazol-5-amine | 433 |   | b |
| 386 | N-[(5-chlorothiophen-2-yl)methyl]-1-[(2-methoxyphenyl)carbonyl]-3-(oxolan-2-yl)-1H-1,2,4-triazol-5-amine | 419 |   | b |
| 387 | N-[(5-chlorothiophen-2-yl)methyl]-1-[(2-methoxyphenyl)carbonyl]-3-(piperidin-4-yl)-1H-1,2,4-triazol-5-amine | 432 | d | a |
| 388 | N-[(5-chlorothiophen-2-yl)methyl]-1-[(2-methoxyphenyl)carbonyl]-3-[1-(pyrrolidine-1-sulfonyl)azetidin-3-yl]-1H-1,2,4-triazol-5-amine | 537 |   | a |
| 389 | N-[(5-chlorothiophen-2-yl)methyl]-1-[(2-methoxyphenyl)carbonyl]-3-[4-(morpholin-4-yl)phenyl]-1H-1,2,4-triazol-5-amine | 510 |   | c |
| 390 | N-[(5-chlorothiophen-2-yl)methyl]-1-[(2-methoxyphenyl)carbonyl]-3-phenyl-1H-1,2,4-triazol-5-amine | 425 |   | b |
| 391 | N-[(5-chlorothiophen-2-yl)methyl]-1-[(2-methylphenyl)carbonyl]-3-(pyridin-2-yl)-1H-1,2,4-triazol-5-amine | 410 | d | b |

TABLE C-continued

| Cmpd No. | IUPAC name | MW | KLK1 Activity | KLKB1 Activity |
|---|---|---|---|---|
| 392 | N-[(5-chlorothiophen-2-yl)methyl]-1-[(furan-3-yl)carbonyl]-3-(oxolan-2-yl)-1H-1,2,4-triazol-5-amine | 379 | | b |
| 393 | N-[(5-chlorothiophen-2-yl)methyl]-3-[4-(dimethylamino)phenyl]-1-[(2-methoxyphenyl)carbonyl]-1H-1,2,4-triazol-5-amine | 468 | d | b |
| 394 | N-benzyl-1-[(2,6-difluorophenyl)carbonyl]-3-(pyridin-2-yl)-1H-1,2,4-triazol-5-amine | 391 | | e |
| 395 | N-benzyl-1-[(2-chlorophenyl)carbonyl]-3-(pyridin-2-yl)-1H-1,2,4-triazol-5-amine | 390 | | b |
| 396 | N-benzyl-1-[(2-chlorophenyl)carbonyl]-3-(thiophen-2-yl)-1H-1,2,4-triazol-5-amine | 395 | | b |
| 397 | N-benzyl-1-[(2-methoxyphenyl)carbonyl]-3-(pyridin-2-yl)-1H-1,2,4-triazol-5-amine | 385 | | c |
| 398 | N-benzyl-1-[(2-methoxyphenyl)carbonyl]-3-(thiophen-2-yl)-1H-1,2,4-triazol-5-amine | 390 | | c |
| 399 | N-benzyl-1-[(4-chlorophenyl)carbonyl]-3-(pyridin-2-yl)-1H-1,2,4-triazol-5-amine | 390 | | b |
| 400 | N-benzyl-1-[(furan-2-yl)carbonyl]-3-(pyridin-4-yl)-1H-1,2,4-triazol-5-amine | 3-(5 | | c |
| 401 | N-benzyl-1-[(furan-3-yl)carbonyl]-3-(pyridin-2-yl)-1H-1,2,4-triazol-5-amine | 3-(5 | | e |
| 402 | N-benzyl-1-[(furan-3-yl)carbonyl]-3-(pyridin-4-yl)-1H-1,2,4-triazol-5-amine | 3-(5 | | d |
| 403 | N-benzyl-3-(furan-2-yl)-1-[(2-methoxyphenyl)carbonyl]-1H-1,2,4-triazol-5-amine | 374 | | c |
| 404 | N-benzyl-3-(pyridin-2-yl)-1-[(thiophen-2-yl)carbonyl]-1H-1,2,4-triazol-5-amine | 361 | | c |
| 405 | N-benzyl-3-(pyridin-2-yl)-1-[(thiophen-3-yl)carbonyl]-1H-1,2,4-triazol-5-amine | 361 | | d |
| 406 | N-benzyl-3-(pyridin-4-yl)-1-[(thiophen-2-yl)carbonyl]-1H-1,2,4-triazol-5-amine | 361 | | e |
| 407 | N-benzyl-3-(pyridin-4-yl)-1-[(thiophen-3-yl)carbonyl]-1H-1,2,4-triazol-5-amine | 361 | e | b |
| 408 | methyl 5-[(4-methylbenzene)amido]-1H-1,2,4-triazole-3-carboxylate | 260 | | e |
| 409 | phenyl 5-[(4-fluorophenyl)methyl]amino-3-(pyridin-3-yl)-1H-1,2,4-triazole-1-carboxylate | 389 | | e |
| 410 | propan-2-yl 5-[(4-fluorophenyl)methyl]amino-3-(pyridin-3-yl)-1H-1,2,4-triazole-1-carboxylate | 355 | | e |
| 411 | tert-butyl 3-(5-[(5-chlorothiophen-2-yl)methyl]amino-1-[(2-methoxyphenyl)carbonyl]-1H-1,2,4-triazol-3-yl)azetidine-1-carboxylate | 504 | | b |
| 412 | tert-butyl 4-(5-[(5-chlorothiophen-2-yl)methyl]amino-1-[(2-methoxyphenyl)carbonyl]-1H-1,2,4-triazol-3-yl)piperidine-1-carboxylate | 532 | | b |
| 413 | tert-butyl 5-[(4-fluorophenyl)methyl]amino-3-(pyridin-3-yl)-1H-1,2,4-triazole-1-carboxylate | 369 | | e |

In some embodiments, there is provided a compound as expressly set forth in Table D following.

TABLE D

| Cmpd No. | IUPAC name | MW | KLKB1 Activity |
|---|---|---|---|
| 414 | (3R)-N-[(3-chloro-1H-indol-5-yl)methyl]-1-[(4-chlorophenyl)methyl]-5-oxopyrrolidine-3-carboxamide | 416 | e |
| 415 | (3S)-1-benzyl-N-[(3-chloro-1H-indol-5-yl)methyl]-5-oxopyrrolidine-3-carboxamide | 382 | e |
| 416 | (3S)-N-[(3-chloro-1-methyl-1H-indol-5-yl)methyl]-1-[(4-chlorophenyl)methyl]-5-oxopyrrolidine-3-carboxamide | 430 | d |
| 417 | (3S)-N-[(3-chloro-1H-indol-5-yl)methyl]-1-[(2-chlorophenyl)methyl]-5-oxopyrrolidine-3-carboxamide | 416 | d |
| 418 | (3S)-N-[(3-chloro-1H-indol-5-yl)methyl]-1-[(3-chlorophenyl)methyl]-5-oxopyrrolidine-3-carboxamide | 416 | e |
| 419 | 2-N-[(2R)-5-amino-1,2,3,4-tetrahydronaphthalen-2-yl]-4-N-(2-fluorophenyl)-4-N,6-dimethylpyrimidine-2,4-diamine | 378 | e |
| 420 | 2-N-[(2R)-5-amino-1,2,3,4-tetrahydronaphthalen-2-yl]-4-N-(3-fluorophenyl)-4-N,6-dimethylpyrimidine-2,4-diamine | 378 | e |

TABLE D-continued

| Cmpd No. | IUPAC name | MW | KLKB1 Activity |
|---|---|---|---|
| 421 | 2-N-[(2R)-5-amino-1,2,3,4-tetrahydronaphthalen-2-yl]-4-N-(4-fluorophenyl)-4-N,6-dimethylpyrimidine-2,4-diamine | 378 | e |
| 422 | 2-N-[(2S)-5-amino-1,2,3,4-tetrahydronaphthalen-2-yl]-4-N,6-dimethyl-4-N-phenylpyrimidine-2,4-diamine | 360 | e |
| 423 | 2-N-[(2S)-5-amino-1,2,3,4-tetrahydronaphthalen-2-yl]-4-N-(2-chlorophenyl)-4-N,6-dimethylpyrimidine-2,4-diamine | 394 | d |
| 424 | 2-N-[(2S)-5-amino-1,2,3,4-tetrahydronaphthalen-2-yl]-4-N-(3-chlorophenyl)-4-N,6-dimethylpyrimidine-2,4-diamine | 394 | e |
| 425 | 2-N-[(2S)-5-amino-1,2,3,4-tetrahydronaphthalen-2-yl]-4-N-(4-chlorophenyl)-4-N,6-dimethylpyrimidine-2,4-diamine | 394 | e |

Compounds disclosed herein also include racemic mixtures, stereoisomers and mixtures of the compounds, including isotopically-labeled and radio-labeled compounds. See e.g., Goding, 1986, MONOCLONAL ANTIBODIES PRINCIPLES AND PRACTICE; Academic Press, p. 104. Such isomers can be isolated by standard resolution techniques, including e.g., fractional crystallization, chiral chromatography, and the like. See e.g., Eliel, E. L. & Wilen S. H., 1993, STEREOCHEMISTRY IN ORGANIC COMPOUNDS; John Wiley & Sons, New York.

In some embodiments, compounds disclosed herein have asymmetric centers and can occur as racemates, racemic mixtures, and as individual enantiomers or diastereoisomers, with all isomeric forms as well as mixtures thereof being contemplated for use in the compounds and methods described herein. The compounds contemplated for use in the compounds and methods described herein do not include those that are known in the art to be too unstable to synthesize and/or isolate.

The compounds disclosed herein can also contain unnatural proportions of atomic isotopes at one or more of the atoms that constitute such compounds. For example, the compounds can be radiolabeled with radioactive isotopes, such as for example tritium ($^3$H), iodine-125 ($^{125}$I), or carbon-14 ($^{14}$C). All isotopic variations of the compounds disclosed herein, whether radioactive or not, are encompassed within the contemplated scope.

In some embodiments, metabolites of the compounds disclosed herein are useful for the methods disclosed herein.

In some embodiments, compounds contemplated herein are provided in the form of a prodrug. The term "prodrug" refers to a compound that can be converted into a compound (e.g., a biologically active compound) described herein in vivo. Prodrugs can be useful for a variety of reason known in the art, including e.g., ease of administration due e.g., to enhanced bioavailability in oral administration, and the like. The prodrug can also have improved solubility in pharmaceutical compositions over the biologically active compounds. An example, without limitation, of a prodrug is a compound which is administered as an ester (i.e., the "prodrug") to facilitate transmittal across a cell membrane where water solubility is detrimental to mobility but which then is metabolically hydrolyzed to the carboxylic acid, the active entity, once inside the cell where water solubility is beneficial. Conventional procedures for the selection and preparation of suitable prodrug derivatives are described, for example, in DESIGN OF PRODRUGS, (ed. H. Bundgaard, Elsevier, 1985), which is hereby incorporated herein by reference for the limited purpose describing procedures and preparation of suitable prodrug derivatives.

Accordingly, in some embodiments, compounds contemplated herein are provided in the form of a prodrug ester. The term "prodrug ester" refers to derivatives of the compounds disclosed herein formed by the addition of any of a variety of ester-forming groups, e.g., groups known in the art, that are hydrolyzed under physiological conditions. Examples of prodrug ester groups include pivaloyloxymethyl, acetoxymethyl, phthalidyl, indanyl and methoxymethyl, as well as other such groups known in the art, including a (5-R-2-oxo-1,3-dioxolen-4-yl)methyl group. Other examples of prodrug ester groups can be found in, for example, T. Higuchi and V. Stella, in "Pro-drugs as Novel Delivery Systems", Vol. 14, A.C.S. Symposium Series, American Chemical Society (1975); and BIOREVERSIBLE CARRIERS IN DRUG DESIGN: THEORY AND APPLICATION, edited by E. B. Roche, Pergamon Press: New York, 14-21 (1987) (providing examples of esters useful as prodrugs for compounds containing carboxyl groups). Each of the above-mentioned references is herein incorporated by reference for the limited purpose of disclosing ester-forming groups that can form prodrug esters.

In some embodiments, prodrugs can be slowly converted to the compounds described herein useful for the methods described herein when placed in a transdermal patch reservoir with a suitable enzyme or chemical reagent.

Certain compounds disclosed herein can exist in unsolvated forms as well as solvated forms, including hydrated forms. In general, the solvated forms are equivalent to unsolvated forms and are encompassed within the scope of contemplated compounds. Certain compounds of the present invention can exist in multiple crystalline or amorphous forms. In general, all physical forms are equivalent for the compounds and methods contemplated herein and are intended to be within the scope disclosed herein.

III. Biological Activities

In some embodiments, compounds described herein exhibit inhibitory activity against thrombin with activities ≥1 μM, e.g., about 1, 2, 3, 4, 5, 6, 7, 8, 9, 10, 11, 12, 13, 14, 16, 18, 20, 22, 24, 26, 28, 30, 32, 34, 36, 38, 40, 45, 50, 55, 60, 65, 70, 75, 80, 85, 90, 95, 100 μM, or even greater. In some embodiments, the compounds exhibit inhibitory activity against thrombin with activities between 0.1 μM and 1 μM, e.g., about 0.1, 0.2, 0.3, 0.4, 0.5, 0.6, 0.7, 0.8, 0.9 or 1.0 μM. In some embodiments, compounds described herein exhibit inhibitory activity against thrombin with activities ≤0.1 μM, e.g., about 1, 2, 5, 10, 15, 20, 30, 40, 50, 60, 70, 80, 90, or 100 nM. Ranges of values using a combination of any of the values recited herein as upper and/or lower limits are also contemplated, for example, but not limited to, 1-10 nM, 10-100 nM, 0.1-1 μM, 1-10 μM, 10-100 μM, 100-200

μM, 200-500 μM, or even 500-1000 μM. In some embodiments, the inhibitory activity is in the range of about 1-10 nM, 10-100 nM, 0.1-1 μM, 1-10 μM, 10-100 μM, 100-200 μM, 200-500 μM, or even 500-1000 μM. It is understood that for purposes of quantification, the terms "activity," "inhibitory activity," "biological activity," "thrombin activity and the like in the context of an inhibitory compound disclosed herein can be quantified in a variety of ways known in the art. Unless indicated otherwise, as used herein such terms refer to $IC_{50}$ in the customary sense (i.e., concentration to achieve half-maximal inhibition).

Inhibitory activity against thrombin in turn inhibits the blood coagulation process. Accordingly, compounds disclosed herein are indicated in the treatment or management of thrombotic disorders. In some embodiments, a dose or a therapeutically effective dose of a compound disclosed herein will be that which is sufficient to achieve a plasma concentration of the compound or its active metabolite(s) within a range set forth herein, e.g., about 1-10 nM, 10-100 nM, 0.1-1 μM, 1-10 μM, 10-100 μM, 100-200 μM, 200-500 μM, or even 500-1000 μM, preferably about 1-10 nM, 10-100 nM, or 0.1-1 μM. Without wishing to be bound by any theory, it is believe that such compounds are indicated in the treatment or management of thrombotic disorders.

In some embodiments, compounds described herein exhibit inhibitory activity against KLK1 and KLKB1 with activities between 1 μM and 10 μM, e.g., about 1, 2, 3, 4, 5, 6, 7, 8, 9 or 10 μM. In some embodiments, compounds described herein exhibit inhibitory activity against KLK1 and KLKB1 with activities ≥10 μM, e.g., about 10, 20, 50, 100, 150, 200, 300, 400, 500, 600, 700, 800, 900, 1000 μM or even greater. In some embodiments, compounds described herein exhibit inhibitory activity against KLK1 and KLKB1 with activities ≤1 μM, e.g., about 900, 800, 700, 600, 500, 400, 300, 200, 100, 50 nM or even lower. Ranges of values using a combination of any of the values recited herein as upper and/or lower limits are also contemplated, for example, but not limited to, 1-10 nM, 10-100 nM, 0.1-1 μM, 1-10 μM, 10-100 μM, 100-200 μM, 200-500 μM, or even 500-1000 μM. In some embodiments, the inhibitory activity is in the range of about 1-10 nM, 10-100 nM, 0.1-1 μM, 1-10 μM, 10-100 μM, 100-200 μM, 200-500 μM, or even 500-1000 μM. It is understood that for purposes of quantification, the terms "activity," "inhibitory activity," "biological activity," "KLK1 activity," "KLKB1 activity" and the like in the context of an inhibitory compound disclosed herein can be quantified in a variety of ways known in the art. Unless indicated otherwise, as used herein such terms refer to $IC_{50}$ in the customary sense (i.e., concentration to achieve half-maximal inhibition).

Inhibitory activity against KLKB1 has an effect on the coagulation cascade and the inflammatory response. Thus, it has been proposed that KLKB1 inhibitors can be useful in the treatment of thrombotic and fibrinolytic diseases and disease conditions.

Accordingly, compounds disclosed herein are indicated in the treatment or management of a variety of diseases or disorders. In some embodiments, a dose or a therapeutically effective dose of a compound disclosed herein will be that which is sufficient to achieve a plasma concentration of the compound or its active metabolite(s) within a range set forth herein, e.g., about 1-10 nM, 10-100 nM, 0.1-1 μM, 1-10 μM, 10-100 μM, 100-200 μM, 200-500 μM, or even 500-1000 μM, preferably about 1-10 nM, 10-100 nM, or 0.1-1 μM. Without wishing to be bound by any theory, it is believe that such compounds are indicated in the treatment or management of diseases associated with thrombin or kallikrein.

IV. Methods of Treating and Preventing Disease

Kallikrein-related diseases or disorders are biological conditions associated with or moderated by kallikrein. They include, but are not limited by, those conditions associated with biological pathways that are moderated by tissue and plasma kallikrein. An example of such a pathway is the kallikrein-kinin system (Moreau, M. E. 2005, *Journal of Pharmacological Sciences,* 99, 6). Kallikrein-related diseases or disorders include, but are not limited to, fibrosis, inflammation, thrombosis, hereditary angioedema, skin disorders, cancer, and ophthalmic diseases. Ophthalmic diseases include, but are not limited to, diabetic macular edema, diabetic retinopathy, and age-related macular degeneration.

Diabetic Macular Edema. In rodent models, it has been shown that activation of KLKB1 in the eye increases retinal vascular permeability; whereas inhibition of the kallikrein-kinin system reduces retinal leakage induced by diabetes and hypertension. These findings suggest that intraocular activation of the KLKB1 pathway can contribute to excessive retinal vascular permeability that can lead to diabetic macular edema. Thus, evidence suggests that KLKB1 inhibitors can provide a new therapeutic opportunity to reduce retinal vascular permeability (Feener, E. P. 2010, *Curr Diab Rep* 10, 270).

Hereditary Angioedema. Ecallantide (Kalbitor) is a 60-amino acid recombinant protein that acts as a potent reversible inhibitor of KLKB1 (Schneider L, et al. 2007, *J Allergy Clin Immunol,* 120, 416) and has been approved by the FDA for the treatment of acute attacks of hereditary angioedema (HAE). Thus plasma kallikrein inhibition can be a useful treatment for HAE, and there is strong interest in the development of plasma kallikrein inhibitors as a therapy for HAE.

Skin. Overexpression of various KLKs in the skin has led to the recognition that certain kallikrein inhibitors can be useful for certain dermatological conditions, including atopic dermatitis, psoriasis and rare skin diseases such as Netherton Syndrome (Freitas et al. *Bioorganic & Medicinal Chemistry Letters* 2012, 22, 6072-6075).

Thrombosis. Thrombotic diseases are the primary indications for thrombin inhibition, because of thrombin's location in the coagulation cascade and, in turn, the importance of the coagulation cascade in the progression of blood clotting processes. However, without wishing to be bound by any theory, it is believed the coagulation cascade in general, and thrombin in particular, is important in a variety other disease states.

It has been discovered that compounds described herein, e.g., multisubstituted aromatic compounds, exhibit inhibitory action against thrombin (activated blood-coagulation factor II; EC 3.4.21.5). This, in turn inhibits the blood coagulation process.

This inhibitory action is useful in the treatment of a variety of thrombotic disorders, such as, but not limited to, acute vascular diseases such as acute coronary syndromes; venous-, arterial- and cardiogenic thromboembolisms; the prevention of other states such as disseminated intravascular coagulation, or other conditions that involve the presence or the potential formation of a blood clot thrombus. Other indications for methods described herein include the following.

Cancer. Tissue kallikreins (KLKs) are subdivided into various types, and have been extensively investigated in cancer and inflammation biology. Various kallikrein KLKs have been found to be up- or down-regulated in various cancer types, such as cervical-, testicular-, and non-small-cell lung adenocarcinoma (Caliendo et al. *J. Med. Chem.,*

2012, 55, 6669). It has been proposed that KLK1 inhibitors will be useful in certain cancers.

It has long been recognized that cancer progression is accompanied by venous thrombosis, but it has not been understood how each disease is related. From several clinical trials studying the treatment of VTE, meta-analyses have shown that low molecular weight heparins (LMWHs) improve overall survival in subgroups of cancer patients. See e.g., Zacharski, L. R. & Lee, A. Y., 2008, *Expert Opin Investig Drugs*, 17:1029-1037; Falanga, A. & Piccioli, A., 2005, *Current Opinion in Pulmonary Medicine*, 11:403-407; Smorenburg, S. M., et al., 1999, *Thromb Haemost*, 82:1600-1604; Hettiarachchi, R. J., et al., 1999, *Thromb Haemost*, 82:947-952. This finding was substantiated in later clinical trials that measured specifically the survival of cancer patients. See e.g., Lee, A. Y. et al., 2005, *J Clin Oncol*, 23:2123-2129; Klerk, C. P. et al., *J Clin Oncol* 2005, 23:2130-2135; Kakkar, A. K., et al., 2004, *J Clin Oncol*, 22:1944-1948; Altinbas, M., et al., 2004, J *Thromb Haemost*, 2:1266-1271.

More recently, researchers have focused on the specific anticancer effect of DTIs. For example, it was shown that heparin significantly prolonged the survival of patients with limited small cell lung cancer. See e.g., Akl, E. A., et al., 2008, *J Exp Clin Cancer Res*, 27:4. Other investigators found that systemic use of argatroban reduced tumor mass and prolonged survival time in rat glioma models leading to the conclusion that argatroban should be considered as a novel therapeutic for glioma, a notoriously difficult to treat cancer type. See e.g., Hua, Y., et al., 2005, *Acta Neurochir*, Suppl 2005, 95:403-406; Hua, Y., et al., 2005, *J Thromb Haemost*, 3:1917-1923. Very recently, it was demonstrated that dabigatran etexilate, a DTI recently FDA-approved (see e.g., Hughes, B., 2010, *Nat Rev Drug Discov*, 9:903-906) for DVT indications, inhibited both the invasion and metastasis of malignant breast tumors. See e.g., DeFeo, K. et al., 2010, *Thrombosis Research*, 125 (Supplement 2): S188-S188; Defeo, K., et al., 2010, *Cancer Biol Ther*, 10:1001-1008. Thus, dabigatran etexilate treatment led to a 50% reduction in tumor volume at 4 weeks with no weight loss in treated mice. Dabigatran etexilate also reduced tumor cells in the blood and liver micrometastases by 50-60%. These investigators concluded that dabigatran etexilate can be beneficial in not only preventing thrombotic events in cancer patients, but also as adjunct therapy to treat malignant tumors.

Further, hirudin and the LMWH nadroparin dramatically reduced the number of lung metastases when administered prior to cancer cell inoculation. See e.g., Hu, L., et al., 2004, *Blood*, 104:2746-51.

The de novo thrombin inhibitor d-Arg-Oic-Pro-d-Ala-Phe (p-Me) has been found to block thrombin-stimulated invasion of prostate cancer cell line PC-3 in a concentration dependent manner. See e.g., Nieman, M. T., et al., 2008, *J Thromb Haemost*, 6:837-845. A reduced rate of tumor growth was observed in mice dosed with the pentapeptide through their drinking water. The mice also showed reduced fold rate in tumor size and reduced overall tumor weight compared to untreated mice. Microscopic examination of treated tumors showed reduced number of large blood vessels thus concluding that the pentapeptide interfered with tumor angiogenesis. Nieman, M. T., et al., *Thromb Haemost*, 104:1044-8.

In view of these and related studies, it is suggested that anticoagulants affect tumor metastasis; that is, angiogenesis, cancer cell adhesion, migration and invasion processes. See e.g., Van Noorden, C. J., et al., 2010, *Thromb Res*, 125 Suppl 2:S77-79.

Fibrosis. Kallikreins are a subgroup of serine proteases, divided into plasma kallikrein (KLKB1) and tissue kallikreins. KLKB1 liberates kinins (bradykinin and kallidin) from the kininogens, peptides responsible for the regulation of blood pressure and activation of inflammation. In the Contact Activation Pathway of the coagulation cascade, KLKB1 assists in the conversion of factor XII to factor XIIa (Keel, M.; Trentz, O. *Injury* 2005, 36, 691-709). Factor XIIa converts FXI into FXIa, which in turn activates FIX, which with its co-factor FVIIIa forms the tenase complex, which finally activates FX to FXa. In the fibrinolysis part of the coagulation cascade, KLKB1 serves to convert plasminogen to plasmin. Thus, it has been proposed that KLKB1 inhibitors can be useful in the treatment of thrombotic and fibrinolytic diseases and disease conditions (U.S. Pat. No. 7,625,944; Bird et al. *Thrombosis and Hemostasis* 2012, 107, 1141).

Several studies have shown the utility of anticoagulant therapy in fibrotic disorders. For example, in a rat model of $CCl_4$-induced chronic liver injury, the DTI SSR182289 decreased liver fibrogenesis significantly after 7 weeks of administration. Similar observations were made in other studies using the LMWHs nadroparin, tinzaparin, enoxaparin, and dalteparin sodium. See e.g., Duplantier, J. G., et al., 2004, Gut, 53:1682-1687; Abdel-Salam, 0. M., et al., 2005, *Pharmacol Res*, 51:59-67; Assy, N., et al., 2007, *Dig Dis Sci*, 52:1187-1193; Abe, W., et al., 2007, *J Hepatol*, 46:286-294. Thus a thrombin inhibitor as an anticoagulant can be useful in the treatment of fibrinolytic diseases.

In another example, the DTI melagatran greatly reduced ischemia reperfusion injury in a kidney transplant model in the large white pig. This led to a drastically improved kidney graft survival at 3 months. See e.g., Favreau, F., et al., 2010, *Am J Transplant*, 10:30-39.

Recent studies have shown that in a bleomycin-induced mouse model of pulmonary fibrosis, dabigatran etexilate treatment reduced important profibrotic events in lung fibroblasts, including the production of collagen and connective tissue growth factor. See e.g., Silver, R. M., et al., 2010, *Am. J. Respir. Crit. Care Med.*, 181:A6780; Bogatkevich, G. S., et al., 2009, *Arthritis Rheum*, 60:3455-3464.

The above experimental evidence points to a close relationship between thrombin and fibrosis and suggests novel therapeutic opportunities for fibrosis using thrombin inhibitors. See e.g., Calvaruso, V., et al., 2008, Gut, 57:1722-1727; Chambers, R. C., 2008, *Br J Pharmacol*, 153 Suppl 1:S367-378; Chambers, R. C. & Laurent, G. J., 2002, *Biochem Soc Trans*, 30:194-200; Howell, D. C., et al., 2001, *Am J Pathol*, 159:1383-1395.

Inflammation. Kallikrein has long been implicated in inflammation (Clements, J. A. *The Molecular Biology of the Kallikreins and Their Roles in Inflammation*, Academic Press: San Diego, Calif., 1997; Vol. 5). There is experimental evidence that KLKB1 is associated with sepsis and inflammatory arthritis (Colman, R. W., 1998, *Clinical Reviews in Allergy and Immunology*, 16: 365). Thus a KLKB1 inhibitor can be useful in the treatment of inflammatory conditions associated with the kallikrein-kinin system, such as systemic inflammatory response syndrome, sepsis, rheumatoid arthritis, and inflammatory bowel disease.

Age-Related Macular Degeneration. KLK1 has been linked to blood vessel growth moderated by the VEGF pathway (Miura S., 2003, *Hypertension*, 41, 1118). Age-related macular degeneration (AMD) is associated with the proliferation of abnormal blood vessels and VEGF expression (Lopez, P. F., 1996, *Investigative Ophthalmology &*

*Visual Science*, 37, 855). Thus, KLK1 inhibitors have been proposed for the treatment of AMD (US Patent #20120264798; Ferrara, N., 2000, *Current Opinion in Biotechnology*, 11, 617).

Alzheimer's Disease. Very recent experiments confirm higher thrombin levels in brain endothelial cells of patients with Alzheimer's disease. While 'normal' thrombin levels are connected to regulatory CNS functions, thrombin accumulation in the brain is toxic. It has also been found that the neural thrombin inhibitor Protease Nexin 1 (PN-1) is significantly reduced in the Alzheimer's disease brain, despite the fact that PN-1 mRNA levels are unchanged. These observations have led some investigators to suggest that reduction of CNS-resident thrombin will prove useful in Alzheimer's Disease (AD) treatment. See e.g., Vaughan, P. J., et al., 1994, *Brain Res*, 668:160-170; Yin, X., et al., 2010, *Am J Pathol*, 176:1600-1606; Akiyama, H., et al., 1992, *Neurosci Lett*, 146:152-154.

Multiple Sclerosis. Investigators found that hirudin treatment in an animal model of Multiple Sclerosis (MS) showed a dramatic improvement in disease severity. See e.g., Han, M. H., et al., 2008, *Nature*, 451:1076-1081. Similar results were obtained following treatment with heparin (a DTI) and dermatan sulfate, another coagulation inhibitor. See e.g., Chelmicka-Szorc, E. & Amason, B. G., 1972, *Arch Neurol*, 27:153-158; Inaba, Y., et al., 1999, *Cell Immunol*, 198:96-102. Other evidence shows that naturally occurring antithrombin III has anti-inflammatory effects in diseases such as endotoxemia and other sepsis-related conditions. See e.g., Wiedermann, C. J. & Romisch, J., 2002, *Acta Med Austriaca*, 29:89-92. Naturally occurring thrombin inhibitors are presumably synthesized in situ and have protective roles in CNS inflammation. Therefore, therapeutic thrombin inhibition has been proposed as a potential MS treatment. See e.g., Luo, W., et al., 2009, In: THROMBIN, Maragoudakis, M. E.; Tsopanoglou, N. E., Eds. Springer New York: 2009; pp 133-159.

Pain. In a rat pain model with partial lesion of the sciatic nerve, intrathecal hirudin prevented the development of neuropathic pain and curbed pain responses for 7 days. The investigators found that following injury, neuropathic pain was mediated by thrombin generation, which in turn activated PAR-1 receptor in the spinal cord. Hirudin inhibited thrombin generation and ultimately led to pain relief. See e.g., Garcia, P. S., et al., 2010, *Thromb Haemost*, 103:1145-1151; Narita, M., et al., 2005, *J Neurosci*, 25:10000-10009. Researchers hypothesize that thrombin and the PARs are involved not just as part of the coagulation cascade, but in inflammation, nociception and neurodevelopment. Development of a DTI to intersect an unexploited pharmacology will lead to pain therapeutics distinct from opioids and NSAIDs, whose shortcomings are well documented. See e.g., Garcia 2010, Id.

Accordingly, in a further aspect, there is provided a method for treating a disease or disorder in a subject in need thereof. The method includes administering a compound of any of Formulae (Ia), (Ib), (IIa), (IIb), (IIc), (III), (IV), (V), (VI) or (VII) as disclosed herein, a compound as set forth in Table A, B, C, or D, pharmaceutically acceptable salt, ester, solvate, or prodrug thereof, or pharmaceutical composition thereof, to a subject in need thereof in an amount effective to treat the disease or disorder. The terms "therapeutically effective amount," "amount effective to treat," "amount effective to prevent" and the like refer to that amount of drug or pharmaceutical agent (e.g., compound or pharmaceutical composition disclosed herein) that will elicit the biological or medical response of a tissue, system, animal, or human that is being sought by a researcher, veterinarian, medical doctor or other clinician.

Compounds useful for methods disclosed herein include the compounds set forth for Formulae (Ia), (Ib), (IIa), (IIb), (IIc), (III), (IV), (V), (VI) or (VII) and for the compounds set forth in Table A, B, C, or D above.

In some embodiments, the diseases or disorders are fibrinolytic diseases. In some embodiments the disease is a fibrotic disorder. In some embodiments, the disease is cancer. In some embodiments, the diseases are inflammatory diseases. In some embodiments the disease is sepsis. In some embodiments the disease is inflammatory arthritis. In some embodiments, the disease is diabetic macular edema. In some embodiments, the disease is hereditary angioedema. In some embodiments, the disease is diabetic retinopathy. In some embodiments, the disease is age-related macular degeneration. In some embodiments, the diseases are various skin diseases which include but are not limited to atopic dermatitis, psoriasis and rare skin diseases such as Netherton Syndrome. In some embodiments, the diseases or disorder is Alzheimer's disease. In some embodiments, the disease is multiple sclerosis. In some embodiments, the disease is pain.

In some embodiments, the disease or disorder is cancer. In some embodiments, the cancer is limited small cell lung cancer. In some embodiments, the cancer is a glioma. In some embodiments, the cancer is malignant breast cancer. In some embodiments, the cancer is a micrometastasis. In some embodiments, the micrometastasis is of the blood or liver. In some embodiments, the cancer is a lung metastasis. In some embodiments, the cancer is prostatic cancer.

In another aspect, there is provided a method for preventing a disease or disorder in a subject. The method includes administering a compound of any of Formulae (Ia), (Ib), (IIa), (IIb), (IIc), (III), (IV), (V), (VI) or (VII) as disclosed herein, compound as set forth in any of Table A, B, C, or D herein, pharmaceutically acceptable salt, ester, solvate, or prodrug thereof, or pharmaceutical composition thereof, to a subject in need thereof in an amount effective to prevent the disease or disorder.

V. Assays

Compounds described herein can be assayed, by a variety of methods known in the art and described herein, for inhibition of biological activity, e.g., protease activity, of a variety of proteins, e.g., thrombin, KLKB1 and KLK1.

The KLKB1 kallikrein activity reported herein (e.g., Tables B, C, and D) was obtained as follows. Human KLKB1 protein was obtained from Enzyme Research Labs. The chromogenic substrate S-2302 was obtained from DiaPharma. KLKB1 was assayed in buffer containing 0.05 M Tris (pH 7.4), 0.01 M NaCl and 0.2% w/v PEG-8000. The final concentration of enzyme used was 3 nM KLKB1. The final concentration of substrate used was 250 µM S-2302 for KLKB1. All assays were performed in 96-well microtiter plates at room temperature (RT). The enzyme and inhibitor were pre-incubated for 10 minutes then substrate was added and read at 405 nm in a SpectraMax Plus Spectrophotometer (Molecular Devices). Inhibitor $IC_{50}$ values were determined by adding test compound as ten point, three-fold serial dilutions in buffer solution, as known in the art. The plate was read at 10 minutes after substrate addition. The $IC_{50}$ was calculated by plotting the percent (%) inhibition against compound concentration and fitting the data to a constrained four parameter sigmoidal curve, as known in the art.

The KLK1 kallikrein activity reported herein (e.g., Tables B and C) was obtained as follows. Recombinant human tissue kallikrein (KLK1) was obtained from R&D Systems.

Pro-Phe-Arg-AMC (1-1295) substrate was obtained from Bachem. KLK1 enzyme is activated by incubating 0.5 mg/ml KLK1 combined with 0.1 µg/ml thermolysin in a buffer of 0.05 M Tres (pH 7.5), 0.15 M NaCl, and 0.01 M CaCl$_2$ for one hour at 37° C. The thermolysin is then deactivated by the addition of equal parts 20 mM 1, 10 phenanthroline solution in water. The activated KLK1 solution is then added to CHES buffer (0.05 M CHES, 0.15 M NaCl, 0.01 M CaCl$_2$, pH 10) for a final concentration of 5 nM along with the test article and incubated for 10 minutes. Substrate is then added at a concentration of 2.75 µM. Substrate activation is read 10 minutes after substrate addition using a Synergy H1 multifunction plate reader (Biotek) programmed with a 360 nm excitation wavelength and a 480 nm emission wavelength Inhibitor response was established by adding test compound as ten point, three-fold serial dilutions, as known in the art. The IC$_{50}$ was calculated by plotting the percent (%) inhibition against compound concentration and fitting the data to a constrained four parameter sigmoidal curve, as known in the art.

The thrombin activity reported herein (e.g., Table A) was obtained as follows. Human thrombin was obtained from Haematologic Technologies Inc. The chromogenic substrate S-2238 was obtained from DiaPharma. Thrombin was assayed in buffer containing 0.05 M Tris (pH 7.4), 0.015 M NaCl and 0.01% PEG-8000. The final concentration of enzyme used was 3 nM thrombin. The final concentration of substrate used was 125 µM S-2238 for thrombin. All assays were performed in 96-well microtiter plates at room temperature (RT). The enzyme and inhibitor were pre-incubated for 10 minutes then substrate was added and read at 405 nm in a SpectraMax Plus Spectrophotometer (Molecular Devices). Inhibitor IC$_{50}$ values were determined by adding test compound as ten point, three-fold serial dilutions in buffer solution, as known in the art. The plate was read at 10 minutes after substrate addition. The IC$_{50}$ was calculated by plotting the percent (%) inhibition against compound concentration and fitting the data to a constrained four parameter sigmoidal curve, as known in the art.

VI. Pharmaceutical Compositions

In another aspect, there is provided a pharmaceutical composition comprising a compound disclosed herein and a pharmaceutically acceptable excipient. The compound is a compound of any of Formulae (Ia), (Ib), (IIa), (IIb), (IIc), (III), (IV), (V), (VI) or (VII) as disclosed herein, a compound as set forth in Table A, B, C, or D herein, or pharmaceutically acceptable salt, ester, solvate, or prodrug thereof. In some embodiments, the compound is set forth in Table A, B, C, or D herein.

The term "pharmaceutically acceptable salts" is meant to include salts of the active compounds that are prepared with relatively nontoxic acids or bases, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds disclosed herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galacturonic acids and the like (see, for example, Berge et al., "Pharmaceutical Salts", *Journal of Pharmaceutical Science*, 1977, 66, 1-19). Certain specific compounds disclosed herein contain both basic and acidic functionalities that allow the compounds to be converted into either base or acid addition salts.

Compounds disclosed herein can exist as salts, such as with pharmaceutically acceptable acids. Accordingly, the compounds contemplated herein include such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts can be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Pharmaceutically acceptable salts of the compounds above, where a basic or acidic group is present in the structure, are also included within the scope of compounds contemplated herein. When an acidic substituent is present, such as —NHSO$_3$H, —COOH and —P(O)(OH)$_2$, there can be formed the ammonium, sodium, potassium, calcium salt, and the like, for use as the dosage form. Basic groups, such as amino or basic heteroaryl radicals, or pyridyl and acidic salts, such as hydrochloride, hydrobromide, acetate, maleate, palmoate, methanesulfonate, p-toluenesulfonate, and the like, can be used as the dosage form.

Also, in the embodiments in which R—COOH is present, pharmaceutically acceptable esters can be employed, e.g., methyl, ethyl, tert-butyl, pivaloyloxymethyl, and the like, and those esters known in the art for modifying solubility or hydrolysis characteristics for use as sustained release or prodrug formulations.

A. Formulations

The compounds disclosed herein can be prepared and administered in a wide variety of ophthalmic, oral, parenteral, and topical dosage forms. The compounds described herein can be administered by eye drop. Also, compounds described herein can be administered by injection (e.g. intravenously, intramuscularly, intravitreally, intracutaneously, subcutaneously, intraduodenally, or intraperitoneally). As such, compounds described herein can also be administered by intravitreal injection. Also, the compounds described herein can be administered by inhalation, for example, intranasally. Additionally, the compounds disclosed herein can be administered transdermally. It is also envisioned that multiple routes of administration (e.g., intramuscular, oral, ocular) can be used to administer the compounds disclosed herein.

In some embodiments, the compounds disclosed herein can be prepared in liquid pharmaceutical compositions for ocular administration. The composition for ocular use can contain one or more agents selected from the group of buffering agents, solubilizing agents, coloring agents, viscosity enhancing agents, and preservation agents in order to produce pharmaceutically elegant and convenient preparations.

In some embodiments, the composition for ocular use can contain preservatives for protection against microbiological contamination, including but not limited to benzalkodium chloride and/or EDTA. Other possible preservatives include but are not limited to benzyl alcohol, methyl parabens, propyl parabens, and chlorobutanol. Preferably, a preservative, or combination of preservatives, will be employed to impart microbiological protection in addition to protection against oxidation of components.

In some embodiments, the compounds disclosed herein can be administered orally as tablets, aqueous or oily suspensions, lozenges, troches, powders, granules, emulsions, capsules, syrups or elixirs. The composition for oral use can contain one or more agents selected from the group of sweetening agents, flavoring agents, coloring agents and preserving agents in order to produce pharmaceutically elegant and palatable preparations. Accordingly, there are also provided pharmaceutical compositions comprising a pharmaceutically acceptable carrier or excipient and one or more compounds disclosed herein.

In some embodiments, tablets contain the acting ingredient in admixture with non-toxic pharmaceutically acceptable excipients that are suitable for the manufacture of tablets. These excipients can be, for example, (1) inert diluents, such as calcium carbonate, lactose, calcium phosphate, carboxymethylcellulose, or sodium phosphate; (2) granulating and disintegrating agents, such as corn starch or alginic acid; (3) binding agents, such as starch, gelatin or *acacia*; and (4) lubricating agents, such as magnesium stearate, stearic acid or talc. These tablets can be uncoated or coated by known techniques to delay disintegration and absorption in the gastrointestinal tract and thereby provide a sustained action over a longer period. For example, a time delay material such as glyceryl monostearate or glyceryl distearate can be employed.

For preparing pharmaceutical compositions from the compounds disclosed herein, pharmaceutically acceptable carriers can be either solid or liquid. Solid form preparations include powders, tablets, pills, capsules, cachets, suppositories, and dispersible granules. A solid carrier can be one or more substance that can also act as diluents, flavoring agents, binders, preservatives, tablet disintegrating agents, or an encapsulating material.

A compound disclosed herein, in the form of a free compound or a pharmaceutically-acceptable pro-drug, metabolite, analogue, derivative, solvate or salt, can be administered, for in vivo application, parenterally by injection or by gradual perfusion over time. Administration can be intravenously, intraperitoneally, intramuscularly, subcutaneously, intracavity, or transdermally. For in vitro studies the compounds can be added or dissolved in an appropriate biologically acceptable buffer and added to a cell or tissue.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds disclosed herein are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds disclosed herein can also be incorporated into liposomes or administered via transdermal pumps or patches. Pharmaceutical admixtures suitable for use in the pharmaceuticals compositions and methods disclosed herein include those described, for example, in PHARMACEUTICAL SCIENCES (17th Ed., Mack Pub. Co., Easton, Pa.) and WO 96/05309, the teachings of both of which are hereby incorporated by reference.

In some embodiments, preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, growth factors and inert gases and the like.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations can contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation can be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds can have limited solubility in water and therefore can require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions can be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions disclosed herein can additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

By the present, there are provided methods for ameliorating wound healing and for mediating tissue repair (including but not limited to treatment of peripheral and coronary vascular disease). According to these methods, a subject having a wound or in need of tissue repair, is treated at the site of the wound or damaged tissue or treated systemically, with a compound disclosed herein in the form of a free compound or a pharmaceutically-acceptable prodrug, metabolite, analogue, derivative, solvate or salt.

Generally, the terms "treating", "treatment" and the like are used herein to mean affecting a subject, tissue or cell to obtain a desired pharmacologic and/or physiologic effect. The effect can be prophylactic in terms of completely or partially preventing a disease or disorder or sign or symptom thereof, and/or can be therapeutic in terms of a partial or complete cure for a disorder and/or adverse effect attributable to it. "Treating" as used herein covers any treatment of, or prevention of a disease or disorder in a vertebrate, a mammal, particularly a human, and includes: (a) preventing the disease or disorder from occurring in a subject that can be predisposed to the disease or disorder, but has not yet been diagnosed as having it; (b) inhibiting the disease or disorder, i.e., arresting its development; or (c) relieving or ameliorating the disease or disorder, i.e., cause regression of the disease or disorder.

There are provided various pharmaceutical compositions useful for ameliorating certain diseases and disorders. The pharmaceutical compositions according to one embodiment are prepared by formulating a compound disclosed herein in the form of a free compound or a pharmaceutically-acceptable pro-drug, metabolite, analogue, derivative, solvate or salt, either alone or together with other pharmaceutical agents, suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers.

Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See e.g., Goodman and Gilman (eds.), 1990, THE PHARMACOLOGICAL BASIS FOR THERAPEUTICS (7th ed.).

The pharmaceutical compositions are preferably prepared and administered in dose units. Solid dose units are tablets, capsules and suppositories. For treatment of a subject, depending on activity of the compound, manner of administration, nature and severity of the disease or disorder, age and body weight of the subject, different daily doses can be used.

Under certain circumstances, however, higher or lower daily doses can be appropriate. The administration of the daily dose can be carried out both by single administration in the form of an individual dose unit or else several smaller dose units and also by multiple administrations of subdivided doses at specific intervals.

The pharmaceutical compositions contemplated herein can be administered locally or systemically in a therapeutically effective dose. Amounts effective for this use will, of course, depend on the severity of the disease or disorder and the weight and general state of the subject. Typically, dosages used in vitro can provide useful guidance in the amounts useful for in situ administration of the pharmaceutical composition, and animal models can be used to determine effective dosages for treatment of particular disorders.

Various considerations are described, e.g., in Langer, 1990, *Science*, 249: 1527; Goodman and Gilman's (eds.), 1990, Id., each of which is herein incorporated by reference and for all purposes. Dosages for parenteral administration of active pharmaceutical agents can be converted into corresponding dosages for oral administration by multiplying parenteral dosages by appropriate conversion factors. As to general applications, the parenteral dosage in mg/mL times 1.8=the corresponding oral dosage in milligrams ("mg"). As to oncology applications, the parenteral dosage in mg/mL times 1.6=the corresponding oral dosage in mg. An average adult weighs about 70 kg. See e.g., Miller-Keane, 1992, ENCYCLOPEDIA & DICTIONARY OF MEDICINE, NURSING & ALLIED HEALTH, 5th Ed., (W. B. Saunders Co.), pp. 1708 and 1651.

The method by which the compound disclosed herein can be administered for oral use would be, for example, in a hard gelatin capsule wherein the active ingredient is mixed with an inert solid diluent, or soft gelatin capsule, wherein the active ingredient is mixed with a co-solvent mixture, such as PEG 400 containing Tween-20. A compound disclosed herein can also be administered in the form of a sterile injectable aqueous or oleaginous solution or suspension. The compound can generally be administered intravenously or as an oral dose of 0.1 µg to 20 mg/kg given, for example, every 3-12 hours.

Formulations for oral use can be in the form of hard gelatin capsules wherein the active ingredient is mixed with an inert solid diluent, for example, calcium carbonate, calcium phosphate or kaolin. They can also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients can be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which can be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions can be in the form of a sterile injectable aqueous or oleagenous suspension. This suspension can be formulated according to known methods using those suitable dispersing or wetting agents and suspending agents that have been mentioned above. The sterile injectable preparation can also a sterile injectable solution or suspension in a non-toxic parenterally-acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

A compound disclosed herein can also be administered in the form of ophthalmic compositions applied topically to the eye, preferably in the form of eye drops. A compound disclosed herein can also be administered in the form of intravitreal injection.

A compound disclosed herein can also be administered in the form of suppositories for rectal administration of the drug. These compositions can be prepared by mixing the drug with a suitable non-irritating excipient that is solid at ordinary temperature but liquid at the rectal temperature and will therefore melt in the rectum to release the drug. Such materials include cocoa butter and polyethylene glycols.

The compounds disclosed herein as used in the methods disclosed herein can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

For topical use, creams, ointments, jellies, solutions or suspensions, etc., containing the compounds disclosed herein, are employed.

In addition, some of the compounds disclosed herein can form solvates with water or common organic solvents. Such solvates are encompassed within the scope of the methods contemplated herein.

B. Effective Dosages

Pharmaceutical compositions provided herein include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to inhibition of thrombin, KLK1, and/or KLKB1); presence of other diseases or other health-related problems; kind of concurrent treatment; and complications from any disease or treatment regimen. Other therapeutic regimens or agents can be used in conjunction with the methods and compounds disclosed herein.

For any compound described herein, the therapeutically effective amount can be initially determined from a variety of techniques known in the art, e.g., biochemical characterization of inhibition of enzyme (thrombin, KLK1, or KLKB1), cell culture assays, and the like. Target concentrations will be those concentrations of active compound(s) that are capable of decreasing enzymatic activity as measured, for example, using the methods described.

Therapeutically effective amounts for use in humans can be determined from animal models. For example, a dose for humans can be formulated to achieve a concentration that has been found to be effective in animals. The dosage in humans can be adjusted by monitoring enzymatic inhibition and adjusting the dosage upwards or downwards, as described above.

Dosages can be varied depending upon the requirements of the patient and the compound being employed. The dose administered to a patient, in the context of the methods disclosed herein, should be sufficient to affect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments of a method disclosed herein, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

Accordingly, in some embodiments, dosage levels of the compounds disclosed herein as used in the present methods are of the order of e.g., about 0.1 mg to about 1 mg, about 1 mg to about 10 mg, about 0.5 mg to about 20 mg per kilogram body weight, an average adult weighing 70 kilograms, with a preferred dosage range between about 0.1 mg to about 20 mg per kilogram body weight per day (from about 7.0 mg to about 1.4 gm per patient per day). The amount of the compound disclosed herein that can be combined with the carrier materials to produce a single dosage will vary depending upon the host treated and the particular mode of administration. For example, a formulation intended for oral administration to humans can contain about 5 μg to 1 g of a compound disclosed herein with an appropriate and convenient amount of carrier material that can vary from about 5 to 95 percent of the total composition. Dosage unit forms will generally contain between from about 0.1 mg to 500 mg of a compound disclosed herein.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from in vitro assays, cell culture assays and/or animal studies can be used in formulating a range of dosages for use in humans. The dosage of such compounds preferably lies within a range of plasma concentrations that include the $ED_{50}$ with little or no toxicity. The dosage can vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual practitioner in view of the patient's condition and the particular method in which the compound is used. For in vitro formulations, the exact formulation and dosage can be chosen by the individual practitioner in view of the patient's condition and the particular method in which the compound is used.

VII. Examples

The examples below are meant to illustrate certain embodiments of the invention and not to limit the scope of the invention. Abbreviations used herein have their conventional meaning in the art, unless indicated otherwise. Specific abbreviations include the following: Å=Ångström; Ac₂O=acetic anhydride; AcOH=acetic acid; aq=aqueous; Bt=benzotriazole; BOC=N-tert-butoxycarbonyl; br=broad; t-BuOH=tert-butanol; ° C.=degree Celsius; d=doublet; DABCO=1,4-diazabicyclo[2.2.2]octane; DCE=1,2-dichloroethane; DCM=dichloromethane; dd=doublet of doublets; DIEA=diethylisopropylamine; DMAP=4-dimethylaminopyridine; DMF=N,N-dimethylformamide; DMSO=dimethylsulfoxide; δ=chemical shift (given in ppm, unless otherwise indicated); EDCI=1-ethyl-3-(3-dimethylaminopropyl)carbodiimide; eq=equivalent; Et₂O=diethyl ether; Et₃N=triethylamine; EtOAc=ethyl acetate; EtOH=ethanol; g=gram; h (or hr)=hour; HOBt=hydroxybenzotriazole; HPLC=high performance liquid chromatography; Hz=Hertz; $IC_{50}$=inhibitory concentration at 50% inhibition; J=coupling constant (given in Hz, unless otherwise indicated); LC=liquid chromatography; LHMDS=lithium hexamethyldisilazide; m=multiplet; M=molar; [M+H]⁺=parent mass spectrum peak plus H⁺; MS=mass spectrum; ms=molecular sieves; MP=melting point; Me₂NH=dimethylamine; MeOH=methanol; mg=milligram; mL=milliliter; mM=millimolar; mmol=millimole; min=minute; μL=microliter; μM=micromolar; ng=nanogram; nM=nanomolar; NMR=nuclear magnetic resonance; ppm=parts per million; q=quartet; $R_f$=retention factor; RT=room temperature; s=singlet; t=triplet; TFA=trifluoroacetic acid; THF=tetrahydrofuran; TLC=thin layer chromatography.

General Scheme I. A synthetic scheme useful for synthesis of compounds described herein is disclosed in General Scheme I following, wherein the terms "$R^x$", "$R^y$", ... and "$R^z$" are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted heterocycloalkenyl, substituted or unsubstituted aryl, or substituted or unsubstituted heteroaryl, or other groups obvious to those skilled in the art.

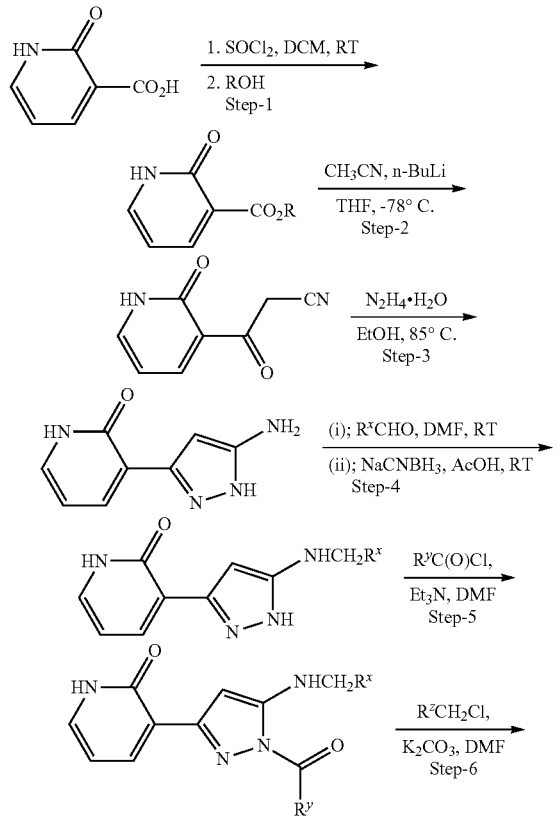

General Scheme I

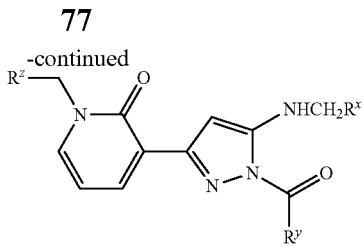

EXAMPLE 1

Preparation of Intermediate 1

The synthesis of Intermediate 1 followed General Procedure 1 following.

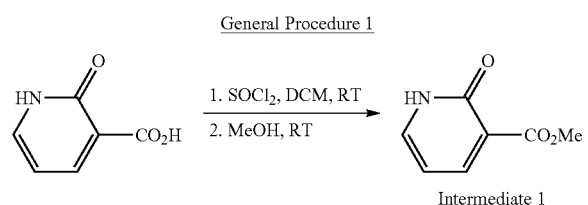 [SMILES: O=C(O)c1ccc[nH]c1=O ; COC(=O)c1ccc[nH]c1=O]

To a solution of 2-hydroxynicotinic acid (50.0 g, 0.359 moles, 1.0 eq.) in dichloromethane (500 mL) at 0° C. was added thionyl chloride (133.6 mL, 1.798 moles, 5.0 eq.) dropwise. After 30 min tetrahydrofuran (500 mL) was added and the reaction stirred for 14-15 hours at ambient temperature. The reaction mixture was cooled to 0° C., to it was added methanol (150 mL) dropwise, and the mixture was stirred for a further 30 min at room temperature. The reaction mixture was concentrated under reduced pressure to obtain a solid, which was then neutralized with aqueous sodium bicarbonate (pH 7-8), and again concentrated to obtain solid product. The solid was dissolved in methanol, filtered, and the filtrate concentrated to give desired product 45.0 g, (yield; 81.8%) m/z 153.99 [M+H]$^+$ $^1$H NMR (DMSO-d6, 400 MHz) δ 8.051-074 (1H, q), 7.661-7.682 (1H, q), 6.259-6.292 (1H, m), 3.734 (3H, s) ppm.

EXAMPLE 2

Preparation of Intermediate 2

The synthesis of Intermediate 2 followed the procedure of General Procedure 2 following.

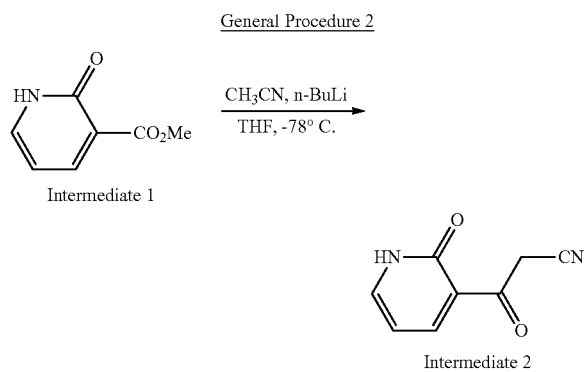

To a cold (−78° C.) solution of acetonitrile (8.18 mL, 0.156 moles, 1.2 eq.) in tetrahydrofuran (300 mL) was added n-BuLi (2.5M in Hexane; 62.68 mL, 0.156 moles, 1.2 eq) dropwise over a period of 60 min. After addition, the reaction was stirred for another 60 min, then to it added methyl 2-oxo-1,2-dihydropyridine-3-carboxylate (Intermediate 1, 20.0 g, 130 mmol, 1.0 eq) portionwise to reaction mixture and maintained −78° C. for 3 hrs. The reaction was quenched with water and washed with ethyl acetate. The aqueous layer was evaporated to obtain crude product, which was suspended in methanol and stirred for 30 min at room temperature. The solid was filtered through suction and dried over high vacuum to afford Intermediate 2 (11.5 g, 54%).

EXAMPLE 3

Preparation of Compound 1

The synthesis of Compound 1 followed the procedure of General Procedure 3 following.

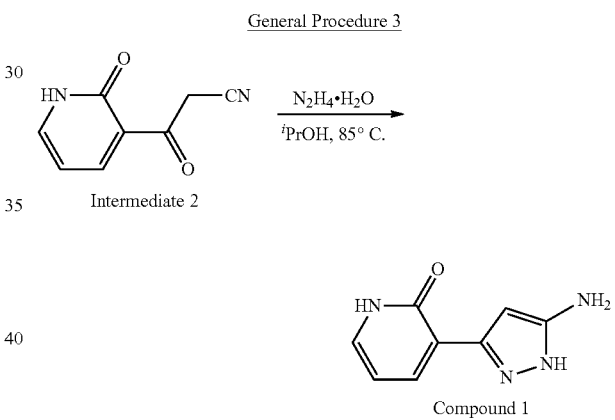

To a solution of Intermediate 2 (20.0 g, 0.123 moles, 1.0 eq) in isopropanol (600 mL) and acetic acid (22.2 mL) was added hydrazine monohydrate (7.40 mL, 0.148 moles, 1.2 eq) dropwise and the reaction was heated at 85° C. for 4-5 Hrs. After cooling, the reaction mixture was concentrated to give crude product, which was purified by column chromatography using neutral silica gel (60-120 mesh), eluting with 10-25% methanol in dichloromethane as gradient to give the desired product Compound 1 13.25 g (yield-61%) m/z 177.06 [M+H]+ 1H NMR (DMSO-d6, 400 MHz) δ 11.831 (1H, s), 7.857-7.879 (1H, q), 7.383-7.403 (1H, q), 6.303-6.336 (1H, m), 6.048 (1H, s) 4.633 (2H, s) ppm.

EXAMPLE 4

Preparation of Compound 2

The synthesis of Compound 2 followed the procedure of General Procedure 4 following.

General Procedure 4

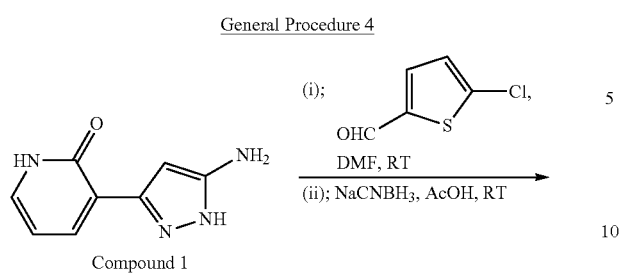

Compound 1

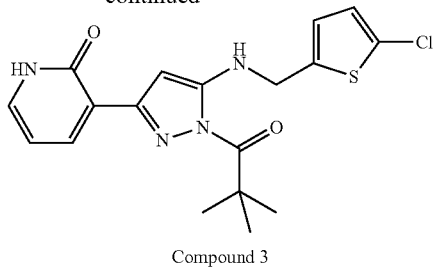

Compound 2

To a solution of Compound 1 in dimethylformamide (100 mL) at 10-15° C. was added acetic acid (11.2 mL) dropwise, followed by 5-chlorothiophene-2-carbaldehyde (9.15 g, 0.0624 moles, 1.1 eq) added portionwise. The reaction was stirred for 30-45 min at room temperature. Sodium cyanoborohydride (5.35 g, 0.0851 moles, 1.5 eq.) was added portionwise over a period of 45 min and reaction was stirred for 2 hours. After completion of reaction, the mixture was poured into ice cold water under stirring and the product was extracted with ethyl acetate. The organic layer was dried over sodium sulfate and concentrated under reduced pressure to obtain crude product, which was purified by column chromatography using neutral silica gel and product was eluted with 10-12% Methanol in dichloromethane as mobile phase to yield pure desired product compound 2 (7.3 g, yield: 42.7%) m/z[M+H]+ 307.10 1H NMR (DMSO-d6, 400 MHz) δ 12.034 (1H, s), 11.815 (1H, s), 7.869-7.882 (1H, q), 7.404-7.415 (1H, d), 6.922-6.931 (1H, d), 6.862-6.871 (1H, d), 6.314-6.331 (1H, d), 6.117 (1H, s), 5.867-5.898 (1H, t), 4.348-4.363 (2H, d) ppm.

EXAMPLE 5

Preparation of Compound 3

The synthesis of Compound 3 followed the procedure of General Procedure 5 following.

General Procedure 5

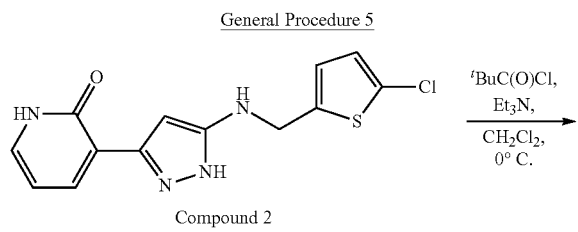

Compound 2

Compound 3

To a cooled (0° C.) solution of compound 2 in triethylamine (2.98 mL, 0.0215 moles, 3.0 eq.) and dichloromethane (40 mL) was added pivaloyl chloride (0.776 g, 0.00647 moles, 0.9 eq) dropwise over a period of 30 minutes. The reaction was stirred for 2-3 hours by maintaining the temperature below 10° C. After completion, the reaction was diluted with ice cold water under stirring and the product was extracted with dichloromethane. The organic phase was dried over sodium sulfate and concentrated under reduced pressure. The resultant crude product was purified by column chromatography using neutral silica gel, eluting with 5-8% methanol in dichloromethane to furnish pure desired product (compound 3, 0.76 g, yield: 43.6%) m/z [M+H]+ 391.24 1H NMR (DMSO-d6, 400 MHz) δ 11.250 (1H, s), 8.086-8.109 (1H, q), 7.731-7.761 (1H, t), 7.484 (1H, s), 6.974-6.984 (1H, d), 6.934-6.944 (1H, d), 6.317-6.350 (1H, t), 6.213 (1H, s), 4.471-4.486 (2H, d), 1.47 (9H, s) ppm.

EXAMPLE 6

Preparation of Compound 4

The synthesis of Compound 4 followed the procedure of General Procedure 6 following.

General Procedure 6

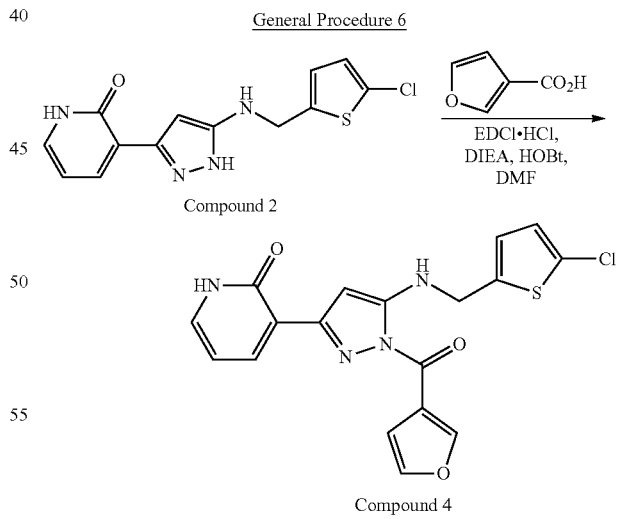

Compound 2

Compound 4

To a solution of furan-3-carboxylic acid (0.338 g, 0.00301 moles, 1.2 eq) in dimethylformamide (5.0 mL) was added EDCI.HCl (0.724 g, 0.00337 moles, 1.5 eq), DIEA (0.811 g, 0.00629 moles, 2.5 eq) and finally HOBt (0.074 g, 0.00048 moles, 0.5 eq). The reaction mixture was stirred at room temperature for 30 min, followed by the addition of compound 2 (0.770 g, 0.00251 moles, 1.0 eq). The mixture was stirred at 14 hours at room temperature. After checking that the reaction had reached completion by LC-MS, the mixture was poured into ice cold water under stirring. The product was extracted with ethyl acetate. The organic phase was dried over sodium sulfate, concentrated under reduced pressure and purified by column chromatography using neutral silica gel (60-120 mesh), eluting with 15-25% ethyl acetate in n-hexane as gradient to give pure desired compound 4 (0.45 g, yield: 45%) m/z[M+H]+ 401.84 1H NMR (DMSO-d6, 400 MHz) δ 11.923 (1H, s), 9.024-9.029 (1H, q), 8.274-8.297 (1H, q), 7.888-7.893 (1H, d), 7.833-7.884 (1H, q), 7.500-7.512 (1H, d), 7.085-7.091 (1H, q), 6.965-6.990 (2H, q), 6.313-6.347 (2H, t), 5.771 (1H, s), 4.445-4.560 (1H, d) ppm.

EXAMPLE 7

Preparation of Compound 5

The synthesis of Compound 5 followed the procedure of General Procedure 7 following.

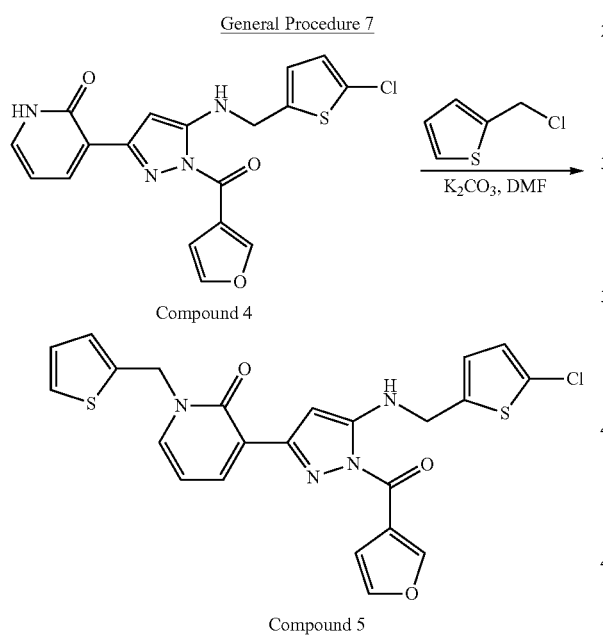

To a solution of compound 4 (0.150 g, 0.375 mmoles, 1.0 eq) in DMF (5.0 mL) was added anhydrous potassium carbonate (0.129 g, 0.937 mmoles, 2.5 eq) and then stirred for 30 minutes at room temperature. 2-(Chloromethyl)thiophene (0.059 g, 0.45 mmoles, 1.2 eq) was added to the reaction mixture and the reaction stirred for a further 2-3 hours at room temperature. The mixture was monitored by TLC and LCMS. After completion of reaction, the reaction mixture was poured into ice cold water under stirring and extracted with ethyl acetate. The organic phase was dried over sodium sulfate, concentrated under reduced pressure and purified by column chromatography using neutral silica gel. The product was eluted with 1-5% ethyl acetate as gradient in n-hexane to furnish compound 5 (0.036 g, yield-19.3%) m/z[M+H]+ 497.23. 1H NMR (DMSO-d6, 400 MHz) δ 9.020 (1H, s), 8.274-8.297 (1H, dd), 7.960-7.981 (1H, dd), 7.885-7.893 (1H, t), 7.833-7.864 (1H, t), 7.519-7.539 (1H, dd), 7.430-7.434 (1H, d), 7.117-7.133 (1H, dd), 7.087-7.091 (1H, d), 6.975-6.987 (1H, t), 6.380-6.427 (1H, t), 6.435 (1H, s), 5.189(2H, s), 4.550-4.565(2H, d) ppm.

EXAMPLE 8

Preparation of Compound 6

The synthesis of Compound 6 followed the procedure of General Procedure 8 following.

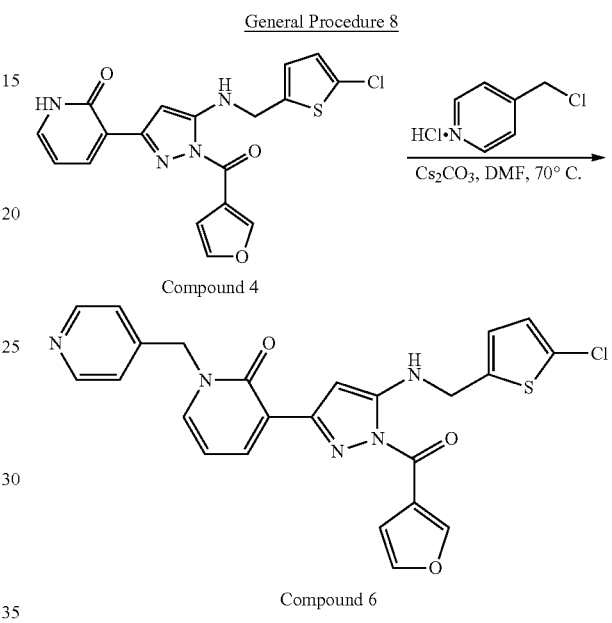

To a solution of compound 4 (0.150 g, 0.375 mmoles, 1.0 eq.) in DMF (5.0 mL) was added cesium carbonate (0.304 g, 0.937 mmoles, 2.5 eq.). The reaction mixture was stirred for 30 min at room temperature, followed by the addition of 4-(chloromethyl)pyridine hydrochloride (0.073 g, 0.45 mmoles, 1.2 eq). The reaction was stirred for 3-4 hours at 70° C. The reaction was monitored by TLC and LCMS. After completion of the reaction, the mixture was poured into ice cold water under stirring and extracted into ethyl acetate. The organic phase was dried over sodium sulfate, filtered and concentrated under reduced pressure. The crude product was purified by column chromatography using neutral silica gel, eluting with 40-55% ethyl acetate as gradient in n-hexane to furnish compound 6 (0.032 g, yield: 17.4%) m/z [M+H]+ 491.95. 1H NMR (DMSO-d6, 400 MHz) δ 9.030 (1H, s), 8.541-8.526 (2H, d), 8.379-8.356 (1H, dd), 8.020-7.999(1H, dd), 7.893-7.836 (2H, m), 7.210-7.195 (2H, d), 7.093-7.089(1H, d), 6.968-6.948(2H, t), 6.498-6.463 (1H, t), 6.294 (1H, s), 5.255 (2H, s), 4.542-4.526 (2H, d) ppm.

EXAMPLE 9

Preparation of Intermediate 3

General Scheme II. A synthetic scheme useful for synthesis of compounds described herein is disclosed in General Scheme II following, wherein the terms "R$^x$", "R$^y$", and "R$^z$" are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted heterocycloalkenyl, substituted or unsubstituted aryl, or substituted or unsubstituted heteroaryl, or other groups obvious to those skilled in the art.

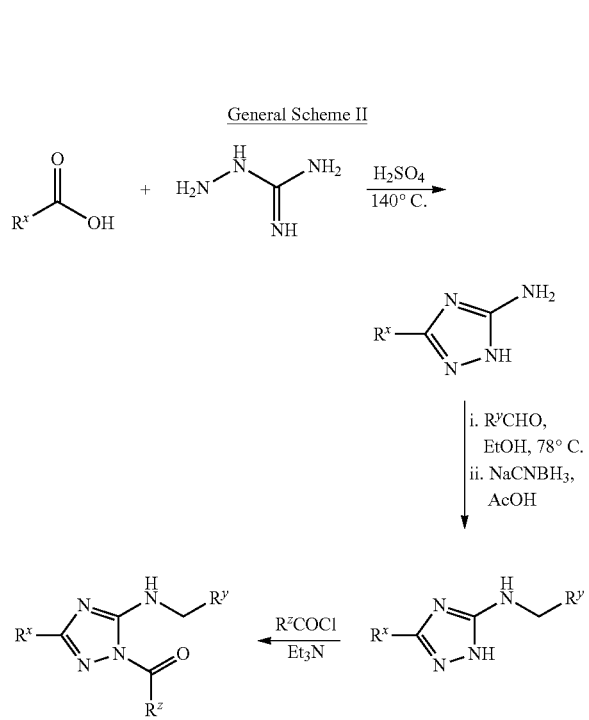

General Scheme II

The synthesis of Intermediate 3 followed General Procedure 9 following.

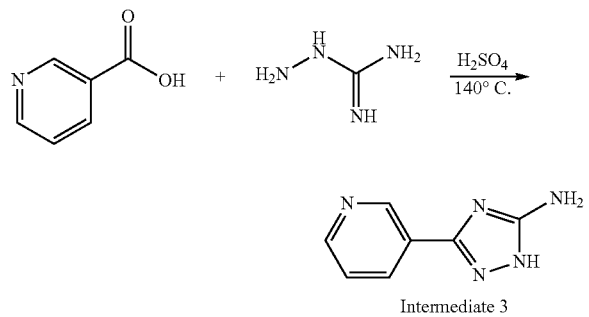

General Procedure 9

A solution of nicotinic acid (9.9 g, 80.9 mmol) in water (30 mL) was added slowly portion-wise to a previously stirred mixture of aminoguanidine sulfate (10 g, 73.5 mmol) in concentrated $H_2SO_4$ (8.8 mL, 162 mmol), and the reaction mixture was stirred at 140° C. for h. The reaction mixture was diluted with water (50 mL) and neutralized with saturated aqueous $K_2CO_3$ (30 mL), and the resultant solid was filtered. The residue was washed with water (2×30 mL), $Et_2O$ (2×30 mL) and dried under vacuum to afford Intermediate 3 (4.6 g, 39%) as an off-white solid. $^1$H NMR: (DMSO-$d_6$) δ 12.23 (s, 1H), 9.05 (s, 1H), 8.54 (d, J=2.8 Hz, 1H), 8.17 (d, J=7.4 Hz, 1H), 7.42-7.52 (m, 1H), 6.19 (s, 2H); MS: 162 [M+H]$^+$; MP: 234-236° C.; TLC: 20% MeOH/NH$_3$ in CHCl$_3$: R$_f$: 0.40.

EXAMPLE 10

Preparation of Intermediate 4

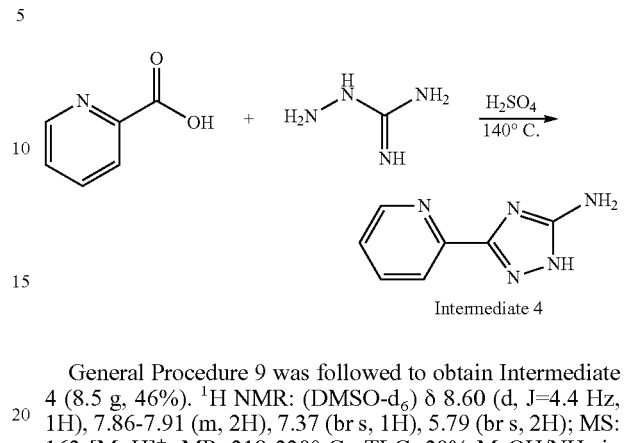

General Procedure 9 was followed to obtain Intermediate 4 (8.5 g, 46%). $^1$H NMR: (DMSO-$d_6$) δ 8.60 (d, J=4.4 Hz, 1H), 7.86-7.91 (m, 2H), 7.37 (br s, 1H), 5.79 (br s, 2H); MS: 162 [M+H]$^+$; MP: 218-220° C.; TLC: 20% MeOH/NH$_3$ in CHCl$_3$: R$_f$: 0.40.

EXAMPLE 11

Preparation of Intermediate 5

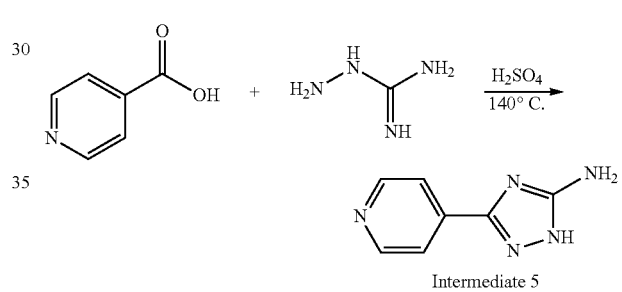

General Procedure 9 was followed to obtain Intermediate 5 (12 g, 67%). $^1$H NMR: (DMSO-$d_6$) δ 12.35 (br s, 1H), 8.59 (d, J=5.5 Hz, 2H), 7.76-7.78 (m, 2H), 6.23 (s, 2H); MS: 162 [M+H]$^+$; TLC: 20% MeOH/NH$_3$ in CHCl$_3$: R$_f$: 0.40.

EXAMPLE 12

Preparation of Intermediate 6

The synthesis of Intermediate 6 followed the procedure of General Procedure 10 following.

General Procedure 10

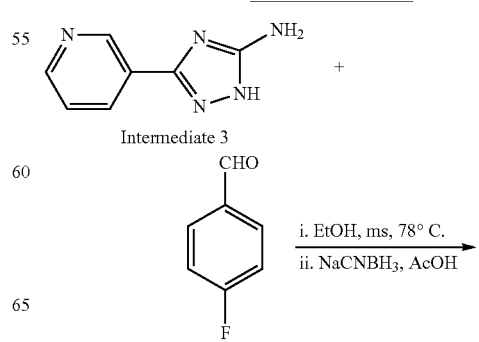

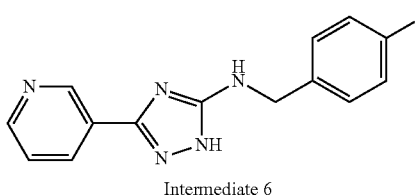

Intermediate 6

4-Fluorobenzaldehyde (3.1 g, 24.8 mmol, 2 eq) and molecular sieves (4 Å powder) were added to a solution of Intermediate 3 (2 g, 12.4 mmol) in EtOH (20 mL) at RT and refluxed for 8 h. Then was added a catalytic quantity of AcOH, NaCNBH$_3$ (1.6 g, 24.8 mmol, eq) at 0° C. and with stirring for 15 h at RT. The solvent was distilled off, and the residue was dissolved in EtOAc (200 mL) and filtered through a Celite® pad to remove inorganic materials. The filtrate was washed with saturated aqueous NaHCO$_3$ (2×20 mL), water (20 mL), brine (20 mL), dried over Na$_2$SO$_4$, filtered and concentrated in vacuo. The resultant compound was purified by column chromatography over silica gel (100-200 mesh) by using a solvent gradient of 0-10% MeOH—CHCl$_3$ as the eluent to afford Intermediate 6 (1.7 g, 51%). $^1$H NMR: (DMSO-d$_6$) δ 12.50 (s, 1H), 9.06 (d, J=1.4 Hz, 1H), 8.53-8.55 (m, 1H), 8.17-8.20 (m, 1H), 7.33-7.45 (m, 4H), 7.12-7.19 (m, 2H), 4.40 (d, J=6.4 Hz, 2H); MS: 270 [M+H]$^+$; MP: 185-186° C.; TLC: 10% MeOH in CHCl$_3$: R$_f$: 0.25.

EXAMPLE 13

Preparation of Intermediate 7

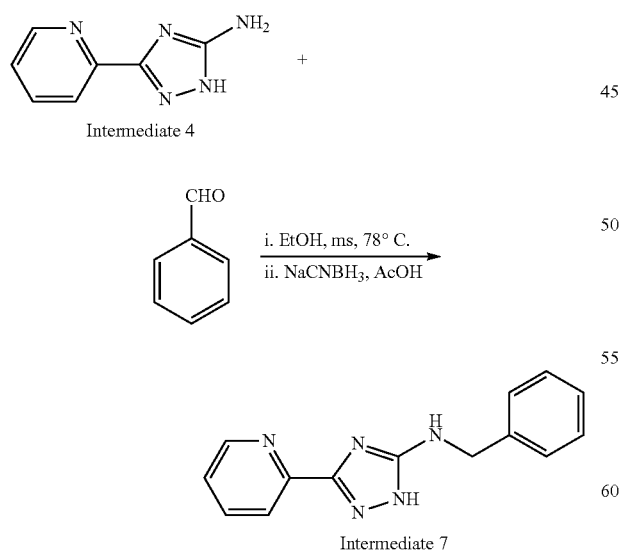

Intermediate 7

General Procedure 10 was followed to obtain Intermediate 7 (2.8 g, 60%). MS: 252 [M+H]$^+$; MP: 226-228° C.; TLC: 10% MeOH in CHCl$_3$: R$_f$: 0.30.

EXAMPLE 14

Preparation of Intermediate 8

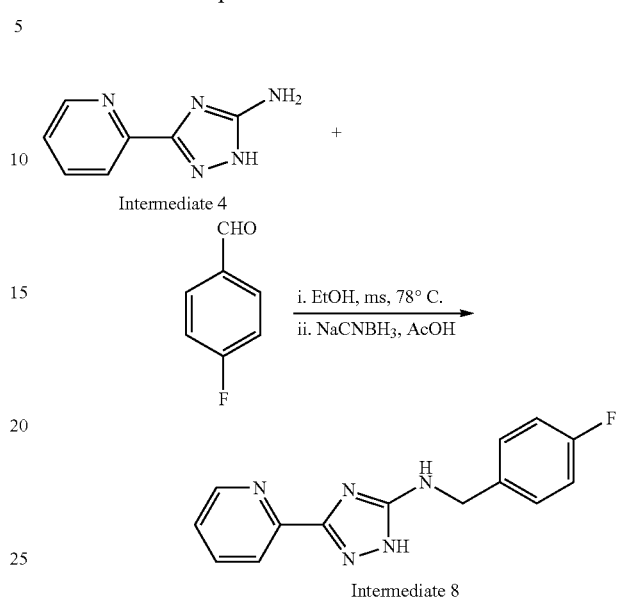

Intermediate 8

General Procedure 10 was followed to obtain Intermediate 8 (1.6 g, 48%). $^1$H NMR: (DMSO-d$_6$) δ 13.15 (br s, 1H), 8.60 (d, J=4.0 Hz, 1H), 7.86-7.93 (m, 2H), 7.30-7.42 (m, 3H), 7.02-7.15 (m, 2H), 6.84 (br s, 1H), 4.37 (d, J=6.2 Hz, 2H); MS: 270 [M+H]$^+$; MP: 219-220° C.; TLC: 10% MeOH in CHCl$_3$: R$_f$: 0.25.

EXAMPLE 15

Preparation of Intermediate 9

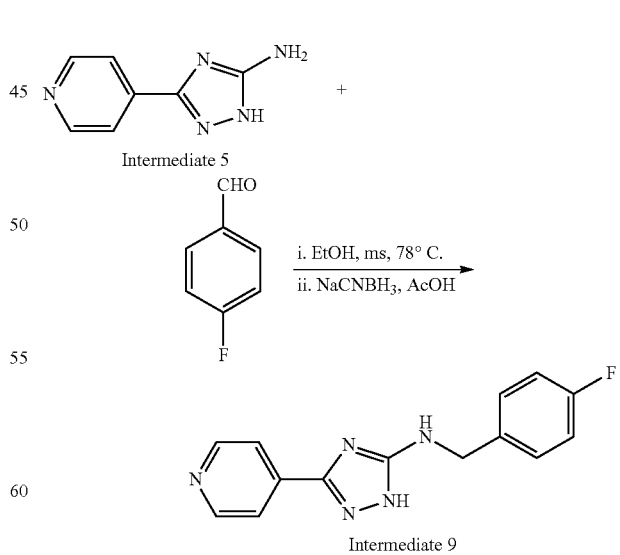

Intermediate 9

General Procedure 10 was followed to obtain Intermediate 9 (1.4 g, 42%). MS: 270 [M+H]$^+$; TLC: 10% MeOH in CHCl$_3$: R$_f$: 0.25.

EXAMPLE 16

Preparation of Compound 7

The synthesis of Compound 7 followed General Procedure 11 following.
General Procedure 11

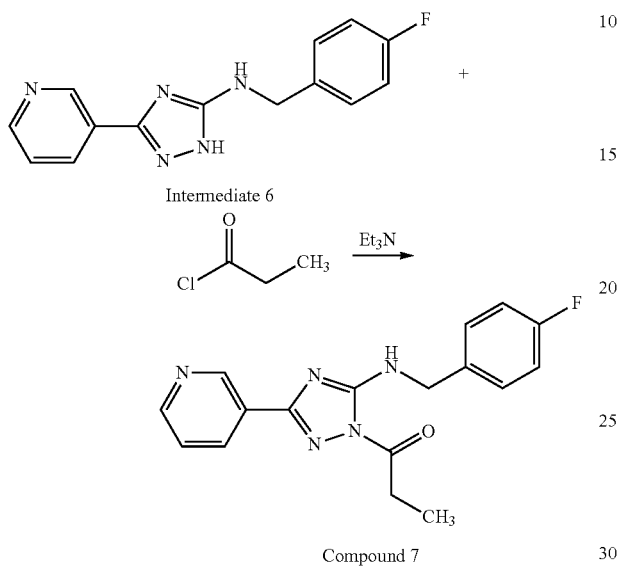

Intermediate 6

Compound 7

Propionyl chloride (39 μL, 0.44 mmol, 1.2 eq) was added to a solution of Intermediate 6 (100 mg, 0.37 mmol) in triethylamine (3 mL) at RT and stirred for 5 h. The reaction mixture was diluted with water (5 mL) and extracted with EtOAc (20 mL). The organic layer washed with water (2×5 mL), saturated aqueous NaHCO₃ (5 mL), brine (5 mL), dried over Na₂SO₄, filtered and concentrated in vacuo. The crude compound was purified by column chromatography over silica gel (100-200 mesh) by using a gradient mixture of 0-30% EtOAc-hexane as the eluent to afford Compound 7 (40 mg, 33%). $^1$H NMR: (DMSO-d$_6$) δ 9.14 (d, J=1.8 Hz, 1H), 8.66-8.67 (m, 1H), 8.28-8.34 (m, 2H), 7.47-7.53 (m, 3H), 7.13-7.17 (m, 2H), 4.63 (d, J=6.2 Hz, 2H), 3.05 (q, J=7.5 Hz, 2H), 1.16 (t, J=7.5 Hz, 3H); MS: 326 [M+H]$^+$; TLC: 50% EtOAc in hexane: R$_f$: 0.60.

EXAMPLE 17

Preparation of Compound 8

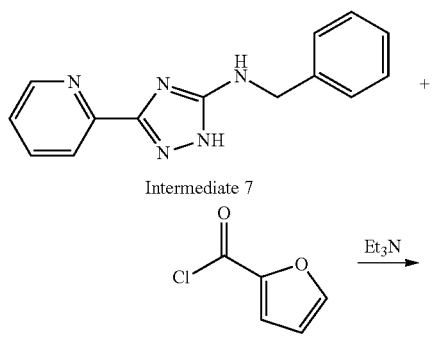

Intermediate 7

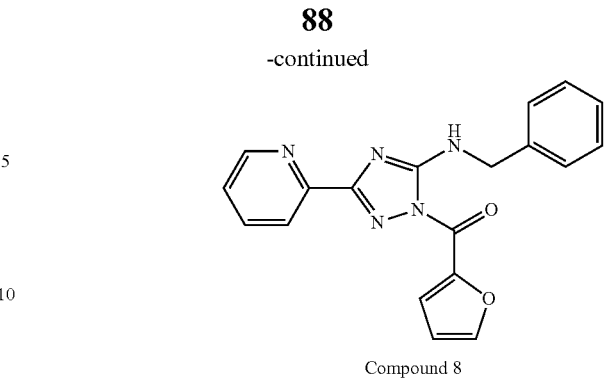

Compound 8

General Procedure 11 was followed to obtain Compound 8 (48 mg, 35%). $^1$H NMR: (DMSO-d$_6$) δ 8.71 (d, J=4.0 Hz, 1H), 8.46 (br s, 1H), 8.13-8.23 (m, 3H), 7.92-7.96 (m, 1H), 7.24-7.52 (m, 6H), 6.88-6.89 (m, 1H), 4.74 (d, J=6.2 Hz, 2H); MS: 346 [M+H]$^+$; MP: 143-145° C.; TLC: 50% EtOAc in hexane: R$_f$: 0.60.

EXAMPLE 18

Preparation of Compound 9

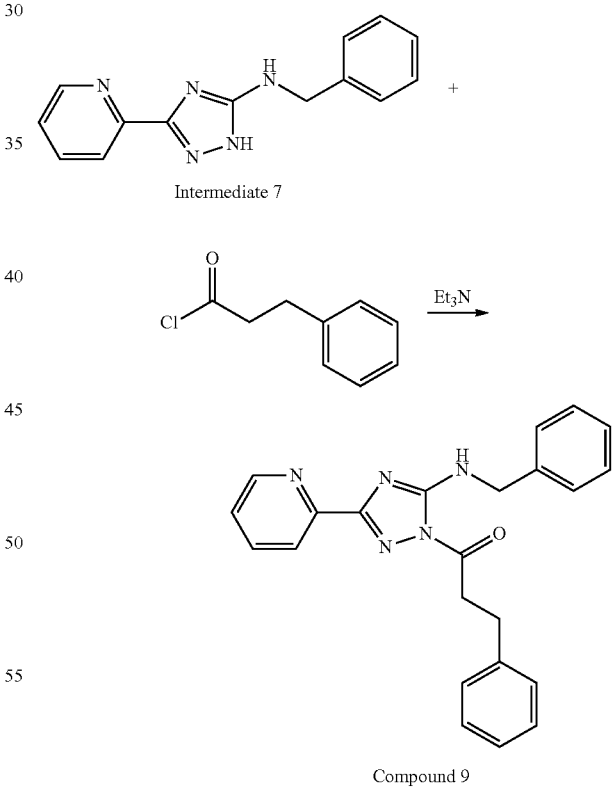

Intermediate 7

Compound 9

General Procedure 11 was followed to obtain Compound 9 (25 mg, 16%). $^1$H NMR: (DMSO-d$_6$) δ 8.65 (d, J=4.0 Hz, 1H), 8.26 (br s, 1H), 8.03 (d, J=8.1 Hz, 1H), 7.90 (t, J=7.7 Hz, 1H), 7.19-7.48 (m, 11H), 4.67 (d, J=6.0 Hz, 2H), 3.30-3.41 (m, 2H), 2.99-3.03 (m, 2H); MS: 384 [M+H]$^+$; MP: 118-120° C.; TLC: 50% EtOAc in hexane: R$_f$: 0.40.

EXAMPLE 19

Preparation of Compound 10

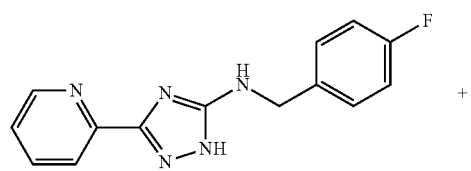

Intermediate 8

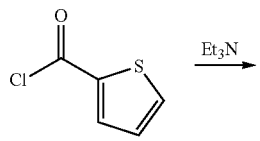

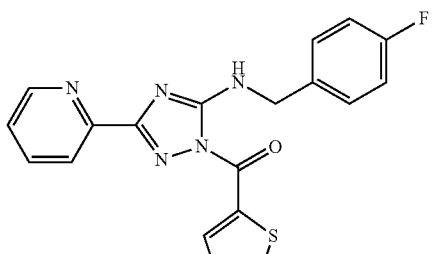

Compound 10

General Procedure 11 was followed to obtain Compound 10 (40 mg, 28%). $^1$H NMR: (DMSO-d$_6$) δ 8.72 (d, J=4.6 Hz, 1H), 8.47-8.54 (m, 2H), 8.12-8.23 (m, 2H), 7.94-7.98 (m, 1H), 7.48-7.52 (m, 3H), 7.34-7.36 (m, 1H), 7.16 (t, J=9.0 Hz, 2H), 4.71 (d, J=6.1 Hz, 2H); MS: 380 [M+H]$^+$; MP: 159-160° C.; TLC: 50% EtOAc in hexane: R$_f$: 0.60.

EXAMPLE 20

Preparation of Compound 11

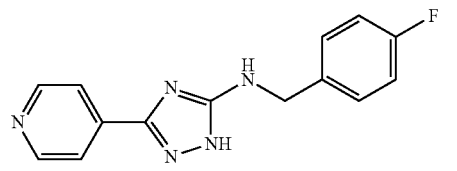

Intermediate 9

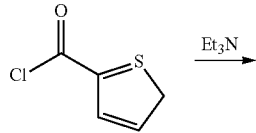

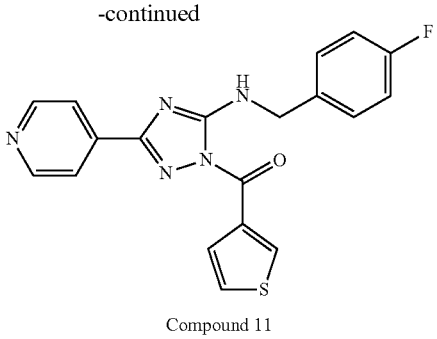

Compound 11

General Procedure 11 was followed to obtain Compound 11 (20 mg, 14%). $^1$H NMR: (DMSO-d$_6$) δ 9.19 (d, J=1.3 Hz, 1H), 8.63-8.73 (m, 3H), 8.00 (d, J=5.7 Hz, 2H), 7.72-7.88 (m, 2H), 7.50-7.54 (m, 2H), 7.17 (t, J=8.8 Hz, 2H), 4.70 (d, J=6.2 Hz, 2H); MS: 380 [M+H]$^+$; MP: 187-188° C.; TLC: 50% EtOAc in hexane: R$_f$: 0.60.

EXAMPLE 21

Preparation of Compound 12

The synthesis of Compound 12 followed General Procedure 12 following.

General Procedure 12

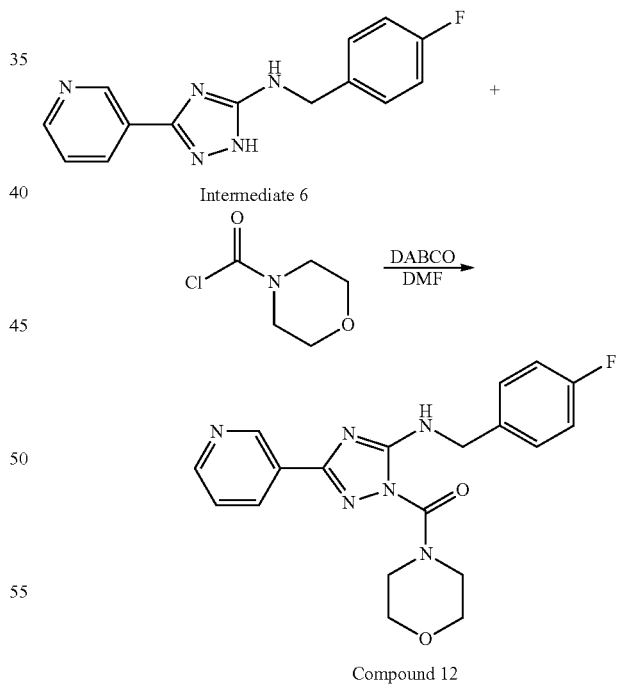

Compound 12

A solution of Intermediate 6 (100 mg, 0.37 mmol) in dry DMF (2 mL) was added to a solution of morpholinecarbonyl chloride (86 μL, 0.74 mmol, 2 eq), DABCO (124 mg, 1.11 mmol, 3 eq) in DMF (3 mL) at RT and stirred for 2 h. The reaction mixture was diluted with water (10 mL) and extracted with EtOAc (30 mL). The organic layer washed with water (2×5 mL), saturated aqueous NaHCO$_3$ (2×5 mL), brine (10 mL), dried over $Na_2SO_4$, filtered and concentrated in vacuo to get a crude residue. The crude compound was purified by column chromatography over silica gel (100-200 mesh) by using a gradient mixture of 0-50% EtOAc-hexane as the eluent to afford Compound 12 (33 mg, 23%). $^1$H NMR: (DMSO-$d_6$) δ 9.11 (s, 1H), 8.64 (d, J=4.8 Hz, 1H), 8.25 (d, J=7.9 Hz, 1H), 7.90 (s, 1H), 7.46-7.52 (m, 3H), 7.16 (t, J=8.8, 2H), 4.59 (d, J=6.2 Hz, 2H), 3.70-3.99 (m, 8H); MS: 383 [M+H]$^+$; TLC: 50% EtOAc in hexane: $R_f$: 0.40.

EXAMPLE 22

Preparation of Compound 13

A useful scheme for the preparation of compounds of the type of Compound 13 is provided in Scheme 1 following.

A solution of cyanogen bromide (1.3 g, 12.6 mmol) in acetone (5 mL) was added portion-wise slowly to a mixture of benzotriazole (3 g, 25.2 mmol, 2 eq) in EtOH (50 mL) followed by 10% aqueous NaOH (6 mL, 12.6 mmol, 1 eq) at 0° C. The reaction mixture was then stirred at RT for 30 min. Solid formation was observed. The solid was filtered and washed with cold EtOH. The resulting material was recrystallized from benzene to afford Intermediate 10 (2.2 g, 33%) as a white solid. $^1$H NMR: (DMSO-$d_6$) δ 11.76 (s, 1H), 8.29-8.39 (m, 2H), 7.86-8.09 (m, 2H), 7.44-7.72 (m, 4H), MS: 264 [M+H]$^+$; TLC: 30% EtOAc in hexane: $R_f$: 0.50.

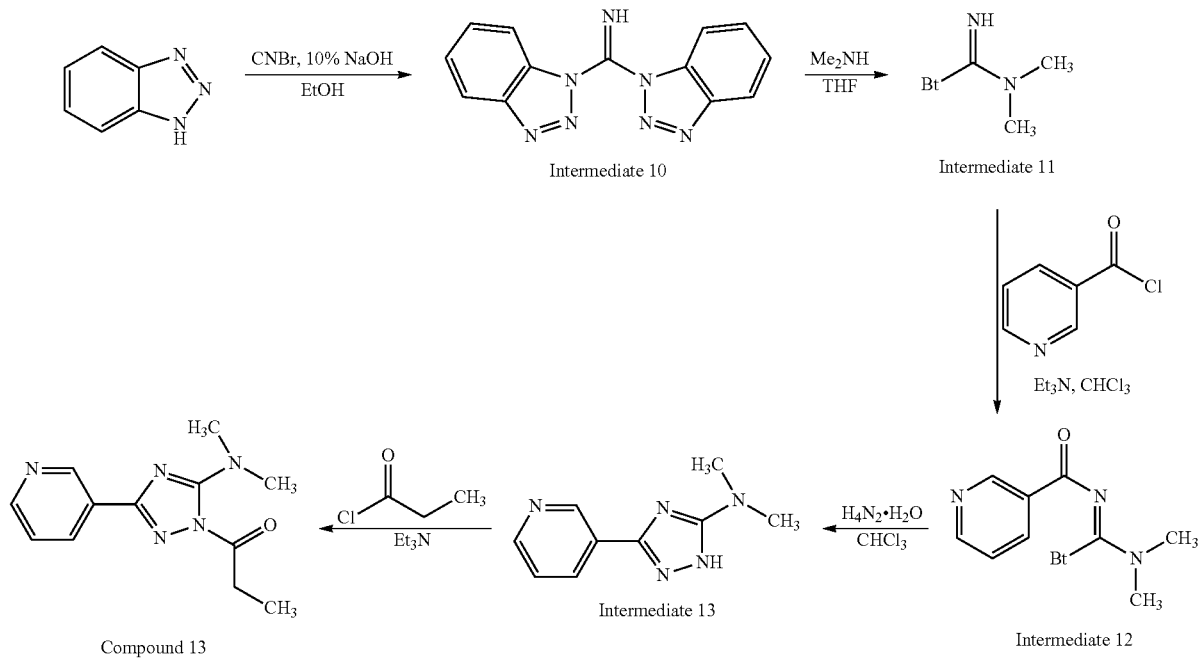

Scheme 1

A detailed description of the preparation of Intermediates 10-13 and Cmpd 24 follows.

Preparation of Intermediate 10

Preparation of Intermediate 11

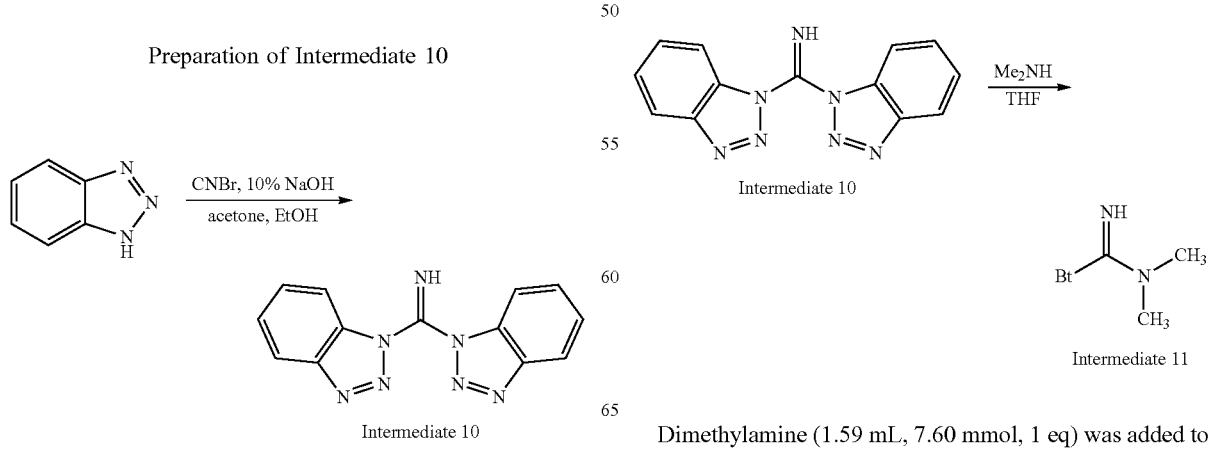

Dimethylamine (1.59 mL, 7.60 mmol, 1 eq) was added to Intermediate 10 (2 g, 7.60 mmol) in THF (30 mL) at RT and the resulting mixture was allowed to stir for 24 h. The solvent was evaporated and the residue was dissolved in DCM (100 mL). The organic layer was washed with 10% Na$_2$CO$_3$ (3×5 mL), brine (10 mL), dried over Na$_2$SO$_4$, filtered and concentrated in vacuo to afford Intermediate 11 (1.2 g, 71%) as a light yellow liquid which was used without additional purification. $^1$H NMR: (DMSO-d$_6$) δ 8.17 (d, J=8.4 Hz, 1H), 7.65-7.80 (m, 3H), 7.49-7.53 (m, 1H), 2.87 (s, 6H); MS: 190 [M+H]$^+$; TLC: 30% EtOAc in hexane: R$_f$: 0.30.

Preparation of Intermediate 12

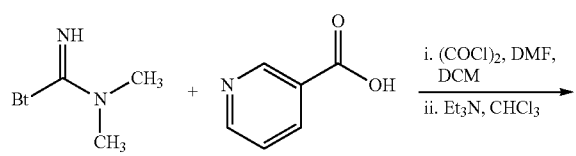

Intermediate 11

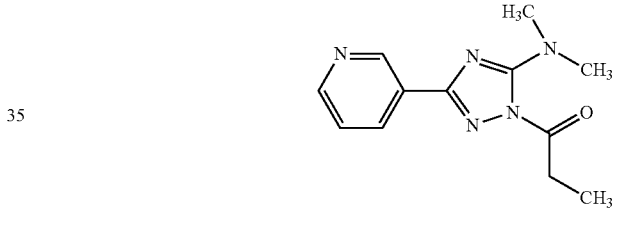

Intermediate 12

Oxalyl chloride (2 mL, 23.3 mmol, 1.4 eq) was added to a solution of nicotinic acid (2 g, 16.3 mmol) in DCM followed by catalytic amount of DMF (0.5 mL) at 0° C. and stirred for 5 h at RT. The solvent was then evaporated to afford nicotinic acid chloride as a yellow solid. Nicotinic acid chloride (1.1 g, 7.93 mmol, 1.5 eq) was then added to a solution of Intermediate 11 (1 g, 5.29 mmol) in CHCl$_3$ (30 mL) followed by Et$_3$N (0.7 mL, 5.29 mmol, 1 eq) at 0° C. The reaction mixture was allowed to warm to RT for stir for 18 h. The mixture was then diluted with CHCl$_3$ (20 mL). The organic layer was washed with water (10 mL), brine (10 mL), dried over Na$_2$SO$_4$, filtered and concentrated in vacuo. The resulting compound was purified by column chromatography over silica gel (100-200 mesh) by using a gradient mixture of 0-50% EtOAc-hexane as the eluent to afford Intermediate 12 (900 mg, 60%) as a white solid. MS: 295 [M+H]$^+$; TLC: 50% EtOAc in DCM: R$_f$: 0.40.

Preparation of Intermediate 13

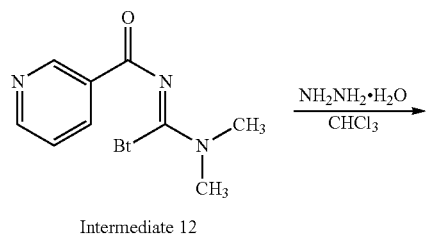

Intermediate 12

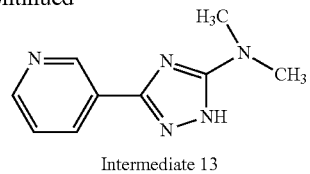

Intermediate 13

Hydrazine hydrate (5 mL) was added solution of Intermediate 12 (900 mg, 25.2 mmol) in chloroform (20 mL) at RT and the resulting mixture was allowed to stir for 24 h. The mixture was diluted with excess CHCl$_3$ (20 mL). The organic layer was then washed with water (15 mL), brine (10 mL), dried over Na$_2$SO$_4$, filtered and concentrated in vacuo. The crude residue was partially purified by column chromatography over silica gel (100-200 mesh) by using a gradient mixture of 0-50% EtOAc-hexane as the eluent to afford Intermediate 13 (150 mg) as a thick brown mass. MS: 190 [M+H]$^+$; TLC: 10% MeOH in CHCl$_3$: R$_f$: 0.30.

Preparation of Compound 13

Compound 13

General Procedure 11 was followed to obtain Compound 13 (13 mg, 6%). $^1$H NMR: (DMSO-d$_6$) δ 9.15 (s, 1H), 8.68 (d, J=3.5 Hz, 1H), 8.31 (d, J=7.9 Hz, 1H), 7.53 (dd, J=7.9, 4.8 Hz, 1H), 3.04-3.14 (m, 8H), 1.15 (t, J=7.3 Hz, 3H); MS: 246 [M+H]$^+$; TLC: 50% EtOAc in DCM: R$_f$: 0.50.

EXAMPLE 23

Preparation of Compound 14

A general chemical scheme for the formation of compounds of the type of Compound 14 is provided in General Scheme III following, wherein the terms "R$^x$", "R$^y$", and "R$^z$" are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted heterocycloalkenyl, substituted or unsubstituted aryl, or substituted or unsubstituted heteroaryl, or other groups obvious to those skilled in the art. General Scheme III

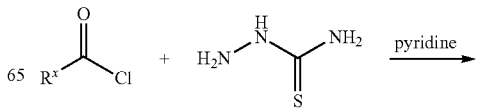

Preparation of Intermediate 14

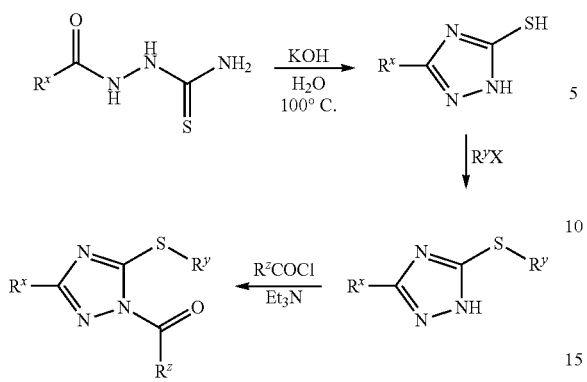

A detailed description of the preparation of Intermediates 14, 15 and Compound 14 follows.

Preparation of Intermediate 14

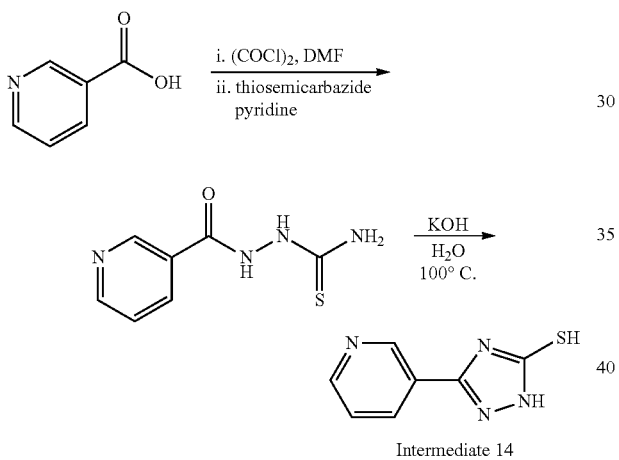

Oxalyl chloride (5.4 mL, 61.0 mmol, 1.5 eq) and DMF (3 mL) was added sequentially to a solution of nicotinic acid (5 g, 40.7 mmol) in dry DCM (300 mL) at RT. The reaction mixture was allowed to stir at RT for 2 h. The solvent was removed and co-distilled with dry toluene (2×50 mL) and to afford 5 g of crude nicotinic acid chloride (5 g, 35.5 mmol). This material was added slowly portion-wise to a solution of thiosemicarbazide (5 g, 54.9 mmol, 1.5 eq) in pyridine (50 mL) at 0° C. over a period of 1 h and then allowed to stir at RT for 14 h. The reaction mixture was neutralized with saturated aqueous NaHCO$_3$ (30 mL) and extracted with t-BuOH (3×100 mL) and dried over Na$_2$SO$_4$, filtered and concentrated in vacuo. The crude residue was dissolved in water (20 mL) along with 10% aqueous KOH (50 mL) and the resulting mixture was allowed to stir at 100° C. for 3 h. The reaction mixture was then cooled to 0° C. and neutralized with 10% aqueous AcOH (60 mL), extracted with EtOAc (2×150 mL), dried over Na$_2$SO$_4$, filtered and concentrated in vacuo to afford crude Intermediate 14 (1.2 g) as an off-white solid. MS: 179 [M+H]$^+$; TLC: 20% MeOH/NH$_3$ in CHCl$_3$: R$_f$: 0.30.

Preparation of Intermediate 15

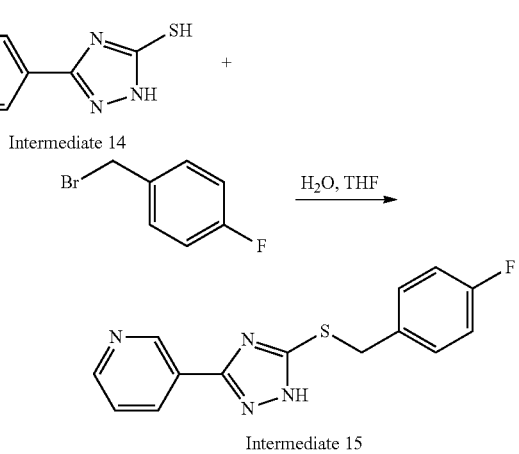

4-Fluorobenzyl bromide (0.12 mL, 1.01 mmol, 0.6 eq) was added to a solution of Intermediate 14 (300 mg, 1.68 mmol) in water (5 mL) and THF (15 mL) at −10° C. and the reaction mixture was allowed to stir at −10° C. for 8 h. The solvent was removed and the residue was diluted with water (10 mL) and extracted with EtOAc (50 mL). The organic layer was washed with water (15 mL), saturated aqueous NaHCO$_3$ (10 mL), brine, dried over Na$_2$SO$_4$, filtered and concentrated in vacuo. The crude compound was purified by column chromatography over silica gel (100-200 mesh) by using a solvent gradient mixture of 0-10% MeOH—CHCl$_3$ as the eluent to afford Intermediate 15 (110 mg, 23%) as an off-white solid. MS: 287 [M+H]$^+$; TLC: EtOAc: R$_f$: 0.40.

Preparation of Compound 14

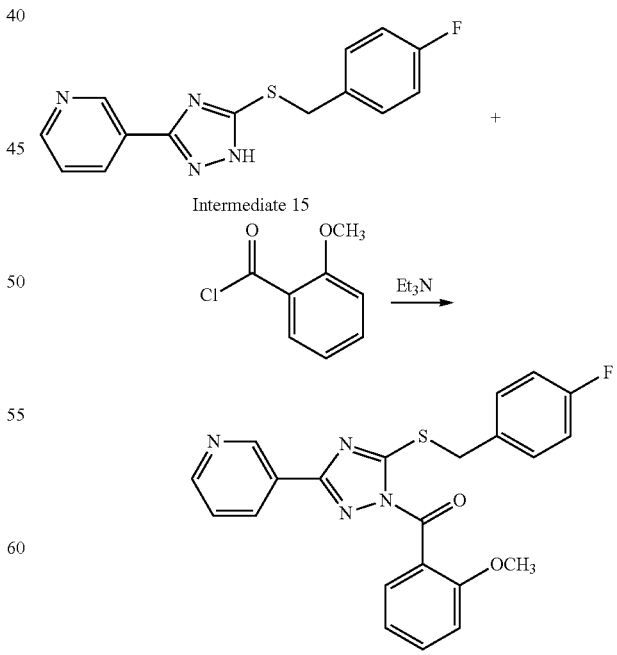

General Procedure 11 was followed to obtain Compound 14 (20 mg, 30%). $^1$H NMR: (DMSO-$d_6$) δ 9.13 (s, 1H), 8.71 (d, J=4.0 Hz, 1H), 8.26 (d, J=7.9 Hz, 1H), 7.53-7.67 (m, 5H), 7.09-7.25 (m, 4H), 4.64 (s, 2H), 3.75 (s, 3H); MS: 421 [M+H]$^+$; MP: 108-112° C.; TLC: 30% EtOAc in hexane: $R_f$: 0.40.

EXAMPLE 24

Preparation of Intermediate 16

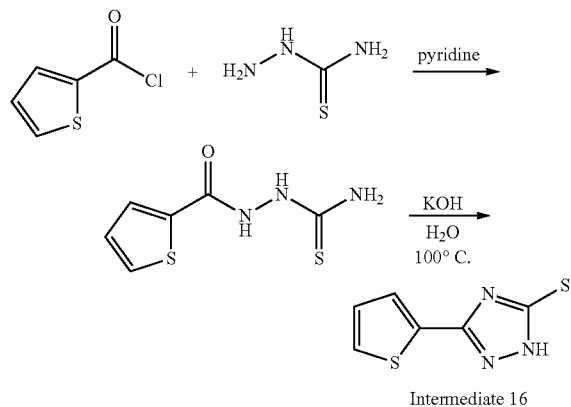

Intermediate 16

2-Thiophene carboxylic acid chloride (6.5 mL, 60.4 mmol) was added slowly portionwise to a solution of thiosemicarbazide (5 g, 54.9 mmol, 1.1 eq) in pyridine (50 mL) at 0° C. over a period of 1 h and then allowed to stir at RT for 14 h. The reaction mixture was neutralized with saturated aqueous NaHCO$_3$ (50 mL) and extracted with t-BuOH (3×100 mL) and dried over Na$_2$SO$_4$, filtered and concentrated in vacuo. The crude residue was dissolved in water (30 mL) along with 10% aqueous KOH (60 mL) and the resulting mixture was allowed to stir at 100° C. for 3 h. The reaction mixture was then cooled to 0° C. and neutralized with 10% aqueous AcOH, extracted with EtOAc (2×150 mL), dried over Na$_2$SO$_4$, filtered and concentrated in vacuo to afford crude Intermediate 16 (1.2 g) as an off-white solid. MS: 184 [M+H]$^+$; TLC: 10% MeOH/NH$_3$ in CHCl$_3$: $R_f$: 0.60.

EXAMPLE 25

Preparation of Intermediate 17

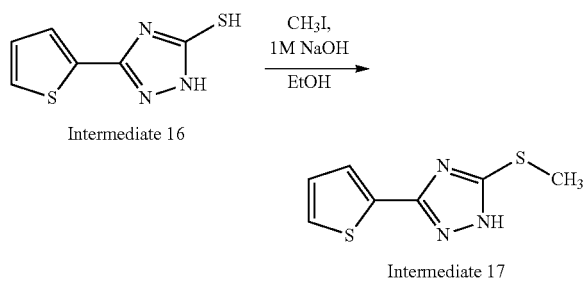

Intermediate 17

A solution of methyl iodide (65 μL, 1.04 mmol, 1.6 eq) in EtOH (2 mL) was added to a solution of Intermediate 16 (120 mg, 0.66 mmol) in 1M aqueous NaOH (3 mL) at RT and the resulting mixture was allowed to stir for 3 h. The reaction mixture was then neutralized with 10% aqueous AcOH (5 mL) and extracted with EtOAc (30 mL). The organic layer was washed with water (10 mL), saturated aqueous NaHCO$_3$ (5 mL), brine, dried over Na$_2$SO$_4$, filtered and concentrated in vacuo. The crude compound was purified by column chromatography over silica gel (100-200 mesh) by using a solvent gradient mixture of 0-10% MeOH—CHCl$_3$ as the eluent to afford Intermediate 17 (90 mg, 70%) as an off-white solid. $^1$H NMR: (DMSO-$d_6$) δ 14.19 (br s, 1H), 7.62-7.67 (m, 2H), 7.16-7.18 (m, 1H), 2.60 (s, 3H); MS: 198 [M+H]$^+$; TLC: 50% EtOAc in hexane: $R_f$: 0.50.

EXAMPLE 26

Preparation of Compound 15

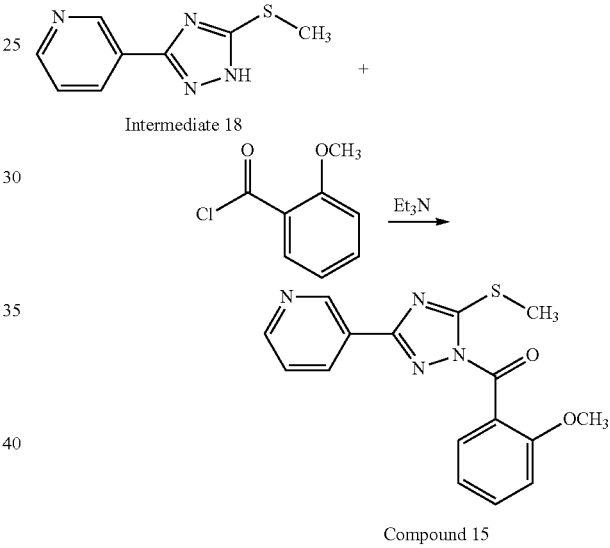

Compound 15

General Procedure 11 was followed to obtain Cmpd 29 (30 mg, 29%). $^1$H NMR: (DMSO-$d_6$) δ 7.72 (d, J=4.8 Hz, 1H), 7.56-7.65 (m, 3H), 7.25 (d, J=8.8 Hz, 1H), 7.09-7.24 (m, 2H), 3.77 (s, 3H), 2.73 (s, 3H); MS: 332 [M+H]$^+$; MP: 165-167° C.; TLC: 30% EtOAc in hexane: $R_f$: 0.40.

EXAMPLE 27

Preparation of Compound 16

General Scheme IV. A synthetic scheme useful for synthesis of compounds described herein including Compound 16 is disclosed in General Scheme IV following, wherein the terms "R$^x$", "R$^y$", and "R$^z$" are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted heterocycloalkenyl, substituted or unsubstituted aryl, or substituted or unsubstituted heteroaryl, or other groups obvious to those skilled in the art.

General Scheme IV

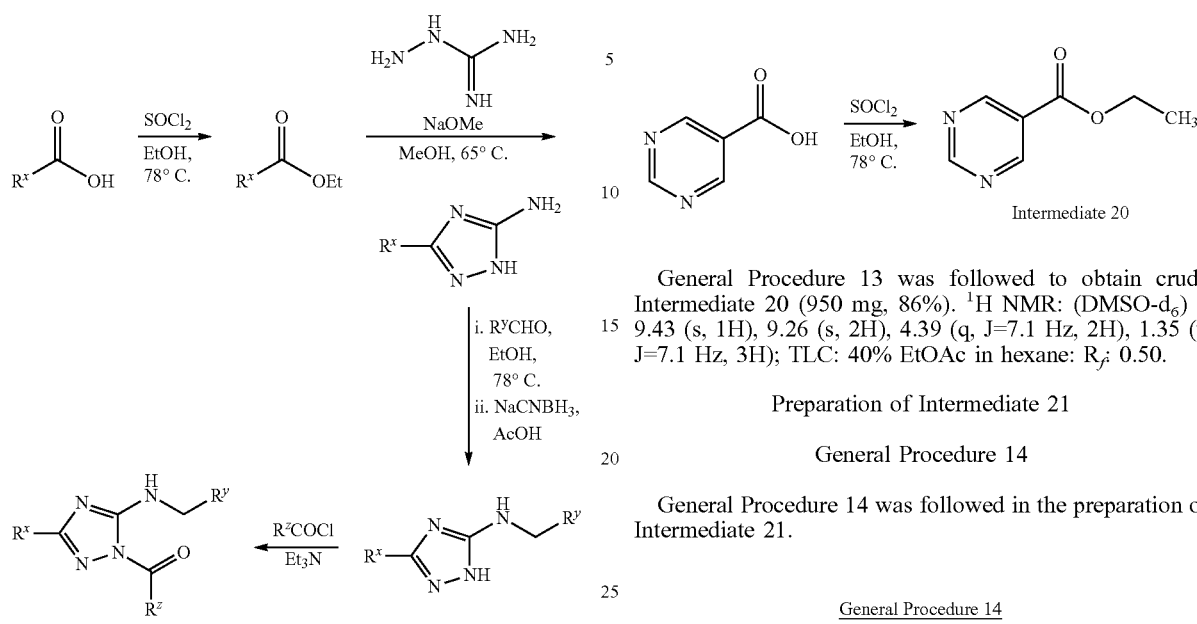

A description of the synthesis of Intermediates 19-24 and Compound 16 follows. Synthesis of Intermediate 19 followed General Procedure 13 following.

Preparation of Intermediate 19
[General Procedure 13]

General Procedure 13 was followed in the preparation of Intermediate 19.

General Procedure 13

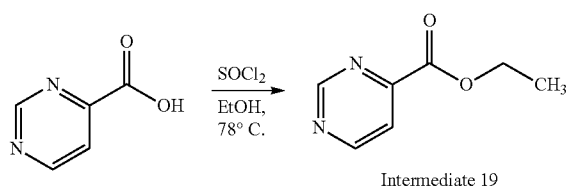

Thionyl chloride (3.55 mL, 48.4 mmol, 3 eq) was added dropwise to a solution of pyrimidine-4-carboxylic acid (2 g, 16.1 mmol) in EtOH (15 mL) and the resulting mixture was heated to reflux for 14 h. The mixture was then cooled to RT and made alkaline with saturated aqueous NaHCO$_3$ to pH 8. The basic solution was then extracted with EtOAc (4×50 mL). The combined organic layers were washed with brine (30 mL), dried over Na$_2$SO$_4$, filtered and concentrated in vacuo to afford Intermediate 19 (1.7 g, 77%). $^1$H NMR: (DMSO-d$_6$) δ 9.40 (d, J=1.0 Hz, 1H), 9.10 (d, J=5.1 Hz, 1H), 8.05 (dd, J=5.1, 1.3 Hz, 1H), 4.39 (q, J=7.1 Hz, 2H), 1.35 (t, J=7.1 Hz, 3H); MS: 153 [M+H]$^+$; TLC: 40% hexane in EtOAc: R$_f$: 0.40.

Preparation of Intermediate 20

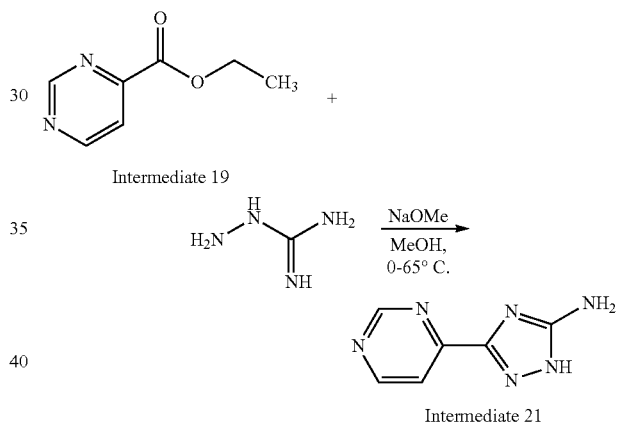

General Procedure 13 was followed to obtain crude Intermediate 20 (950 mg, 86%). $^1$H NMR: (DMSO-d$_6$) δ 9.43 (s, 1H), 9.26 (s, 2H), 4.39 (q, J=7.1 Hz, 2H), 1.35 (t, J=7.1 Hz, 3H); TLC: 40% EtOAc in hexane: R$_f$: 0.50.

Preparation of Intermediate 21

General Procedure 14

General Procedure 14 was followed in the preparation of Intermediate 21.

General Procedure 14

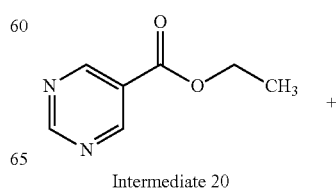

Intermediate 19 (1.6 g, 10.5 mmol) was added dropwise to a vigorously stirring mixture of aminoguanidine sulfate (10.3 g, 42.1 mmol, 4 eq) in freshly prepared NaOMe (using 968 mg, 42.1 mmol of Na in 28 mL of dry MeOH) at 0° C. The resulting mixture was heated to reflux for 20 h. The mixture was then cooled to RT, carefully poured over ice cold water (20 mL) and concentrated in vacuo. The crude residue was purified over neutral alumina using 4-10% MeOH—CHCl$_3$ as the eluent to give Intermediate 21 (500 mg, 26%). MS: 163 [M+H]$^+$; TLC: 20% MeOH in CHCl$_3$: R$_f$: 0.20.

Preparation of Intermediate 22

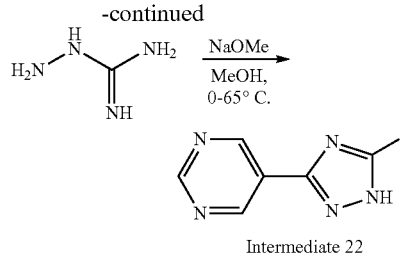

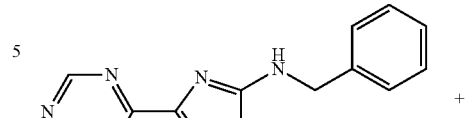

General Procedure 14 was followed to obtain Intermediate 22 (500 mg, 45%). $^1$H NMR: (DMSO-$d_6$) δ 12.44 (br s, 1H), 9.17-9.18 (m, 3H), 6.32 (s, 2H); TLC: 20% MeOH in CHCl$_3$: $R_f$: 0.20.

Preparation of Intermediate 23

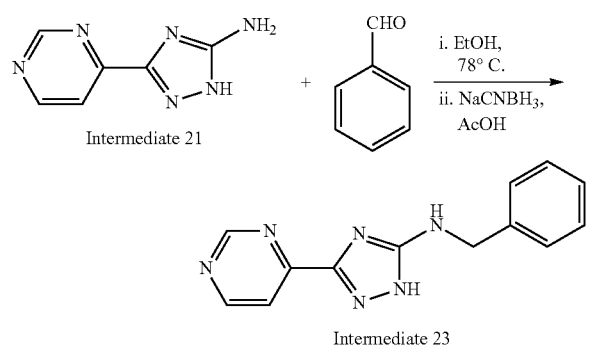

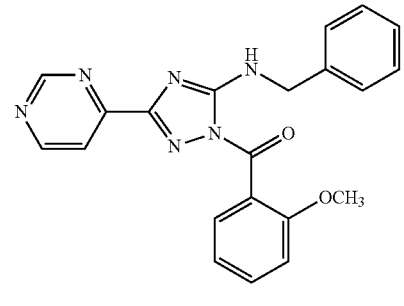

General Procedure 10 was followed to obtain Intermediate 23 (210 mg, 34%). $^1$H NMR: (DMSO-$d_6$) δ 12.80 (s, 1H), 9.18 (s, 1H), 8.83 (s, 1H), 7.92 (d, J=4.4 Hz, 1H), 7.25-7.40 (m, 5H), 4.44 (d, J=5.7 Hz, 2H); TLC: EtOAc: $R_f$: 0.30.

Preparation of Intermediate 24

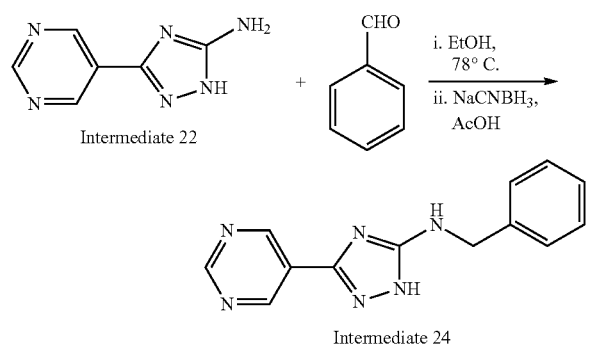

General Procedure 10 was followed to obtain Intermediate 24 (160 mg, 20%). MS: 253 [M+H]$^+$; TLC: EtOAc: $R_f$: 0.30.

Preparation of Compound 16

General Procedure 11

General Procedure 11 was followed in the preparation of Compound 16.

General Procedure 11

2-Methoxybenzoyl chloride (72 μL, 0.54 mmol, 2 eq) was added to a solution of Intermediate 23 (70 mg, 0.27 mmol) in Et$_3$N (0.18 mL, 1.35 mmol) and DCM (3 mL) at 0° C. The resulting mixture was allowed to stir at RT for 2 h. The reaction mixture was then diluted with water (5 mL) and extracted with DCM (3×15 mL). The combined organic layers were washed with saturated aqueous NaHCO$_3$ (10 mL), water (2×5 mL), brine (15 mL), dried over Na$_2$SO$_4$, filtered and concentrated in vacuo. The crude material was purified by column chromatography over silica gel (100-200 mesh) using a gradient mixture of 0-70% EtOAc-hexane as the eluent to afford Compound 16 (45 mg, 29%). $^1$H NMR: (DMSO-$d_6$) δ 9.21 (s, 1H), 8.90 (d, J=5.1 Hz, 1H), 8.59 (t, J=6.0 Hz, 1H), 7.93 (d, J=5.1 Hz, 1H), 7.08-7.60 (m, 10H), 4.72 (d, J=5.7 Hz, 2H), 3.77 (s, 3H); MS: 387 [M+H]$^+$; MP: 192-195° C.; TLC: 40% hexane in EtOAc: $R_f$: 0.30.

EXAMPLE 28

Preparation of Compound 17

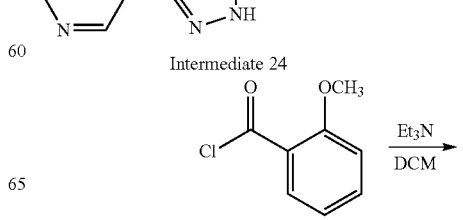

-continued

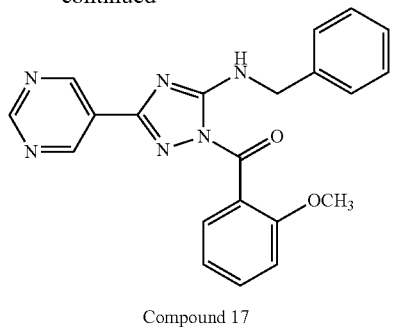

Compound 17

General Procedure 11 was followed by preparative HPLC purification to obtain Compound 17 (30 mg, 16%). $^1$H NMR: (DMSO-$d_6$) δ 9.26 (s, 1H), 9.11 (s, 2H), 8.64 (t, J=6.3 Hz, 1H), 7.07-7.60 (m, 9H), 4.71 (d, J=6.3 Hz, 2H), 3.78 (s, 3H); MS: 387 [M+H][1]; MP: 154-157° C.; TLC: 40% EtOAc in hexane: $R_f$: 0.20.

EXAMPLE 29

Preparation of Compound 18

General Scheme V. A synthetic scheme useful for synthesis of compounds described herein including Compound 18 is disclosed in General Scheme V following, wherein the terms "$R^x$", "$R^y$", and "$R^z$" are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted heterocycloalkenyl, substituted or unsubstituted aryl, or substituted or unsubstituted heteroaryl, or other groups obvious to those skilled in the art. General Scheme V

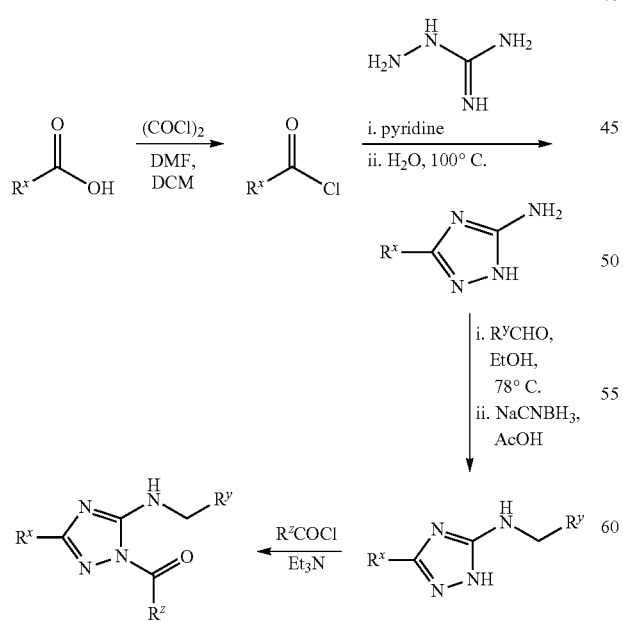

A description of the synthesis of Intermediates 25, 26 and Compound 18 follows.

Preparation of Intermediate 25

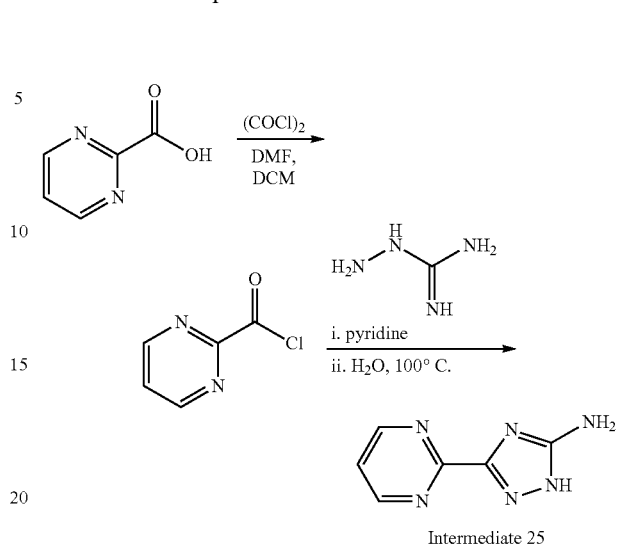

Intermediate 25

Oxalyl chloride (2.36 mL, 24.2 mmol, 1.5 eq) and a catalytic quantity of DMF were added to a solution of pyrimidine-2-carboxylic acid (2 g, 16.1 mmol) in dry DCM (30 mL) at 0° C. The resulting mixture was allowed to warm to RT and stir for 3 h. The volatiles were removed in vacuo and the residue was thoroughly dried to afford pyrimidine-2-carboxylic acid chloride (2.1 g, 14.8 mmol) as a black solid. The crude material was added portion-wise to a solution of aminoguanidine sulfate (5.5 g, 22.2 mmol, 1.5 eq) in pyridine (20 mL) at 0° C. The resulting mixture was allowed to warm to RT and stir for 14 h. The mixture was then neutralized with saturated aqueous NaHCO$_3$, extracted with t-BuOH (5×50 mL), dried over Na$_2$SO$_4$, filtered and concentrated in vacuo. The crude material was dissolved in water (45 mL) and the resulting solution was heated to 100° C. for 24 h. The reaction mixture was then cooled to RT, extracted with t-BuOH (5×30 mL), dried over Na$_2$SO$_4$, filtered and concentrated in vacuo to afford Intermediate 25 (650 mg, 25%) as off-white solid. TLC: 30% MeOH in CHCl$_3$: $R_f$: 0.20.

Preparation of Intermediate 26

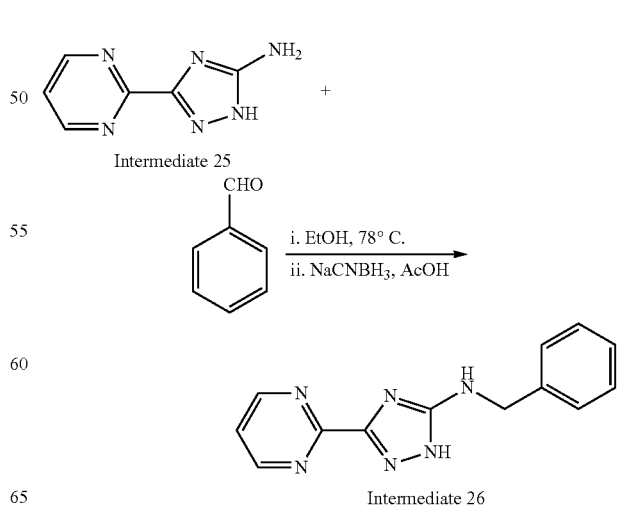

Intermediate 26

General Procedure 10 was followed to obtain Intermediate 26 (120 mg, 17%). MS: 253 [M+H]+; TLC: EtOAc: $R_f$: 0.30.

Preparation of Compound 18

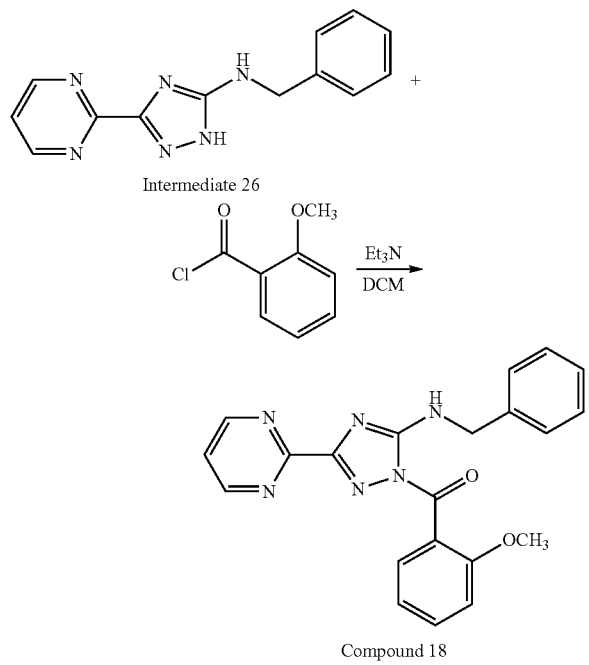

Compound 18

General Procedure 11 was followed to obtain Compound 18 (32 mg, 21%). $^1$H NMR: (DMSO-$d_6$) δ 8.86 (d, J=5.1 Hz, 2H), 8.44 (t, J=6.0 Hz, 1H), 7.08-7.59 (m, 10H), 4.73 (d, J=6.3 Hz, 2H), 3.77 (s, 3H); MS: 387 [M+H]+; MP: 203-205° C.; TLC: 40% hexane in EtOAc: $R_f$: 0.40.

EXAMPLE 30

Preparation of Compound 19

General Scheme VI. A synthetic scheme useful for synthesis of compounds described herein including Compound 19 is disclosed in General Scheme VI following, wherein the terms "$R^x$", "$R^y$", and "$R^z$" are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted heterocycloalkenyl, substituted or unsubstituted aryl, or substituted or unsubstituted heteroaryl, or other groups obvious to those skilled in the art.

General Scheme VI

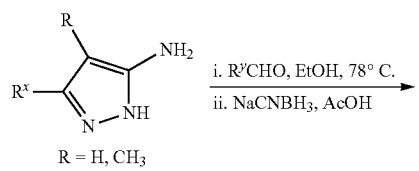

R = H, CH$_3$

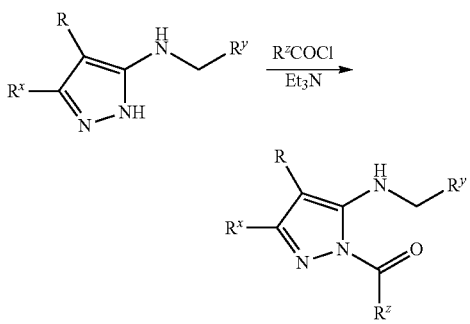

Preparation of Intermediate 27

General Procedure 10 was followed in the preparation of Intermediate 27.

General Procedure 10

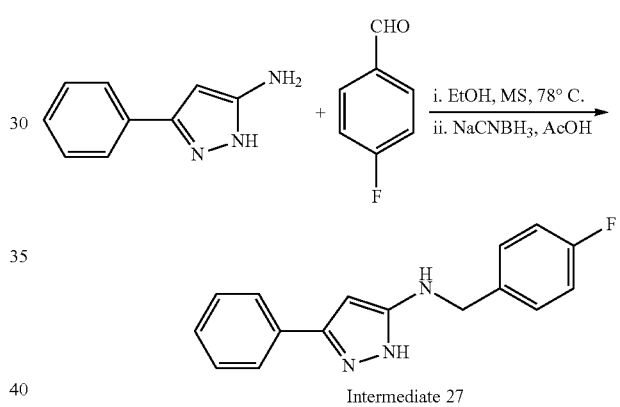

Intermediate 27

4-Fluorobenzaldehyde (0.54 mL, 5.03 mmol, 2 eq) and molecular sieves (4 Å powder) were added to a solution of 3-amino-5-phenylpyrazole (400 mg, 2.51 mmol) in EtOH (20 mL) at RT and the resulting mixture was heated to reflux. After 8 h, the reaction mixture was cooled to 0° C. and AcOH (0.4 mL) and NaCNBH$_3$ (316 mg, 5.03 mmol, 2 eq) were added. The mixture was then allowed to warm to RT and stir for 15 h. The solvent was evaporated and the residue was dissolved in EtOAc (100 mL) and filtered through a Celite pad to remove inorganic materials. The filtrate was then washed with saturated aqueous NaHCO$_3$ (2×20 mL), water (20 mL), brine (20 mL), dried over Na$_2$SO$_4$, filtered and concentrated in vacuo. The crude material was purified by column chromatography over silica gel (100-200 mesh) by using a solvent gradient of 0-50% EtOAc-petroleum ether as the eluent to afford Intermediate 27 (240 mg, 36%) as an off white solid. MS: 268 [M+H]+; TLC: EtOAc: $R_f$: 0.60.

Preparation of Compound 19

General Procedure 15 was followed in the preparation of Compound 19.

General Procedure 15

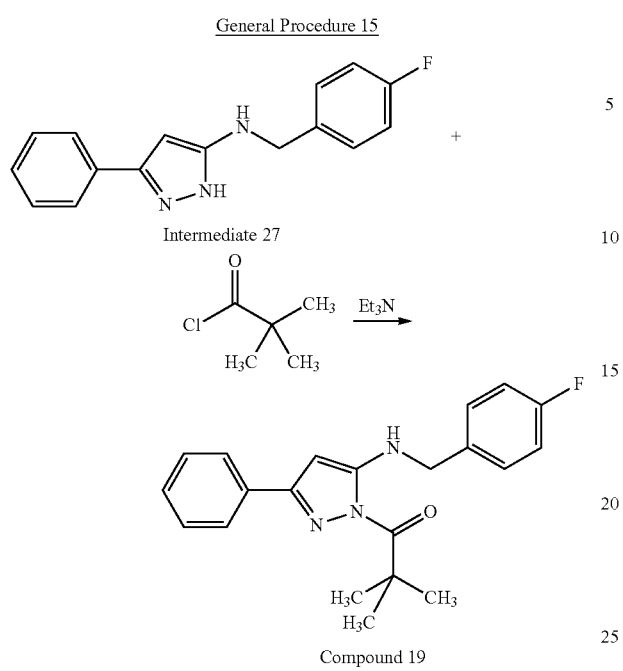

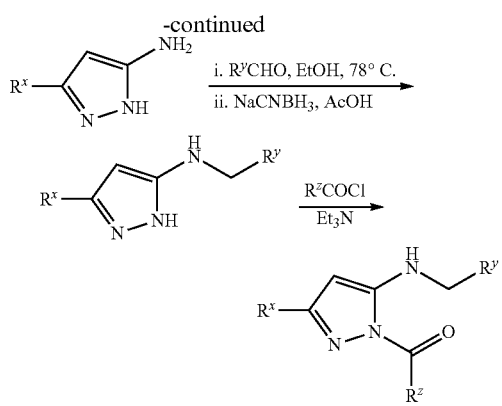

Pivaloyl chloride (32 µL, 0.26 mmol, 1.2 eq) was added to a solution of Intermediate 27 (60 mg, 0.22 mmol) in triethylamine (3 mL) at RT and stirred for 3 h. The reaction mixture was diluted with water (5 mL) and extracted with EtOAc (20 mL). The organic layer was washed with water (2×5 mL), saturated aqueous NaHCO$_3$ (5 mL), brine (5 mL), dried over Na$_2$SO$_4$, filtered and concentrated in vacuo. The crude compound was purified by column chromatography over silica gel (100-200 mesh) by using a gradient mixture of 0-10% EtOAc-hexane as the eluent to afford Compound 19 (23 mg, 29%). $^1$H NMR: (DMSO-d$_6$) δ 7.79-7.84 (m, 3H), 7.37-7.49 (m, 5H), 7.17 (t, J=8.8 Hz, 2H), 5.89 (s, 1H), 4.38 (d, J=6.2 Hz, 2H), 1.49 (s, 9H); MS: 352 [M+H]$^+$; TLC: 20% EtOAc in hexane: R$_f$: 0.60.

EXAMPLE 31

Preparation of Compound 20

General Scheme VII. A synthetic scheme useful for synthesis of compounds described herein including Compound 20 is disclosed in General Scheme VII following, wherein the terms "R$^x$", "R$^y$", and "R$^z$" are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted heterocycloalkenyl, substituted or unsubstituted aryl, or substituted or unsubstituted heteroaryl, or other groups obvious to those skilled in the art.

A description of the syntheses of Intermediates 28-31 and Compound 20 follows.

Preparation of Intermediate 28
[General Procedure 16]

General Procedure 16 was followed in the preparation of Intermediate 28.

General Procedure 16

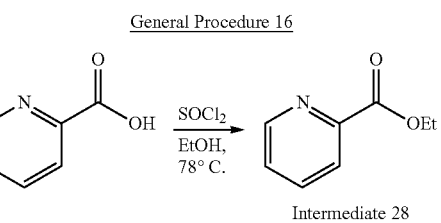

Thionyl chloride (5.4 mL, 73.2 mmol, 3 eq) was added to a solution of picolinic acid (3 g, 24.4 mmol) in EtOH (50 mL) at 0° C. The resulting mixture was heated to reflux and allowed to stir for 2 h. The mixture was then cooled and the solvent was evaporated. The resulting residue was poured into saturated aqueous NaHCO$_3$ and extracted with EtOAc (2×50 mL). The combined organic layers were dried over Na$_2$SO$_4$, filtered and concentrated in vacuo. The crude material was purified by column chromatography over silica gel (100-200 mesh) by using DCM as the eluent to afford Intermediate 28 (3 g, 81%) as a colorless liquid. MS: 152 [M+H]$^+$; TLC: 10% MeOH/NH$_3$ in CHCl$_3$: R$_f$: 0.70.

Preparation of Intermediate 29
[General Procedure 17]

General Procedure 17 was followed in the preparation of Intermediate 29.

General Scheme VII

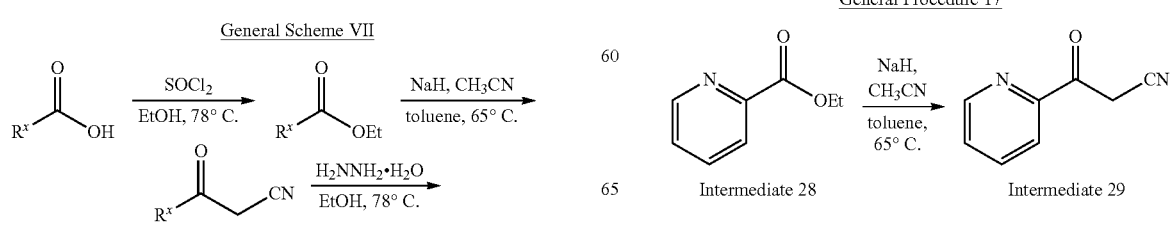

General Procedure 17

A solution of Intermediate 28 (3 g, 19.6 mmol) and CH₃CN (0.8 mL, 19.6 mmol, 1 eq) in dry toluene (10 mL) was slowly added to a mixture of NaH (784 mg, 19.6 mmol, 1 eq, 60% in mineral oil) in toluene (50 mL) at 65° C. The resulting mixture was allowed to stir at 65° C. for 16 h. The reaction mixture was then cooled to RT and quenched with ice cold water (20 mL). The resulting solid was filtered to afford Intermediate 29 (1.5 g, 53%) as a brown solid. $^1$H NMR: (CDCl₃) δ 8.70 (d, J=4.8 Hz, 1H), 8.12 (d, J=7.5 Hz, 1H), 7.90-7.94 (m, 1H), 7.56-7.60 (m, 1H), 4.41 (s, 2H); MS: 147 [M+H]$^+$; TLC: EtOAc: R$_f$: 0.40.

Preparation of Intermediate 30
[General Procedure 18]

General Procedure 18 was followed in the preparation of Intermediate 30.

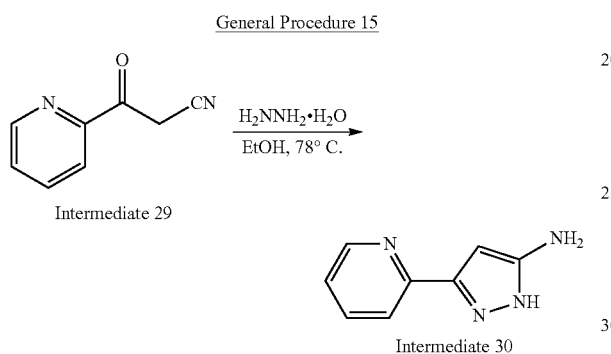

Hydrazine hydrate (0.34 mL, 6.8 mmol, 1 eq) was added to a solution of Intermediate 29 (1 g, 6.8 mmol) in EtOH (30 mL) at RT. The mixture was then heated to reflux and allowed to stir for 20 h. The solvent was then evaporated. The resulting crude material was triturated with Et₂O (2×20 mL) and dried under vacuum to afford Intermediate (700 mg, 64%) as a brown liquid. $^1$H NMR: (DMSO-d₆) δ 8.53 (d, J=4.4 Hz, 1H), 7.78 (d, J=4.4 Hz, 2H), 7.23-7.26 (m, 1H), 5.95 (s, 1H), 4.84 (br s, 2H); MS: 161 [M+H]$^+$; TLC: EtOAc: R$_f$: 0.20.

Preparation of Intermediate 31

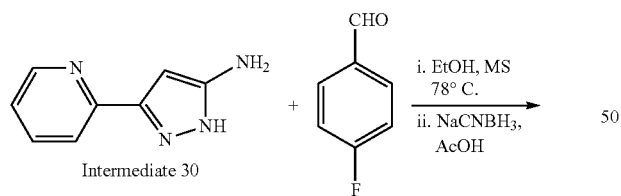

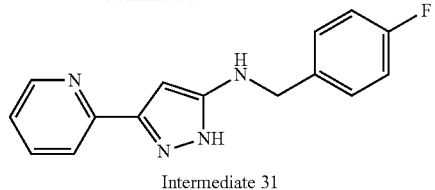

Intermediate 31

General Procedure 10 was followed to afford Intermediate 31 (450 mg). MS: 269 [M+H]$^+$; TLC: EtOAc: R$_f$: 0.40.

Preparation of Compound 20

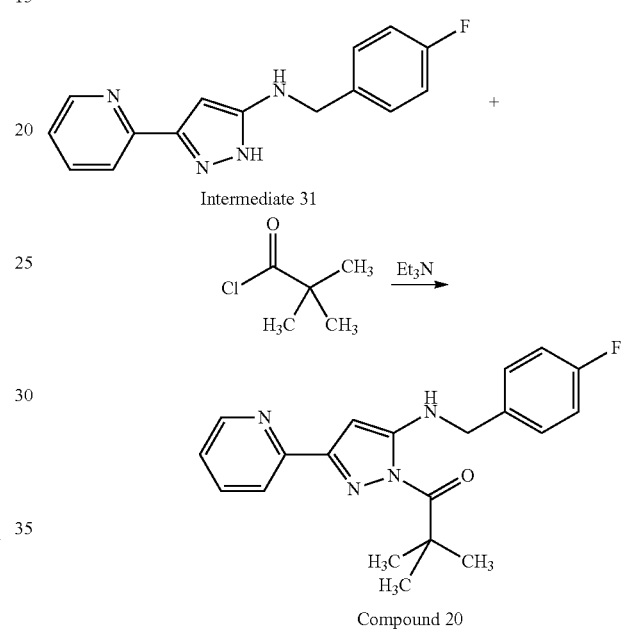

General Procedure 11 was followed to afford Compound 20 (40 mg, 30%). $^1$H NMR: (DMSO-d₆) δ 8.58 (d, J=4.4 Hz, 1H), 7.86-7.98 (m, 3H), 7.38-7.46 (m, 3H), 7.18 (t, J=8.8 Hz, 2H), 5.84 (s, 1H), 4.40 (d, J=6.2 Hz, 2H), 1.50 (s, 9H); MS: 353 [M+H]$^+$; MP: 102-103° C.; TLC: 20% EtOAc in hexane: R$_f$: 0.60.

EXAMPLE 33

General Scheme VIII

A synthetic scheme useful for synthesis of compounds described herein is disclosed in General Scheme VIII following, wherein the terms "Ar," "R$^1$" and "R$^2$" are as defined in Example 1.

General Scheme VIII

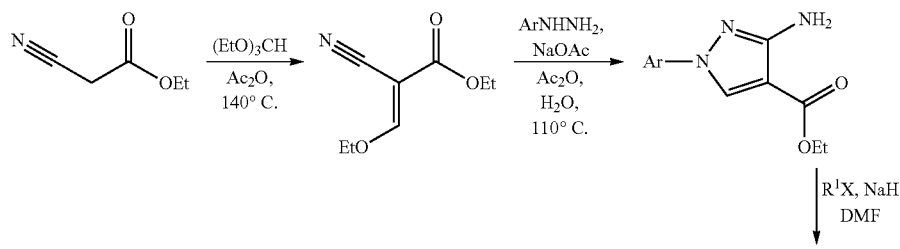

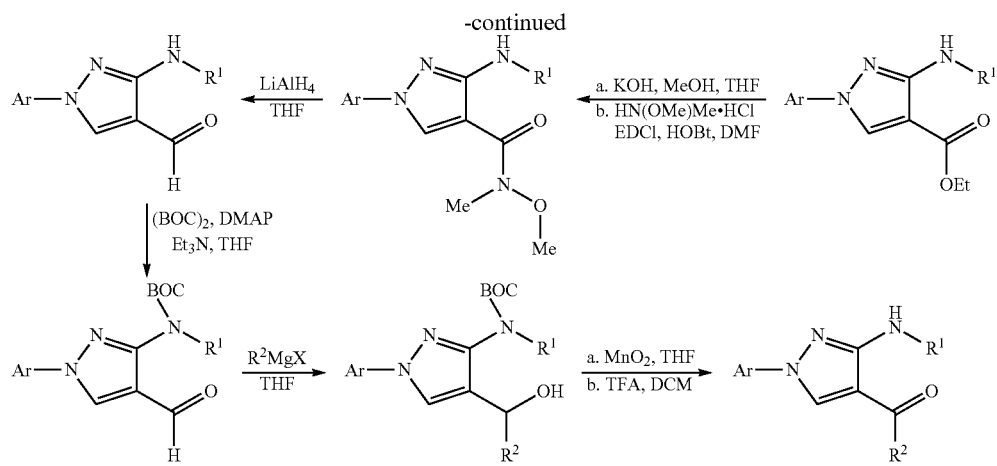

EXAMPLE 34

Preparation of Intermediate 32

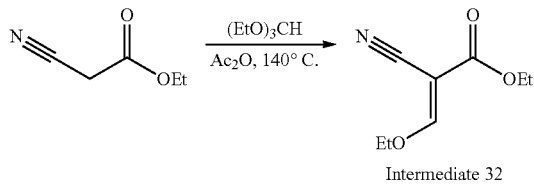 [SMILES: "(EtO)3CH" ; CCOC(=O)CC#N ; CCO/C=C(\C#N)C(=O)OCC]

Intermediate 32

A solution of ethyl cyanoacetate (20 g, 176.8 mmol) and triethyl orthoformate (29.4 mL, 176.8 mmol) in acetic anhydride (100 mL) was heated to 140° C. and allowed to stir for 5 h. The solvent was then evaporated to afford crude Intermediate 32 (23 g, 76%) as a low melting solid. MS: 170 [M+H]$^+$; TLC: 30% EtOAc in hexane: R$_f$: 0.40.

EXAMPLE 35

Preparation of Intermediate 33

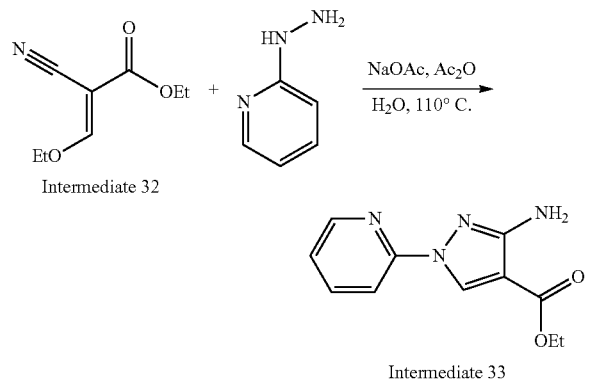

Sodium acetate (8.2 g, 100 mmol, 2 eq) was added to a solution of Intermediate 32 (8.45 g, 50.0 mmol) and 2-hydrazinopyridine (5 g, 45.5 mmol, 0.9 eq) in AcOH (100 mL) and water (20 mL). The resulting mixture was heated at 110° C. and allowed to stir for 16 h. The mixture was then allowed to cool and ice-cold water was added. The precipitate was collected by filtration and washed with Et$_2$O and dried under vacuum to afford Intermediate (4 g, 38%) as a pale yellow solid. $^1$H NMR: (DMSO-d$_6$) δ 8.48-8.49 (m, 1H), 8.00-8.04 (m, 1H), 7.87 (d, J=8.3 Hz, 1H), 7.79 (s, 1H), 7.65 (br s, 2H), 7.33-7.36 (m, 1H), 4.22 (q, J=7.0 Hz, 2H), 1.28 (t, J=7.0 Hz, 3H); MS: 233 [M+H]$^+$; TLC: 15% EtOAc in hexane: R$_f$: 0.50.

EXAMPLE 36

Preparation of Compound 21

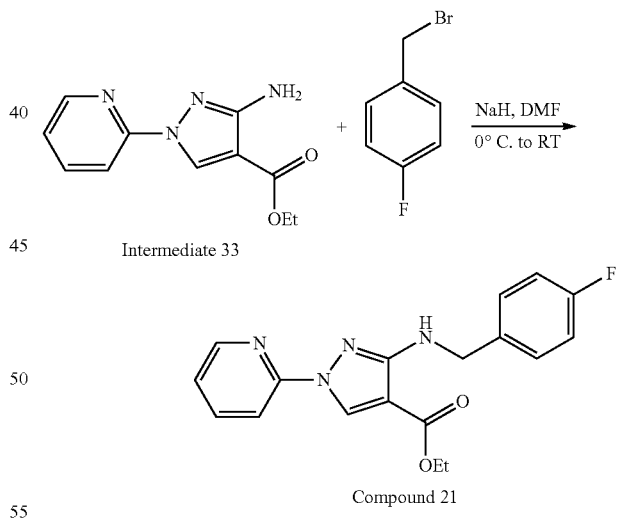

Sodium hydride (603 mg, 15.1 mmol, 1 eq, 60% in mineral oil) was added to a solution of Intermediate 33 (3.5 g, 15.1 mmol) in DMF (300 mL) at 0° C. After 30 minutes, a solution of 4-fluorobenzyl bromide (2.85 g, 15.1 mmol, 1 eq) in DMF (50 mL) was added and the resulting mixture was allowed to warm to RT. After 5 h, the reaction mixture was diluted with water (100 mL) and extracted with EtOAc (3×100 mL). The combined organic layers were washed with water (5×50 mL), brine (50 mL), dried over Na$_2$SO$_4$, filtered and concentrated in vacuo. The crude material was purified by column chromatography over silica gel (100-200 mesh) by using a gradient mixture of 0-5% EtOAc-hexane as the eluent to afford a partially pure product. The material was then recrystallized from Et₂O and pentane to afford Compound 21 (2.8 g, 55%) as a pale yellow solid. $^1$H NMR: (DMSO-d$_6$) δ 9.50 (t, J=6.6 Hz, 1H), 8.45-8.46 (m, 1H), 8.00-8.05 (m, 1H), 7.82-7.89 (m, 2H), 7.24-7.38 (m, 3H), 7.11 (t, J=8.8 Hz, 2H), 4.88 (d, J=6.6 Hz, 2H), 4.17 (q, J=7.0 Hz, 2H), 1.24 (t, J=7.0 Hz, 3H); MS: 341 [M+H]$^+$; MP: 99-100° C.; TLC: 15% EtOAc in hexane: R$_f$: 0.40.

EXAMPLE 37

Trans-corneal Permeability of Compounds 4 and 22

In this example, trans-corneal permeability of compounds are measured in-vitro across excised rabbit corneas. Excised rabbit cornea are acquired from Pel-Freez and delivered in DMEM culture media on ice overnight. The test apparatus is a curved 9 mm Franz chamber (Permegear) suitable for rabbit eyes. Test compound is prepared in PBS buffer. The compound solution is added to the donor chamber of the Franz chamber and the entire apparatus placed in an incubator at 37° C. for four hours. During incubation and at every subsequent hour, a sample is removed from the receiver chamber and analyzed by HPLC (Shimadzu Prominence) using a C18 column (Phenomenex 00F-4605-E0) in reverse phase with acetonitrile in water. The apparent permeability coefficient P$_{app}$(cm/s) is calculated as $$P_{app} = \frac{1}{AC_D} \times \frac{dM}{dt}$$

where dM/dt is the flux (nmol/s) across the cell layers or cornea, A is the exposed surface area (cm$^2$) of the insert membrane of rabbit cornea, and C$_0$ is the initial drug concentration (μM) in the donor compartment.

In Table E following, measured trans-corneal permeability P$_{app}$ in units of cm/s is presented for example compounds.

TABLE E

| Cmpd No. | P$_{app}$ |
|---|---|
| 4 | 2.5 × 10$^{-6}$ |
| 22 | 5.7 × 10$^{-6}$ |

EXAMPLE 38

Pharmacokinetics in Mice

In this example, pharmacokinetics in mice is presented for series of example compounds #4, #23, #24, #25, #26. Each compound is administered intravenously (i.v.) as a single dose via tail vein or orally (p.o.) as a single dose via gastric gavage to male CD-1 mice of nominal weights between 20 g and 26 g. Nominal doses are 1 mg/kg and 5 mg/kg for i.v. and p.o., respectively. In some examples (dose type A), both p.o. and i.v. doses are prepared by dissolving the test compound in 5% dimethyl acetamide and diluted in tetraethylene glycol for a final concentration of 0.25 mg/mL. In other examples (dose type B), i.v. doses are prepared by dissolving test compounds in 20% dimethyl acetamide, 40% polyethylene glycol and 40% phosphate buffered saline, and p.o. doses are prepared by dissolving test compounds in carboxymethyl cellulose suspension (1% by weight) in water and 2.5% dimethyl acetamide.

Animals are housed in standard holding cages with food and water available ad libitum except for animals used for p.o. dosing which are fasted overnight prior to dosing. Samples are taken in triplicate via cardiac puncture at times prior to dosing and at 0.083 (i.v. only), 0.25, 0.5, 1, 2, 4, 8, and 24 hours after administration. Plasma is obtained by centrifuge and stored frozen until analyzed by LC-MS/MS using a Shimadzu VP System HPLC coupled to a Applied Biosystems MDS SCIEX API 3000 triple quadrapole MS. Assay results are calibrated using reference samples prepared in a range between 1.5 and 5000 ng/mL.

Pharmacokinetic parameters are calculated from mean concentration values using a non-compartmental analysis as described in the following and as apparent to those of ordinary skill in the art. Half-lives (t$_{1/2}$) and elimination rate constants (λ) are determined by log linear regression using equal weighting on the last three finite sample time points. Concentration at time zero (C$_0$) for the i.v. data is established by the extrapolation of log linear regression using equal weighting on the first three sample time points. Area under the curve (AUC) values are calculated using linear trapezoidal integration. Systemic clearance (CL) is calculated as the ratio of dosage and AUC. The apparent volume of distribution (V$_d$) is calculated as the ratio of CL and λ. Percent oral bioavailability (% F) is determined from the ratio of i.v. and p.o. AUC values weighted by dosage.

In Table F following resulting pharmacokinetic parameters are listed for five example compounds, rounded to the nearest significant digit.

TABLE F

| Cmpd No | 4 | 23 | 24 | 25 | 26 |
|---|---|---|---|---|---|
| Dose type | A | A | A | B | B |
| i.v. t$_{1/2}$ (h) | 1 | 0.5 | 1 | 0.3 | 0.3 |
| i.v. C$_0$ (ng/ml) | 300 | 400 | 200 | 100 | 200 |
| i.v. AUC (h · ng/ml) | 100 | 100 | 200 | 40 | 50 |
| i.v. V$_d$ (ml/kg) | 10000 | 5000 | 8000 | 6000 | 5000 |
| i.v. CL (ml/kg/h) | 10000 | 8000 | 5000 | 10000 | 10000 |
| p.o. t$_{1/2}$ (h) | 6 | 0.6 | 1 | >0.3 | >0.3 |
| p.o. AUC (h · ng/ml) | 300 | 80 | 600 | 10 | 20 |
| % F | 60 | 10 | 70 | 9 | 8 |

The contents of all references, patents, and published applications cited herein are hereby incorporated by reference in their entirety and for all purposes.

While the invention has been described in detail with reference to certain preferred embodiments thereof, it will be understood that modifications and variations are within the spirit and scope of that which is described and claimed.

What is claimed is:
1. A compound with structure of Formula (V):

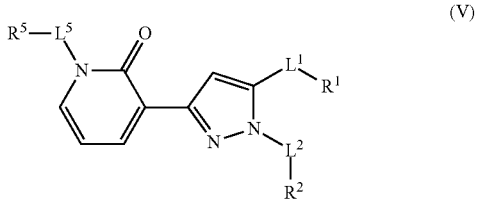

or pharmaceutically acceptable salt thereof;

wherein
L¹ is —NR⁷—;
L² a bond, substituted or unsubstituted alkylene, —SO₂—, or —C(=O)—, provided that if L² is a bond, R² is hydrogen;
L⁵ is a bond or substituted or unsubstituted alkylene, provided that if L⁵ is a bond, R⁵ is hydrogen;
R¹ is hydrogen, substituted or unsubstituted alkyl, substituted or unsubstituted heteroalkyl, ubstituted or unsubstituted heterocycloalkyl, substituted or unsubstituted heterocycloalkenyl, substituted or unsubstituted aryl, substituted or unsubstituted fused ring aryl, or substituted or unsubstituted heteroaryl;
R² and R⁵ are independently hydrogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl; and
R⁷ is hydrogen, or substituted or unsubstituted alkyl.

2. The compound according to claim 1, wherein L² is substituted or unsubstituted alkylene or —C(O)—, and R² is substituted or unsubstituted alkyl, substituted or unsubstituted cycloalkyl, substituted or unsubstituted cycloalkenyl, substituted or unsubstituted heteroalkyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl.

3. The compound according to claim 2, wherein R² is substituted or unsubstituted aryl or substituted or unsubstituted heteroaryl.

4. The compound according to claim 3, wherein R² is heteroaryl selected from the group consisting of substituted or unsubstituted pyridyl, substituted or unsubstituted pyridazinyl, substituted or unsubstituted pyrimidinyl, substituted or unsubstituted thienyl, and substituted or unsubstituted furyl.

5. The compound according to claim 2, wherein R² is substituted or unsubstituted alkyl, substituted or unsubstituted cycloalkyl, or substituted or unsubstituted heterocycloalkyl.

6. The compound according to claim 5, wherein R² is heterocycloalkyl selected from the group consisting of substituted or unsubstituted oxanyl, substituted or unsubstituted oxetanyl, and substituted or unsubstituted morpholinyl.

7. The compound according to claim 2, wherein R² is fused ring aryl selected from the group consisting of substituted or unsubstituted benzodioxinyl and substituted or unsubstituted naphthyl.

8. The compound according to claim 1, wherein R¹ is hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl.

9. The compound according to claim 8, wherein R¹ is substituted alkyl having at least one substituent comprising heteroaryl selected from the group consisting of substituted or unsubstituted pyridyl, substituted or unsubstituted pyridazinyl, substituted or unsubstituted pyrimidinyl, substituted or unsubstituted thienyl, and substituted or unsubstituted furyl.

10. The compound according to claim 9, wherein R¹ is substituted alkyl having at least one substituent comprising chloro-substituted thienyl.

11. The compound according to claim 8, wherein R¹ is substituted alkyl having at least one substituent comprising heterocycloalkyl selected from the group consisting of substituted or unsubstituted morpholinyl, substituted or unsubstituted oxanyl, and substituted or unsubstituted oxetanyl.

12. The compound according to claim 8, wherein R¹ is substituted alkyl having at least one substituent comprising fused ring aryl selected from the group consisting of substituted or unsubstituted benzodioxinyl and substituted or unsubstituted naphthyl.

13. The compound according to claim 2, wherein L⁵ is substituted or unsubstituted alkylene, and R⁵ is substituted or unsubstituted aryl, substituted or unsubstituted fused ring aryl, or substituted or unsubstituted heteroaryl.

14. The compound according to claim 13, wherein R⁵ is heteroaryl selected from the group consisting of substituted or unsubstituted pyridyl, substituted or unsubstituted pyridazinyl, substituted or unsubstituted pyrimidinyl, substituted or unsubstituted thienyl, and substituted or unsubstituted furyl.

15. The compound according to claim 13, wherein R⁵ is fused ring aryl selected from the group consisting of substituted or unsubstituted benzodioxinyl and substituted or unsubstituted naphthyl.

16. The compound according to claim 2, wherein L⁵ is substituted or unsubstituted alkylene, and R⁵ is substituted or unsubstituted heterocycloalkyl.

17. The compound according to claim 16, wherein R⁵ is heterocycloalkyl selected from the group consisting of substituted or unsubstituted morpholinyl, substituted or unsubstituted oxanyl, and substituted or unsubstituted oxetanyl.

18. A pharmaceutical composition comprising a pharmaceutically acceptable excipient in combination with a compound according to claim 1, or a compound as set forth below:

Compound 1, 3-(5-amino-1H-pyrazol-3-yl)-1,2-dihydropyridin-2-one;
Compound 2, 3-(5-[(5-chlorothiophen-2-yl)methyl]amino-1H-pyrazol-3-yl)-1,2-dihydropyridin-2-one;
Compound 3, 3-(5-[(5-chlorothiophen-2-yl)methyl]amino-1-(2,2-dimethylpropanoyl)-1H-pyrazol-3-yl)-1,2-dihydropyridin-2-one;
Compound 4, 3-(5-[(5-chlorothiophen-2-yl)methyl]amino-1-[(furan-3-yl)carbonyl]-1H-pyrazol-3-yl)-1,2-dihydropyridin-2-one;
Compound 5, 3-(5-[(5-chlorothiophen-2-yl)methyl]amino-1-[(furan-3-yl)carbonyl]-1H-pyrazol-3-yl)-1-(thiophen-2-ylmethyl)-1,2-dihydropyridin-2-one;
Compound 6, 3-(5-[(5-chlorothiophen-2-yl)methyl]amino-1-[(furan-3-yl)carbonyl]-1H-pyrazol-3-yl)-1-(pyridin-4-ylmethyl)-1,2-dihydropyridin-2-one;
Compound 23, 3-(5-[(5-chlorothiophen-2-yl)methyl]amino-1-[(furan-3-yl)carbonyl]-1H-pyrazol-3-yl)-1-methyl-1,2-dihydropyridin-2-one;
Compound 25, 3-(5-[(5-chlorothiophen-2-yl)methyl]amino-1-[(furan-3-yl)carbonyl]-1H-pyrazol-3-yl)-1-(pyridin-2-ylmethyl)-1,2-dihydropyridin-2-one;
Compound 26, 3-(5-[(5-chlorothiophen-2-yl)methyl]amino-1-[(furan-3-yl)carbonyl]-1H-pyrazol-3-yl)-1-(furan-2-ylmethyl)-1,2-dihydropyridin-2-one;
Compound 27, 1-[(2-chlorophenyl)methyl]-3-(5-[(5-chlorothiophen-2-yl)methyl]amino-1-(2,2-dimethylpropanoyl)-1H-pyrazol-3-yl)-1,2-dihydropyridin-2-one;

Compound 28, 1-[(2-chlorophenyl)methyl]-3-(5-[(5-chlorothiophen-2-yl)methyl]amino-1-[(2-methoxyphenyl)carbonyl]-1H-pyrazol-3-yl)-1,2-dihydropyridin-2-one;

Compound 29, 1-[(2-chlorophenyl)methyl]-3-(5-[(5-chlorothiophen-2-yl)methyl]amino-1-[(furan-3-yl)carbonyl]-1H-pyrazol-3-yl)-1,2-dihydropyridin-2-one;

Compound 30, 1-[(2-chlorophenyl)methyl]-3-(5-[(5-chlorothiophen-2-yl)methyl]amino-1H-pyrazol-3-yl)-1,2-dihydropyridin-2-one;

Compound 31, 1-[(3-chlorophenyl)methyl]-3-(5-[(5-chlorothiophen-2-yl)methyl]amino-1-(2,2-dimethylpropanoyl)-1H-pyrazol-3-yl)-1,2-dihydropyridin-2-one;

Compound 32, 1-[(3-chlorophenyl)methyl]-3-(5-[(5-chlorothiophen-2-yl)methyl]amino-1-[(2-methoxyphenyl)carbonyl]-1H-pyrazol-3-yl)-1,2-dihydropyridin-2-one;

Compound 33, 1-[(3-chlorophenyl)methyl]-3-(5-[(5-chlorothiophen-2-yl)methyl]amino-1-[(furan-3-yl)carbonyl]-1H-pyrazol-3-yl)-1,2-dihydropyridin-2-one;

Compound 34, 1-[(3-chlorophenyl)methyl]-3-(5-[(5-chlorothiophen-2-yl)methyl]amino-1H-pyrazol-3-yl)-1,2-dihydropyridin-2-one;

Compound 35, 1-[(4-chlorophenyl)methyl]-3-(5-[(5-chlorothiophen-2-yl)methyl]amino-1-(2,2-dimethylpropanoyl)-1H-pyrazol-3-yl)-1,2-dihydropyridin-2-one;

Compound 36, 1-[(4-chlorophenyl)methyl]-3-(5-[(5-chlorothiophen-2-yl)methyl]amino-1-[(2-methoxyphenyl)carbonyl]-1H-pyrazol-3-yl)-1,2-dihydropyridin-2-one;

Compound 37, 1-[(4-chlorophenyl)methyl]-3-(5-[(5-chlorothiophen-2-yl)methyl]amino-1-[(furan-3-yl)carbonyl]-1H-pyrazol-3-yl)-1,2-dihydropyridin-2-one;

Compound 38, 1-[(4-chlorophenyl)methyl]-3-(5-[(5-chlorothiophen-2-yl)methyl]amino-1H-pyrazol-3-yl)-1,2-dihydropyridin-2-one;

Compound 39, 1-[(5-chlorothiophen-2-yl)methyl]-3-(5-[(5-chlorothiophen-2-yl)methyl]amino-1-(2,2-dimethylpropanoyl)-1H-pyrazol-3-yl)-1,2-dihydropyridin-2-one;

Compound 40, 1-[(5-chlorothiophen-2-yl)methyl]-3-(5-[(5-chlorothiophen-2-yl)methyl]amino-1-[(2-methoxyphenyl)carbonyl]-1H-pyrazol-3-yl)-1,2-dihydropyridin-2-one;

Compound 41, 1-[(5-chlorothiophen-2-yl)methyl]-3-(5-[(5-chlorothiophen-2-yl)methyl]amino-1-[(furan-3-yl)carbonyl]-1H-pyrazol-3-yl)-1,2-dihydropyridin-2-one;

Compound 42, 1-[(5-chlorothiophen-2-yl)methyl]-3-(5-[(5-chlorothiophen-2-yl)methyl]amino-1H-pyrazol-3-yl)-1,2-dihydropyridin-2-one;

Compound 43, 1-benzyl-3-(5-[(5-chlorothiophen-2-yl)methyl]amino-1-(2,2-dimethylpropanoyl)-1H-pyrazol-3-yl)-1,2-dihydropyridin-2-one;

Compound 44, 1-benzyl-3-(5-[(5-chlorothiophen-2-yl)methyl]amino-1-(3-methoxy-2,2-dimethylpropanoyl)-1H-pyrazol-3-yl)-1,2-dihydropyridin-2-one;

Compound 45, 1-benzyl-3-(5-[(5-chlorothiophen-2-yl)methyl]amino-1-[(2,3-dihydro-1,4-benzodioxin-5-yl)carbonyl]-1H-pyrazol-3-yl)-1,2-dihydropyridin-2-one;

Compound 46, 1-benzyl-3-(5-[(5-chlorothiophen-2-yl)methyl]amino-1-[(2,4-dimethoxyphenyl)carbonyl]-1H-pyrazol-3-yl)-1,2-dihydropyridin-2-one;

Compound 47, 1-benzyl-3-(5-[(5-chlorothiophen-2-yl)methyl]amino-1-[(2-methoxyphenyl)carbonyl]-1H-pyrazol-3-yl)-1,2-dihydropyridin-2-one;

Compound 48, 1-benzyl-3-(5-[(5-chlorothiophen-2-yl)methyl]amino-1-[(4-methyloxan-4-yl)carbonyl]-1H-pyrazol-3-yl)-1,2-dihydropyridin-2-one;

Compound 49, 1-benzyl-3-(5-[(5-chlorothiophen-2-yl)methyl]amino-1-[(furan-2-yl)carbonyl]-1H-pyrazol-3-yl)-1,2-dihydropyridin-2-one;

Compound 50, 1-benzyl-3-(5-[(5-chlorothiophen-2-yl)methyl]amino-1-[(furan-3-yl)carbonyl]-1H-pyrazol-3-yl)-1,2-dihydropyridin-2-one;

Compound 51, 1-benzyl-3-(5-[(5-chlorothiophen-2-yl)methyl]amino-1-[(thiophen-2-yl)carbonyl]-1H-pyrazol-3-yl)-1,2-dihydropyridin-2-one;

Compound 52, 1-benzyl-3-(5-[(5-chlorothiophen-2-yl)methyl]amino-1-[(thiophen-3-yl)carbonyl]-1H-pyrazol-3-yl)-1,2-dihydropyridin-2-one;

Compound 53, 1-benzyl-3-(5-[(5-chlorothiophen-2-yl)methyl]amino-1-[4-(morpholin-4-yl)phenyl]carbonyl-1H-pyrazol-3-yl)-1,2-dihydropyridin-2-one;

Compound 54, 1-benzyl-3-(5-[(5-chlorothiophen-2-yl)methyl]amino-1H-pyrazol-3-yl)-1,2-dihydropyridin-2-one;

Compound 55, 1-benzyl-3-1-[(2-chlorophenyl)carbonyl]-5-[(5-chlorothiophen-2-yl)methyl]amino-1H-pyrazol-3-yl-1,2-dihydropyridin-2-one;

Compound 56, 2-[3-(5-[(5-chlorothiophen-2-yl)methyl]amino-1-(2,2-dimethylpropanoyl)-1H-pyrazol-3-yl)-2-oxo-1,2-dihydropyridin-1-yl]acetonitrile;

Compound 57, 2-[3-(5-[(5-chlorothiophen-2-yl)methyl]amino-1-[(2-methoxyphenyl)carbonyl]-1H-pyrazol-3-yl)-2-oxo-1,2-dihydropyridin-1-yl]acetonitrile;

Compound 58, 2-[3-(5-[(5-chlorothiophen-2-yl)methyl]amino-1-[(furan-3-yl)carbonyl]-1H-pyrazol-3-yl)-2-oxo-1,2-dihydropyridin-1-yl]acetonitrile;

Compound 59, 2-[3-(5-[(5-chlorothiophen-2-yl)methyl]amino-1H-pyrazol-3-yl)-2-oxo-1,2-dihydropyridin-1-yl]acetic acid;

Compound 60, 2-[3-(5-[(5-chlorothiophen-2-yl)methyl]amino-1H-pyrazol-3-yl)-2-oxo-1,2-dihydropyridin-1-yl]acetonitrile;

Compound 61, 3-(1-benzoyl-5-[(5-chlorothiophen-2-yl)methyl]amino-1H-pyrazol-3-yl)-1,2-dihydropyridin-2-one;

Compound 62, 3-(1-benzoyl-5-[(5-chlorothiophen-2-yl)methyl]amino-1H-pyrazol-3-yl)-1-(2-methoxyethyl)-1,2-dihydropyridin-2-one;

Compound 63, 3-(1-benzoyl-5-[(5-chlorothiophen-2-yl)methyl]amino-1H-pyrazol-3-yl)-1-(furan-2-ylmethyl)-1,2-dihydropyridin-2-one;

Compound 64, 3-(1-benzoyl-5-[(5-chlorothiophen-2-yl)methyl]amino-1H-pyrazol-3-yl)-1-(furan-3-ylmethyl)-1,2-dihydropyridin-2-one;

Compound 65, 3-(1-benzoyl-5-[(5-chlorothiophen-2-yl)methyl]amino-1H-pyrazol-3-yl)-1-(pyridazin-3-ylmethyl)-1,2-dihydropyridin-2-one;

Compound 66, 3-(1-benzoyl-5-[(5-chlorothiophen-2-yl)methyl]amino-1H-pyrazol-3-yl)-1-(pyridin-2-ylmethyl)-1,2-dihydropyridin-2-one;

Compound 67, 3-(1-benzoyl-5-[(5-chlorothiophen-2-yl)methyl]amino-1H-pyrazol-3-yl)-1-(pyridin-3-ylmethyl)-1,2-dihydropyridin-2-one;

Compound 68, 3-(1-benzoyl-5-[(5-chlorothiophen-2-yl)methyl]amino-1H-pyrazol-3-yl)-1-(pyridin-4-ylmethyl)-1,2-dihydropyridin-2-one;

Compound 69, 3-(1-benzoyl-5-[(5-chlorothiophen-2-yl)methyl]amino-1H-pyrazol-3-yl)-1-(pyrimidin-2-ylmethyl)-1,2-dihydropyridin-2-one;

Compound 70, 3-(1-benzoyl-5-[(5-chlorothiophen-2-yl)methyl]amino-1H-pyrazol-3-yl)-1-(thiophen-2-ylmethyl)-1,2-dihydropyridin-2-one;

Compound 71, 3-(1-benzoyl-5-[(5-chlorothiophen-2-yl)methyl]amino-1H-pyrazol-3-yl)-1-(thiophen-3-ylmethyl)-1,2-dihydropyridin-2-one;

Compound 72, 3-(1-benzoyl-5-[(5-chlorothiophen-2-yl)methyl]amino-1H-pyrazol-3-yl)-1-b enzyl-1,2-dihydropyridin-2-one;

Compound 73, 3-(1-benzoyl-5-[(5-chlorothiophen-2-yl)methyl]amino-1H-pyrazol-3-yl)-1-methyl-1,2-dihydropyridin-2-one;

Compound 74, 3-(5-[(4-fluorophenyl)methyl]amino-1-[(furan-2-yl)carbonyl]-1H-pyrazol-3-yl)-1-(pyridin-2-ylmethyl)-1,2-dihydropyridin-2-one;

Compound 75, 3-(5-[(5-chlorothiophen-2-yl)methyl]amino-1-(2,2-dimethylpropanoyl)-1H-pyrazol-3-yl)-1-(2-methoxyethyl)-1,2-dihydropyridin-2-one;

Compound 76, 3-(5-[(5-chlorothiophen-2-yl)methyl]amino-1-(2,2-dimethylpropanoyl)-1H-pyrazol-3-yl)-1-(2-phenylethyl)-1,2-dihydropyridin-2-one;

Compound 77, 3-(5-[(5-chlorothiophen-2-yl)methyl]amino-1-(2,2-dimethylpropanoyl)-1H-pyrazol-3-yl)-1-(furan-2-ylmethyl)-1,2-dihydropyridin-2-one;

Compound 78, 3-(5-[(5-chlorothiophen-2-yl)methyl]amino-1-(2,2-dimethylpropanoyl)-1H-pyrazol-3-yl)-1-(furan-3-ylmethyl)-1,2-dihydropyridin-2-one;

Compound 79, 3-(5-[(5-chlorothiophen-2-yl)methyl]amino-1-(2,2-dimethylpropanoyl)-1H-pyrazol-3-yl)-1-(naphthalen-1-ylmethyl)-1,2-dihydropyridin-2-one;

Compound 80, 3-(5-[(5-chlorothiophen-2-yl)methyl]amino-1-(2,2-dimethylpropanoyl)-1H-pyrazol-3-yl)-1-(naphthalen-2-ylmethyl)-1,2-dihydropyridin-2-one;

Compound 81, 3-(5-[(5-chlorothiophen-2-yl)methyl]amino-1-(2,2-dimethylpropanoyl)-1H-pyrazol-3-yl)-1-(pyridazin-3-ylmethyl)-1,2-dihydropyridin-2-one;

Compound 82, 3-(5-[(5-chlorothiophen-2-yl)methyl]amino-1-(2,2-dimethylpropanoyl)-1H-pyrazol-3-yl)-1-(pyridin-2-ylmethyl)-1,2-dihydropyridin-2-one;

Compound 83, 3-(5-[(5-chlorothiophen-2-yl)methyl]amino-1-(2,2-dimethylpropanoyl)-1H-pyrazol-3-yl)-1-(pyridin-3-ylmethyl)-1,2-dihydropyridin-2-one;

Compound 84, 3-(5-[(5-chlorothiophen-2-yl)methyl]amino-1-(2,2-dimethylpropanoyl)-1H-pyrazol-3-yl)-1-(pyridin-4-ylmethyl)-1,2-dihydropyridin-2-one;

Compound 85, 3-(5-[(5-chlorothiophen-2-yl)methyl]amino-1-(2,2-dimethylpropanoyl)-1H-pyrazol-3-yl)-1-(pyrimidin-2-ylmethyl)-1,2-dihydropyridin-2-one;

Compound 86, 3-(5-[(5-chlorothiophen-2-yl)methyl]amino-1-(2,2-dimethylpropanoyl)-1H-pyrazol-3-yl)-1-(thiophen-2-ylmethyl)-1,2-dihydropyridin-2-one;

Compound 87, 3-(5-[(5-chlorothiophen-2-yl)methyl]amino-1-(2,2-dimethylpropanoyl)-1H-pyrazol-3-yl)-1-(thiophen-3-ylmethyl)-1,2-dihydropyridin-2-one;

Compound 88, 3-(5-[(5-chlorothiophen-2-yl)methyl]amino-1-(2,2-dimethylpropanoyl)-1H-pyrazol-3-yl)-1-[2-(morpholin-4-yl)-2-oxoethyl]-1,2-dihydropyridin-2-one;

Compound 89, 3-(5-[(5-chlorothiophen-2-yl)methyl]amino-1-(2,2-dimethylpropanoyl)-1H-pyrazol-3-yl)-1-[2-(morpholin-4-yl)ethyl]-1,2-dihydropyridin-2-one;

Compound 90, 3-(5-[(5-chlorothiophen-2-yl)methyl]amino-1-(2,2-dimethylpropanoyl)-1H-pyrazol-3-yl)-1-methyl-1,2-dihydropyridin-2-one;

Compound 91, 3-(5-[(5-chlorothiophen-2-yl)methyl]amino-1-(3-hydroxy-2,2-dimethylpropanoyl)-1H-pyrazol-3-yl)-1,2-dihydropyridin-2-one;

Compound 92, 3-(5-[(5-chlorothiophen-2-yl)methyl]amino-1-(3-hydroxy-2,2-dimethylpropanoyl)-1H-pyrazol-3-yl)-1-(2-methoxyethyl)-1,2-dihydropyridin-2-one;

Compound 93, 3-(5-[(5-chlorothiophen-2-yl)methyl]amino-1-(3-hydroxy-2,2-dimethylpropanoyl)-1H-pyrazol-3-yl)-1-(furan-2-ylmethyl)-1,2-dihydropyridin-2-one;

Compound 94, 3-(5-[(5-chlorothiophen-2-yl)methyl]amino-1-(3-hydroxy-2,2-dimethylpropanoyl)-1H-pyrazol-3-yl)-1-(pyridin-3-ylmethyl)-1,2-dihydropyridin-2-one;

Compound 95, 3-(5-[(5-chlorothiophen-2-yl)methyl]amino-1-(3-hydroxy-2,2-dimethylpropanoyl)-1H-pyrazol-3-yl)-1-(thiophen-2-ylmethyl)-1,2-dihydropyridin-2-one;

Compound 96, 3-(5-[(5-chlorothiophen-2-yl)methyl]amino-1-(3-methoxy-2,2-dimethylpropanoyl)-1H-pyrazol-3-yl)-1,2-dihydropyridin-2-one;

Compound 97, 3-(5-[(5-chlorothiophen-2-yl)methyl]amino-1-(3-methoxy-2,2-dimethylpropanoyl)-1H-pyrazol-3-yl)-1-(2-methoxyethyl)-1,2-dihydropyridin-2-one;

Compound 98, 3-(5-[(5-chlorothiophen-2-yl)methyl]amino-1-(3-methoxy-2,2-dimethylpropanoyl)-1H-pyrazol-3-yl)-1-(furan-2-ylmethyl)-1,2-dihydropyridin-2-one;

Compound 99, 3-(5-[(5-chlorothiophen-2-yl)methyl]amino-1-(3-methoxy-2,2-dimethylpropanoyl)-1H-pyrazol-3-yl)-1-(furan-3-ylmethyl)-1,2-dihydropyridin-2-one;

Compound 100, 3-(5-[(5-chlorothiophen-2-yl)methyl]amino-1-(3-methoxy-2,2-dimethylpropanoyl)-1H-pyrazol-3-yl)-1-(pyridazin-3-ylmethyl)-1,2-dihydropyridin-2-one;

Compound 101, 3-(5-[(5-chlorothiophen-2-yl)methyl]amino-1-(3-methoxy-2,2-dimethylpropanoyl)-1H-pyrazol-3-yl)-1-(pyridin-2-ylmethyl)-1,2-dihydropyridin-2-one;

Compound 102, 3-(5-[(5-chlorothiophen-2-yl)methyl]amino-1-(3-methoxy-2,2-dimethylpropanoyl)-1H-pyrazol-3-yl)-1-(pyridin-3-ylmethyl)-1,2-dihydropyridin-2-one;

Compound 103, 3-(5-[(5-chlorothiophen-2-yl)methyl]amino-1-(3-methoxy-2,2-dimethylpropanoyl)-1H-pyrazol-3-yl)-1-(pyridin-4-ylmethyl)-1,2-dihydropyridin-2-one;

Compound 104, 3-(5-[(5-chlorothiophen-2-yl)methyl]amino-1-(3-methoxy-2,2-dimethylpropanoyl)-1H-pyrazol-3-yl)-1-(pyrimidin-2-ylmethyl)-1,2-dihydropyridin-2-one;

Compound 105, 3-(5-[(5-chlorothiophen-2-yl)methyl]amino-1-(3-methoxy-2,2-dimethylpropanoyl)-1H-pyrazol-3-yl)-1-(thiophen-2-ylmethyl)-1,2-dihydropyridin-2-one;

Compound 106, 3-(5-[(5-chlorothiophen-2-yl)methyl]amino-1-(3-methoxy-2,2-dimethylpropanoyl)-1H-pyrazol-3-yl)-1-(thiophen-3-ylmethyl)-1,2-dihydropyridin-2-one;

Compound 107, 3-(5-[(5-chlorothiophen-2-yl)methyl]amino-1-(3-methoxy-2,2-dimethylpropanoyl)-1H-pyrazol-3-yl)-1-[2-(morpholin-4-yl)ethyl]-1,2-dihydropyridin-2-one;

Compound 108, 3-(5-[(5-chlorothiophen-2-yl)methyl]amino-1-[(2,3-dihydro-1,4-benzodioxin-5-yl)carbonyl]-1H-pyrazol-3-yl)-1,2-dihydropyridin-2-one;

Compound 109, 3-(5-[(5-chlorothiophen-2-yl)methyl]amino-1-[(2,3-dihydro-1,4-benzodioxin-5-yl)carbonyl]-1H-pyrazol-3-yl)-1-(2-methoxyethyl)-1,2-dihydropyridin-2-one;

Compound 110, 3-(5-[(5-chlorothiophen-2-yl)methyl]amino-1-[(2,3-dihydro-1,4-benzodioxin-5-yl)carbonyl]-1H-pyrazol-3-yl)-1-(furan-2-ylmethyl)-1,2-dihydropyridin-2-one;

Compound 111, 3-(5-[(5-chlorothiophen-2-yl)methyl]amino-1-[(2,3-dihydro-1,4-benzodioxin-5-yl)carbonyl]-1H-pyrazol-3-yl)-1-(furan-3-ylmethyl)-1,2-dihydropyridin-2-one;

Compound 112, 3-(5-[(5-chlorothiophen-2-yl)methyl]amino-1-[(2,3-dihydro-1,4-benzodioxin-5-yl)carbonyl]-1H-pyrazol-3-yl)-1-(pyridazin-3-ylmethyl)-1,2-dihydropyridin-2-one;

Compound 113, 3-(5-[(5-chlorothiophen-2-yl)methyl]amino-1-[(2,3-dihydro-1,4-benzodioxin-5-yl)carbonyl]-1H-pyrazol-3-yl)-1-(pyridin-2-ylmethyl)-1,2-dihydropyridin-2-one;

Compound 114, 3-(5-[(5-chlorothiophen-2-yl)methyl]amino-1-[(2,3-dihydro-1,4-benzodioxin-5-yl)carbonyl]-1H-pyrazol-3-yl)-1-(pyridin-3-ylmethyl)-1,2-dihydropyridin-2-one;

Compound 115, 3-(5-[(5-chlorothiophen-2-yl)methyl]amino-1-[(2,3-dihydro-1,4-benzodioxin-5-yl)carbonyl]-1H-pyrazol-3-yl)-1-(pyridin-4-ylmethyl)-1,2-dihydropyridin-2-one;

Compound 116, 3-(5-[(5-chlorothiophen-2-yl)methyl]amino-1-[(2,3-dihydro-1,4-benzodioxin-5-yl)carbonyl]-1H-pyrazol-3-yl)-1-(pyrimidin-2-ylmethyl)-1,2-dihydropyridin-2-one;

Compound 117, 3-(5-[(5-chlorothiophen-2-yl)methyl]amino-1-[(2,3-dihydro-1,4-benzodioxin-5-yl)carbonyl]-1H-pyrazol-3-yl)-1-(thiophen-2-ylmethyl)-1,2-dihydropyridin-2-one;

Compound 118, 3-(5-[(5-chlorothiophen-2-yl)methyl]amino-1-[(2,3-dihydro-1,4-benzodioxin-5-yl)carbonyl]-1H-pyrazol-3-yl)-1-(thiophen-3-ylmethyl)-1,2-dihydropyridin-2-one;

Compound 119, 3-(5-[(5-chlorothiophen-2-yl)methyl]amino-1-[(2,3-dihydro-1,4-benzodioxin-5-yl)carbonyl]-1H-pyrazol-3-yl)-1-[2-(morpholin-4-yl)ethyl]-1,2-dihydropyridin-2-one;

Compound 120, 3-(5-[(5-chlorothiophen-2-yl)methyl]amino-1-[(2,3-dihydro-1,4-benzodioxin-5-yl)carbonyl]-1H-pyrazol-3-yl)-1-methyl-1,2-dihydropyridin-2-one;

Compound 121, 3-(5-[(5-chlorothiophen-2-yl)methyl]amino-1-[(2,4-dimethoxyphenyl)carbonyl]-1H-pyrazol-3-yl)-1,2-dihydropyridin-2-one;

Compound 122, 3-(5-[(5-chlorothiophen-2-yl)methyl]amino-1-[(2,4-dimethoxyphenyl)carbonyl]-1H-pyrazol-3-yl)-1-(2-methoxyethyl)-1,2-dihydropyridin-2-one;

Compound 123, 3-(5-[(5-chlorothiophen-2-yl)methyl]amino-1-[(2,4-dimethoxyphenyl)carbonyl]-1H-pyrazol-3-yl)-1-(furan-3-ylmethyl)-1,2-dihydropyridin-2-one;

Compound 124, 3-(5-[(5-chlorothiophen-2-yl)methyl]amino-1-[(2,4-dimethoxyphenyl)carbonyl]-1H-pyrazol-3-yl)-1-(pyridazin-3-ylmethyl)-1,2-dihydropyridin-2-one;

Compound 125, 3-(5-[(5-chlorothiophen-2-yl)methyl]amino-1-[(2,4-dimethoxyphenyl)carbonyl]-1H-pyrazol-3-yl)-1-(pyridin-2-ylmethyl)-1,2-dihydropyridin-2-one;

Compound 126, 3-(5-[(5-chlorothiophen-2-yl)methyl]amino-1-[(2,4-dimethoxyphenyl)carbonyl]-1H-pyrazol-3-yl)-1-(pyridin-3-ylmethyl)-1,2-dihydropyridin-2-one;

Compound 127, 3-(5-[(5-chlorothiophen-2-yl)methyl]amino-1-[(2,4-dimethoxyphenyl)carbonyl]-1H-pyrazol-3-yl)-1-(pyridin-4-ylmethyl)-1,2-dihydropyridin-2-one;

Compound 128, 3-(5-[(5-chlorothiophen-2-yl)methyl]amino-1-[(2,4-dimethoxyphenyl)carbonyl]-1H-pyrazol-3-yl)-1-(pyrimidin-2-ylmethyl)-1,2-dihydropyridin-2-one;

Compound 129, 3-(5-[(5-chlorothiophen-2-yl)methyl]amino-1-[(2,4-dimethoxyphenyl)carbonyl]-1H-pyrazol-3-yl)-1-(thiophen-2-ylmethyl)-1,2-dihydropyridin-2-one;

Compound 130, 3-(5-[(5-chlorothiophen-2-yl)methyl]amino-1-[(2,4-dimethoxyphenyl)carbonyl]-1H-pyrazol-3-yl)-1-(thiophen-3-ylmethyl)-1,2-dihydropyridin-2-one;

Compound 131, 3-(5-[(5-chlorothiophen-2-yl)methyl]amino-1-[(2,4-dimethoxyphenyl)carbonyl]-1H-pyrazol-3-yl)-1-[2-(morpholin-4-yl)ethyl]-1,2-dihydropyridin-2-one;

Compound 132, 3-(5-[(5-chlorothiophen-2-yl)methyl]amino-1-[(2-methoxyphenyl)carbonyl]-1H-pyrazol-3-yl)-1,2-dihydropyridin-2-one;

Compound 133, 3-(5-[(5-chlorothiophen-2-yl)methyl]amino-1-[(2-methoxyphenyl)carbonyl]-1H-pyrazol-3-yl)-1-(2-methoxyethyl)-1,2-dihydropyridin-2-one;

Compound 134, 3-(5-[(5-chlorothiophen-2-yl)methyl]amino-1-[(2-methoxyphenyl)carbonyl]-1H-pyrazol-3-yl)-1-(2-phenylethyl)-1,2-dihydropyridin-2-one;

Compound 135, 3-(5-[(5-chlorothiophen-2-yl)methyl]amino-1-[(2-methoxyphenyl)carbonyl]-1H-pyrazol-3-yl)-1-(furan-2-ylmethyl)-1,2-dihydropyridin-2-one;

Compound 136, 3-(5-[(5-chlorothiophen-2-yl)methyl]amino-1-[(2-methoxyphenyl)carbonyl]-1H-pyrazol-3-yl)-1-(furan-3-ylmethyl)-1,2-dihydropyridin-2-one;

Compound 137, 3-(5-[(5-chlorothiophen-2-yl)methyl]amino-1-[(2-methoxyphenyl)carbonyl]-1H-pyrazol-3-yl)-1-(naphthalen-2-ylmethyl)-1,2-dihydropyridin-2-one;

Compound 138, 3-(5-[(5-chlorothiophen-2-yl)methyl]amino-1-[(2-methoxyphenyl)carbonyl]-1H-pyrazol-3-yl)-1-(pyridazin-3-ylmethyl)-1,2-dihydropyridin-2-one;

Compound 139, 3-(5-[(5-chlorothiophen-2-yl)methyl]amino-1-[(2-methoxyphenyl)carbonyl]-1H-pyrazol-3-yl)-1-(pyridin-2-ylmethyl)-1,2-dihydropyridin-2-one;

Compound 140, 3-(5-[(5-chlorothiophen-2-yl)methyl]amino-1-[(2-methoxyphenyl)carbonyl]-1H-pyrazol-3-yl)-1-(pyridin-3-ylmethyl)-1,2-dihydropyridin-2-one;

Compound 141, 3-(5-[(5-chlorothiophen-2-yl)methyl]amino-1-[(2-methoxyphenyl)carbonyl]-1H-pyrazol-3-yl)-1-(pyridin-4-ylmethyl)-1,2-dihydropyridin-2-one;

Compound 142, 3-(5-[(5-chlorothiophen-2-yl)methyl]amino-1-[(2-methoxyphenyl)carbonyl]-1H-pyrazol-3-yl)-1-(pyrimidin-2-ylmethyl)-1,2-dihydropyridin-2-one;

Compound 143, 3-(5-[(5-chlorothiophen-2-yl)methyl]amino-1-[(2-methoxyphenyl)carbonyl]-1H-pyrazol-3-yl)-1-(thiophen-2-ylmethyl)-1,2-dihydropyridin-2-one;

Compound 144, 3-(5-[(5-chlorothiophen-2-yl)methyl]amino-1-[(2-methoxyphenyl)carbonyl]-1H-pyrazol-3-yl)-1-(thiophen-3-ylmethyl)-1,2-dihydropyridin-2-one;

Compound 145, 3-(5-[(5-chlorothiophen-2-yl)methyl] amino-1-[(2-methoxyphenyl)carbonyl]-1H-pyrazol-3-yl)-1-[2-(morpholin-4-yl)-2-oxoethyl]-1,2-dihydropyridin-2-one;

Compound 146, 3-(5-[(5-chlorothiophen-2-yl)methyl] amino-1-[(2-methoxyphenyl)carbonyl]-1H-pyrazol-3-yl)-1-[2-(morpholin-4-yl)ethyl]-1,2-dihydropyridin-2-one;

Compound 147, 3-(5-[(5-chlorothiophen-2-yl)methyl] amino-1-[(2-methoxyphenyl)carbonyl]-1H-pyrazol-3-yl)-1-methyl-1,2-dihydropyridin-2-one;

Compound 148, 3-(5-[(5-chlorothiophen-2-yl)methyl] amino-1-[(3-methyloxetan-3-yl)carbonyl]-1H-pyrazol-3-yl)-1-methyl-1,2-dihydropyridin-2-one;

Compound 149, 3-(5-[(5-chlorothiophen-2-yl)methyl] amino-1-[(4-methyloxan-4-yl)carbonyl]-1H-pyrazol-3-yl)-1-(2-methoxyethyl)-1,2-dihydropyridin-2-one;

Compound 150, 3-(5-[(5-chlorothiophen-2-yl)methyl] amino-1-[(4-methyloxan-4-yl)carbonyl]-1H-pyrazol-3-yl)-1-(furan-2-ylmethyl)-1,2-dihydropyridin-2-one;

Compound 151, 3-(5-[(5-chlorothiophen-2-yl)methyl] amino-1-[(4-methyloxan-4-yl)carbonyl]-1H-pyrazol-3-yl)-1-(furan-3-ylmethyl)-1,2-dihydropyridin-2-one;

Compound 152, 3-(5-[(5-chlorothiophen-2-yl)methyl] amino-1-[(4-methyloxan-4-yl)carbonyl]-1H-pyrazol-3-yl)-1-(pyridazin-3-ylmethyl)-1,2-dihydropyridin-2-one;

Compound 153, 3-(5-[(5-chlorothiophen-2-yl)methyl] amino-1-[(4-methyloxan-4-yl)carbonyl]-1H-pyrazol-3-yl)-1-(pyridin-2-ylmethyl)-1,2-dihydropyridin-2-one;

Compound 154, 3-(5-[(5-chlorothiophen-2-yl)methyl] amino-1-[(4-methyloxan-4-yl)carbonyl]-1H-pyrazol-3-yl)-1-(pyridin-3-ylmethyl)-1,2-dihydropyridin-2-one;

Compound 155, 3-(5-[(5-chlorothiophen-2-yl)methyl] amino-1-[(4-methyloxan-4-yl)carbonyl]-1H-pyrazol-3-yl)-1-(pyridin-4-ylmethyl)-1,2-dihydropyridin-2-one;

Compound 156, 3-(5-[(5-chlorothiophen-2-yl)methyl] amino-1-[(4-methyloxan-4-yl)carbonyl]-1H-pyrazol-3-yl)-1-(pyrimidin-2-ylmethyl)-1,2-dihydropyridin-2-one;

Compound 157, 3-(5-[(5-chlorothiophen-2-yl)methyl] amino-1-[(4-methyloxan-4-yl)carbonyl]-1H-pyrazol-3-yl)-1-(thiophen-2-ylmethyl)-1,2-dihydropyridin-2-one;

Compound 158, 3-(5-[(5-chlorothiophen-2-yl)methyl] amino-1-[(4-methyloxan-4-yl)carbonyl]-1H-pyrazol-3-yl)-1-(thiophen-3-ylmethyl)-1,2-dihydropyridin-2-one;

Compound 159, 3-(5-[(5-chlorothiophen-2-yl)methyl] amino-1-[(4-methyloxan-4-yl)carbonyl]-1H-pyrazol-3-yl)-1-[2-(morpholin-4-yl)ethyl]-1,2-dihydropyridin-2-one;

Compound 160, 3-(5-[(5-chlorothiophen-2-yl)methyl] amino-1-[(furan-2-yl)carbonyl]-1H-pyrazol-3-yl)-1-(2-methoxyethyl)-1,2-dihydropyridin-2-one;

Compound 161, 3-(5-[(5-chlorothiophen-2-yl)methyl] amino-1-[(furan-2-yl)carbonyl]-1H-pyrazol-3-yl)-1-(furan-2-ylmethyl)-1,2-dihydropyridin-2-one;

Compound 162, 3-(5-[(5-chlorothiophen-2-yl)methyl] amino-1-[(furan-2-yl)carbonyl]-1H-pyrazol-3-yl)-1-(furan-3-ylmethyl)-1,2-dihydropyridin-2-one;

Compound 163, 3-(5-[(5-chlorothiophen-2-yl)methyl] amino-1-[(furan-2-yl)carbonyl]-1H-pyrazol-3-yl)-1-(pyridazin-3-ylmethyl)-1,2-dihydropyridin-2-one;

Compound 164, 3-(5-[(5-chlorothiophen-2-yl)methyl] amino-1-[(furan-2-yl)carbonyl]-1H-pyrazol-3-yl)-1-(pyridin-2-ylmethyl)-1,2-dihydropyridin-2-one;

Compound 165, 3-(5-[(5-chlorothiophen-2-yl)methyl] amino-1-[(furan-2-yl)carbonyl]-1H-pyrazol-3-yl)-1-(pyridin-3-ylmethyl)-1,2-dihydropyridin-2-one;

Compound 166, 3-(5-[(5-chlorothiophen-2-yl)methyl] amino-1-[(furan-2-yl)carbonyl]-1H-pyrazol-3-yl)-1-(pyridin-4-ylmethyl)-1,2-dihydropyridin-2-one;

Compound 167, 3-(5-[(5-chlorothiophen-2-yl)methyl] amino-1-[(furan-2-yl)carbonyl]-1H-pyrazol-3-yl)-1-(pyrimidin-2-ylmethyl)-1,2-dihydropyridin-2-one;

Compound 168, 3-(5-[(5-chlorothiophen-2-yl)methyl] amino-1-[(furan-2-yl)carbonyl]-1H-pyrazol-3-yl)-1-(thiophen-2-ylmethyl)-1,2-dihydropyridin-2-one;

Compound 169, 3-(5-[(5-chlorothiophen-2-yl)methyl] amino-1-[(furan-2-yl)carbonyl]-1H-pyrazol-3-yl)-1-(thiophen-3-ylmethyl)-1,2-dihydropyridin-2-one;

Compound 170, 3-(5-[(5-chlorothiophen-2-yl)methyl] amino-1-[(furan-2-yl)carbonyl]-1H-pyrazol-3-yl)-1-[2-(morpholin-4-yl)ethyl]-1,2-dihydropyridin-2-one;

Compound 171, 3-(5-[(5-chlorothiophen-2-yl)methyl] amino-1-[(furan-3-yl)carbonyl]-1H-pyrazol-3-yl)-1-(2-methoxyethyl)-1,2-dihydropyridin-2-one;

Compound 172, 3-(5-[(5-chlorothiophen-2-yl)methyl] amino-1-[(furan-3-yl)carbonyl]-1H-pyrazol-3-yl)-1-(2-phenylethyl)-1,2-dihydropyridin-2-one;

Compound 173, 3-(5-[(5-chlorothiophen-2-yl)methyl] amino-1-[(furan-3-yl)carbonyl]-1H-pyrazol-3-yl)-1-(furan-3-ylmethyl)-1,2-dihydropyridin-2-one;

Compound 174, 3-(5-[(5-chlorothiophen-2-yl)methyl] amino-1-[(furan-3-yl)carbonyl]-1H-pyrazol-3-yl)-1-(naphthalen-1-ylmethyl)-1,2-dihydropyridin-2-one;

Compound 175, 3-(5-[(5-chlorothiophen-2-yl)methyl] amino-1-[(furan-3-yl)carbonyl]-1H-pyrazol-3-yl)-1-(naphthalen-2-ylmethyl)-1,2-dihydropyridin-2-one;

Compound 176, 3-(5-[(5-chlorothiophen-2-yl)methyl] amino-1-[(furan-3-yl)carbonyl]-1H-pyrazol-3-yl)-1-(pyridazin-3-ylmethyl)-1,2-dihydropyridin-2-one;

Compound 177, 3-(5-[(5-chlorothiophen-2-yl)methyl] amino-1-[(furan-3-yl)carbonyl]-1H-pyrazol-3-yl)-1-(pyridin-3-ylmethyl)-1,2-dihydropyridin-2-one;

Compound 178, 3-(5-[(5-chlorothiophen-2-yl)methyl] amino-1-[(furan-3-yl)carbonyl]-1H-pyrazol-3-yl)-1-(pyrimidin-2-ylmethyl)-1,2-dihydropyridin-2-one;

Compound 179, 3-(5-[(5-chlorothiophen-2-yl)methyl] amino-1-[(furan-3-yl)carbonyl]-1H-pyrazol-3-yl)-1-(thiophen-3-ylmethyl)-1,2-dihydropyridin-2-one;

Compound 180, 3-(5-[(5-chlorothiophen-2-yl)methyl] amino-1-[(furan-3-yl)carbonyl]-1H-pyrazol-3-yl)-1-[2-(morpholin-4-yl)-2-oxoethyl]-1,2-dihydropyridin-2-one;

Compound 181, 3-(5-[(5-chlorothiophen-2-yl)methyl] amino-1-[(furan-3-yl)carbonyl]-1H-pyrazol-3-yl)-1-[2-(morpholin-4-yl)ethyl]-1,2-dihydropyridin-2-one;

Compound 182, 3-(5-[(5-chlorothiophen-2-yl)methyl] amino-1-[(thiophen-2-yl)carbonyl]-1H-pyrazol-3-yl)-1-(2-methoxyethyl)-1,2-dihydropyridin-2-one;

Compound 183, 3-(5-[(5-chlorothiophen-2-yl)methyl] amino-1-[(thiophen-2-yl)carbonyl]-1H-pyrazol-3-yl)-1-(furan-2-ylmethyl)-1,2-dihydropyridin-2-one;

Compound 184, 3-(5-[(5-chlorothiophen-2-yl)methyl] amino-1-[(thiophen-2-yl)carbonyl]-1H-pyrazol-3-yl)-1-(furan-3-ylmethyl)-1,2-dihydropyridin-2-one;

Compound 185, 3-(5-[(5-chlorothiophen-2-yl)methyl] amino-1-[(thiophen-2-yl)carbonyl]-1H-pyrazol-3-yl)-1-(pyridazin-3-ylmethyl)-1,2-dihydropyridin-2-one;

Compound 186, 3-(5-[(5-chlorothiophen-2-yl)methyl]amino-1-[(thiophen-2-yl)carbonyl]-1H-pyrazol-3-yl)-1-(pyridin-2-ylmethyl)-1,2-dihydropyridin-2-one;

Compound 187, 3-(5-[(5-chlorothiophen-2-yl)methyl]amino-1-[(thiophen-2-yl)carbonyl]-1H-pyrazol-3-yl)-1-(pyridin-3-ylmethyl)-1,2-dihydropyridin-2-one;

Compound 188, 3-(5-[(5-chlorothiophen-2-yl)methyl]amino-1-[(thiophen-2-yl)carbonyl]-1H-pyrazol-3-yl)-1-(pyridin-4-ylmethyl)-1,2-dihydropyridin-2-one;

Compound 189, 3-(5-[(5-chlorothiophen-2-yl)methyl]amino-1-[(thiophen-2-yl)carbonyl]-1H-pyrazol-3-yl)-1-(pyrimidin-2-ylmethyl)-1,2-dihydropyridin-2-one;

Compound 190, 3-(5-[(5-chlorothiophen-2-yl)methyl]amino-1-[(thiophen-2-yl)carbonyl]-1H-pyrazol-3-yl)-1-(thiophen-2-ylmethyl)-1,2-dihydropyridin-2-one;

Compound 191, 3-(5-[(5-chlorothiophen-2-yl)methyl]amino-1-[(thiophen-2-yl)carbonyl]-1H-pyrazol-3-yl)-1-(thiophen-3-ylmethyl)-1,2-dihydropyridin-2-one;

Compound 192, 3-(5-[(5-chlorothiophen-2-yl)methyl]amino-1-[(thiophen-2-yl)carbonyl]-1H-pyrazol-3-yl)-1-[2-(morpholin-4-yl)ethyl]-1,2-dihydropyridin-2-one;

Compound 193, 3-(5-[(5-chlorothiophen-2-yl)methyl]amino-1-[(thiophen-3-yl)carbonyl]-1H-pyrazol-3-yl)-1,2-dihydropyridin-2-one;

Compound 194, 3-(5-[(5-chlorothiophen-2-yl)methyl]amino-1-[(thiophen-3-yl)carbonyl]-1H-pyrazol-3-yl)-1-(2-methoxyethyl)-1,2-dihydropyridin-2-one;

Compound 195, 3-(5-[(5-chlorothiophen-2-yl)methyl]amino-1-[(thiophen-3-yl)carbonyl]-1H-pyrazol-3-yl)-1-(furan-2-ylmethyl)-1,2-dihydropyridin-2-one;

Compound 196, 3-(5-[(5-chlorothiophen-2-yl)methyl]amino-1-[(thiophen-3-yl)carbonyl]-1H-pyrazol-3-yl)-1-(furan-3-ylmethyl)-1,2-dihydropyridin-2-one;

Compound 197, 3-(5-[(5-chlorothiophen-2-yl)methyl]amino-1-[(thiophen-3-yl)carbonyl]-1H-pyrazol-3-yl)-1-(pyridazin-3-ylmethyl)-1,2-dihydropyridin-2-one;

Compound 198, 3-(5-[(5-chlorothiophen-2-yl)methyl]amino-1-[(thiophen-3-yl)carbonyl]-1H-pyrazol-3-yl)-1-(pyridin-2-ylmethyl)-1,2-dihydropyridin-2-one;

Compound 199, 3-(5-[(5-chlorothiophen-2-yl)methyl]amino-1-[(thiophen-3-yl)carbonyl]-1H-pyrazol-3-yl)-1-(pyridin-3-ylmethyl)-1,2-dihydropyridin-2-one;

Compound 200, 3-(5-[(5-chlorothiophen-2-yl)methyl]amino-1-[(thiophen-3-yl)carbonyl]-1H-pyrazol-3-yl)-1-(pyridin-4-ylmethyl)-1,2-dihydropyridin-2-one;

Compound 201, 3-(5-[(5-chlorothiophen-2-yl)methyl]amino-1-[(thiophen-3-yl)carbonyl]-1H-pyrazol-3-yl)-1-(pyrimidin-2-ylmethyl)-1,2-dihydropyridin-2-one;

Compound 202, 3-(5-[(5-chlorothiophen-2-yl)methyl]amino-1-[(thiophen-3-yl)carbonyl]-1H-pyrazol-3-yl)-1-(thiophen-2-ylmethyl)-1,2-dihydropyridin-2-one;

Compound 203, 3-(5-[(5-chlorothiophen-2-yl)methyl]amino-1-[(thiophen-3-yl)carbonyl]-1H-pyrazol-3-yl)-1-(thiophen-3-ylmethyl)-1,2-dihydropyridin-2-one;

Compound 204, 3-(5-[(5-chlorothiophen-2-yl)methyl]amino-1-[(thiophen-3-yl)carbonyl]-1H-pyrazol-3-yl)-1-[2-(morpholin-4-yl)ethyl]-1,2-dihydropyridin-2-one;

Compound 205, 3-(5-[(5-chlorothiophen-2-yl)methyl]amino-1-[2-(morpholin-4-yl)phenyl]carbonyl-1H-pyrazol-3-yl)-1,2-dihydropyridin-2-one;

Compound 206, 3-(5-[(5-chlorothiophen-2-yl)methyl]amino-1-[4-(2-methoxyethoxy)phenyl]carbonyl-1H-pyrazol-3-yl)-1,2-dihydropyridin-2-one;

Compound 207, 3-(5-[(5-chlorothiophen-2-yl)methyl]amino-1-[4-(morpholin-4-yl)phenyl]carbonyl-1H-pyrazol-3-yl)-1,2-dihydropyridin-2-one;

Compound 208, 3-(5-[(5-chlorothiophen-2-yl)methyl]amino-1-[4-(morpholin-4-yl)phenyl]carbonyl-1H-pyrazol-3-yl)-1-(2-methoxyethyl)-1,2-dihydropyridin-2-one;

Compound 209, 3-(5-[(5-chlorothiophen-2-yl)methyl]amino-1-[4-(morpholin-4-yl)phenyl]carbonyl-1H-pyrazol-3-yl)-1-(furan-2-ylmethyl)-1,2-dihydropyridin-2-one;

Compound 210, 3-(5-[(5-chlorothiophen-2-yl)methyl]amino-1-[4-(morpholin-4-yl)phenyl]carbonyl-1H-pyrazol-3-yl)-1-(furan-3-ylmethyl)-1,2-dihydropyridin-2-one;

Compound 211, 3-(5-[(5-chlorothiophen-2-yl)methyl]amino-1-[4-(morpholin-4-yl)phenyl]carbonyl-1H-pyrazol-3-yl)-1-(pyridazin-3-ylmethyl)-1,2-dihydropyridin-2-one;

Compound 212, 3-(5-[(5-chlorothiophen-2-yl)methyl]amino-1-[4-(morpholin-4-yl)phenyl]carbonyl-1H-pyrazol-3-yl)-1-(pyridin-2-ylmethyl)-1,2-dihydropyridin-2-one;

Compound 213, 3-(5-[(5-chlorothiophen-2-yl)methyl]amino-1-[4-(morpholin-4-yl)phenyl]carbonyl-1H-pyrazol-3-yl)-1-(pyridin-3-ylmethyl)-1,2-dihydropyridin-2-one;

Compound 214, 3-(5-[(5-chlorothiophen-2-yl)methyl]amino-1-[4-(morpholin-4-yl)phenyl]carbonyl-1H-pyrazol-3-yl)-1-(pyridin-4-ylmethyl)-1,2-dihydropyridin-2-one;

Compound 215, 3-(5-[(5-chlorothiophen-2-yl)methyl]amino-1-[4-(morpholin-4-yl)phenyl]carbonyl-1H-pyrazol-3-yl)-1-(pyrimidin-2-ylmethyl)-1,2-dihydropyridin-2-one;

Compound 216, 3-(5-[(5-chlorothiophen-2-yl)methyl]amino-1-[4-(morpholin-4-yl)phenyl]carbonyl-1H-pyrazol-3-yl)-1-(thiophen-2-ylmethyl)-1,2-dihydropyridin-2-one;

Compound 217, 3-(5-[(5-chlorothiophen-2-yl)methyl]amino-1-[4-(morpholin-4-yl)phenyl]carbonyl-1H-pyrazol-3-yl)-1-(thiophen-3-ylmethyl)-1,2-dihydropyridin-2-one;

Compound 218, 3-(5-[(5-chlorothiophen-2-yl)methyl]amino-1-[4-(morpholin-4-yl)phenyl]carbonyl-1H-pyrazol-3-yl)-1-[2-(morpholin-4-yl)ethyl]-1,2-dihydropyridin-2-one;

Compound 219, 3-(5-[(5-chlorothiophen-2-yl)methyl]amino-1H-pyrazol-3-yl)-1-(1H-1,2,3,4-tetrazol-5-ylmethyl)-1,2-dihydropyridin-2-one;

Compound 220, 3-(5-[(5-chlorothiophen-2-yl)methyl]amino-1H-pyrazol-3-yl)-1-(2-methoxyethyl)-1,2-dihydropyridin-2-one;

Compound 221, 3-(5-[(5-chlorothiophen-2-yl)methyl]amino-1H-pyrazol-3-yl)-1-(2-phenylethyl)-1,2-dihydropyridin-2-one;

Compound 222, 3-(5-[(5-chlorothiophen-2-yl)methyl]amino-1H-pyrazol-3-yl)-1-(furan-2-ylmethyl)-1,2-dihydropyridin-2-one;

Compound 223, 3-(5-[(5-chlorothiophen-2-yl)methyl]amino-1H-pyrazol-3-yl)-1-(furan-3-ylmethyl)-1,2-dihydropyridin-2-one;

Compound 224, 3-(5-[(5-chlorothiophen-2-yl)methyl]amino-1H-pyrazol-3-yl)-1-(naphthalen-1-ylmethyl)-1,2-dihydropyridin-2-one;

Compound 225, 3-(5-[(5-chlorothiophen-2-yl)methyl]amino-1H-pyrazol-3-yl)-1-(naphthalen-2-ylmethyl)-1,2-dihydropyridin-2-one;

Compound 226, 3-(5-[(5-chlorothiophen-2-yl)methyl]amino-1H-pyrazol-3-yl)-1-(pyridazin-3-ylmethyl)-1,2-dihydropyridin-2-one;
Compound 227, 3-(5-[(5-chlorothiophen-2-yl)methyl]amino-1H-pyrazol-3-yl)-1-(pyridin-2-ylmethyl)-1,2-dihydropyridin-2-one;
Compound 228, 3-(5-[(5-chlorothiophen-2-yl)methyl]amino-1H-pyrazol-3-yl)-1-(pyridin-3-ylmethyl)-1,2-dihydropyridin-2-one;
Compound 229, 3-(5-[(5-chlorothiophen-2-yl)methyl]amino-1H-pyrazol-3-yl)-1-(pyridin-4-ylmethyl)-1,2-dihydropyridin-2-one;
Compound 230, 3-(5-[(5-chlorothiophen-2-yl)methyl]amino-1H-pyrazol-3-yl)-1-(pyrimidin-2-ylmethyl)-1,2-dihydropyridin-2-one;
Compound 231, 3-(5-[(5-chlorothiophen-2-yl)methyl]amino-1H-pyrazol-3-yl)-1-(thiophen-2-ylmethyl)-1,2-dihydropyridin-2-one;
Compound 232, 3-(5-[(5-chlorothiophen-2-yl)methyl]amino-1H-pyrazol-3-yl)-1-(thiophen-3-ylmethyl)-1,2-dihydropyridin-2-one;
Compound 233, 3-(5-[(5-chlorothiophen-2-yl)methyl]amino-1H-pyrazol-3-yl)-1-[2-(morpholin-4-yl)-2-oxoethyl]-1,2-dihydropyridin-2-one;
Compound 234, 3-(5-[(5-chlorothiophen-2-yl)methyl]amino-1H-pyrazol-3-yl)-1-[2-(morpholin-4-yl)ethyl]-1,2-dihydropyridin-2-one;
Compound 235, 3-(5-[(5-chlorothiophen-2-yl)methyl]amino-1H-pyrazol-3-yl)-1-[2-(pyridin-2-yl)ethyl]-1,2-dihydropyridin-2-one;
Compound 236, 3-(5-[(5-chlorothiophen-2-yl)methyl]amino-1H-pyrazol-3-yl)-1-methyl-1,2-dihydropyridin-2-one;
Compound 237, 3-[5-(benzylamino)-1-[(furan-2-yl)carbonyl]-1H-pyrazol-3-yl]-1,2-dihydropyridin-2-one;
Compound 238, 3-[5-(benzylamino)-1-[(furan-2-yl)carbonyl]-1H-pyrazol-3-yl]-1-(pyridin-2-ylmethyl)-1,2-dihydropyridin-2-one;
Compound 239, 3-[5-(dimethylamino)-1-[(furan-2-yl)carbonyl]-1H-pyrazol-3-yl]-1,2-dihydropyridin-2-one;
Compound 240, 3-[5-(dimethylamino)-1-[(furan-2-yl)carbonyl]-1H-pyrazol-3-yl]-1-(pyridin-2-ylmethyl)-1,2-dihydropyridin-2-one;
Compound 241, 3-1-[(2-aminophenyl)carbonyl]-5-[(5-chlorothiophen-2-yl)methyl]amino-1H-pyrazol-3-yl-1,2-dihydropyridin-2-one;
Compound 242, 3-1-[(2-chlorophenyl)carbonyl]-5-[(5-chlorothiophen-2-yl)methyl]amino-1H-pyrazol-3-yl-1-(2-methoxyethyl)-1,2-dihydropyridin-2-one;
Compound 243, 3-1-[(2-chlorophenyl)carbonyl]-5-[(5-chlorothiophen-2-yl)methyl]amino-1H-pyrazol-3-yl-1-(furan-2-ylmethyl)-1,2-dihydropyridin-2-one;
Compound 244, 3-1-[(2-chlorophenyl)carbonyl]-5-[(5-chlorothiophen-2-yl)methyl]amino-1H-pyrazol-3-yl-1-(furan-3-ylmethyl)-1,2-dihydropyridin-2-one;
Compound 245, 3-1-[(2-chlorophenyl)carbonyl]-5-[(5-chlorothiophen-2-yl)methyl]amino-1H-pyrazol-3-yl-1-(pyridazin-3-ylmethyl)-1,2-dihydropyridin-2-one;
Compound 246, 3-1-[(2-chlorophenyl)carbonyl]-5-[(5-chlorothiophen-2-yl)methyl]amino-1H-pyrazol-3-yl-1-(pyridin-2-ylmethyl)-1,2-dihydropyridin-2-one;
Compound 247, 3-1-[(2-chlorophenyl)carbonyl]-5-[(5-chlorothiophen-2-yl)methyl]amino-1H-pyrazol-3-yl-1-(pyridin-3-ylmethyl)-1,2-dihydropyridin-2-one;
Compound 248, 3-1-[(2-chlorophenyl)carbonyl]-5-[(5-chlorothiophen-2-yl)methyl]amino-1H-pyrazol-3-yl-1-(pyridin-4-ylmethyl)-1,2-dihydropyridin-2-one;
Compound 249, 3-1-[(2-chlorophenyl)carbonyl]-5-[(5-chlorothiophen-2-yl)methyl]amino-1H-pyrazol-3-yl-1-(pyrimidin-2-ylmethyl)-1,2-dihydropyridin-2-one;
Compound 250, 3-1-[(2-chlorophenyl)carbonyl]-5-[(5-chlorothiophen-2-yl)methyl]amino-1H-pyrazol-3-yl-1-(thiophen-2-ylmethyl)-1,2-dihydropyridin-2-one;
Compound 251, 3-1-[(2-chlorophenyl)carbonyl]-5-[(5-chlorothiophen-2-yl)methyl]amino-1H-pyrazol-3-yl-1-(thiophen-3-ylmethyl)-1,2-dihydropyridin-2-one;
Compound 252, 3-1-[(2-chlorophenyl)carbonyl]-5-[(5-chlorothiophen-2-yl)methyl]amino-1H-pyrazol-3-yl-1-[2-(morpholin-4-yl)ethyl]-1,2-dihydropyridin-2-one;
Compound 253, 3-1-[(4-tert-butylphenyl)carbonyl]-5-[(5-chlorothiophen-2-yl)methyl]amino-1H-pyrazol-3-yl-1,2-dihydropyridin-2-one;
Compound 254, 3-1-[(4-tert-butylphenyl)carbonyl]-5-[(5-chlorothiophen-2-yl)methyl]amino-1H-pyrazol-3-yl-1-methyl-1,2-dihydropyridin-2-one;
Compound 255, 3-5-amino-1-[(furan-2-yl)carbonyl]-1H-pyrazol-3-yl-1,2-dihydropyridin-2-one;
Compound 256, 3-5-amino-1-[(furan-2-yl)carbonyl]-1H-pyrazol-3-yl-1-(pyridin-2-ylmethyl)-1,2-dihydropyridin-2-one;
Compound 257, ethyl 2-[3-(5-[(5-chlorothiophen-2-yl)methyl]amino-1-(2,2-dimethylpropanoyl)-1H-pyrazol-3-yl)-2-oxo-1,2-dihydropyridin-1-yl]acetate;
Compound 258, ethyl 2-[3-(5-[(5-chlorothiophen-2-yl)methyl]amino-1-[(2-methoxyphenyl)carbonyl]-1H-pyrazol-3-yl)-2-oxo-1,2-dihydropyridin-1-yl]acetate;
Compound 259, ethyl 2-[3-(5-[(5-chlorothiophen-2-yl)methyl]amino-1-[(furan-3-yl)carbonyl]-1H-pyrazol-3-yl)-2-oxo-1,2-dihydropyridin-1-yl]acetate;
Compound 260, ethyl 2-[3-(5-[(5-chlorothiophen-2-yl)methyl]amino-1H-pyrazol-3-yl)-2-oxo-1,2-dihydropyridin-1-yl]acetate;
Compound 261, tert-butyl 2-[3-(5-[(5-chlorothiophen-2-yl)methyl]amino-1-(2,2-dimethylpropanoyl)-1H-pyrazol-3-yl)-2-oxo-1,2-dihydropyridin-1-yl]acetate;
Compound 262, tert-butyl 2-[3-(5-[(5-chlorothiophen-2-yl)methyl]amino-1-[(2-methoxyphenyl)carbonyl]-1H-pyrazol-3-yl)-2-oxo-1,2-dihydropyridin-1-yl]acetate;
Compound 263, tert-butyl 2-[3-(5-[(5-chlorothiophen-2-yl)methyl]amino-1-[(furan-3-yl)carbonyl]-1H-pyrazol-3-yl)-2-oxo-1,2-dihydropyridin-1-yl]acetate;
Compound 264, tert-butyl 2-[3-(5-[(5-chlorothiophen-2-yl)methyl]amino-1H-pyrazol-3-yl)-2-oxo-1,2-dihydropyridin-1-yl]acetate;
Compound 265, 1-[(5-[(5-chlorothiophen-2-yl)methyl]amino-3-(1-methyl-2-oxo-1,2-dihydropyridin-3-yl)-1H-pyrazol-1-yl)carbonyl]cyclopropylmethyl 1-(hydroxymethyl)cyclopropane-1-carboxylate.

19. The compound of claim 1, as set forth below:
Compound 1, 3-(5-amino-1H-pyrazol-3-yl)-1,2-dihydropyridin-2-one;
Compound 2, 3-(5-[(5-chlorothiophen-2-yl)methyl]amino-1H-pyrazol-3-yl)-1,2-dihydropyridin-2-one;
Compound 3, 3-(5-[(5-chlorothiophen-2-yl)methyl]amino-1-(2,2-dimethylpropanoyl)-1H-pyrazol-3-yl)-1,2-dihydropyridin-2-one;
Compound 4, 3-(5-[(5-chlorothiophen-2-yl)methyl]amino-1-[(furan-3-yl)carbonyl]-1H-pyrazol-3-yl)-1,2-dihydropyridin-2-one;
Compound 5, 3-(5-[(5-chlorothiophen-2-yl)methyl]amino-1-[(furan-3-yl)carbonyl]-1H-pyrazol-3-yl)-1-(thiophen-2-ylmethyl)-1,2-dihydropyridin-2-one;

Compound 6, 3-(5-[(5-chlorothiophen-2-yl)methyl]amino-1-[(furan-3-yl)carbonyl]-1H-pyrazol-3-yl)-1-(pyridin-4-ylmethyl)-1,2-dihydropyridin-2-one; ;

Compound 23, 3-(5-[(5-chlorothiophen-2-yl)methyl]amino-1-[(furan-3-yl)carbonyl]-1H-pyrazol-3-yl)-1-methyl-1,2-dihydropyridin-2-one; ;

Compound 25, 3-(5-[(5-chlorothiophen-2-yl)methyl]amino-1-[(furan-3-yl)carbonyl]-1H-pyrazol-3-yl)-1-(pyridin-2-ylmethyl)-1,2-dihydropyridin-2-one;

Compound 26, 3-(5-[(5-chlorothiophen-2-yl)methyl]amino-1-[(furan-3-yl)carbonyl]-1H-pyrazol-3-yl)-1-(furan-2-ylmethyl)-1,2-dihydropyridin-2-one;

Compound 27, 1-[(2-chlorophenyl)methyl]-3-(5-[(5-chlorothiophen-2-yl)methyl]amino-1-(2,2-dimethylpropanoyl)-1H-pyrazol-3-yl)-1,2-dihydropyridin-2-one;

Compound 28, 1-[(2-chlorophenyl)methyl]-3-(5-[(5-chlorothiophen-2-yl)methyl]amino-1-[(2-methoxyphenyl)carbonyl]-1H-pyrazol-3-yl)-1,2-dihydropyridin-2-one;

Compound 29, 1-[(2-chlorophenyl)methyl]-3-(5-[(5-chlorothiophen-2-yl)methyl]amino-1-[(furan-3-yl)carbonyl]-1H-pyrazol-3-yl)-1,2-dihydropyridin-2-one;

Compound 30, 1-[(2-chlorophenyl)methyl]-3-(5-[(5-chlorothiophen-2-yl)methyl]amino-1H-pyrazol-3-yl)-1,2-dihydropyridin-2-one;

Compound 31, 1-[(3-chlorophenyl)methyl]-3-(5-[(5-chlorothiophen-2-yl)methyl]amino-1-(2,2-dimethylpropanoyl)-1H-pyrazol-3-yl)-1,2-dihydropyridin-2-one;

Compound 32, 1-[(3-chlorophenyl)methyl]-3-(5-[(5-chlorothiophen-2-yl)methyl]amino-1-[(2-methoxyphenyl)carbonyl]-1H-pyrazol-3-yl)-1,2-dihydropyridin-2-one;

Compound 33, 1-[(3-chlorophenyl)methyl]-3-(5-[(5-chlorothiophen-2-yl)methyl]amino-1-[(furan-3-yl)carbonyl]-1H-pyrazol-3-yl)-1,2-dihydropyridin-2-one;

Compound 34, 1-[(3-chlorophenyl)methyl]-3-(5-[(5-chlorothiophen-2-yl)methyl]amino-1H-pyrazol-3-yl)-1,2-dihydropyridin-2-one;

Compound 35, 1-[(4-chlorophenyl)methyl]-3-(5-[(5-chlorothiophen-2-yl)methyl]amino-1-(2,2-dimethylpropanoyl)-1H-pyrazol-3-yl)-1,2-dihydropyridin-2-one;

Compound 36, 1-[(4-chlorophenyl)methyl]-3-(5-[(5-chlorothiophen-2-yl)methyl]amino-1-[(2-methoxyphenyl)carbonyl]-1H-pyrazol-3-yl)-1,2-dihydropyridin-2-one;

Compound 37, 1-[(4-chlorophenyl)methyl]-3-(5-[(5-chlorothiophen-2-yl)methyl]amino-1-[(furan-3-yl)carbonyl]-1H-pyrazol-3-yl)-1,2-dihydropyridin-2-one;

Compound 38, 1-[(4-chlorophenyl)methyl]-3-(5-[(5-chlorothiophen-2-yl)methyl]amino-1H-pyrazol-3-yl)-1,2-dihydropyridin-2-one;

Compound 39, 1-[(5-chlorothiophen-2-yl)methyl]-3-(5-[(5-chlorothiophen-2-yl)methyl]amino-1-(2,2-dimethylpropanoyl)-1H-pyrazol-3-yl)-1,2-dihydropyridin-2-one;

Compound 40, 1-[(5-chlorothiophen-2-yl)methyl]-3-(5-[(5-chlorothiophen-2-yl)methyl]amino-1-[(2-methoxyphenyl)carbonyl]-1H-pyrazol-3-yl)-1,2-dihydropyridin-2-one;

Compound 41, 1-[(5-chlorothiophen-2-yl)methyl]-3-(5-[(5-chlorothiophen-2-yl)methyl]amino-1-[(furan-3-yl)carbonyl]-1H-pyrazol-3-yl)-1,2-dihydropyridin-2-one;

Compound 42, 1-[(5-chlorothiophen-2-yl)methyl]-3-(5-[(5-chlorothiophen-2-yl)methyl]amino-1H-pyrazol-3-yl)-1,2-dihydropyridin-2-one;

Compound 43, 1-benzyl-3-(5-[(5-chlorothiophen-2-yl)methyl]amino-1-(2,2-dimethylpropanoyl)-1H-pyrazol-3-yl)-1,2-dihydropyridin-2-one;

Compound 44, 1-benzyl-3-(5-[(5-chlorothiophen-2-yl)methyl]amino-1-(3-methoxy-2,2-dimethylpropanoyl)-1H-pyrazol-3-yl)-1,2-dihydropyridin-2-one;

Compound 45, 1-benzyl-3-(5-[(5-chlorothiophen-2-yl)methyl]amino-1-[(2,3-dihydro-1,4-benzodioxin-5-yl)carbonyl]-1H-pyrazol-3-yl)-1,2-dihydropyridin-2-one;

Compound 46, 1-benzyl-3-(5-[(5-chlorothiophen-2-yl)methyl]amino-1-[(2,4-dimethoxyphenyl)carbonyl]-1H-pyrazol-3-yl)-1,2-dihydropyridin-2-one;

Compound 47, 1-benzyl-3-(5-[(5-chlorothiophen-2-yl)methyl]amino-1-[(2-methoxyphenyl)carbonyl]-1H-pyrazol-3-yl)-1,2-dihydropyridin-2-one;

Compound 48, 1-benzyl-3-(5-[(5-chlorothiophen-2-yl)methyl]amino-1-[(4-methyloxan-4-yl)carbonyl]-1H-pyrazol-3-yl)-1,2-dihydropyridin-2-one;

Compound 49, 1-benzyl-3-(5-[(5-chlorothiophen-2-yl)methyl]amino-1-[(furan-2-yl)carbonyl]-1H-pyrazol-3-yl)-1,2-dihydropyridin-2-one;

Compound 50, 1-benzyl-3-(5-[(5-chlorothiophen-2-yl)methyl]amino-1-[(furan-3-yl)carbonyl]-1H-pyrazol-3-yl)-1,2-dihydropyridin-2-one;

Compound 51, 1-benzyl-3-(5-[(5-chlorothiophen-2-yl)methyl]amino-1-[(thiophen-2-yl)carbonyl]-1H-pyrazol-3-yl)-1,2-dihydropyridin-2-one;

Compound 52, 1-benzyl-3-(5-[(5-chlorothiophen-2-yl)methyl]amino-1-[(thiophen-3-yl)carbonyl]-1H-pyrazol-3-yl)-1,2-dihydropyridin-2-one;

Compound 53, 1-benzyl-3-(5-[(5-chlorothiophen-2-yl)methyl]amino-1-[4-(morpholin-4-yl)phenyl]carbonyl-1H-pyrazol-3-yl)-1,2-dihydropyridin-2-one;

Compound 54, 1-benzyl-3-(5-[(5-chlorothiophen-2-yl)methyl]amino-1H-pyrazol-3-yl)-1,2-dihydropyridin-2-one;

Compound 55, 1-benzyl-3-1-[(2-chlorophenyl)carbonyl]-5-[(5-chlorothiophen-2-yl)methyl]amino-1H-pyrazol-3-yl-1,2-dihydropyridin-2-one;

Compound 56, 2-[3-(5-[(5-chlorothiophen-2-yl)methyl]amino-1-(2,2-dimethylpropanoyl)-1H-pyrazol-3-yl)-2-oxo-1,2-dihydropyridin-1-yl]acetonitrile;

Compound 57, 2-[3-(5-[(5-chlorothiophen-2-yl)methyl]amino-1-[(2-methoxyphenyl)carbonyl]-1H-pyrazol-3-yl)-2-oxo-1,2-dihydropyridin-1-yl]acetonitrile;

Compound 58, 2-[3-(5-[(5-chlorothiophen-2-yl)methyl]amino-1-[(furan-3-yl)carbonyl]-1H-pyrazol-3-yl)-2-oxo-1,2-dihydropyridin-1-yl]acetonitrile;

Compound 59, 2-[3-(5-[(5-chlorothiophen-2-yl)methyl]amino-1H-pyrazol-3-yl)-2-oxo-1,2-dihydropyridin-1-yl]acetic acid;

Compound 60, 2-[3-(5-[(5-chlorothiophen-2-yl)methyl]amino-1H-pyrazol-3-yl)-2-oxo-1,2-dihydropyridin-1-yl]acetonitrile;

Compound 61, 3-(1-benzoyl-5-[(5-chlorothiophen-2-yl)methyl]amino-1H-pyrazol-3-yl)-1,2-dihydropyridin-2-one;

Compound 62, 3-(1-benzoyl-5-[(5-chlorothiophen-2-yl)methyl]amino-1H-pyrazol-3-yl)-1-(2-methoxyethyl)-1,2-dihydropyridin-2-one;

Compound 63, 3-(1-benzoyl-5-[(5-chlorothiophen-2-yl)methyl]amino-1H-pyrazol-3-yl)-1-(furan-2-ylmethyl)-1,2-dihydropyridin-2-one;

Compound 64, 3-(1-benzoyl-5-[(5-chlorothiophen-2-yl)methyl]amino-1H-pyrazol-3-yl)-1-(furan-3-ylmethyl)-1,2-dihydropyridin-2-one;

Compound 65, 3-(1-benzoyl-5-[(5-chlorothiophen-2-yl)methyl]amino-1H-pyrazol-3-yl)-1-(pyridazin-3-ylmethyl)-1,2-dihydropyridin-2-one;

Compound 66, 3-(1-benzoyl-5-[(5-chlorothiophen-2-yl)methyl]amino-1H-pyrazol-3-yl)-1-(pyridin-2-ylmethyl)-1,2-dihydropyridin-2-one;

Compound 67, 3-(1-benzoyl-5-[(5-chlorothiophen-2-yl)methyl]amino-1H-pyrazol-3-yl)-1-(pyridin-3-ylmethyl)-1,2-dihydropyridin-2-one;

Compound 68, 3-(1-benzoyl-5-[(5-chlorothiophen-2-yl)methyl]amino-1H-pyrazol-3-yl)-1-(pyridin-4-ylmethyl)-1,2-dihydropyridin-2-one;

Compound 69, 3-(1-benzoyl-5-[(5-chlorothiophen-2-yl)methyl]amino-1H-pyrazol-3-yl)-1-(pyrimidin-2-ylmethyl)-1,2-dihydropyridin-2-one;

Compound 70, 3-(1-benzoyl-5-[(5-chlorothiophen-2-yl)methyl]amino-1H-pyrazol-3-yl)-1-(thiophen-2-ylmethyl)-1,2-dihydropyridin-2-one;

Compound 71, 3-(1-benzoyl-5-[(5-chlorothiophen-2-yl)methyl]amino-1H-pyrazol-3-yl)-1-(thiophen-3-ylmethyl)-1,2-dihydropyridin-2-one;

Compound 72, 3-(1-benzoyl-5-[(5-chlorothiophen-2-yl)methyl]amino-1H-pyrazol-3-yl)-1-benzyl-1,2-dihydropyridin-2-one;

Compound 73, 3-(1-benzoyl-5-[(5-chlorothiophen-2-yl)methyl]amino-1H-pyrazol-3-yl)-1-methyl-1,2-dihydropyridin-2-one;

Compound 74, 3-(5-[(4-fluorophenyl)methyl]amino-1-[(furan-2-yl)carbonyl]-1H-pyrazol-3-yl)-1-(pyridin-2-ylmethyl)-1,2-dihydropyridin-2-one;

Compound 75, 3-(5-[(5-chlorothiophen-2-yl)methyl]amino-1-(2,2-dimethylpropanoyl)-1H-pyrazol-3-yl)-1-(2-methoxyethyl)-1,2-dihydropyridin-2-one;

Compound 76, 3-(5-[(5-chlorothiophen-2-yl)methyl]amino-1-(2,2-dimethylpropanoyl)-1H-pyrazol-3-yl)-1-(2-phenylethyl)-1,2-dihydropyridin-2-one;

Compound 77, 3-(5-[(5-chlorothiophen-2-yl)methyl]amino-1-(2,2-dimethylpropanoyl)-1H-pyrazol-3-yl)-1-(furan-2-ylmethyl)-1,2-dihydropyridin-2-one;

Compound 78, 3-(5-[(5-chlorothiophen-2-yl)methyl]amino-1-(2,2-dimethylpropanoyl)-1H-pyrazol-3-yl)-1-(furan-3-ylmethyl)-1,2-dihydropyridin-2-one;

Compound 79, 3-(5-[(5-chlorothiophen-2-yl)methyl]amino-1-(2,2-dimethylpropanoyl)-1H-pyrazol-3-yl)-1-(naphthalen-1-ylmethyl)-1,2-dihydropyridin-2-one;

Compound 80, 3-(5-[(5-chlorothiophen-2-yl)methyl]amino-1-(2,2-dimethylpropanoyl)-1H-pyrazol-3-yl)-1-(naphthalen-2-ylmethyl)-1,2-dihydropyridin-2-one;

Compound 81, 3-(5-[(5-chlorothiophen-2-yl)methyl]amino-1-(2,2-dimethylpropanoyl)-1H-pyrazol-3-yl)-1-(pyridazin-3-ylmethyl)-1,2-dihydropyridin-2-one;

Compound 82, 3-(5-[(5-chlorothiophen-2-yl)methyl]amino-1-(2,2-dimethylpropanoyl)-1H-pyrazol-3-yl)-1-(pyridin-2-ylmethyl)-1,2-dihydropyridin-2-one;

Compound 83, 3-(5-[(5-chlorothiophen-2-yl)methyl]amino-1-(2,2-dimethylpropanoyl)-1H-pyrazol-3-yl)-1-(pyridin-3-ylmethyl)-1,2-dihydropyridin-2-one;

Compound 84, 3-(5-[(5-chlorothiophen-2-yl)methyl]amino-1-(2,2-dimethylpropanoyl)-1H-pyrazol-3-yl)-1-(pyridin-4-ylmethyl)-1,2-dihydropyridin-2-one;

Compound 85, 3-(5-[(5-chlorothiophen-2-yl)methyl]amino-1-(2,2-dimethylpropanoyl)-1H-pyrazol-3-yl)-1-(pyrimidin-2-ylmethyl)-1,2-dihydropyridin-2-one;

Compound 86, 3-(5-[(5-chlorothiophen-2-yl)methyl]amino-1-(2,2-dimethylpropanoyl)-1H-pyrazol-3-yl)-1-(thiophen-2-ylmethyl)-1,2-dihydropyridin-2-one;

Compound 87, 3-(5-[(5-chlorothiophen-2-yl)methyl]amino-1-(2,2-dimethylpropanoyl)-1H-pyrazol-3-yl)-1-(thiophen-3-ylmethyl)-1,2-dihydropyridin-2-one;

Compound 88, 3-(5-[(5-chlorothiophen-2-yl)methyl]amino-1-(2,2-dimethylpropanoyl)-1H-pyrazol-3-yl)-1-[2-(morpholin-4-yl)-2-oxoethyl]-1,2-dihydropyridin-2-one;

Compound 89, 3-(5-[(5-chlorothiophen-2-yl)methyl]amino-1-(2,2-dimethylpropanoyl)-1H-pyrazol-3-yl)-1-[2-(morpholin-4-yl)ethyl]-1,2-dihydropyridin-2-one;

Compound 90, 3-(5-[(5-chlorothiophen-2-yl)methyl]amino-1-(2,2-dimethylpropanoyl)-1H-pyrazol-3-yl)-1-methyl-1,2-dihydropyridin-2-one;

Compound 91, 3-(5-[(5-chlorothiophen-2-yl)methyl]amino-1-(3-hydroxy-2,2-dimethylpropanoyl)-1H-pyrazol-3-yl)-1,2-dihydropyridin-2-one;

Compound 92, 3-(5-[(5-chlorothiophen-2-yl)methyl]amino-1-(3-hydroxy-2,2-dimethylpropanoyl)-1H-pyrazol-3-yl)-1-(2-methoxyethyl)-1,2-dihydropyridin-2-one;

Compound 93, 3-(5-[(5-chlorothiophen-2-yl)methyl]amino-1-(3-hydroxy-2,2-dimethylpropanoyl)-1H-pyrazol-3-yl)-1-(furan-2-ylmethyl)-1,2-dihydropyridin-2-one;

Compound 94, 3-(5-[(5-chlorothiophen-2-yl)methyl]amino-1-(3-hydroxy-2,2-dimethylpropanoyl)-1H-pyrazol-3-yl)-1-(pyridin-3-ylmethyl)-1,2-dihydropyridin-2-one;

Compound 95, 3-(5-[(5-chlorothiophen-2-yl)methyl]amino-1-(3-hydroxy-2,2-dimethylpropanoyl)-1H-pyrazol-3-yl)-1-(thiophen-2-ylmethyl)-1,2-dihydropyridin-2-one;

Compound 96, 3-(5-[(5-chlorothiophen-2-yl)methyl]amino-1-(3-methoxy-2,2-dimethylpropanoyl)-1H-pyrazol-3-yl)-1,2-dihydropyridin-2-one;

Compound 97, 3-(5-[(5-chlorothiophen-2-yl)methyl]amino-1-(3-methoxy-2,2-dimethylpropanoyl)-1H-pyrazol-3-yl)-1-(2-methoxyethyl)-1,2-dihydropyridin-2-one;

Compound 98, 3-(5-[(5-chlorothiophen-2-yl)methyl]amino-1-(3-methoxy-2,2-dimethylpropanoyl)-1H-pyrazol-3-yl)-1-(furan-2-ylmethyl)-1,2-dihydropyridin-2-one;

Compound 99, 3-(5-[(5-chlorothiophen-2-yl)methyl]amino-1-(3-methoxy-2,2-dimethylpropanoyl)-1H-pyrazol-3-yl)-1-(furan-3-ylmethyl)-1,2-dihydropyridin-2-one;

Compound 100, 3-(5-[(5-chlorothiophen-2-yl)methyl]amino-1-(3-methoxy-2,2-dimethylpropanoyl)-1H-pyrazol-3-yl)-1-(pyridazin-3-ylmethyl)-1,2-dihydropyridin-2-one;

Compound 101, 3-(5-[(5-chlorothiophen-2-yl)methyl]amino-1-(3-methoxy-2,2-dimethylpropanoyl)-1H-pyrazol-3-yl)-1-(pyridin-2-ylmethyl)-1,2-dihydropyridin-2-one;

Compound 102, 3-(5-[(5-chlorothiophen-2-yl)methyl]amino-1-(3-methoxy-2,2-dimethylpropanoyl)-1H-pyrazol-3-yl)-1-(pyridin-3-ylmethyl)-1,2-dihydropyridin-2-one;

Compound 103, 3-(5-[(5-chlorothiophen-2-yl)methyl]amino-1-(3-methoxy-2,2-dimethylpropanoyl)-1H-pyrazol-3-yl)-1-(pyridin-4-ylmethyl)-1,2-dihydropyridin-2-one;

Compound 104, 3-(5-[(5-chlorothiophen-2-yl)methyl]amino-1-(3-methoxy-2,2-dimethylpropanoyl)-1H-pyrazol-3-yl)-1-(pyrimidin-2-ylmethyl)-1,2-dihydropyridin-2-one;

Compound 105, 3-(5-[(5-chlorothiophen-2-yl)methyl]amino-1-(3-methoxy-2,2-dimethylpropanoyl)-1H-pyrazol-3-yl)-1-(thiophen-2-ylmethyl)-1,2-dihydropyridin-2-one;

Compound 106, 3-(5-[(5-chlorothiophen-2-yl)methyl]amino-1-(3-methoxy-2,2-dimethylpropanoyl)-1H-pyrazol-3-yl)-1-(thiophen-3-ylmethyl)-1,2-dihydropyridin-2-one;

Compound 107, 3-(5-[(5-chlorothiophen-2-yl)methyl]amino-1-(3-methoxy-2,2-dimethylpropanoyl)-1H-pyrazol-3-yl)-1-[2-(morpholin-4-yl)ethyl]-1,2-dihydropyridin-2-one;

Compound 108, 3-(5-[(5-chlorothiophen-2-yl)methyl]amino-1-[(2,3-dihydro-1,4-benzodioxin-5-yl)carbonyl]-1H-pyrazol-3-yl)-1,2-dihydropyridin-2-one;

Compound 109, 3-(5-[(5-chlorothiophen-2-yl)methyl]amino-1-[(2,3-dihydro-1,4-benzodioxin-5-yl)carbonyl]-1H-pyrazol-3-yl)-1-(2-methoxyethyl)-1,2-dihydropyridin-2-one;

Compound 110, 3-(5-[(5-chlorothiophen-2-yl)methyl]amino-1-[(2,3-dihydro-1,4-benzodioxin-5-yl)carbonyl]-1H-pyrazol-3-yl)-1-(furan-2-ylmethyl)-1,2-dihydropyridin-2-one;

Compound 111, 3-(5-[(5-chlorothiophen-2-yl)methyl]amino-1-[(2,3-dihydro-1,4-benzodioxin-5-yl)carbonyl]-1H-pyrazol-3-yl)-1-(furan-3-ylmethyl)-1,2-dihydropyridin-2-one;

Compound 112, 3-(5-[(5-chlorothiophen-2-yl)methyl]amino-1-[(2,3-dihydro-1,4-benzodioxin-5-yl)carbonyl]-1H-pyrazol-3-yl)-1-(pyridazin-3-ylmethyl)-1,2-dihydropyridin-2-one;

Compound 113, 3-(5-[(5-chlorothiophen-2-yl)methyl]amino-1-[(2,3-dihydro-1,4-benzodioxin-5-yl)carbonyl]-1H-pyrazol-3-yl)-1-(pyridin-2-ylmethyl)-1,2-dihydropyridin-2-one;

Compound 114, 3-(5-[(5-chlorothiophen-2-yl)methyl]amino-1-[(2,3-dihydro-1,4-benzodioxin-5-yl)carbonyl]-1H-pyrazol-3-yl)-1-(pyridin-3-ylmethyl)-1,2-dihydropyridin-2-one;

Compound 115, 3-(5-[(5-chlorothiophen-2-yl)methyl]amino-1-[(2,3-dihydro-1,4-benzodioxin-5-yl)carbonyl]-1H-pyrazol-3-yl)-1-(pyridin-4-ylmethyl)-1,2-dihydropyridin-2-one;

Compound 116, 3-(5-[(5-chlorothiophen-2-yl)methyl]amino-1-[(2,3-dihydro-1,4-benzodioxin-5-yl)carbonyl]-1H-pyrazol-3-yl)-1-(pyrimidin-2-ylmethyl)-1,2-dihydropyridin-2-one;

Compound 117, 3-(5-[(5-chlorothiophen-2-yl)methyl]amino-1-[(2,3-dihydro-1,4-benzodioxin-5-yl)carbonyl]-1H-pyrazol-3-yl)-1-(thiophen-2-ylmethyl)-1,2-dihydropyridin-2-one;

Compound 118, 3-(5-[(5-chlorothiophen-2-yl)methyl]amino-1-[(2,3-dihydro-1,4-benzodioxin-5-yl)carbonyl]-1H-pyrazol-3-yl)-1-(thiophen-3-ylmethyl)-1,2-dihydropyridin-2-one;

Compound 119, 3-(5-[(5-chlorothiophen-2-yl)methyl]amino-1-[(2,3-dihydro-1,4-benzodioxin-5-yl)carbonyl]-1H-pyrazol-3-yl)-1-[2-(morpholin-4-yl)ethyl]-1,2-dihydropyridin-2-one;

Compound 120, 3-(5-[(5-chlorothiophen-2-yl)methyl]amino-1-[(2,3-dihydro-1,4-benzodioxin-5-yl)carbonyl]-1H-pyrazol-3-yl)-1-methyl-1,2-dihydropyridin-2-one;

Compound 121, 3-(5-[(5-chlorothiophen-2-yl)methyl]amino-1-[(2,4-dimethoxyphenyl)carbonyl]-1H-pyrazol-3-yl)-1,2-dihydropyridin-2-one;

Compound 122, 3-(5-[(5-chlorothiophen-2-yl)methyl]amino-1-[(2,4-dimethoxyphenyl)carbonyl]-1H-pyrazol-3-yl)-1-(2-methoxyethyl)-1,2-dihydropyridin-2-one;

Compound 123, 3-(5-[(5-chlorothiophen-2-yl)methyl]amino-1-[(2,4-dimethoxyphenyl)carbonyl]-1H-pyrazol-3-yl)-1-(furan-3-ylmethyl)-1,2-dihydropyridin-2-one;

Compound 124, 3-(5-[(5-chlorothiophen-2-yl)methyl]amino-1-[(2,4-dimethoxyphenyl)carbonyl]-1H-pyrazol-3-yl)-1-(pyridazin-3-ylmethyl)-1,2-dihydropyridin-2-one;

Compound 125, 3-(5-[(5-chlorothiophen-2-yl)methyl]amino-1-[(2,4-dimethoxyphenyl)carbonyl]-1H-pyrazol-3-yl)-1-(pyridin-2-ylmethyl)-1,2-dihydropyridin-2-one;

Compound 126, 3-(5-[(5-chlorothiophen-2-yl)methyl]amino-1-[(2,4-dimethoxyphenyl)carbonyl]-1H-pyrazol-3-yl)-1-(pyridin-3-ylmethyl)-1,2-dihydropyridin-2-one;

Compound 127, 3-(5-[(5-chlorothiophen-2-yl)methyl]amino-1-[(2,4-dimethoxyphenyl)carbonyl]-1H-pyrazol-3-yl)-1-(pyridin-4-ylmethyl)-1,2-dihydropyridin-2-one;

Compound 128, 3-(5-[(5-chlorothiophen-2-yl)methyl]amino-1-[(2,4-dimethoxyphenyl)carbonyl]-1H-pyrazol-3-yl)-1-(pyrimidin-2-ylmethyl)-1,2-dihydropyridin-2-one;

Compound 129, 3-(5-[(5-chlorothiophen-2-yl)methyl]amino-1-[(2,4-dimethoxyphenyl)carbonyl]-1H-pyrazol-3-yl)-1-(thiophen-2-ylmethyl)-1,2-dihydropyridin-2-one;

Compound 130, 3-(5-[(5-chlorothiophen-2-yl)methyl]amino-1-[(2,4-dimethoxyphenyl)carbonyl]-1H-pyrazol-3-yl)-1-(thiophen-3-ylmethyl)-1,2-dihydropyridin-2-one;

Compound 131, 3-(5-[(5-chlorothiophen-2-yl)methyl]amino-1-[(2,4-dimethoxyphenyl)carbonyl]-1H-pyrazol-3-yl)-1-[2-(morpholin-4-yl)ethyl]-1,2-dihydropyridin-2-one;

Compound 132, 3-(5-[(5-chlorothiophen-2-yl)methyl]amino-1-[(2-methoxyphenyl)carbonyl]-1H-pyrazol-3-yl)-1,2-dihydropyridin-2-one;

Compound 133, 3-(5-[(5-chlorothiophen-2-yl)methyl]amino-1-[(2-methoxyphenyl)carbonyl]-1H-pyrazol-3-yl)-1-(2-methoxyethyl)-1,2-dihydropyridin-2-one;

Compound 134, 3-(5-[(5-chlorothiophen-2-yl)methyl]amino-1-[(2-methoxyphenyl)carbonyl]-1H-pyrazol-3-yl)-1-(2-phenylethyl)-1,2-dihydropyridin-2-one;

Compound 135, 3-(5-[(5-chlorothiophen-2-yl)methyl]amino-1-[(2-methoxyphenyl)carbonyl]-1H-pyrazol-3-yl)-1-(furan-2-ylmethyl)-1,2-dihydropyridin-2-one;

Compound 136, 3-(5-[(5-chlorothiophen-2-yl)methyl]amino-1-[(2-methoxyphenyl)carbonyl]-1H-pyrazol-3-yl)-1-(furan-3-ylmethyl)-1,2-dihydropyridin-2-one;

Compound 137, 3-(5-[(5-chlorothiophen-2-yl)methyl]amino-1-[(2-methoxyphenyl)carbonyl]-1H-pyrazol-3-yl)-1-(naphthalen-2-ylmethyl)-1,2-dihydropyridin-2-one;

Compound 138, 3-(5-[(5-chlorothiophen-2-yl)methyl]amino-1-[(2-methoxyphenyl)carbonyl]-1H-pyrazol-3-yl)-1-(pyridazin-3-ylmethyl)-1,2-dihydropyridin-2-one;

Compound 139, 3-(5-[(5-chlorothiophen-2-yl)methyl]amino-1-[(2-methoxyphenyl)carbonyl]-1H-pyrazol-3-yl)-1-(pyridin-2-ylmethyl)-1,2-dihydropyridin-2-one;

Compound 140, 3-(5-[(5-chlorothiophen-2-yl)methyl]amino-1-[(2-methoxyphenyl)carbonyl]-1H-pyrazol-3-yl)-1-(pyridin-3-ylmethyl)-1,2-dihydropyridin-2-one;

Compound 141, 3-(5-[(5-chlorothiophen-2-yl)methyl]amino-1-[(2-methoxyphenyl)carbonyl]-1H-pyrazol-3-yl)-1-(pyridin-4-ylmethyl)-1,2-dihydropyridin-2-one;

Compound 142, 3-(5-[(5-chlorothiophen-2-yl)methyl]amino-1-[(2-methoxyphenyl)carbonyl]-1H-pyrazol-3-yl)-1-(pyrimidin-2-ylmethyl)-1,2-dihydropyridin-2-one;

Compound 143, 3-(5-[(5-chlorothiophen-2-yl)methyl]amino-1-[(2-methoxyphenyl)carbonyl]-1H-pyrazol-3-yl)-1-(thiophen-2-ylmethyl)-1,2-dihydropyridin-2-one;

Compound 144, 3-(5-[(5-chlorothiophen-2-yl)methyl]amino-1-[(2-methoxyphenyl)carbonyl]-1H-pyrazol-3-yl)-1-(thiophen-3-ylmethyl)-1,2-dihydropyridin-2-one;

Compound 145, 3-(5-[(5-chlorothiophen-2-yl)methyl]amino-1-[(2-methoxyphenyl)carbonyl]-1H-pyrazol-3-yl)-1-[2-(morpholin-4-yl)-2-oxoethyl]-1,2-dihydropyridin-2-one;

Compound 146, 3-(5-[(5-chlorothiophen-2-yl)methyl]amino-1-[(2-methoxyphenyl)carbonyl]-1H-pyrazol-3-yl)-1-[2-(morpholin-4-yl)ethyl]-1,2-dihydropyridin-2-one;

Compound 147, 3-(5-[(5-chlorothiophen-2-yl)methyl]amino-1-[(2-methoxyphenyl)carbonyl]-1H-pyrazol-3-yl)-1-methyl-1,2-dihydropyridin-2-one;

Compound 148, 3-(5-[(5-chlorothiophen-2-yl)methyl]amino-1-[(3-methyloxetan-3-yl)carbonyl]-1H-pyrazol-3-yl)-1-methyl-1,2-dihydropyridin-2-one;

Compound 149, 3-(5-[(5-chlorothiophen-2-yl)methyl]amino-1-[(4-methyloxan-4-yl)carbonyl]-1H-pyrazol-3-yl)-1-(2-methoxyethyl)-1,2-dihydropyridin-2-one;

Compound 150, 3-(5-[(5-chlorothiophen-2-yl)methyl]amino-1-[(4-methyloxan-4-yl)carbonyl]-1H-pyrazol-3-yl)-1-(furan-2-ylmethyl)-1,2-dihydropyridin-2-one;

Compound 151, 3-(5-[(5-chlorothiophen-2-yl)methyl]amino-1-[(4-methyloxan-4-yl)carbonyl]-1H-pyrazol-3-yl)-1-(furan-3-ylmethyl)-1,2-dihydropyridin-2-one;

Compound 152, 3-(5-[(5-chlorothiophen-2-yl)methyl]amino-1-[(4-methyloxan-4-yl)carbonyl]-1H-pyrazol-3-yl)-1-(pyridazin-3-ylmethyl)-1,2-dihydropyridin-2-one;

Compound 153, 3-(5-[(5-chlorothiophen-2-yl)methyl]amino-1-[(4-methyloxan-4-yl)carbonyl]-1H-pyrazol-3-yl)-1-(pyridin-2-ylmethyl)-1,2-dihydropyridin-2-one;

Compound 154, 3-(5-[(5-chlorothiophen-2-yl)methyl]amino-1-[(4-methyloxan-4-yl)carbonyl]-1H-pyrazol-3-yl)-1-(pyridin-3-ylmethyl)-1,2-dihydropyridin-2-one;

Compound 155, 3-(5-[(5-chlorothiophen-2-yl)methyl]amino-1-[(4-methyloxan-4-yl)carbonyl]-1H-pyrazol-3-yl)-1-(pyridin-4-ylmethyl)-1,2-dihydropyridin-2-one;

Compound 156, 3-(5-[(5-chlorothiophen-2-yl)methyl]amino-1-[(4-methyloxan-4-yl)carbonyl]-1H-pyrazol-3-yl)-1-(pyrimidin-2-ylmethyl)-1,2-dihydropyridin-2-one;

Compound 157, 3-(5-[(5-chlorothiophen-2-yl)methyl]amino-1-[(4-methyloxan-4-yl)carbonyl]-1H-pyrazol-3-yl)-1-(thiophen-2-ylmethyl)-1,2-dihydropyridin-2-one;

Compound 158, 3-(5-[(5-chlorothiophen-2-yl)methyl]amino-1-[(4-methyloxan-4-yl)carbonyl]-1H-pyrazol-3-yl)-1-(thiophen-3-ylmethyl)-1,2-dihydropyridin-2-one;

Compound 159, 3-(5-[(5-chlorothiophen-2-yl)methyl]amino-1-[(4-methyloxan-4-yl)carbonyl]-1H-pyrazol-3-yl)-1-[2-(morpholin-4-yl)ethyl]-1,2-dihydropyridin-2-one;

Compound 160, 3-(5-[(5-chlorothiophen-2-yl)methyl]amino-1-[(furan-2-yl)carbonyl]-1H-pyrazol-3-yl)-1-(2-methoxyethyl)-1,2-dihydropyridin-2-one;

Compound 161, 3-(5-[(5-chlorothiophen-2-yl)methyl]amino-1-[(furan-2-yl)carbonyl]-1H-pyrazol-3-yl)-1-(furan-2-ylmethyl)-1,2-dihydropyridin-2-one;

Compound 162, 3-(5-[(5-chlorothiophen-2-yl)methyl]amino-1-[(furan-2-yl)carbonyl]-1H-pyrazol-3-yl)-1-(furan-3-ylmethyl)-1,2-dihydropyridin-2-one;

Compound 163, 3-(5-[(5-chlorothiophen-2-yl)methyl]amino-1-[(furan-2-yl)carbonyl]-1H-pyrazol-3-yl)-1-(pyridazin-3-ylmethyl)-1,2-dihydropyridin-2-one;

Compound 164, 3-(5-[(5-chlorothiophen-2-yl)methyl]amino-1-[(furan-2-yl)carbonyl]-1H-pyrazol-3-yl)-1-(pyridin-2-ylmethyl)-1,2-dihydropyridin-2-one;

Compound 165, 3-(5-[(5-chlorothiophen-2-yl)methyl]amino-1-[(furan-2-yl)carbonyl]-1H-pyrazol-3-yl)-1-(pyridin-3-ylmethyl)-1,2-dihydropyridin-2-one;

Compound 166, 3-(5-[(5-chlorothiophen-2-yl)methyl]amino-1-[(furan-2-yl)carbonyl]-1H-pyrazol-3-yl)-1-(pyridin-4-ylmethyl)-1,2-dihydropyridin-2-one;

Compound 167, 3-(5-[(5-chlorothiophen-2-yl)methyl]amino-1-[(furan-2-yl)carbonyl]-1H-pyrazol-3-yl)-1-(pyrimidin-2-ylmethyl)-1,2-dihydropyridin-2-one;

Compound 168, 3-(5-[(5-chlorothiophen-2-yl)methyl]amino-1-[(furan-2-yl)carbonyl]-1H-pyrazol-3-yl)-1-(thiophen-2-ylmethyl)-1,2-dihydropyridin-2-one;

Compound 169, 3-(5-[(5-chlorothiophen-2-yl)methyl]amino-1-[(furan-2-yl)carbonyl]-1H-pyrazol-3-yl)-1-(thiophen-3-ylmethyl)-1,2-dihydropyridin-2-one;

Compound 170, 3-(5-[(5-chlorothiophen-2-yl)methyl]amino-1-[(furan-2-yl)carbonyl]-1H-pyrazol-3-yl)-1-[2-(morpholin-4-yl)ethyl]-1,2-dihydropyridin-2-one;

Compound 171, 3-(5-[(5-chlorothiophen-2-yl)methyl]amino-1-[(furan-3-yl)carbonyl]-1H-pyrazol-3-yl)-1-(2-methoxyethyl)-1,2-dihydropyridin-2-one;

Compound 172, 3-(5-[(5-chlorothiophen-2-yl)methyl]amino-1-[(furan-3-yl)carbonyl]-1H-pyrazol-3-yl)-1-(2-phenylethyl)-1,2-dihydropyridin-2-one;

Compound 173, 3-(5-[(5-chlorothiophen-2-yl)methyl]amino-1-[(furan-3-yl)carbonyl]-1H-pyrazol-3-yl)-1-(furan-3-ylmethyl)-1,2-dihydropyridin-2-one;

Compound 174, 3-(5-[(5-chlorothiophen-2-yl)methyl]amino-1-[(furan-3-yl)carbonyl]-1H-pyrazol-3-yl)-1-(naphthalen-1-ylmethyl)-1,2-dihydropyridin-2-one;

Compound 175, 3-(5-[(5-chlorothiophen-2-yl)methyl]amino-1-[(furan-3-yl)carbonyl]-1H-pyrazol-3-yl)-1-(naphthalen-2-ylmethyl)-1,2-dihydropyridin-2-one;

Compound 176, 3-(5-[(5-chlorothiophen-2-yl)methyl]amino-1-[(furan-3-yl)carbonyl]-1H-pyrazol-3-yl)-1-(pyridazin-3-ylmethyl)-1,2-dihydropyridin-2-one;

Compound 177, 3-(5-[(5-chlorothiophen-2-yl)methyl]amino-1-[(furan-3-yl)carbonyl]-1H-pyrazol-3-yl)-1-(pyridin-3-ylmethyl)-1,2-dihydropyridin-2-one;

Compound 178, 3-(5-[(5-chlorothiophen-2-yl)methyl]amino-1-[(furan-3-yl)carbonyl]-1H-pyrazol-3-yl)-1-(pyrimidin-2-ylmethyl)-1,2-dihydropyridin-2-one;

Compound 179, 3-(5-[(5-chlorothiophen-2-yl)methyl]amino-1-[(furan-3-yl)carbonyl]-1H-pyrazol-3-yl)-1-(thiophen-3-ylmethyl)-1,2-dihydropyridin-2-one;

Compound 180, 3-(5-[(5-chlorothiophen-2-yl)methyl]amino-1-[(furan-3-yl)carbonyl]-1H-pyrazol-3-yl)-1-[2-(morpholin-4-yl)-2-oxoethyl]-1,2-dihydropyridin-2-one;

Compound 181, 3-(5-[(5-chlorothiophen-2-yl)methyl]amino-1-[(furan-3-yl)carbonyl]-1H-pyrazol-3-yl)-1-[2-(morpholin-4-yl)ethyl]-1,2-dihydropyridin-2-one;

Compound 182, 3-(5-[(5-chlorothiophen-2-yl)methyl]amino-1-[(thiophen-2-yl)carbonyl]-1H-pyrazol-3-yl)-1-(2-methoxyethyl)-1,2-dihydropyridin-2-one;

Compound 183, 3-(5-[(5-chlorothiophen-2-yl)methyl]amino-1-[(thiophen-2-yl)carbonyl]-1H-pyrazol-3-yl)-1-(furan-2-ylmethyl)-1,2-dihydropyridin-2-one;

Compound 184, 3-(5-[(5-chlorothiophen-2-yl)methyl]amino-1-[(thiophen-2-yl)carbonyl]-1H-pyrazol-3-yl)-1-(furan-3-ylmethyl)-1,2-dihydropyridin-2-one;

Compound 185, 3-(5-[(5-chlorothiophen-2-yl)methyl]amino-1-[(thiophen-2-yl)carbonyl]-1H-pyrazol-3-yl)-1-(pyridazin-3-ylmethyl)-1,2-dihydropyridin-2-one;

Compound 186, 3-(5-[(5-chlorothiophen-2-yl)methyl]amino-1-[(thiophen-2-yl)carbonyl]-1H-pyrazol-3-yl)-1-(pyridin-2-ylmethyl)-1,2-dihydropyridin-2-one;

Compound 187, 3-(5-[(5-chlorothiophen-2-yl)methyl]amino-1-[(thiophen-2-yl)carbonyl]-1H-pyrazol-3-yl)-1-(pyridin-3-ylmethyl)-1,2-dihydropyridin-2-one;

Compound 188, 3-(5-[(5-chlorothiophen-2-yl)methyl]amino-1-[(thiophen-2-yl)carbonyl]-1H-pyrazol-3-yl)-1-(pyridin-4-ylmethyl)-1,2-dihydropyridin-2-one;

Compound 189, 3-(5-[(5-chlorothiophen-2-yl)methyl]amino-1-[(thiophen-2-yl)carbonyl]-1H-pyrazol-3-yl)-1-(pyrimidin-2-ylmethyl)-1,2-dihydropyridin-2-one;

Compound 190, 3-(5-[(5-chlorothiophen-2-yl)methyl]amino-1-[(thiophen-2-yl)carbonyl]-1H-pyrazol-3-yl)-1-(thiophen-2-ylmethyl)-1,2-dihydropyridin-2-one;

Compound 191, 3-(5-[(5-chlorothiophen-2-yl)methyl]amino-1-[(thiophen-2-yl)carbonyl]-1H-pyrazol-3-yl)-1-(thiophen-3-ylmethyl)-1,2-dihydropyridin-2-one;

Compound 192, 3-(5-[(5-chlorothiophen-2-yl)methyl]amino-1-[(thiophen-2-yl)carbonyl]-1H-pyrazol-3-yl)-1-[2-(morpholin-4-yl)ethyl]-1,2-dihydropyridin-2-one;

Compound 193, 3-(5-[(5-chlorothiophen-2-yl)methyl]amino-1-[(thiophen-3-yl)carbonyl]-1H-pyrazol-3-yl)-1,2-dihydropyridin-2-one;

Compound 194, 3-(5-[(5-chlorothiophen-2-yl)methyl]amino-1-[(thiophen-3-yl)carbonyl]-1H-pyrazol-3-yl)-1-(2-methoxyethyl)-1,2-dihydropyridin-2-one;

Compound 195, 3-(5-[(5-chlorothiophen-2-yl)methyl]amino-1-[(thiophen-3-yl)carbonyl]-1H-pyrazol-3-yl)-1-(furan-2-ylmethyl)-1,2-dihydropyridin-2-one;

Compound 196, 3-(5-[(5-chlorothiophen-2-yl)methyl]amino-1-[(thiophen-3-yl)carbonyl]-1H-pyrazol-3-yl)-1-(furan-3-ylmethyl)-1,2-dihydropyridin-2-one;

Compound 197, 3-(5-[(5-chlorothiophen-2-yl)methyl]amino-1-[(thiophen-3-yl)carbonyl]-1H-pyrazol-3-yl)-1-(pyridazin-3-ylmethyl)-1,2-dihydropyridin-2-one;

Compound 198, 3-(5-[(5-chlorothiophen-2-yl)methyl]amino-1-[(thiophen-3-yl)carbonyl]-1H-pyrazol-3-yl)-1-(pyridin-2-ylmethyl)-1,2-dihydropyridin-2-one;

Compound 199, 3-(5-[(5-chlorothiophen-2-yl)methyl]amino-1-[(thiophen-3-yl)carbonyl]-1H-pyrazol-3-yl)-1-(pyridin-3-ylmethyl)-1,2-dihydropyridin-2-one;

Compound 200, 3-(5-[(5-chlorothiophen-2-yl)methyl]amino-1-[(thiophen-3-yl)carbonyl]-1H-pyrazol-3-yl)-1-(pyridin-4-ylmethyl)-1,2-dihydropyridin-2-one;

Compound 201, 3-(5-[(5-chlorothiophen-2-yl)methyl]amino-1-[(thiophen-3-yl)carbonyl]-1H-pyrazol-3-yl)-1-(pyrimidin-2-ylmethyl)-1,2-dihydropyridin-2-one;

Compound 202, 3-(5-[(5-chlorothiophen-2-yl)methyl]amino-1-[(thiophen-3-yl)carbonyl]-1H-pyrazol-3-yl)-1-(thiophen-2-ylmethyl)-1,2-dihydropyridin-2-one;

Compound 203, 3-(5-[(5-chlorothiophen-2-yl)methyl]amino-1-[(thiophen-3-yl)carbonyl]-1H-pyrazol-3-yl)-1-(thiophen-3-ylmethyl)-1,2-dihydropyridin-2-one;

Compound 204, 3-(5-[(5-chlorothiophen-2-yl)methyl]amino-1-[(thiophen-3-yl)carbonyl]-1H-pyrazol-3-yl)-1-[2-(morpholin-4-yl)ethyl]-1,2-dihydropyridin-2-one;

Compound 205, 3-(5-[(5-chlorothiophen-2-yl)methyl]amino-1-[2-(morpholin-4-yl)phenyl]carbonyl-1H-pyrazol-3-yl)-1,2-dihydropyridin-2-one;

Compound 206, 3-(5-[(S-chi orothiophen-2-yl)methyl]amino-1-[4-(2-methoxyethoxy)phenyl]carbonyl-1H-pyrazol-3-yl)-1,2-dihydropyridin-2-one;

Compound 207, 3-(5-[(5-chlorothiophen-2-yl)methyl]amino-1-[4-(morpholin-4-yl)phenyl]carbonyl-1H-pyrazol-3-yl)-1,2-dihydropyridin-2-one;

Compound 208, 3-(5-[(5-chlorothiophen-2-yl)methyl]amino-1-[4-(morpholin-4-yl)phenyl]carbonyl-1H-pyrazol-3-yl)-1-(2-methoxyethyl)-1,2-dihydropyridin-2-one;

Compound 209, 3-(5-[(5-chlorothiophen-2-yl)methyl]amino-1-[4-(morpholin-4-yl)phenyl]carbonyl-1H-pyrazol-3-yl)-1-(furan-2-ylmethyl)-1,2-dihydropyridin-2-one;

Compound 210, 3-(5-[(5-chlorothiophen-2-yl)methyl]amino-1-[4-(morpholin-4-yl)phenyl]carbonyl-1H-pyrazol-3-yl)-1-(furan-3-ylmethyl)-1,2-dihydropyridin-2-one;

Compound 211, 3-(5-[(5-chlorothiophen-2-yl)methyl]amino-1-[4-(morpholin-4-yl)phenyl]carbonyl-1H-pyrazol-3-yl)-1-(pyridazin-3-ylmethyl)-1,2-dihydropyridin-2-one;

Compound 212, 3-(5-[(5-chlorothiophen-2-yl)methyl]amino-1-[4-(morpholin-4-yl)phenyl]carbonyl-1H-pyrazol-3-yl)-1-(pyridin-2-ylmethyl)-1,2-dihydropyridin-2-one;

Compound 213, 3-(5-[(5-chlorothiophen-2-yl)methyl]amino-1-[4-(morpholin-4-yl)phenyl]carbonyl-1H-pyrazol-3-yl)-1-(pyridin-3-ylmethyl)-1,2-dihydropyridin-2-one;

Compound 214, 3-(5-[(5-chlorothiophen-2-yl)methyl]amino-1-[4-(morpholin-4-yl)phenyl]carbonyl-1H-pyrazol-3-yl)-1-(pyridin-4-ylmethyl)-1,2-dihydropyridin-2-one;

Compound 215, 3-(5-[(5-chlorothiophen-2-yl)methyl]amino-1-[4-(morpholin-4-yl)phenyl]carbonyl-1H-pyrazol-3-yl)-1-(pyrimidin-2-ylmethyl)-1,2-dihydropyridin-2-one;

Compound 216, 3-(5-[(5-chlorothiophen-2-yl)methyl]amino-1-[4-(morpholin-4-yl)phenyl]carbonyl-1H-pyrazol-3-yl)-1-(thiophen-2-ylmethyl)-1,2-dihydropyridin-2-one;

Compound 217, 3-(5-[(5-chlorothiophen-2-yl)methyl]amino-1-[4-(morpholin-4-yl)phenyl]carbonyl-1H-pyrazol-3-yl)-1-(thiophen-3-ylmethyl)-1,2-dihydropyridin-2-one;

Compound 218, 3-(5-[(5-chlorothiophen-2-yl)methyl]amino-1-[4-(morpholin-4-yl)phenyl]carbonyl-1H-pyrazol-3-yl)-1-[2-(morpholin-4-yl)ethyl]-1,2-dihydropyridin-2-one;

Compound 219, 3-(5-[(5-chlorothiophen-2-yl)methyl] amino-1H-pyrazol-3-yl)-1-(1H-1,2,3,4-tetrazol-5-ylmethyl)-1,2-dihydropyridin-2-one;
Compound 220, 3-(5-[(5-chlorothiophen-2-yl)methyl] amino-1H-pyrazol-3-yl)-1-(2-methoxyethyl)-1,2-dihydropyridin-2-one;
Compound 221, 3-(5-[(5-chlorothiophen-2-yl)methyl] amino-1H-pyrazol-3-yl)-1-(2-phenylethyl)-1,2-dihydropyridin-2-one;
Compound 222, 3-(5-[(5-chlorothiophen-2-yl)methyl] amino-1H-pyrazol-3-yl)-1-(furan-2-ylmethyl)-1,2-dihydropyridin-2-one;
Compound 223, 3-(5-[(5-chlorothiophen-2-yl)methyl] amino-1H-pyrazol-3-yl)-1-(furan-3-ylmethyl)-1,2-dihydropyridin-2-one;
Compound 224, 3-(5-[(5-chlorothiophen-2-yl)methyl] amino-1H-pyrazol-3-yl)-1-(naphthalen-1-ylmethyl)-1,2-dihydropyridin-2-one;
Compound 225, 3-(5-[(5-chlorothiophen-2-yl)methyl] amino-1H-pyrazol-3-yl)-1-(naphthalen-2-ylmethyl)-1,2-dihydropyridin-2-one;
Compound 226, 3-(5-[(5-chlorothiophen-2-yl)methyl] amino-1H-pyrazol-3-yl)-1-(pyridazin-3-ylmethyl)-1,2-dihydropyridin-2-one;
Compound 227, 3-(5-[(5-chlorothiophen-2-yl)methyl] amino-1H-pyrazol-3-yl)-1-(pyridin-2-ylmethyl)-1,2-dihydropyridin-2-one;
Compound 228, 3-(5-[(5-chlorothiophen-2-yl)methyl] amino-1H-pyrazol-3-yl)-1-(pyridin-3-ylmethyl)-1,2-dihydropyridin-2-one;
Compound 229, 3-(5-[(5-chlorothiophen-2-yl)methyl] amino-1H-pyrazol-3-yl)-1-(pyridin-4-ylmethyl)-1,2-dihydropyridin-2-one;
Compound 230, 3-(5-[(5-chlorothiophen-2-yl)methyl] amino-1H-pyrazol-3-yl)-1-(pyrimidin-2-ylmethyl)-1,2-dihydropyridin-2-one;
Compound 231, 3-(5-[(5-chlorothiophen-2-yl)methyl] amino-1H-pyrazol-3-yl)-1-(thiophen-2-ylmethyl)-1,2-dihydropyridin-2-one;
Compound 232, 3-(5-[(5-chlorothiophen-2-yl)methyl] amino-1H-pyrazol-3-yl)-1-(thiophen-3-ylmethyl)-1,2-dihydropyridin-2-one;
Compound 233, 3-(5-[(5-chlorothiophen-2-yl)methyl] amino-1H-pyrazol-3-yl)-1-[2-(morpholin-4-yl)-2-oxoethyl]-1,2-dihydropyridin-2-one;
Compound 234, 3-(5-[(5-chlorothiophen-2-yl)methyl] amino-1H-pyrazol-3-yl)-1-[2-(morpholin-4-yl)ethyl]-1,2-dihydropyridin-2-one;
Compound 235, 3-(5-[(5-chlorothiophen-2-yl)methyl] amino-1H-pyrazol-3-yl)-1-[2-(pyridin-2-yl)ethyl]-1,2-dihydropyridin-2-one;
Compound 236, 3-(5-[(5-chlorothiophen-2-yl)methyl] amino-1H-pyrazol-3-yl)-1-methyl-1,2-dihydropyridin-2-one;
Compound 237, 3-[5-(benzylamino)-1-[(furan-2-yl)carbonyl]-1H-pyrazol-3-yl]-1,2-dihydropyridin-2-one;
Compound 238, 3-[5-(benzylamino)-1-[(furan-2-yl)carbonyl]-1H-pyrazol-3-yl]-1-(pyridin-2-ylmethyl)-1,2-dihydropyridin-2-one;
Compound 239, 3-[5-(dimethylamino)-1-[(furan-2-yl)carbonyl]-1H-pyrazol-3-yl]-1,2-dihydropyridin-2-one;
Compound 240, 3-[5-(dimethylamino)-1-[(furan-2-yl)carbonyl]-1H-pyrazol-3-yl]-1-(pyridin-2-ylmethyl)-1,2-dihydropyridin-2-one;
Compound 241, 3-1-[(2-aminophenyl)carbonyl]-5-[(5-chlorothiophen-2-yl)methyl]amino-1H-pyrazol-3-yl-1,2-dihydropyridin-2-one;
Compound 242, 3-1-[(2-chlorophenyl)carbonyl]-5-[(5-chlorothiophen-2-yl)methyl]amino-1H-pyrazol-3-yl-1-(2-methoxyethyl)-1,2-dihydropyridin-2-one;
Compound 243, 3-1-[(2-chlorophenyl)carbonyl]-5-[(5-chlorothiophen-2-yl)methyl]amino-1H-pyrazol-3-yl-1-(furan-2-ylmethyl)-1,2-dihydropyridin-2-one;
Compound 244, 3-1-[(2-chlorophenyl)carbonyl]-5-[(5-chlorothiophen-2-yl)methyl]amino-1H-pyrazol-3-yl-1-(furan-3-ylmethyl)-1,2-dihydropyridin-2-one;
Compound 245, 3-1-[(2-chlorophenyl)carbonyl]-5-[(5-chlorothiophen-2-yl)methyl]amino-1H-pyrazol-3-yl-1-(pyridazin-3-ylmethyl)-1,2-dihydropyridin-2-one;
Compound 246, 3-1-[(2-chlorophenyl)carbonyl]-5-[(5-chlorothiophen-2-yl)methyl]amino-1H-pyrazol-3-yl-1-(pyridin-2-ylmethyl)-1,2-dihydropyridin-2-one;
Compound 247, 3-1-[(2-chlorophenyl)carbonyl]-5-[(5-chlorothiophen-2-yl)methyl]amino-1H-pyrazol-3-yl-1-(pyridin-3-ylmethyl)-1,2-dihydropyridin-2-one;
Compound 248, 3-1-[(2-chlorophenyl)carbonyl]-5-[(5-chlorothiophen-2-yl)methyl]amino-1H-pyrazol-3-yl-1-(pyridin-4-ylmethyl)-1,2-dihydropyridin-2-one;
Compound 249, 3-1-[(2-chlorophenyl)carbonyl]-5-[(5-chlorothiophen-2-yl)methyl]amino-1H-pyrazol-3-yl-1-(pyrimidin-2-ylmethyl)-1,2-dihydropyridin-2-one;
Compound 250, 3-1-[(2-chlorophenyl)carbonyl]-5-[(5-chlorothiophen-2-yl)methyl]amino-1H-pyrazol-3-yl-1-(thiophen-2-ylmethyl)-1,2-dihydropyridin-2-one;
Compound 251, 3-1-[(2-chlorophenyl)carbonyl]-5-[(5-chlorothiophen-2-yl)methyl]amino-1H-pyrazol-3-yl-1-(thiophen-3-ylmethyl)-1,2-dihydropyridin-2-one;
Compound 252, 3-1-[(2-chlorophenyl)carbonyl]-5-[(5-chlorothiophen-2-yl)methyl]amino-1H-pyrazol-3-yl 1 [2-(morpholin-4-yl)ethyl]-1,2-dihydropyridin-2-one;
Compound 253, 3-1-[(4-tert-butylphenyl)carbonyl]-5-[(5-chlorothiophen-2-yl)methyl]amino-1H-pyrazol-3-yl-1,2-dihydropyridin-2-one;
Compound 254, 3-1-[(4-tert-butylphenyl)carbonyl]-5-[(5-chlorothiophen-2-yl)methyl]amino-1H-pyrazol-3-yl-1-methyl-1,2-dihydropyridin-2-one;
Compound 255, 3-5-amino-1-[(furan-2-yl)carbonyl]-1H-pyrazol-3-yl-1,2-dihydropyridin-2-one;
Compound 256, 3-5-amino-1-[(furan-2-yl)carbonyl]-1H-pyrazol-3-yl-1-(pyridin-2-ylmethyl)-1,2-dihydropyridin-2-one;
Compound 257, ethyl 2-[3-(5-[(5-chlorothiophen-2-yl) methyl]amino-1-(2,2-dimethylpropanoyl)-1H-pyrazol-3-yl)-2-oxo-1,2-dihydropyridin-1-yl]acetate;
Compound 258, ethyl 2-[3-(5-[(5-chlorothiophen-2-yl) methyl]amino-1-[(2-methoxyphenyl)carbonyl]-1H-pyrazol-3-yl)-2-oxo-1,2-dihydropyridin-1-yl]acetate;
Compound 259, ethyl 2-[3-(5-[(5-chlorothiophen-2-yl) methyl]amino-1-[(furan-3-yl)carbonyl]-1H-pyrazol-3-yl)-2-oxo-1,2-dihydropyridin-1-yl]acetate;
Compound 260, ethyl 2-[3-(5-[(5-chlorothiophen-2-yl) methyl]amino-1H-pyrazol-3-yl)-2-oxo-1,2-dihydropyridin-1-yl]acetate;
Compound 261, tert-butyl 2-[3-(5-[(5-chlorothiophen-2-yl)methyl]amino-1-(2,2-dimethylpropanoyl)-1H-pyrazol-3-yl)-2-oxo-1,2-dihydropyridin-1-yl]acetate;
Compound 262, tert-butyl 2-[3-(5-[(5-chlorothiophen-2-yl)methyl]amino-1-[(2-methoxyphenyl)carbonyl]-1H-pyrazol-3-yl)-2-oxo-1,2-dihydropyridin-1-yl]acetate;
Compound 263, tert-butyl 2-[3-(5-[(5-chlorothiophen-2-yl)methyl]amino-1-[(furan-3-yl)carbonyl]-1H-pyrazol-3-yl)-2-oxo-1,2-dihydropyridin-1-yl]acetate;

Compound 264, tert-butyl 2-[3-(5-[(5-chlorothiophen-2-yl)methyl]amino-1H-pyrazol-3-yl)-2-oxo-1,2-dihydropyridin-1-yl]acetate;

Compound 265, 1-[(5-[(5-chlorothiophen-2-yl)methyl]amino-3-(1-methyl-2-oxo-1,2-dihydropyridin-3-yl)-1H-pyrazol-1-yl)carbonyl]cyclopropylmethyl 1-(hydroxymethyl)cyclopropane-1-carboxylate.

20. The compound of claim 1, wherein $R^5$ is substituted or unsubstituted $C_1$-$C_8$ heteroalkyl having O or N as a heteroatom.

21. The compound of claim 1, wherein $R^5$ is substituted $C_1$-$C_8$ alkyl having one or more substituent group selected from the group consisting of —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN, —NO$_2$, —CF$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R', R", R"', and R"" each independently is hydrogen, substituted or unsubstituted heteroalkyl, substituted or unsubstituted cycloalkyl, substituted or unsubstituted heterocycloalkyl, substituted or unsubstituted aryl, substituted or unsubstituted alkyl, substituted or unsubstituted alkoxy, substituted or unsubstituted thioalkoxy, or substituted or unsubstituted arylalkyl.

22. The compound of claim 1, wherein $R^2$ is substituted or unsubstituted cycloalkyl.

23. The compound of claim 22, wherein $R^2$ is substituted or unsubstituted cycloalkyl selected from the group consisting of substituted or unsubstituted cyclopropyl, substituted or unsubstituted cyclobutyl, substituted or unsubstituted cyclopentyl, and substituted or unsubstituted cyclohexyl.

24. The compound of claim 1, wherein $R^7$ is substituted or unsubstituted methyl.

25. The compound of claim 1, wherein $R^7$ is hydrogen.

* * * * *